US010570420B2

(12) United States Patent
Daviet et al.

(10) Patent No.: US 10,570,420 B2
(45) **Date of Patent: *Feb. 25, 2020**

(54) METHOD FOR PRODUCING FRAGRANT ALCOHOLS

(71) Applicant: FIRMENICH SA, Geneva (CH)

(72) Inventors: Laurent Daviet, Geneva (CH); Letizia Rocci, Geneva (CH); Michel Schalk, Geneva (CH)

(73) Assignee: Firmenich SA, Satigny (CH)

( * ) Notice: Subject to any disclaimer, the term of this patent is extended or adjusted under 35 U.S.C. 154(b) by 0 days.

This patent is subject to a terminal disclaimer.

(21) Appl. No.: 15/877,183

(22) Filed: Jan. 22, 2018

(65) Prior Publication Data

US 2018/0208946 A1 Jul. 26, 2018

Related U.S. Application Data

(62) Division of application No. 15/023,640, filed as application No. PCT/EP2014/070060 on Sep. 19, 2014, now Pat. No. 9,909,145.

(60) Provisional application No. 61/880,149, filed on Sep. 19, 2013.

(51) Int. Cl.

*C12P 5/00* (2006.01)
*C12N 9/02* (2006.01)
*C12P 7/02* (2006.01)

(52) U.S. Cl.

CPC ............ *C12P 5/007* (2013.01); *C12N 9/0071* (2013.01); *C12N 9/0079* (2013.01); *C12P 7/02* (2013.01); *C12Y 114/13* (2013.01); *C12Y 114/14001* (2013.01)

(58) Field of Classification Search

CPC ........... C12Y 114/13; C12Y 114/14001; C12P 5/007; C12P 7/02; C12N 9/0079; C12N 9/0071

See application file for complete search history.

(56) References Cited

U.S. PATENT DOCUMENTS

| | | | | |
|---|---|---|---|---|
| 9,909,145 | B2 * | 3/2018 | Daviet ................. | C12Y 114/13 |
| 2011/0008836 | A1 | 1/2011 | Schalk | |
| 2011/0281257 | A1 | 11/2011 | Schalk | |
| 2016/0108374 | A1 | 4/2016 | Bohlmann | |

FOREIGN PATENT DOCUMENTS

| | | | |
|---|---|---|---|
| WO | 2003025193 | A1 | 3/2003 |
| WO | 2009109597 | A1 | 9/2009 |
| WO | 2010067309 | A1 | 6/2010 |
| WO | 2013064411 | A1 | 5/2013 |
| WO | 2014067007 | A1 | 5/2014 |

OTHER PUBLICATIONS

Diaz-Chavez, M., et al. "Biosynthesis of sandalwood oil: santalum album CYP76F Cytochromes P450 produce santalols and bergamotol," Plos One, vol. 8, Issue 9, 2013.
Broun et al., Catalytic plasticity of fatty acid modification enzymes underlying chemical diversity of plant lipids. Science, 1998, vol. 282: 1315-1317.
Devos et al., Practical limits of function prediction. Proteins: Structure, Function, and Genetics. 2000, vol. 41: 98-107.
Seffernick et al., Melamine deaminase and Atrazine chlorohydrolase: 98 percent identical but functionally different. J. Bacteriol., 2001, vol. 183 (8): 2405-2410.
Whisstock et al., Prediction of protein function from protein sequence. Q. Rev. Biophysics., 2003, vol. 36 (3): 307-340.
Witkowski et al., Conversion of b-ketoacyl synthase to a Malonyl Decarboxylase by replacement of the active cysteine with glutamine. Biochemistry, 1999, vol. 38: 11643-11650.
Altschul et al., J. Mol. Biol. 215,1990, p. 403-410.
Altschul, J. Mol. Biol. , 1991, 219, p. 555-565.
Barnes H.J, Method Enzymol., 272,1996, p. 3-14.
Cankar et al, FEBS Letters, 2011, p. 178-182.
Gotoh O., J Biol Chem, 267(1), 1992, p. 83-90.
Halkier et al, Arch. Biochem. Biophys., 322,1995, p. 369-377.
Haudenschield et al, Arch. Biochem. Biophys., 379, 2000, p. 127-136.
Jensen et al., Phytochemistry, vol. 71, 2010, p. 132-141.
Maurer et al, Advanced Synthesis & Catalysis, 345, 2003, p. 802-810.
Seifert et al., Chembiochem, 2009, vol. 10, p. 853.
Takahashi, et al., "Metabolic Engineering of Sesquiterpene Metabolism in Yeast", J. Biotechnology and Bioengineenng, 2007, vol. 97(1), p. 170-181.
Tatusova et al., "BLAST 2 Sequences, a new tool for comaring protein and nucleotide sequences", FEMS Microbiology Letters, 1999, vol. 174, p. 247-250.
Teoh et al., "*Artemisia annua* L. (Asteraceae) trichome-specific cDNAs reveal CYP71AV1, a cytochrome P450 with a key role . . . ", FEBS Letters, 2006, vol. 580, p. 1411-1416.
Tresse et al., "Comparative evaluation of adhesion, surface properties, and surface protein composition of Listeria . . . ", Journal of Applied Microbiology, 2006, 101, p. 53-62.
Wu et al., "Redirection of cytosolic or plastidic isoprenoid precursors elevates terpene production in plants", Nat. Biotechnol., 2006, vol. 24(11), p. 1441-1447.
Martin et al., "Engineering a mevalonate pathway in *Escherichia coli* for production of terpenoids", Nat. Biotechnol., 2003, vol. 21, 796-802.
Meinhold et al., "Engineering Cytochrome P450 BM3 for Terminal Alkane Hydroxylation", Advanced Synthesis & Catalysis, 2006, vol. 348, p. 763-772.
Murashige et al., "A Revised Medium for Rapid Growth and Bio Assays with Tobacco Tissue Cultures", Physiologia Plantarum, 1962, vol. 15, p. 473-497.
International Search Report and Written Opinion of the International Searching Authority dated Mar. 10, 2015 for application No. PCT/EP2014/070060 filed Sep. 19, 2014.

(Continued)

*Primary Examiner* — Ganapathirama Raghu
(74) *Attorney, Agent, or Firm* — Armstrong Teasdale LLP

(57) ABSTRACT

This invention relates generally to methods and compositions for producing a sesquiterpene alcohol comprising contacting a sesquiterpene with a P450 polypeptide with monooxygenase activity.

6 Claims, 31 Drawing Sheets

Specification includes a Sequence Listing.

(56) References Cited

OTHER PUBLICATIONS

International Preliminary Report on Patentability dated Mar. 22, 2016 for application No. PCT/EP2014/070060 filed Sep. 19, 2014.
Omura et al., "The Carbon Monoxide-binding Pigment of Liver Microsomes II.", J. Biol. Chem., Jul. 1964, vol. 239 (7) , p. 2379-2385.
Schalk et al., "Toward a Biosynthetic Route to Sclaeol and Amber Odorants", J. Am Chem. Soc., 2012, vol. 134, p. 18900-18903.
Schalk et al., "A single amino acid substitution (F363I) converts the regiochemistry of the spearmint (−)-limonene . . . ", Proc Natl Acad Sci USA , 2000,vol. 97(22), p. 11948-11953.
Schardl et al., "Design and construction of a versatile system for the expression of foreign genes in plants", Gene, 1987, vol. 61, p. 1-11.
Bohlmann, et al., XP2733709, Accession BBF82151, "Santalum album santalene synthase (SaSSY) polypeptide SEQ: 17", Jul. 3, 2014.
Han, et al., "Full=Cytochrome P450 CYP736A12", XP002736380, UniProt Accession H2DH18, Mar. 21, 2012.
Cankar, et al., "valencene oxidase [Cichorium intybus]", NCBI GenBank Accession No. ADM86719.1, Jan. 24, 2011.
Siminszky, et al., "CYP71D10p [Glycine max]", GenBank Accession No. AAB94588.1, Mar. 2, 1999.
Martin, et al., E,E-alpha-famesene synthase [Picea abies], GenBank Accession No. AAS47697.1, Aug. 29, 2004.
Picaud, et al., (E)-beta-famesene synthase [Artemisia annua], GenBank Accession No. AAX39387.1, Jun. 1, 2005.
Ro, et al., "amorpha-4,11-diene C-12 oxidase [Artemisia annua]", GenBank Accession No. ABB82944.1, Apr. 13, 2006.
Kong, et al., "cytochrome P450 reductase [Artemisia annua]", GenBank Accession No. ABM88789.1, Jan. 28, 2007.
Rocci, et al., "sesquisabinene B synthase [Santalum album]", GenBank Accession No. ADP37190.1, Nov. 7, 2010.
Rocci, et al., "Tps2-1 [Clausena lansium]", GenBank Accession No. ADR71055.1, Dec. 11, 2010.
Rocci, et al., "(−)-beta-bisabolene synthase [Santalum album]", GenBank Accession No. ADP37189.1, Nov. 7, 2010.
Rocci, et al., "santalene bergamotene synthase 2 [Santalum album]", GenBank Accession No. ADP30867, Nov. 6, 2010.

* cited by examiner

- Figure 1 -

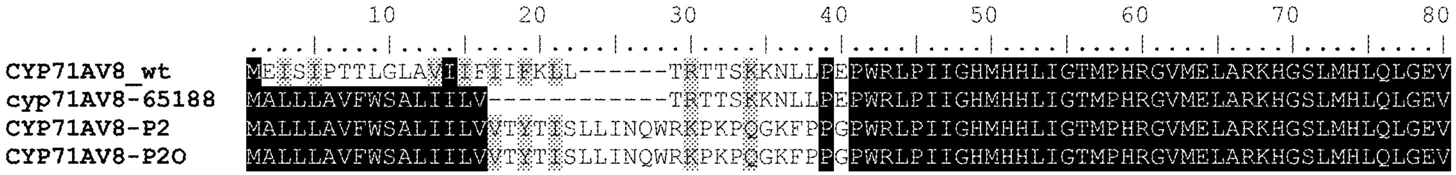

- Figure 1 -

```
                    .    |    .    |    .    |    .    |    .    |    .    |    .    |    .    |
                         10        20        30        40        50        60        70        80
CYP71AV8_wt        ME SPTTLGLA I F IEKL------T TTSKNLLPE PWRLPIIGHMHHLIGTMPHRGVMELARKHGSLMHLQLGEV
CYP71AV8-65188     MALLAVFWSALIILV          T TTSKNLLPE PWRLPIIGHMHHLIGTMPHRGVMELARKHGSLMHLQLGEV
CYP71AV8-P2        MALLAVFWSALIILV T T SLLINQWR PKP GKFPP GPWRLPIIGHMHHLIGTMPHRGVMELARKHGSLMHLQLGEV
CYP71AV8-P20       MALLAVFWSALIILV T T SLLINQWR PKP GKFPP GPWRLPIIGHMHHLIGTMPHRGVMELARKHGSLMHLQLGEV
```

- Figure 2A -
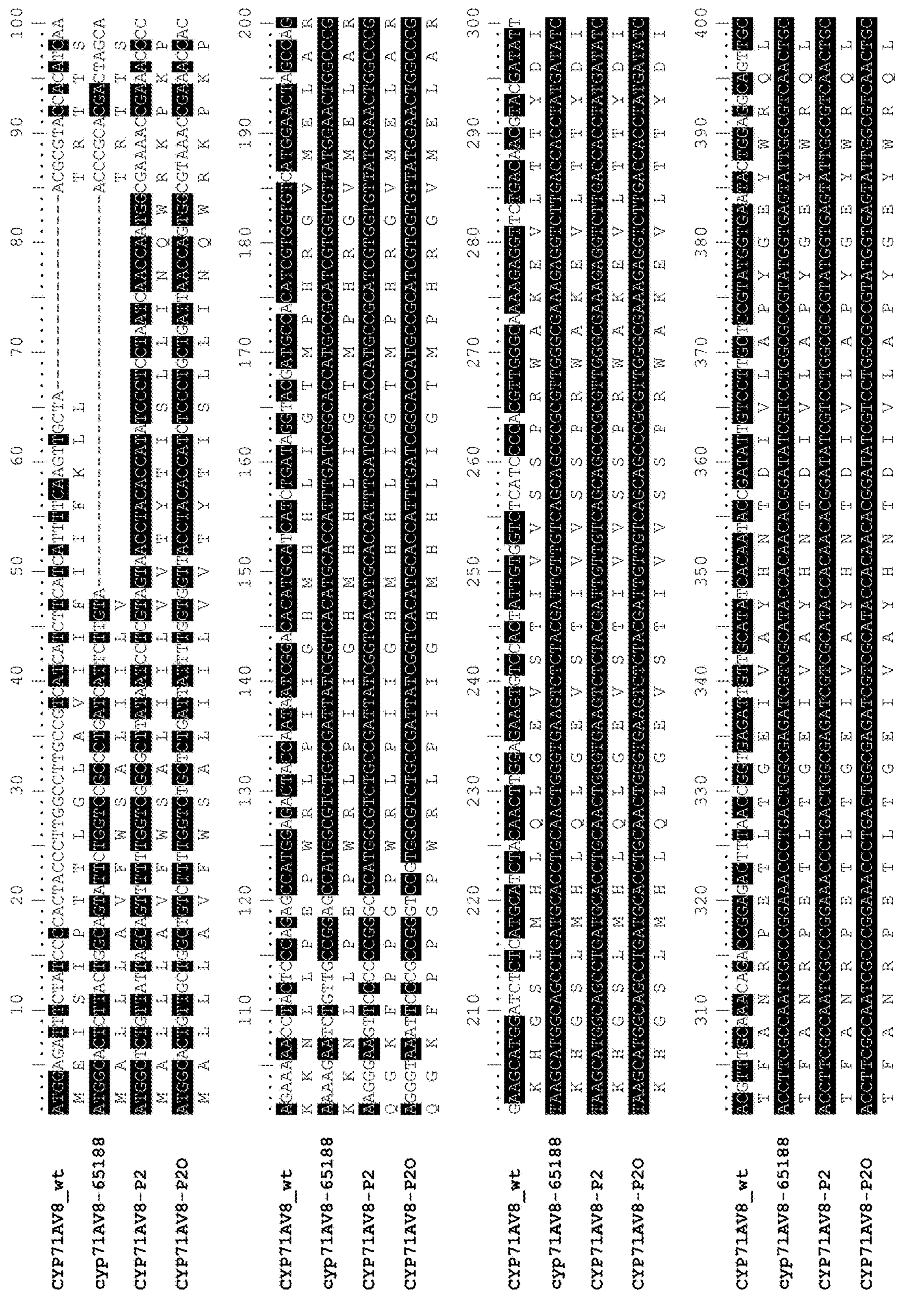

- Figure 2B -
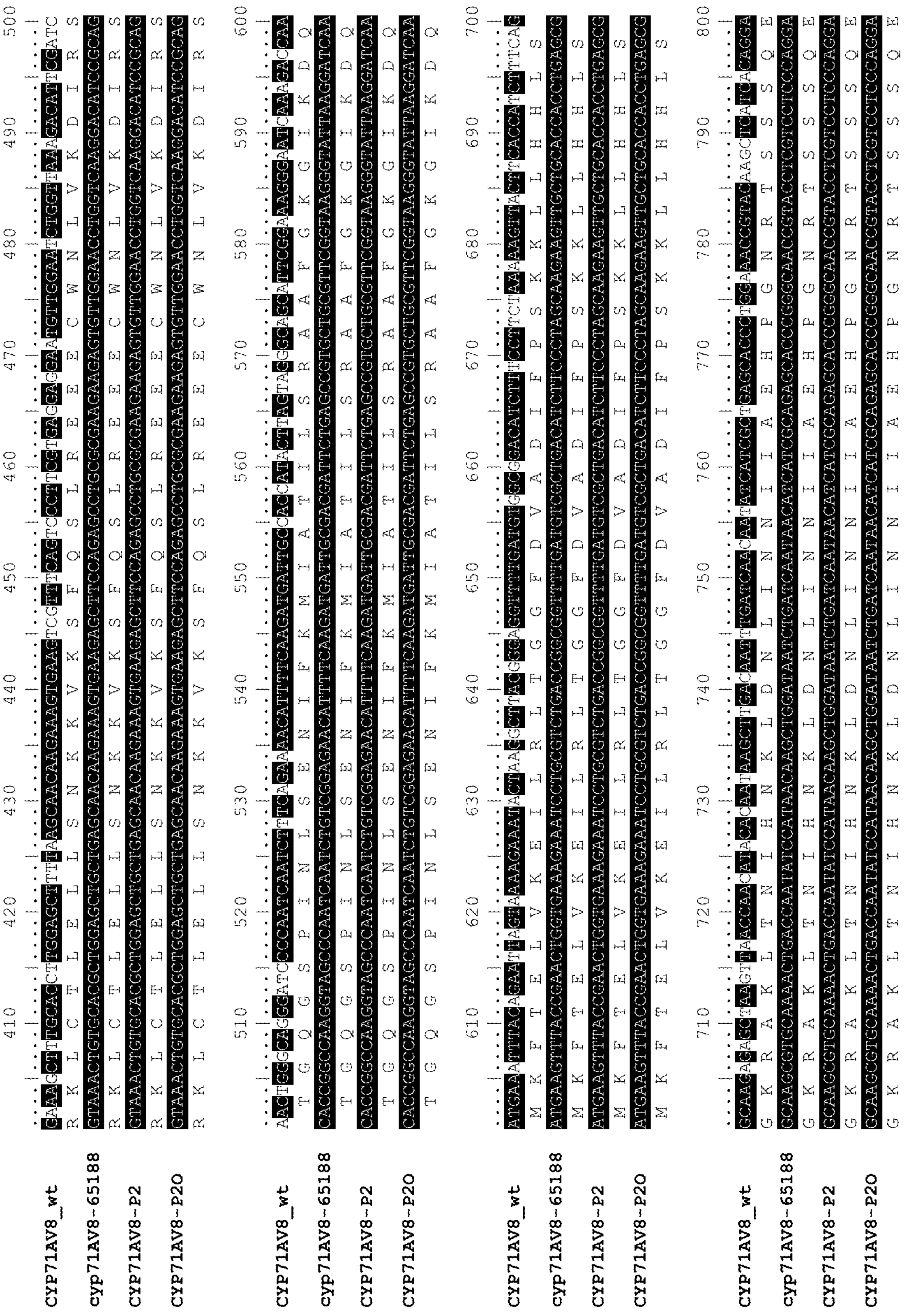

- Figure 2C -
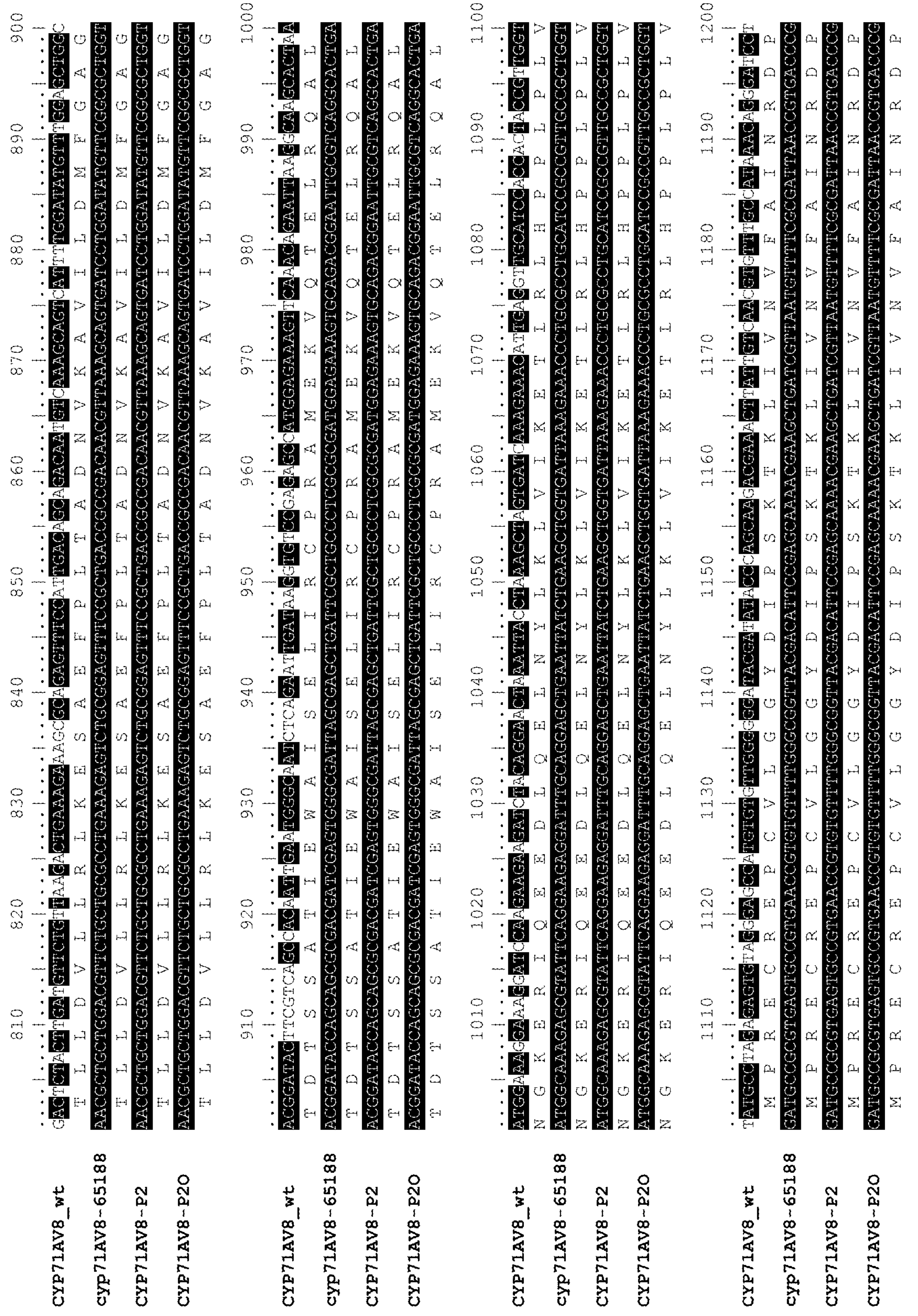

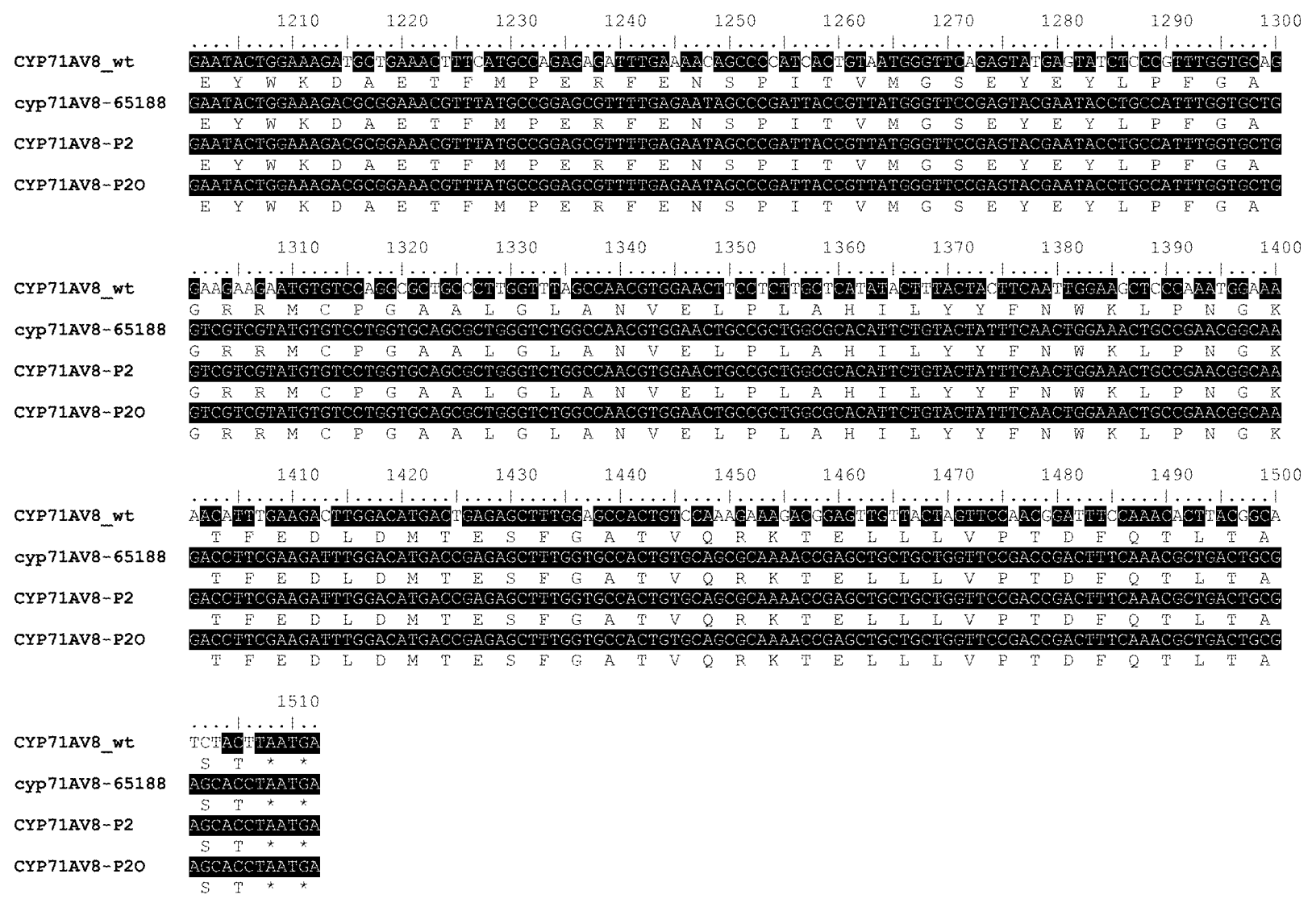

- Figure 2D -

```
                        1210      1220      1230      1240      1250      1260      1270      1280      1290      1300
                    ....|....|....|....|....|....|....|....|....|....|....|....|....|....|....|....|....|....|....|....|
CYP71AV8_wt         GAATACTGGAAAGATGCTGAAACTTTCATGCCAGAGAGATTTGAAAACAGCCCCATCACTGTAATGGGTTCAGAGTATGAGTATCTCCCGTTTGGTGCAG
                     E  Y  W  K  D  A  E  T  F  M  P  E  R  F  E  N  S  P  I  T  V  M  G  S  E  Y  E  Y  L  P  F  G  A
cyp71AV8-65188      GAATACTGGAAAGACGCGGAAACGTTTATGCCGGAGCGTTTTGAGAATAGCCCGATTACCGTTATGGGTTCCGAGTACGAATACCTGCCATTTGGTGCTG
                     E  Y  W  K  D  A  E  T  F  M  P  E  R  F  E  N  S  P  I  T  V  M  G  S  E  Y  E  Y  L  P  F  G  A
CYP71AV8-P2         GAATACTGGAAAGACGCGGAAACGTTTATGCCGGAGCGTTTTGAGAATAGCCCGATTACCGTTATGGGTTCCGAGTACGAATACCTGCCATTTGGTGCTG
                     E  Y  W  K  D  A  E  T  F  M  P  E  R  F  E  N  S  P  I  T  V  M  G  S  E  Y  E  Y  L  P  F  G  A
CYP71AV8-P2O        GAATACTGGAAAGACGCGGAAACGTTTATGCCGGAGCGTTTTGAGAATAGCCCGATTACCGTTATGGGTTCCGAGTACGAATACCTGCCATTTGGTGCTG
                     E  Y  W  K  D  A  E  T  F  M  P  E  R  F  E  N  S  P  I  T  V  M  G  S  E  Y  E  Y  L  P  F  G  A

                        1310      1320      1330      1340      1350      1360      1370      1380      1390      1400
                    ....|....|....|....|....|....|....|....|....|....|....|....|....|....|....|....|....|....|....|....|
CYP71AV8_wt         GAAGAAGAATGTGTCCAGGCGCTGCCCTTGGTTTAGCCAACGTGGAACTTCCTCTTGCTCATATACTTTACTACTTCAATTGGAAGCTCCCAAATGGAAA
                    G  R  R  M  C  P  G  A  A  L  G  L  A  N  V  E  L  P  L  A  H  I  L  Y  Y  F  N  W  K  L  P  N  G  K
cyp71AV8-65188      GTCGTCGTATGTGTCCTGGTGCAGCGCTGGGTCTGGCCAACGTGGAACTGCCGCTGGCGCACATTCTGTACTATTTCAACTGGAAACTGCCGAACGGCAA
                    G  R  R  M  C  P  G  A  A  L  G  L  A  N  V  E  L  P  L  A  H  I  L  Y  Y  F  N  W  K  L  P  N  G  K
CYP71AV8-P2         GTCGTCGTATGTGTCCTGGTGCAGCGCTGGGTCTGGCCAACGTGGAACTGCCGCTGGCGCACATTCTGTACTATTTCAACTGGAAACTGCCGAACGGCAA
                    G  R  R  M  C  P  G  A  A  L  G  L  A  N  V  E  L  P  L  A  H  I  L  Y  Y  F  N  W  K  L  P  N  G  K
CYP71AV8-P2O        GTCGTCGTATGTGTCCTGGTGCAGCGCTGGGTCTGGCCAACGTGGAACTGCCGCTGGCGCACATTCTGTACTATTTCAACTGGAAACTGCCGAACGGCAA
                    G  R  R  M  C  P  G  A  A  L  G  L  A  N  V  E  L  P  L  A  H  I  L  Y  Y  F  N  W  K  L  P  N  G  K

                        1410      1420      1430      1440      1450      1460      1470      1480      1490      1500
                    ....|....|....|....|....|....|....|....|....|....|....|....|....|....|....|....|....|....|....|....|
CYP71AV8_wt         AACATTTGAAGACTTGGACATGACTGAGAGCTTTGGAGCCACTGTCCAAAGAAAGACGGAGTTGTTACTAGTTCCAACGGATTTCCAAACACTTACGGCA
                      T  F  E  D  L  D  M  T  E  S  F  G  A  T  V  Q  R  K  T  E  L  L  L  V  P  T  D  F  Q  T  L  T  A
cyp71AV8-65188      GACCTTCGAAGATTTGGACATGACCGAGAGCTTTGGTGCCACTGTGCAGCGCAAAACCGAGCTGCTGCTGGTTCCGACCGACTTTCAAACGCTGACTGCG
                      T  F  E  D  L  D  M  T  E  S  F  G  A  T  V  Q  R  K  T  E  L  L  L  V  P  T  D  F  Q  T  L  T  A
CYP71AV8-P2         GACCTTCGAAGATTTGGACATGACCGAGAGCTTTGGTGCCACTGTGCAGCGCAAAACCGAGCTGCTGCTGGTTCCGACCGACTTTCAAACGCTGACTGCG
                      T  F  E  D  L  D  M  T  E  S  F  G  A  T  V  Q  R  K  T  E  L  L  L  V  P  T  D  F  Q  T  L  T  A
CYP71AV8-P2O        GACCTTCGAAGATTTGGACATGACCGAGAGCTTTGGTGCCACTGTGCAGCGCAAAACCGAGCTGCTGCTGGTTCCGACCGACTTTCAAACGCTGACTGCG
                      T  F  E  D  L  D  M  T  E  S  F  G  A  T  V  Q  R  K  T  E  L  L  L  V  P  T  D  F  Q  T  L  T  A

                        1510
                    ....|....|..
CYP71AV8_wt         TCTACTTAATGA
                     S  T  *  *
cyp71AV8-65188      AGCACCTAATGA
                     S  T  *  *
CYP71AV8-P2         AGCACCTAATGA
                     S  T  *  *
CYP71AV8-P2O        AGCACCTAATGA
                     S  T  *  *
```

– Figure 3 -
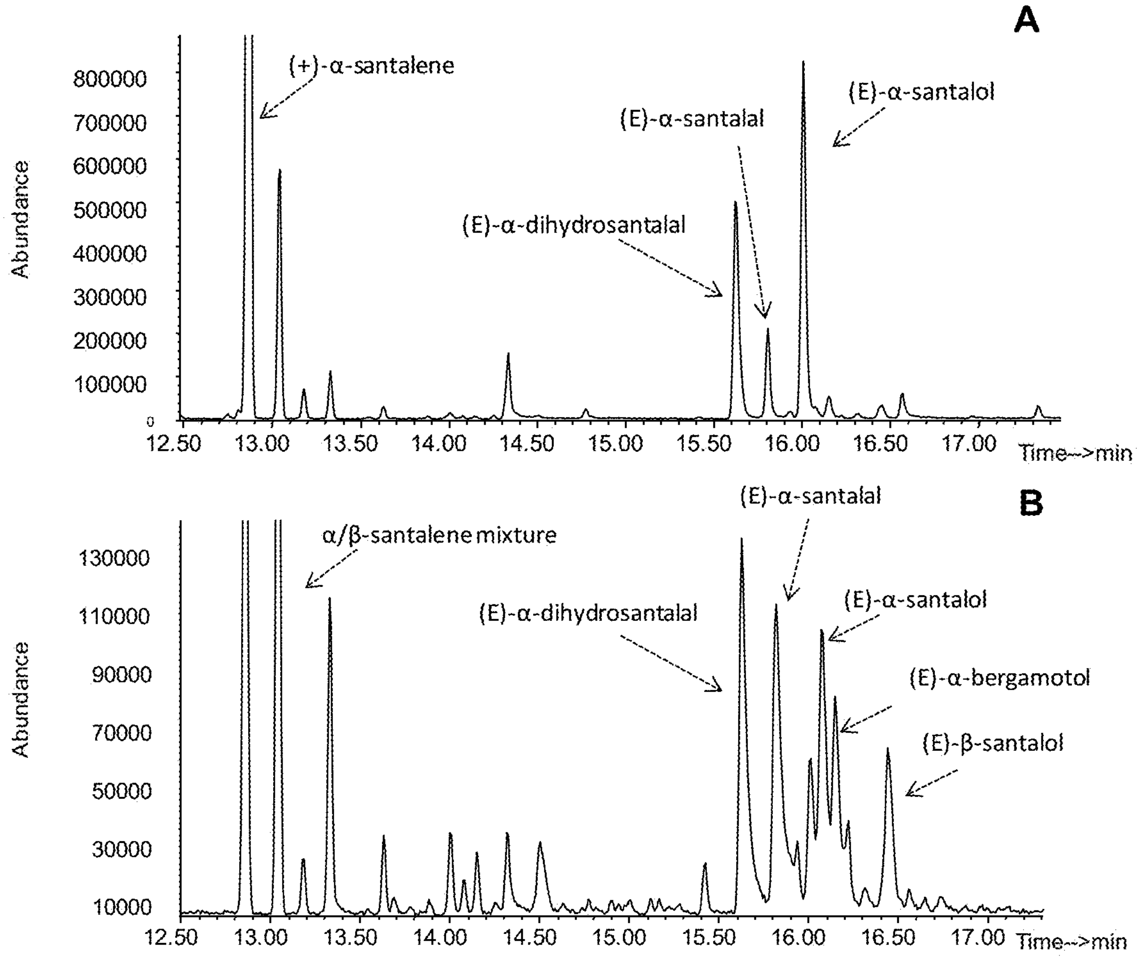

– Figure 4 –
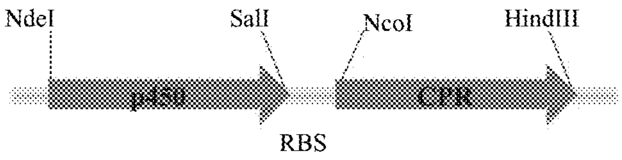

– Figure 5 –
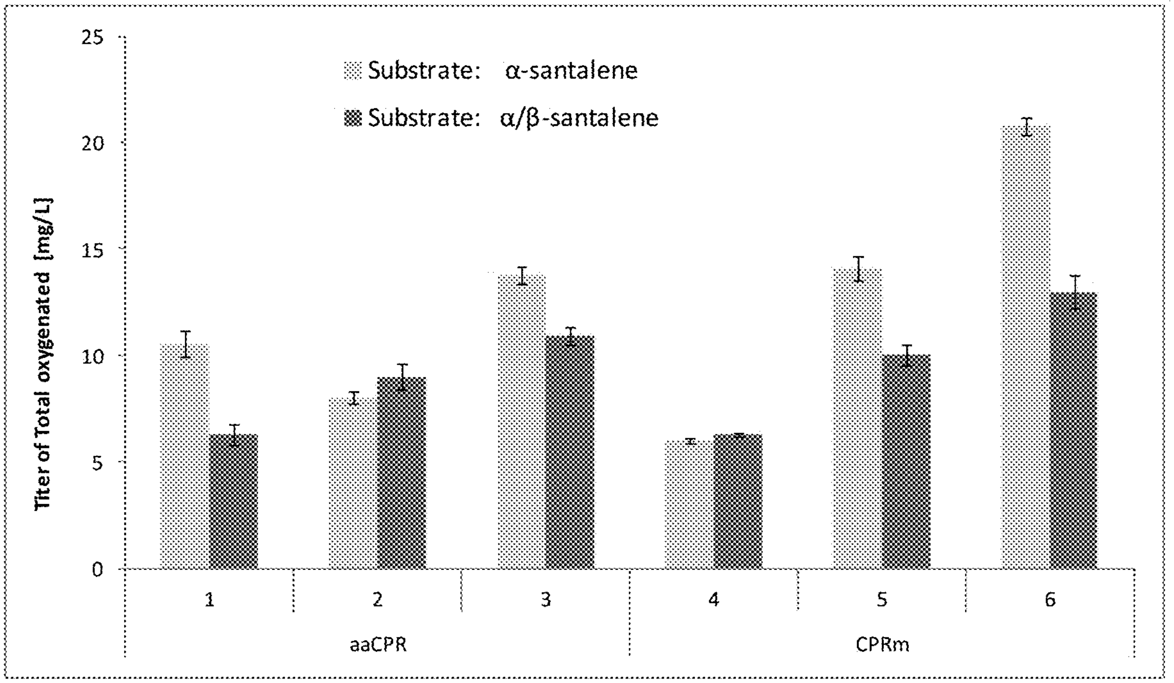

– Figure 6 –
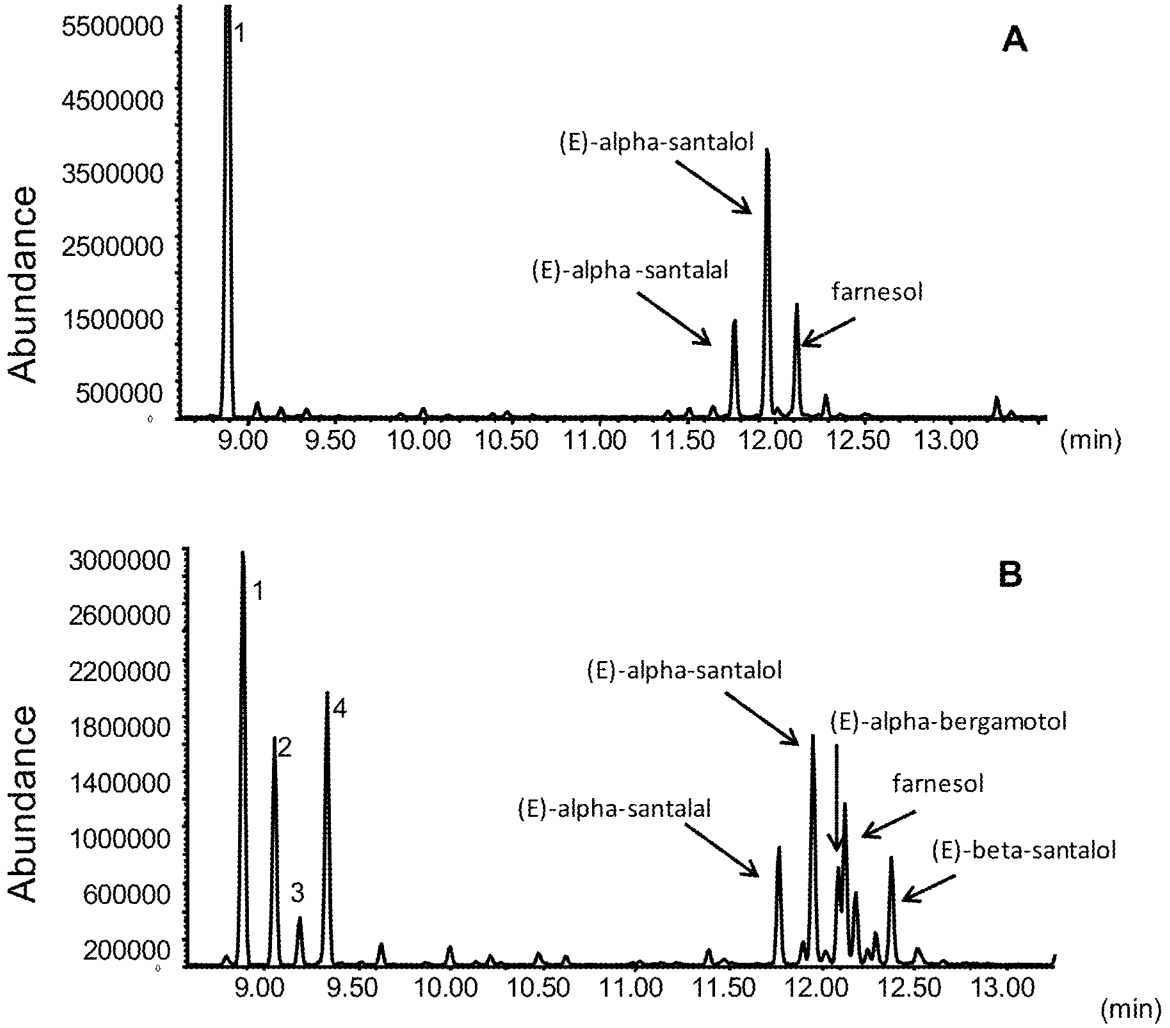

-Figure 7 –
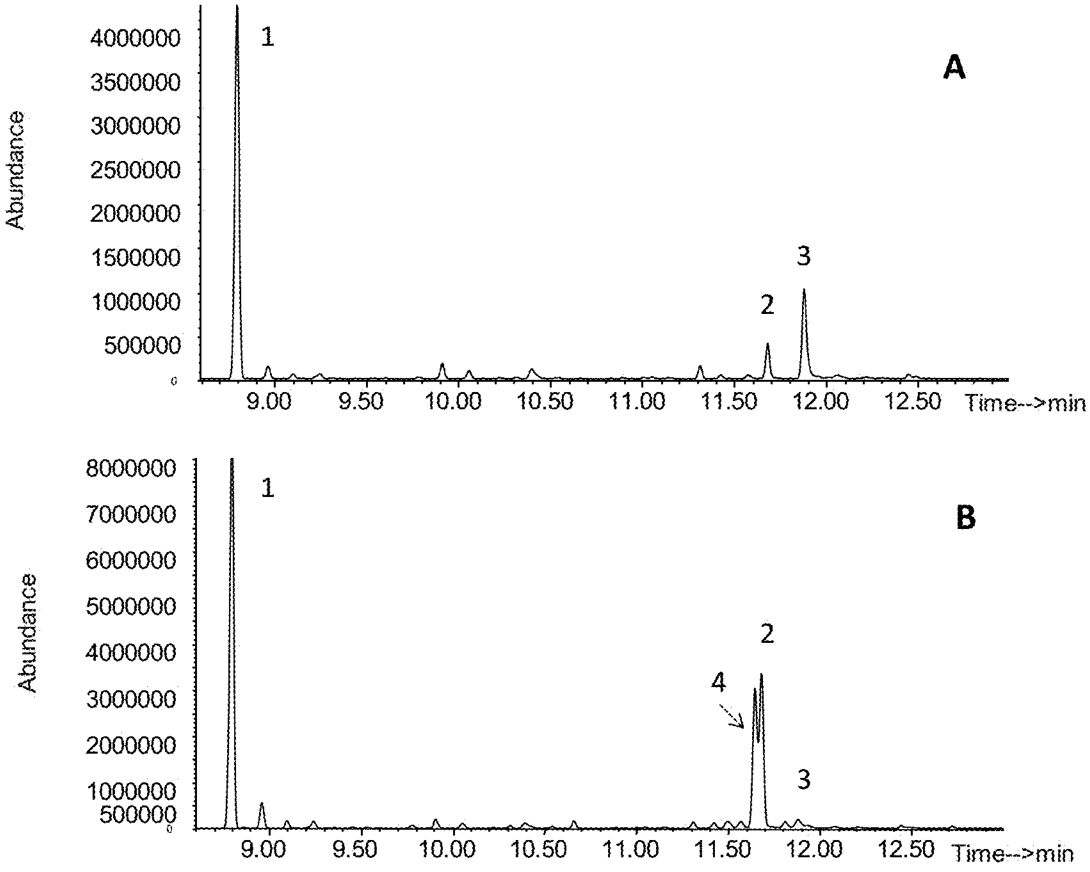

– Figure 8 –
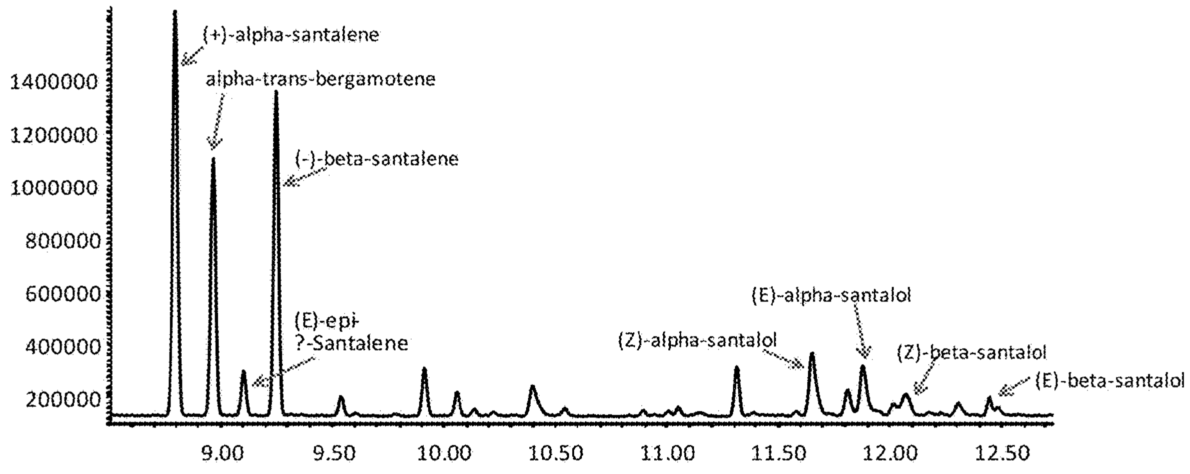

- Figure 9 -
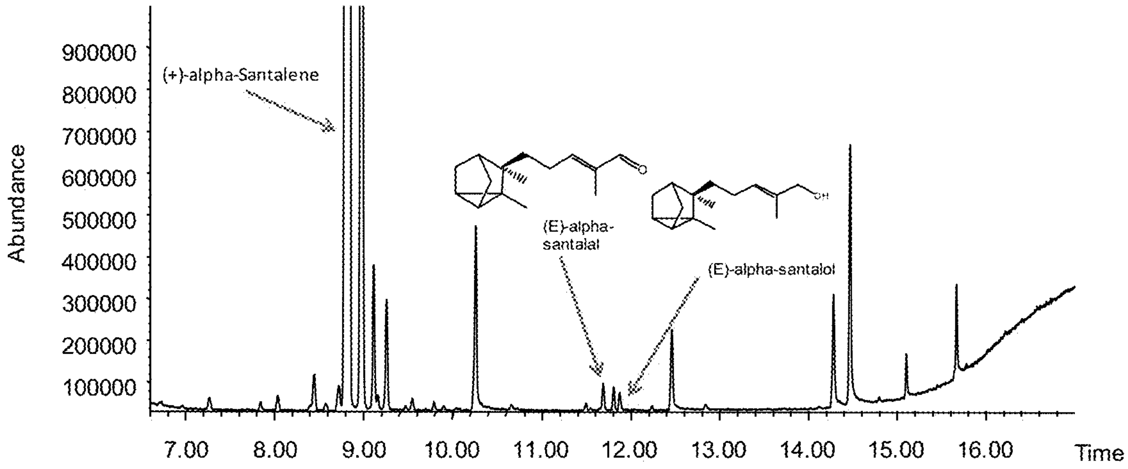

- Figure 10-
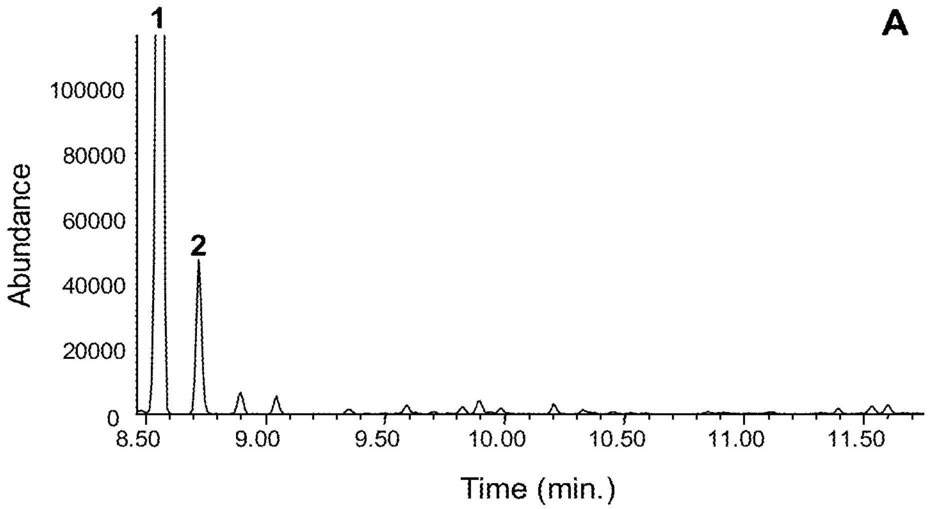
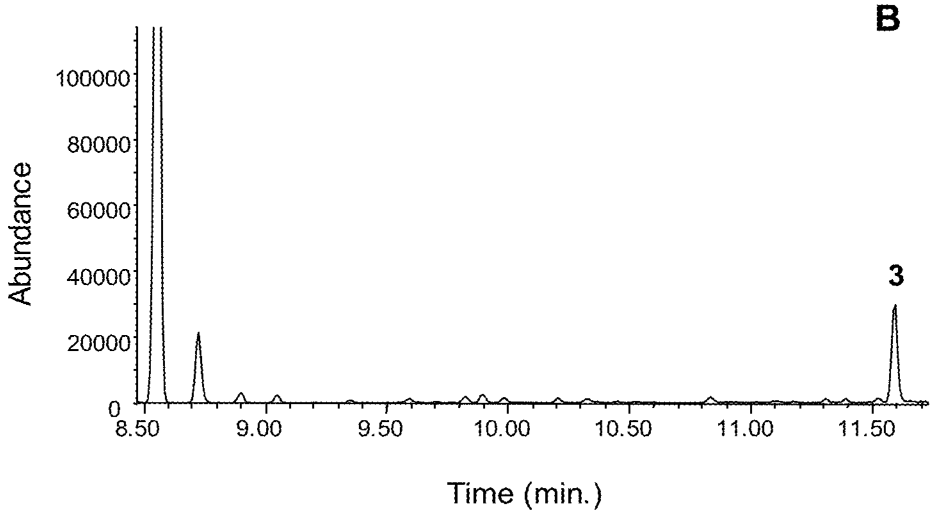

- Figure 11 -
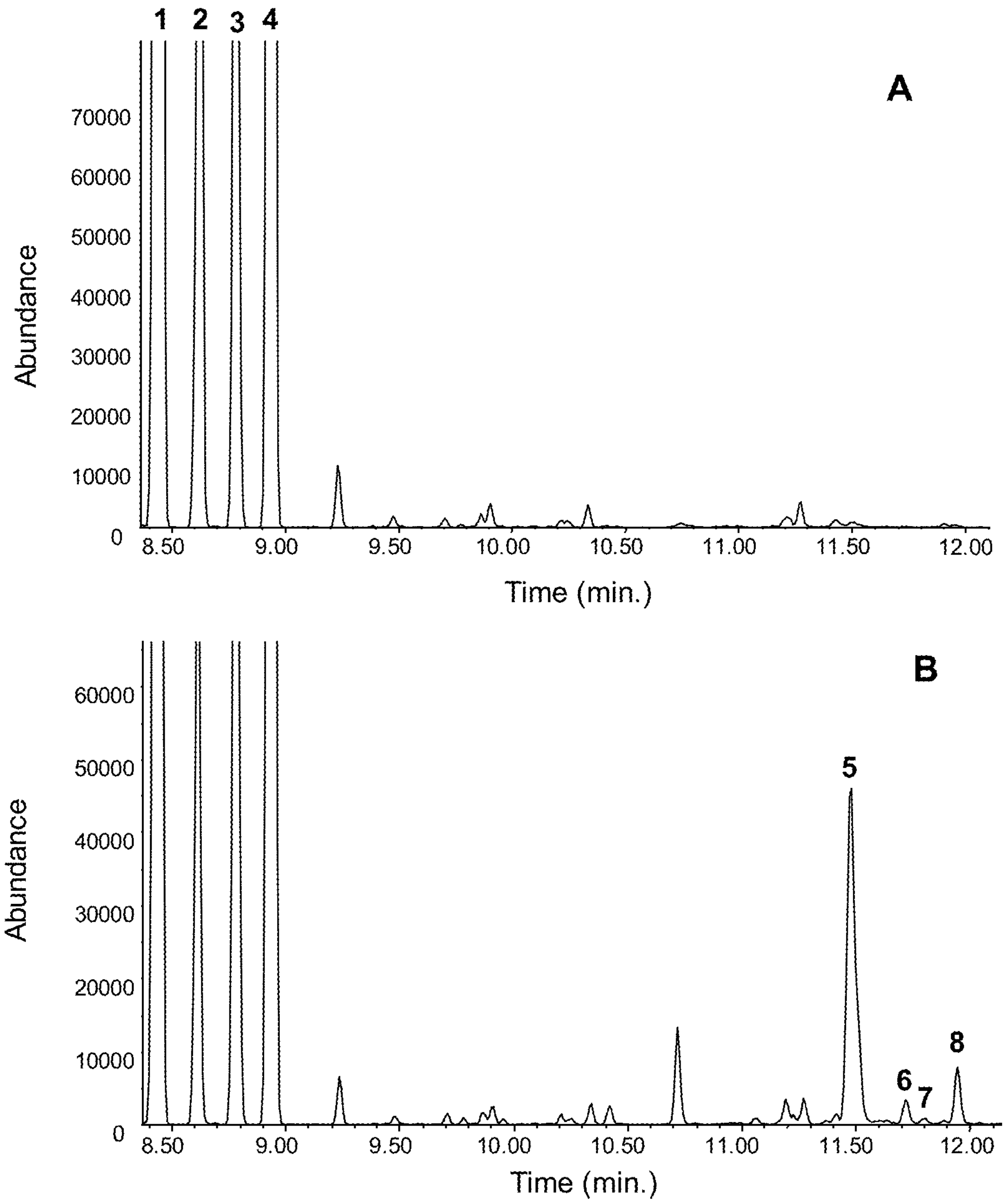

- Figure 12 -
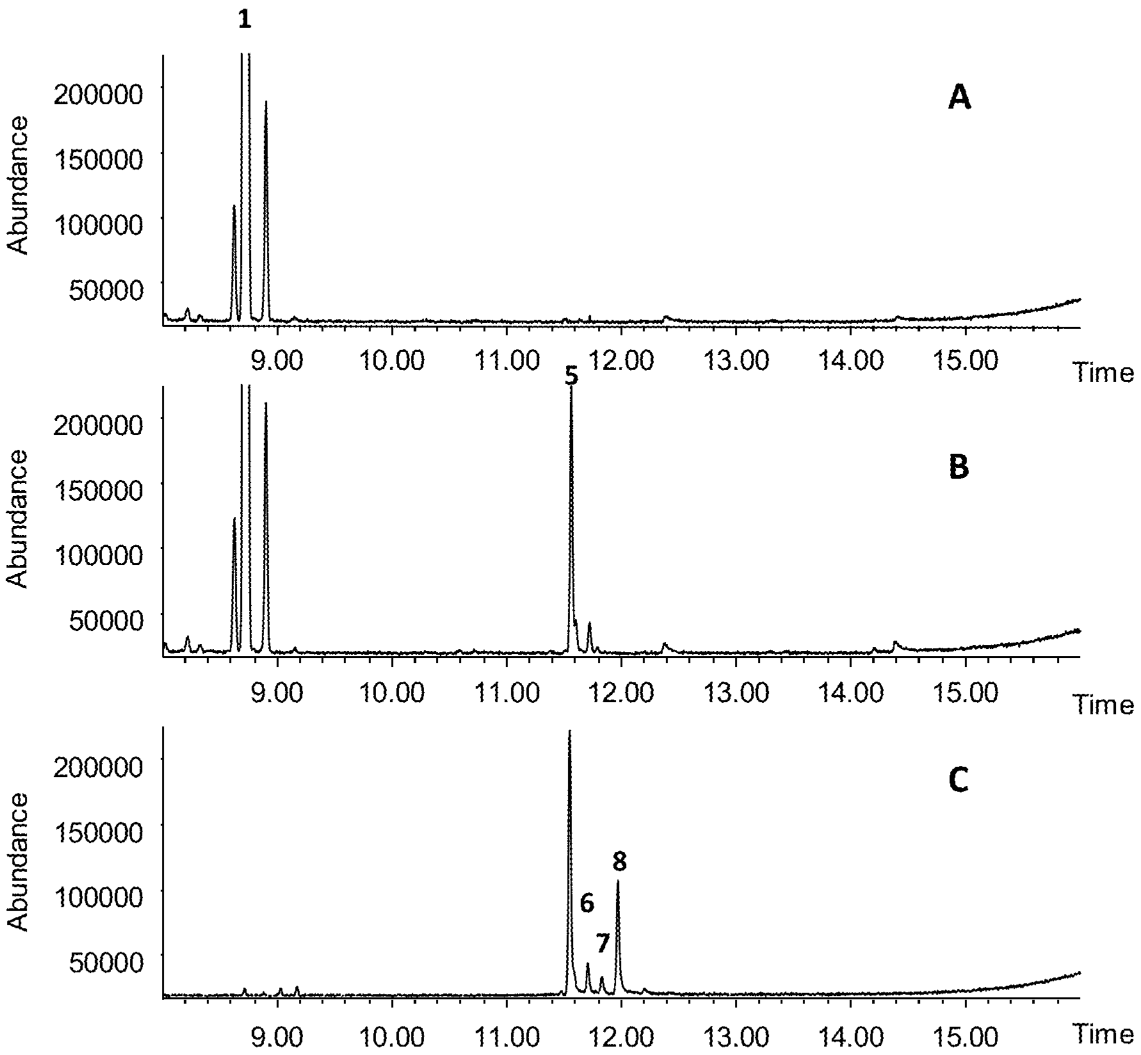

- Figure 13 -
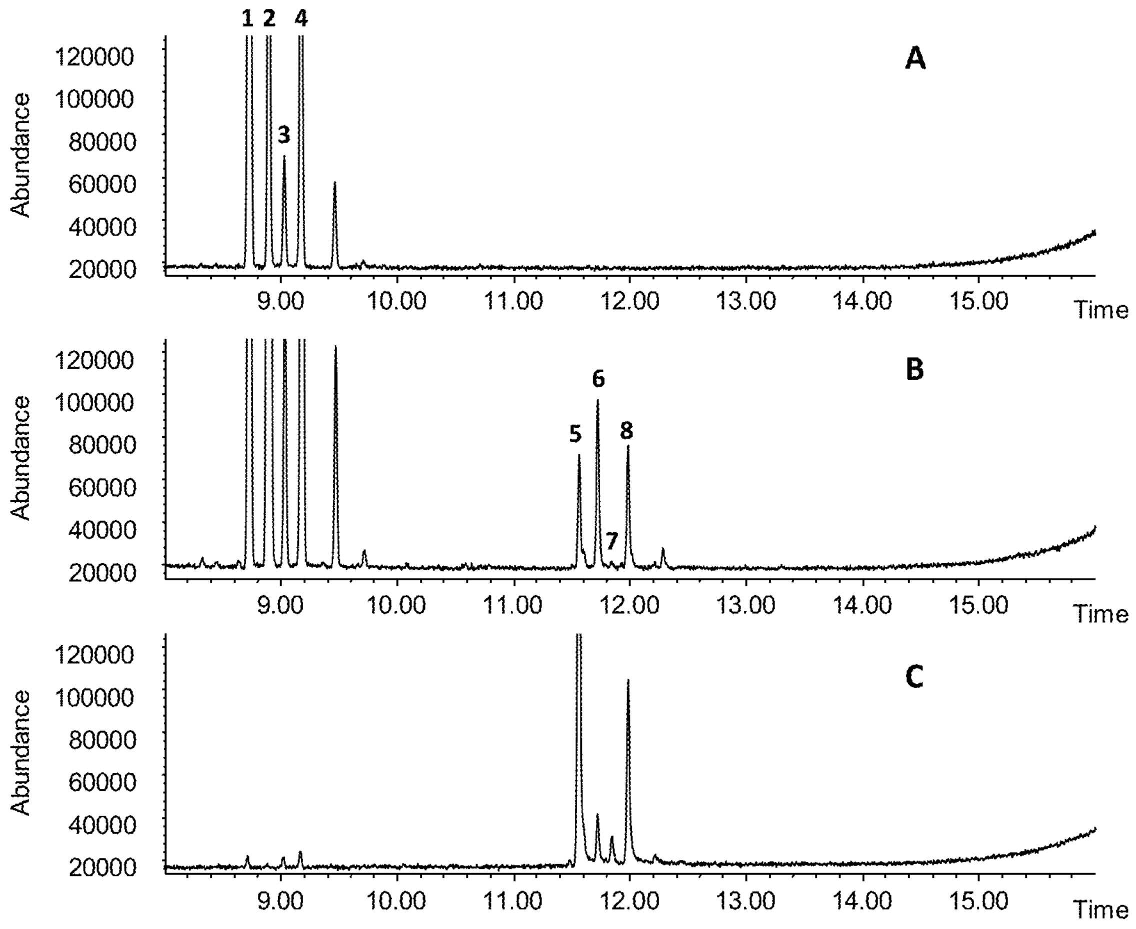

- Figure 14 -
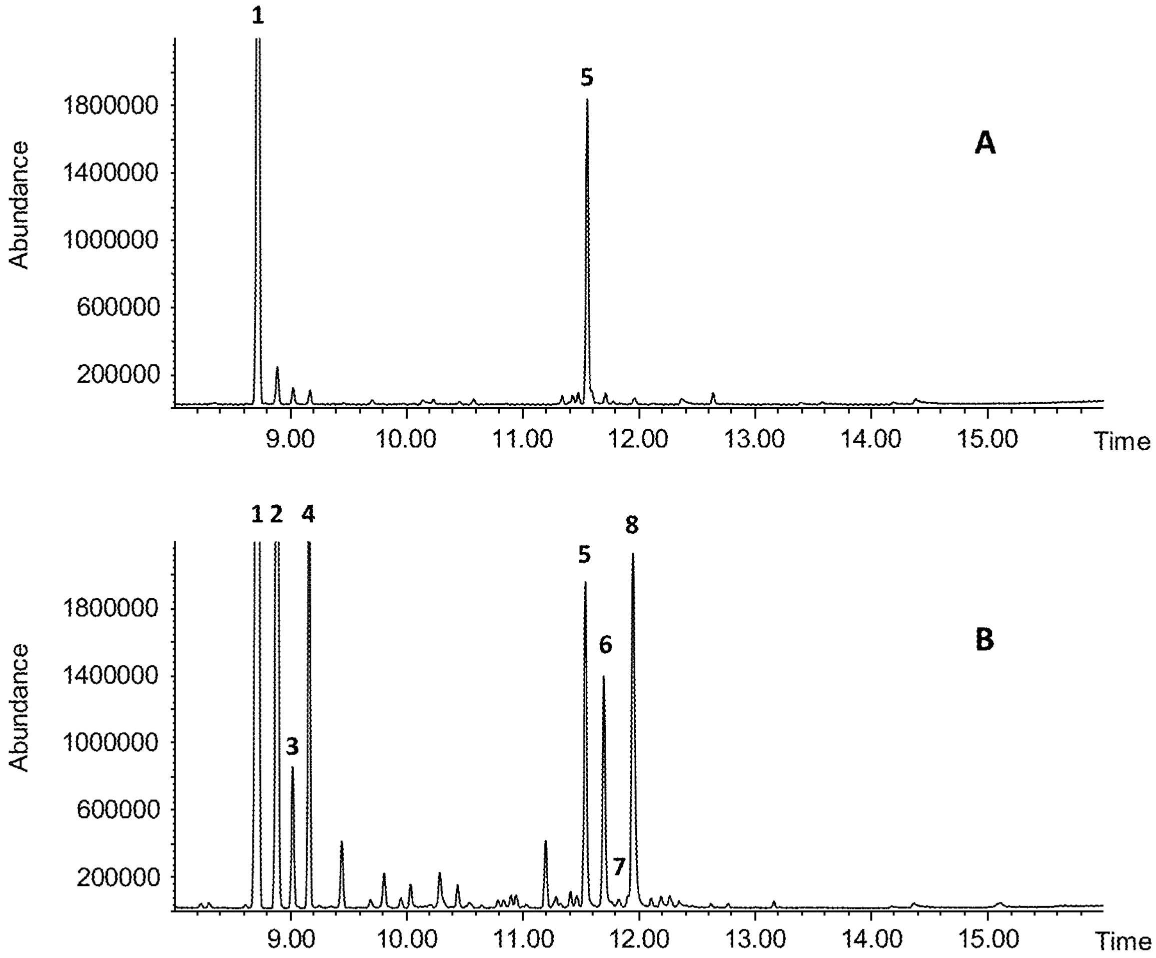

– Figure 15 –
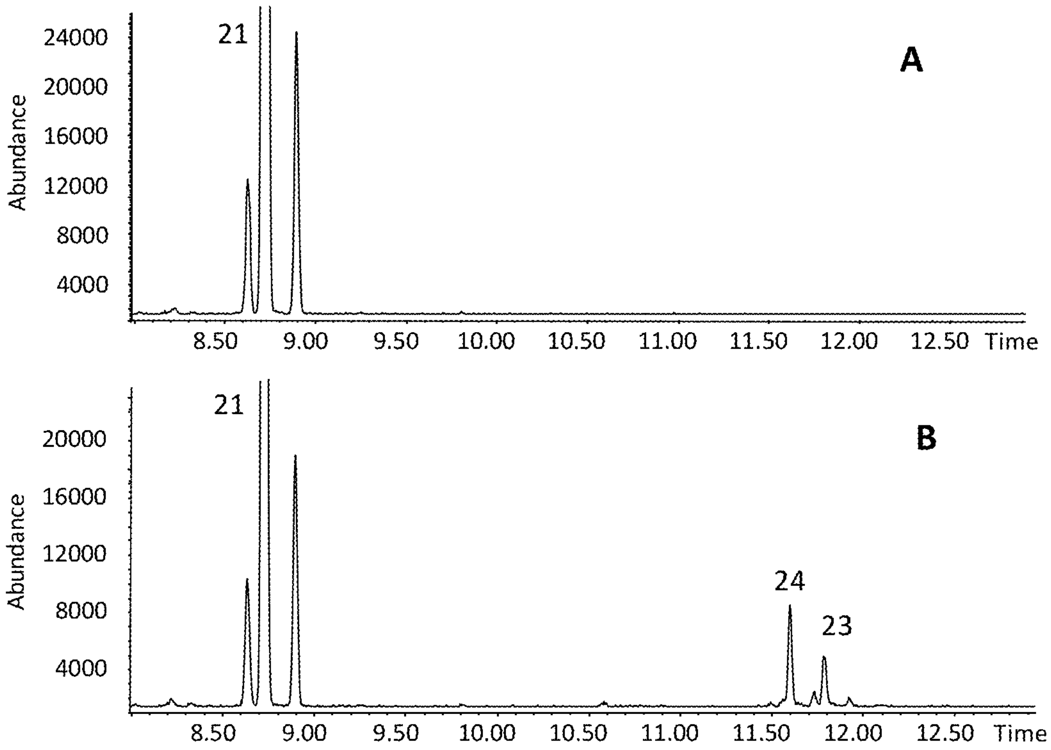

- Figure 16 -
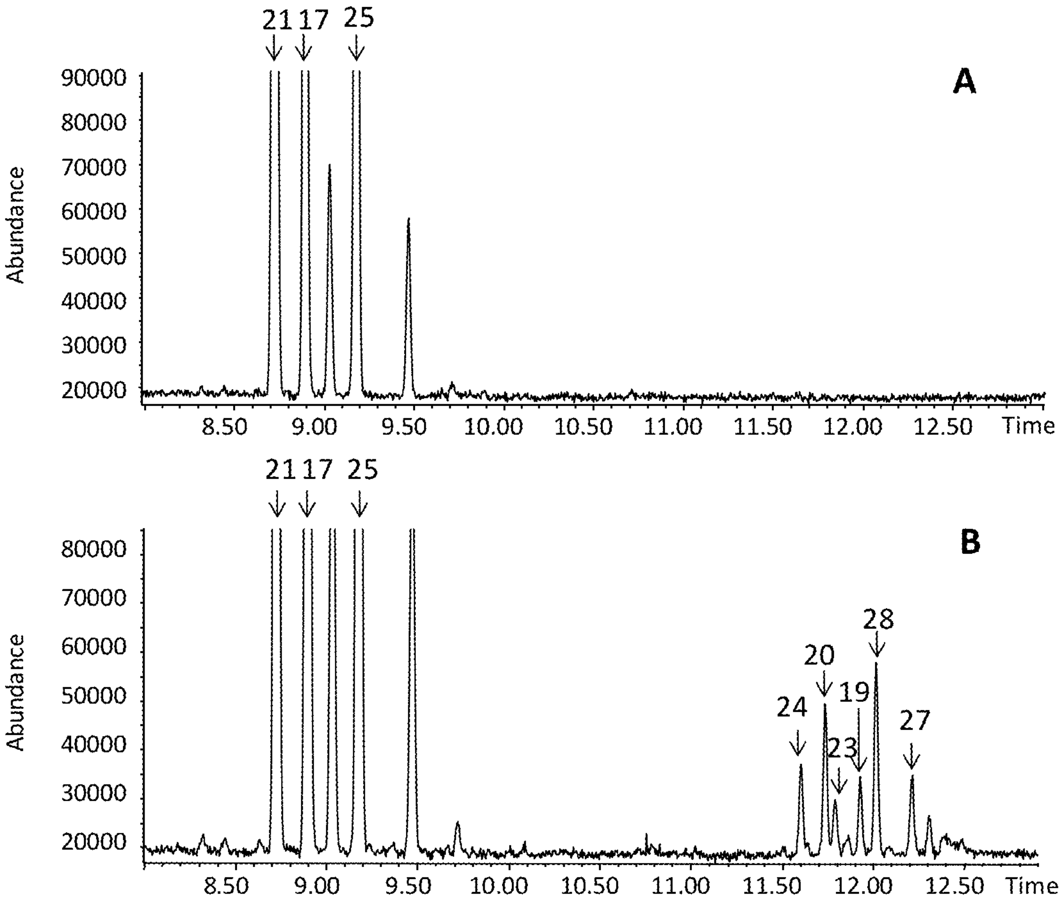

- Figure 17 –
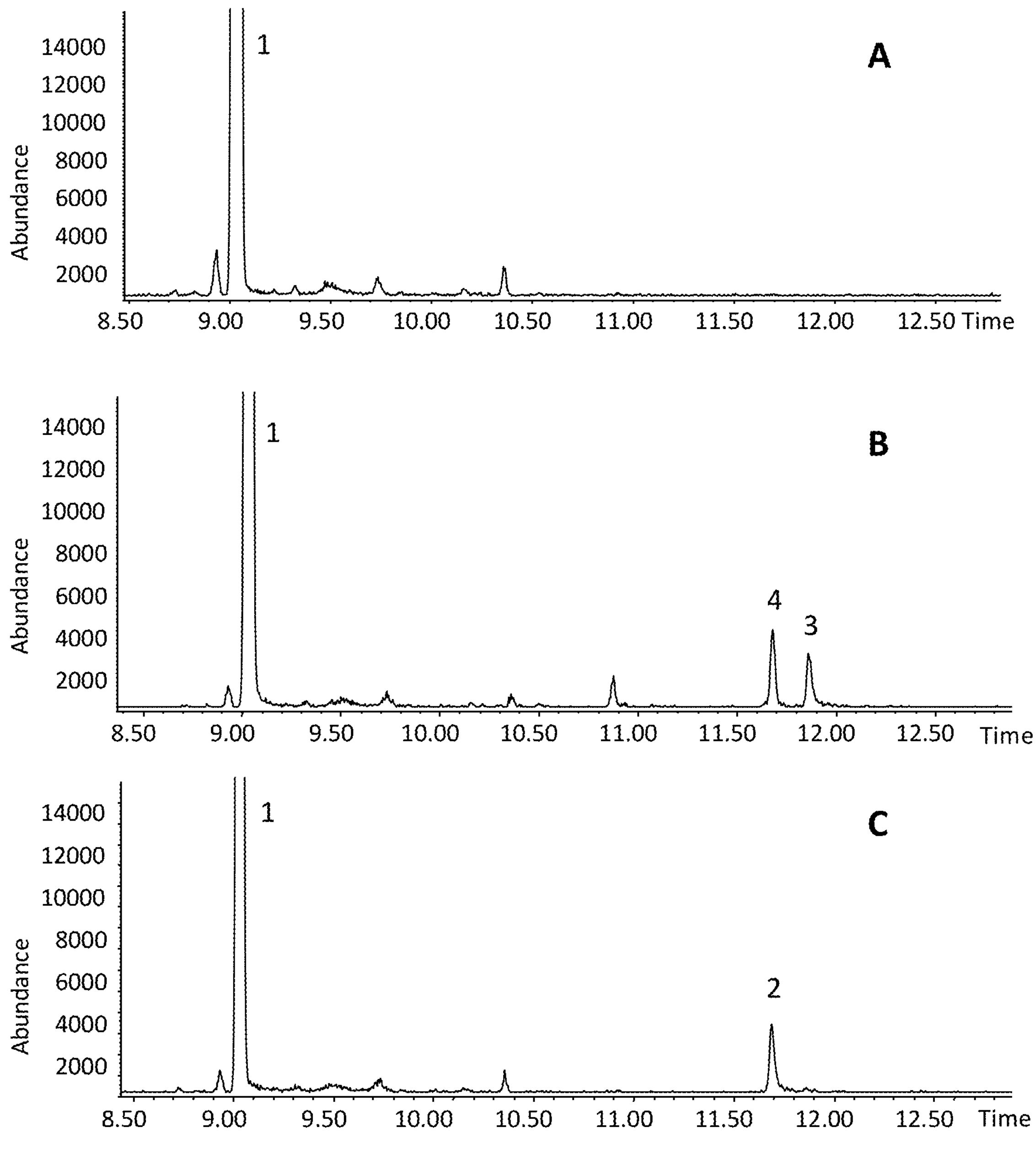

- Figure 18—
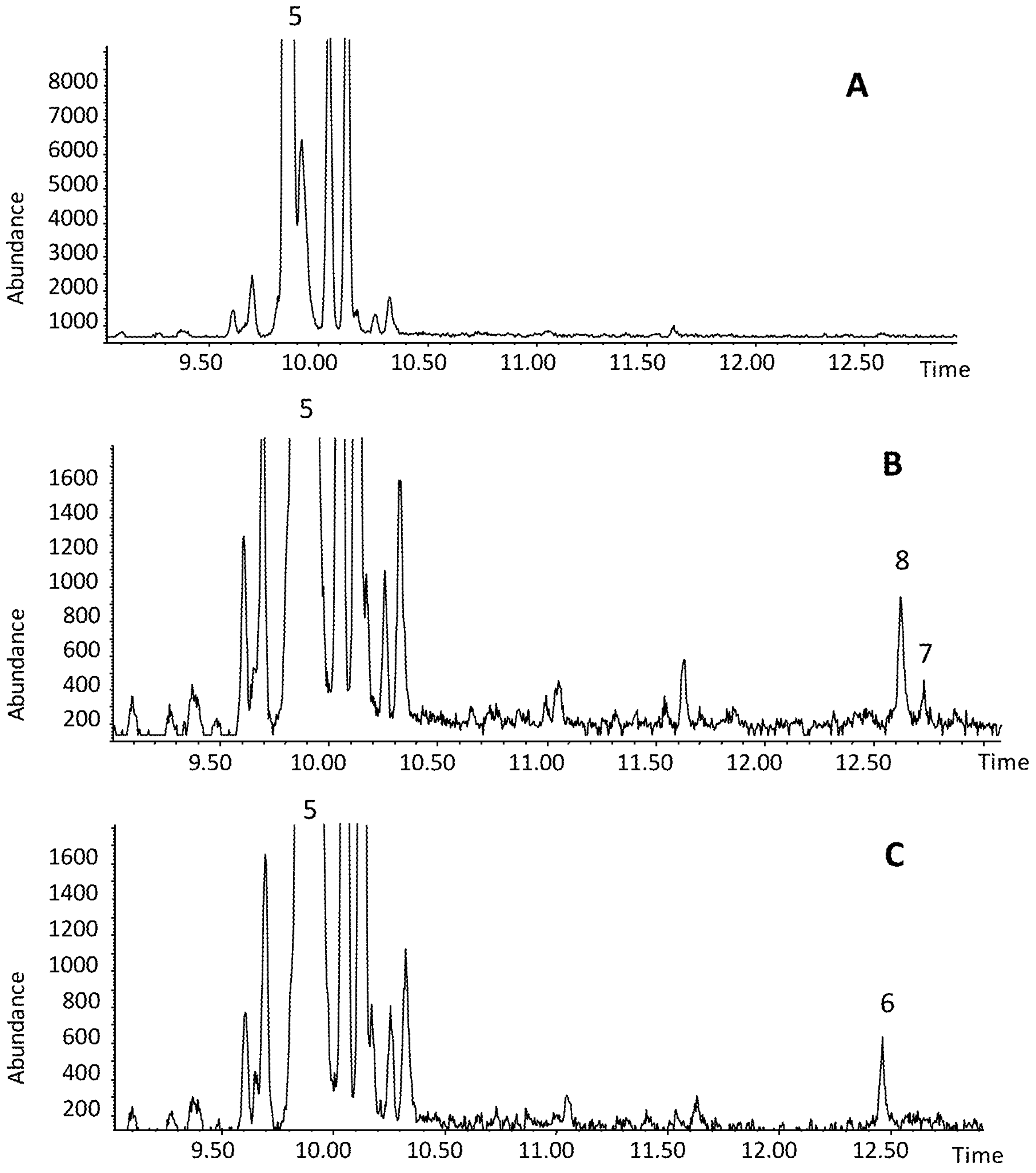

- Figure 19 –
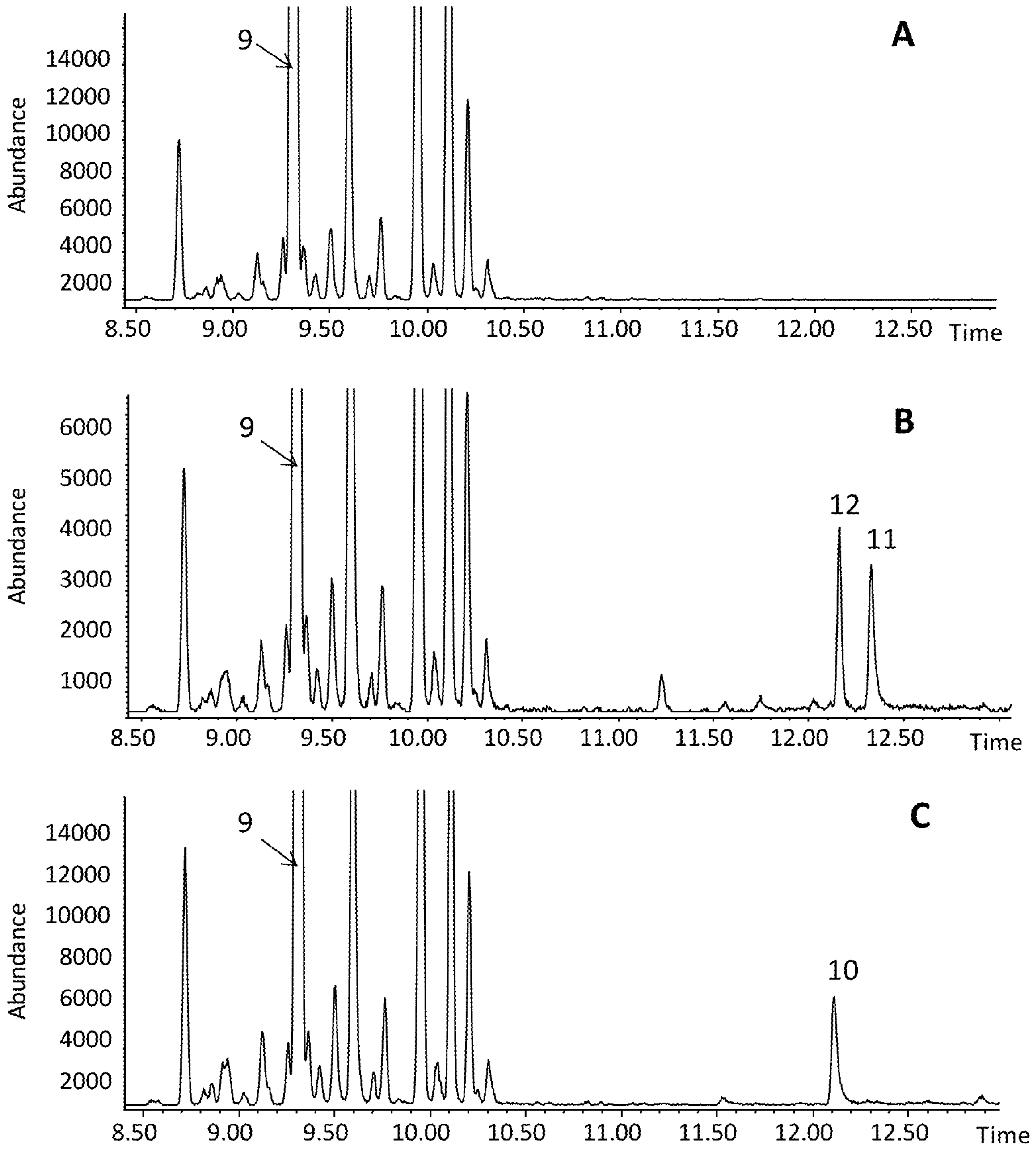

- Figure 20—
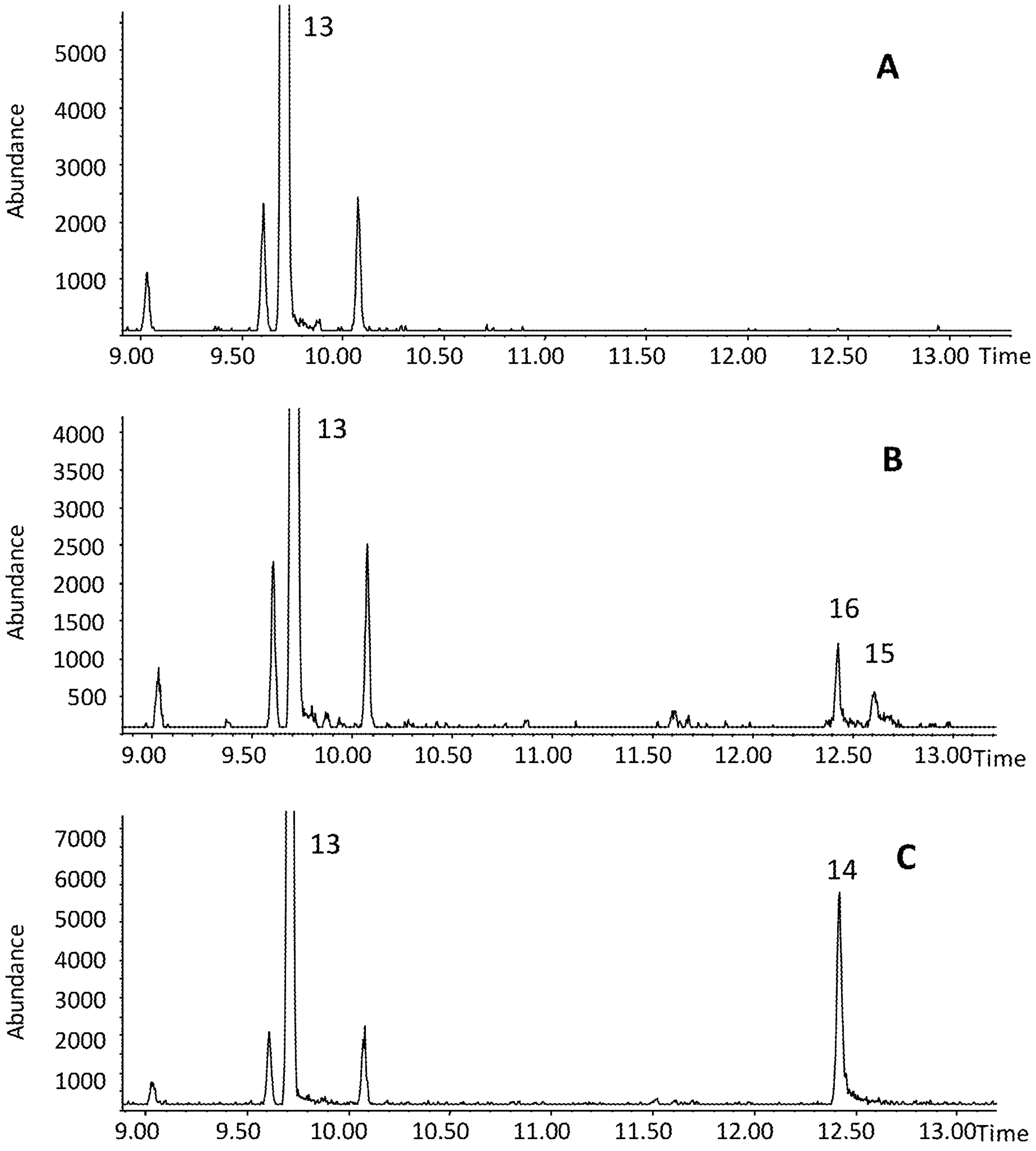

- Figure 21 –
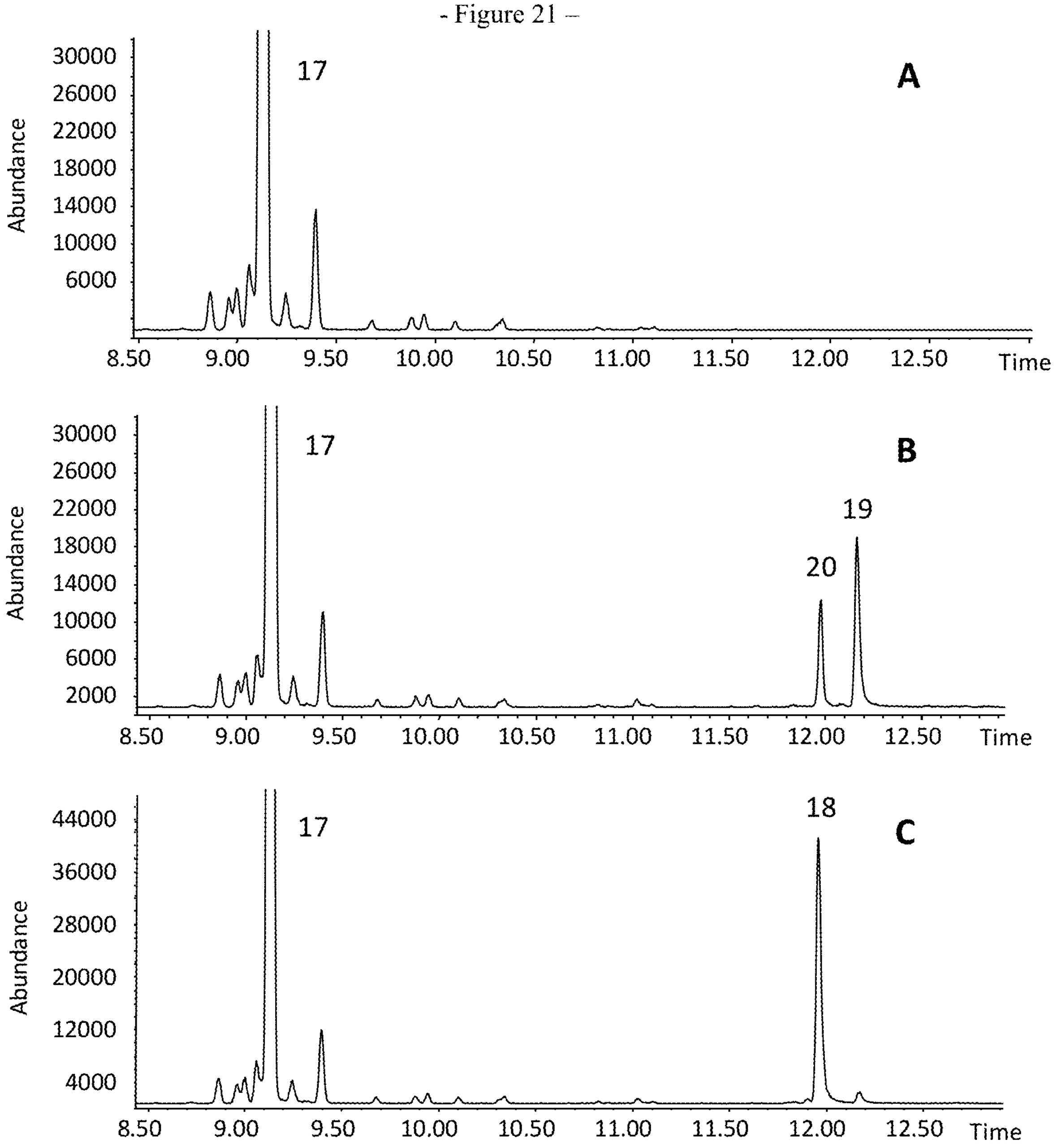

- Figure 22 –
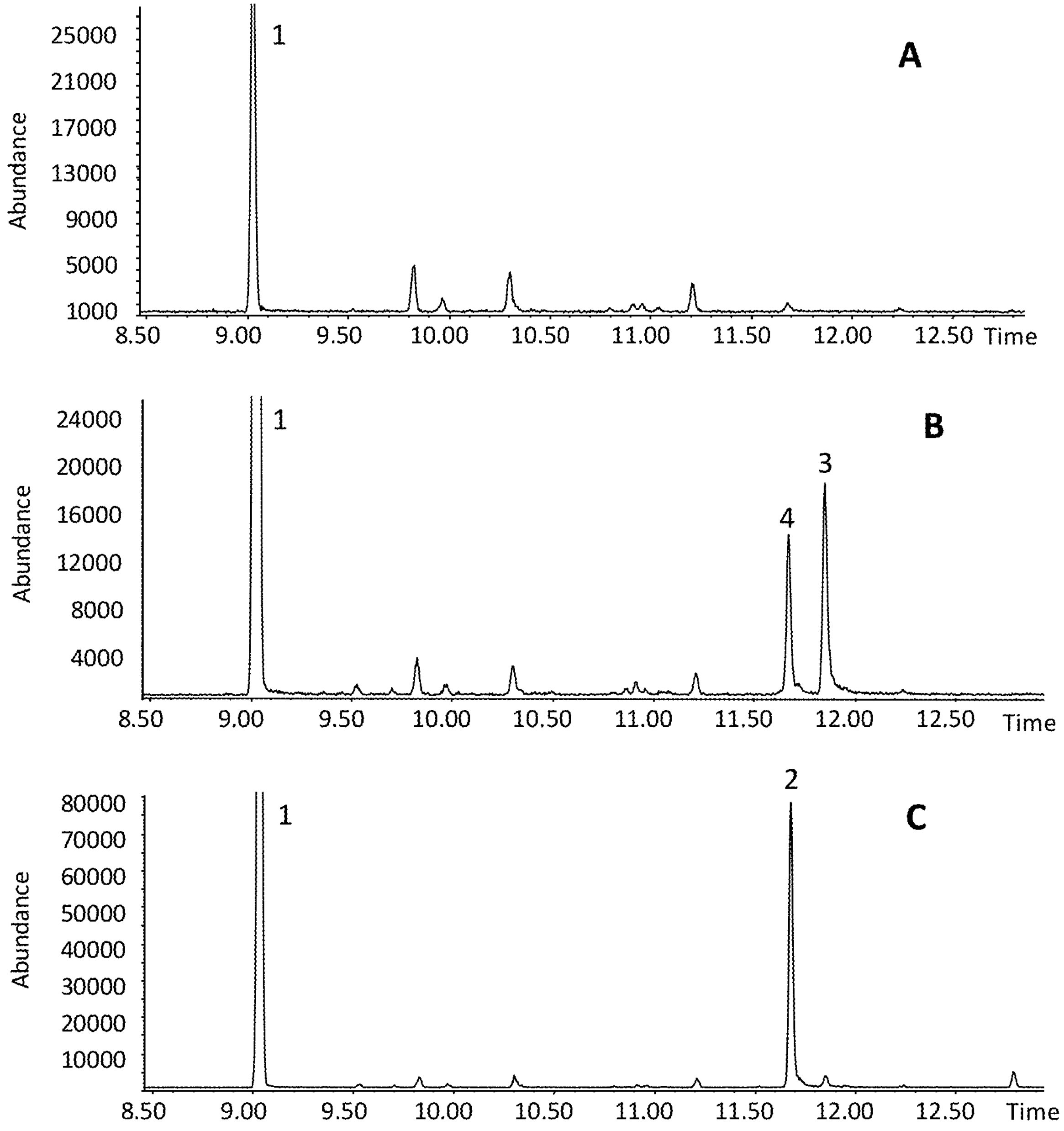

- Figure 23 –
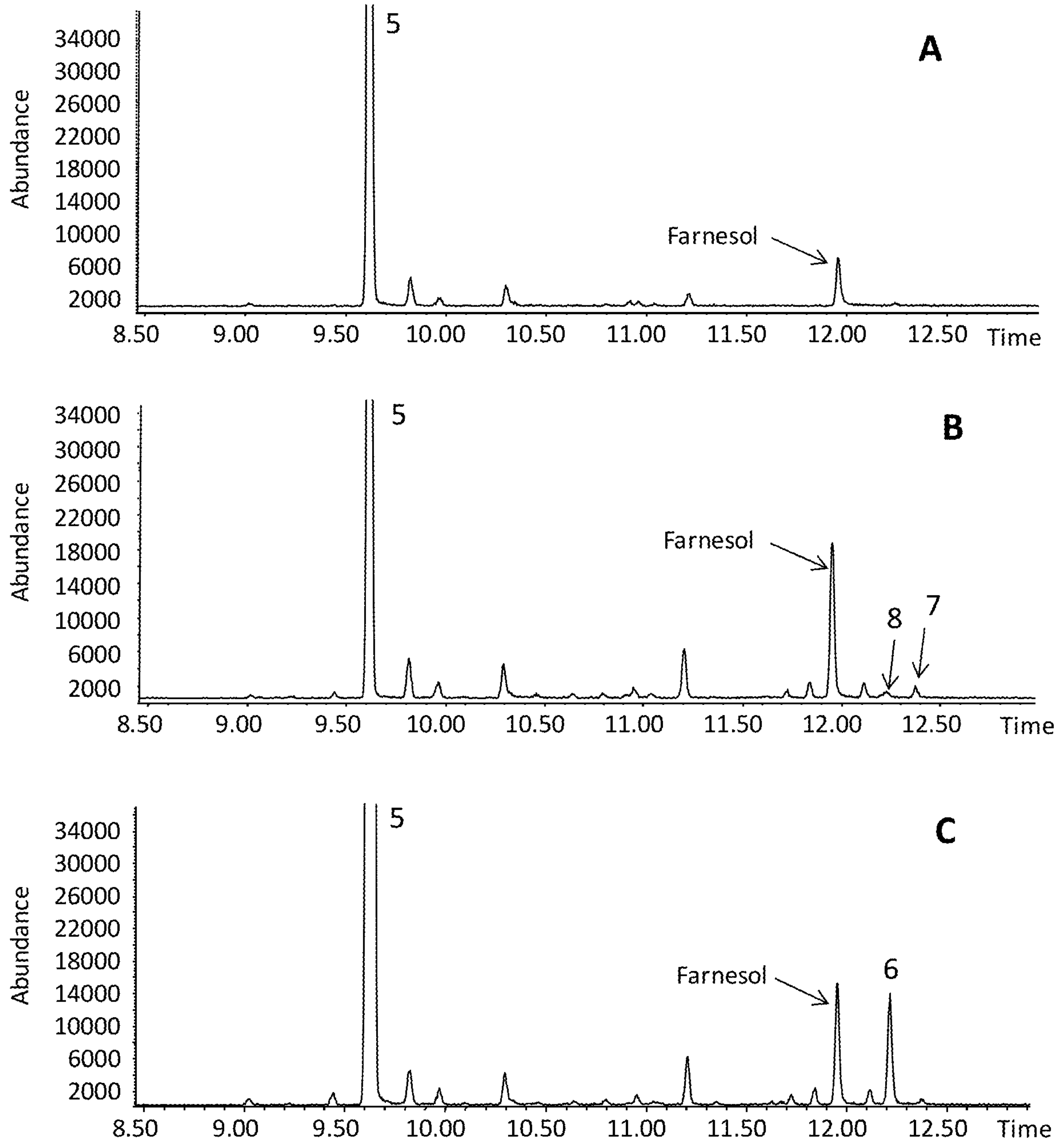

- Figure 24 –
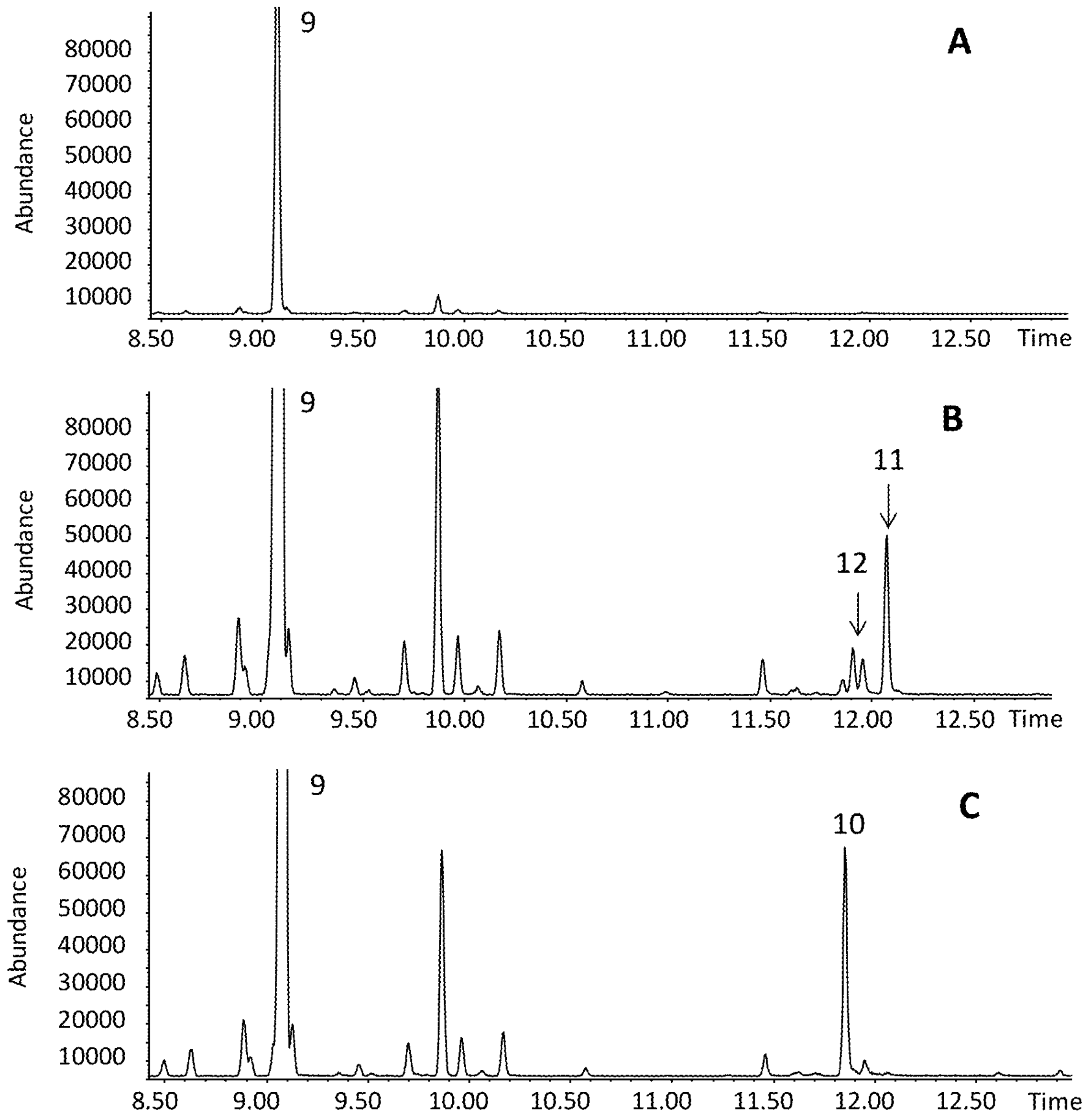

- Figure 25 –
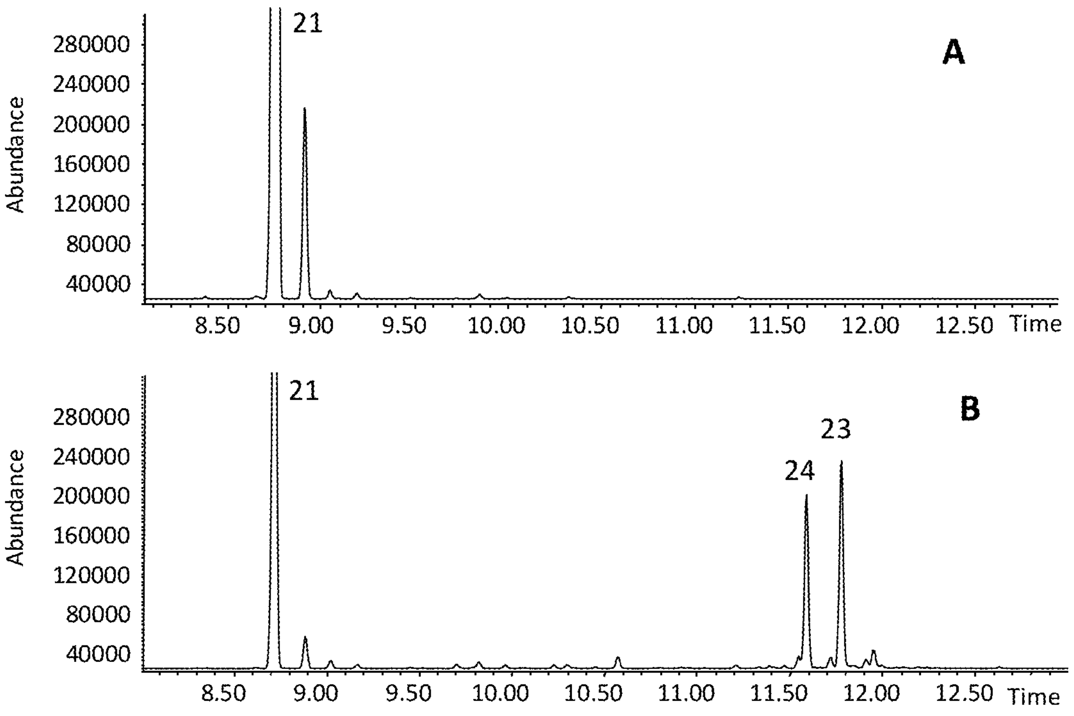

- Figure 26 -
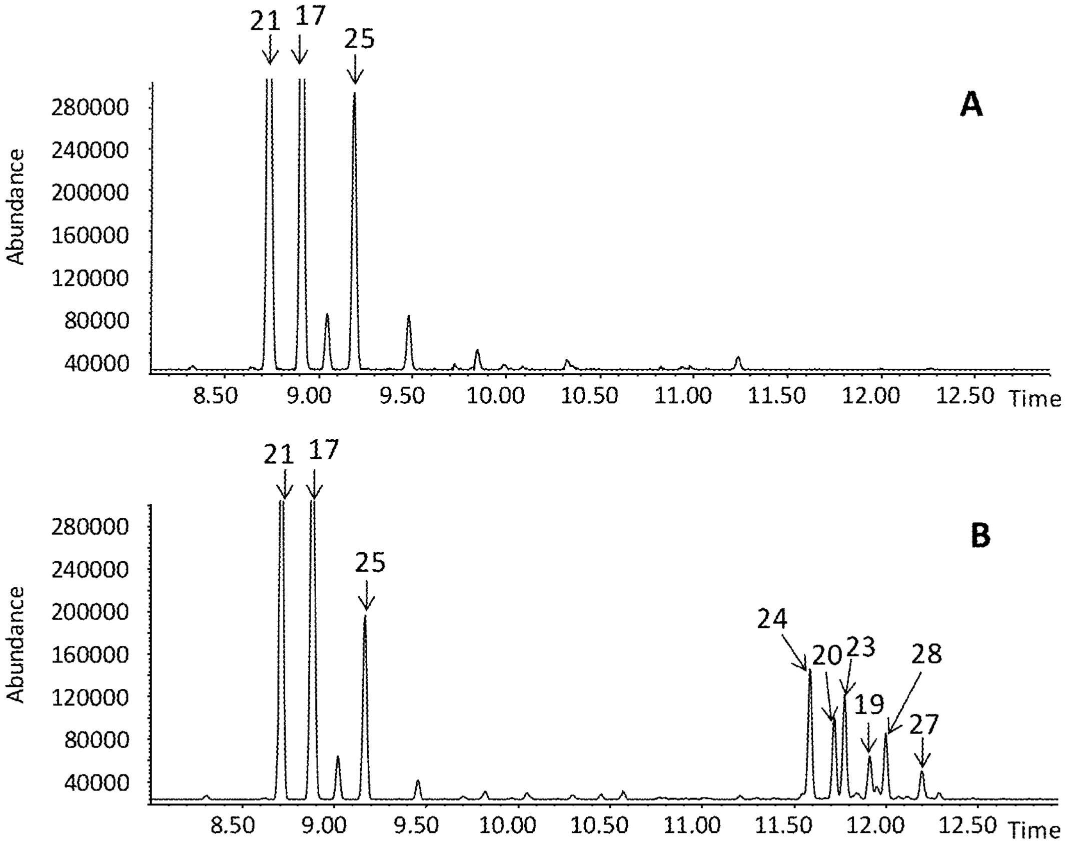

- Figure 27A -

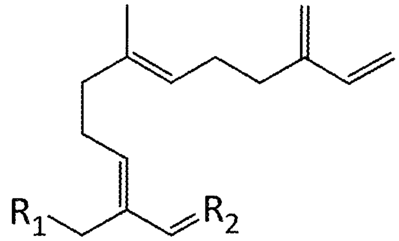

1. *trans-β*-farnesene; $R_1$ = H, $R_2$ = H,H
2. *(2Z,6E)-β*-sinensol; $R_1$ = OH, $R_2$ = H,H
3. *(2E,6E)-β*-sinensol; $R_1$ = H, $R_2$ = OH,H
4. *(2E,6E)-β*-sinensal; $R_1$ = H, $R_2$ = O

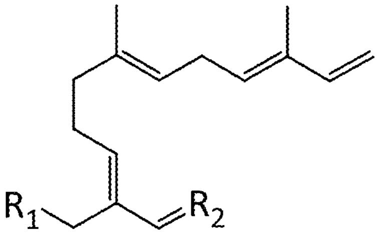

5. *trans-α*-farnesene: $R_1$ = H, $R_2$ = H,H
6. *(2Z,6E,9E)-α*-sinensol; $R_1$ = OH, $R_2$ = H,H
7. *(2E,6E,9E)-α*-sinensol; $R_1$ = H, $R_2$ = OH,H
8. *(2E,6E,9E)-α*-sinensal; $R_1$ = H, $R_2$ = O

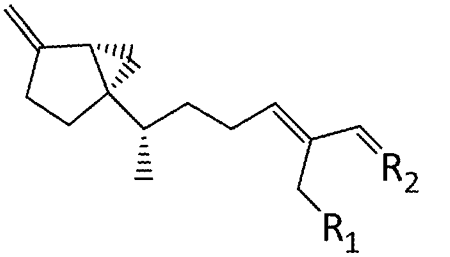

9. *(-)*-Sesquisabinene B; $R_1$ = H, $R_2$ = H,H
10. $R_1$ = OH, $R_2$ = H,H
11. $R_1$ = H, $R_2$ = OH,H
12. $R_1$ = H, $R_2$ = O

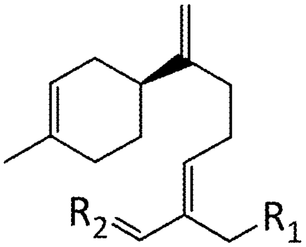

13. *(-)-β*-Bisabolene; $R_1$ = H, $R_2$ = H,H
14. *(-)-(Z)*-lanceol; $R_1$ = OH, $R_2$ = H,H
15. *(E)*-lanceol; $R_1$ = H, $R_2$ = OH,H
16. *(E)*-lanceal $R_1$ = H, $R_2$ = O

- Figure 27B -
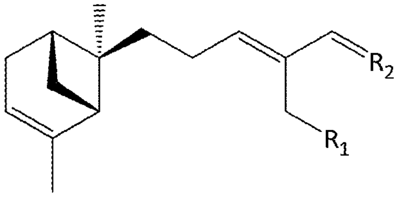
17. *(-)-trans-α*-Bergamotene;$R_1$ = H, $R_2$ = H,H
18. *(-)-(Z)-trans-α*-bergamotol; $R_1$ = OH, $R_2$ = H,H
19. *(-)-(E)-trans-α*-bergamotol; $R_1$ = H, $R_2$ = OH,H
20. *(E)-trans-α*-bergamotal; $R_1$ = H, $R_2$ = O
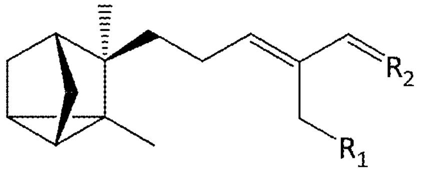
21. *(+)-α*-santalene; $R_1$ = H, $R_2$ = H,H
22. *(+)-(Z)-α*-santalol; $R_1$ = OH, $R_2$ = H,H
23. *(+)-(E)-α*-santalol; $R_1$ = H, $R_2$ = OH,H
24. *(E)-α*-santalal; $R_1$ = H, $R_2$ = O
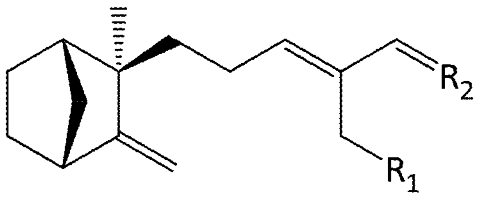
25. *(-)-β*-santalene; $R_1$ = H, $R_2$ = H,H
26. *(-)-(Z)- β*-santalol; $R_1$ = OH, $R_2$ = H,H
27. *(-)-(E)- β*-santalol; $R_1$ = H, $R_2$ = OH,H
28. *(-)-(E)- β*-santalal; $R_1$ = H, $R_2$ = O

METHOD FOR PRODUCING FRAGRANT ALCOHOLS

RELATED APPLICATIONS

This application is a divisional application of U.S. patent application Ser. No. 15/023,640 filed Mar. 21, 2016, now U.S. Pat. No. 9,909,145, which is a national stage application under 35 U.S.C. § 371 of International Patent Application PCT/EP2014/070060 filed on Sep. 19, 2014, which claims the benefit of U.S. provisional application 61/880,149, filed on Sep. 19, 2013. The entire contents of each of these applications are hereby incorporated by reference herein in their entirety.

SUBMISSION OF SEQUENCE LISTING

The Sequence Listing associated with this application is filed in electronic format via EFS-Web and hereby incorporated by reference into the specification in its entirety. The name of the text file containing the Sequence Listing is 9000US_DIV_SequenceListing. The size of the text file is 423 KB, and the text file was created on Jan. 16, 2018.

FIELD

The field relates to cytochrome P450s and uses to produce sesquiterpene alcohols.

BACKGROUND

Terpenes hydrocarbons such as alpha and beta santalenes have been produced via biochemical processes for example such as through genetically altered cells. These terpenes and the alcohol derived from them are major constituents of sandalwood oil and the alcohols are important perfumery ingredients typically obtained commercially through the distillation of the heartwood of *Santalum* species (e.g., Sandalwood). Examples of such alcohols include α-sinensol, β-sinensol, α-santalol, β-santalol, α-trans-bergamotol and epi-β-santalol. Although new biochemical pathways have been developed, including genetically engineered cells, to generate the terpene hydrocarbons, it is desirable to find a biochemical pathway to generate and produce the alcohols derived from the santalenes. It is further desirable to use a biochemical pathway to not only generate such alcohols but it is further desirable to selectively produce, via a biochemical pathway, cis-isomers of the alcohols such as iso-α-sinensol, iso-β-sinensol, (Z)-α-santalol, (Z)-β-santalol, (Z)-α-trans-bergamotol and (Z)-epi-β-santalol.

Cytochrome P450s represent a family of enzymes of oxidases. P450s commonly catalyze a monooxygenase reaction. Cytochrome P450 enzymes are classified into families and subfamilies based on the amino acid sequences homology. Members of a same subfamily share over 55% amino acid sequence identity and have usually similar enzymatic activities (substrate and/or product selectivity). CYP71AV1 (NCBI accession No ABB82944.1, SEQ ID No. 51 and 52) and CYP71AV8 (NCBI accession No ADM86719.1, SEQ ID No. 1 and 2) are two members of the CYP71AV subfamily and shares 78% sequence identity. CYP71AV1 has previously been shown to oxidize amorphadiene (Teoh et al, *FEBS letters* 580 (2006) 1411-1416). CYP71AV8 has previously been shown to oxidize (+)-valencene, germacrene A and amorphadiene (Cankar et al, *FEBS Lett.* 585(1), 178-182 (2011)).

Processes using engineered cells have been reported that use terpene synthases to catalyze the production of a diterpene or sesquiterpene. The diterpenes or sesquiterpenes were further processed using a cytochromeP450 polypeptide to catalyze the hydroxylation, oxidation, demethylation or methylation of the diterpene or sesquiterpene produced by the cell.

SUMMARY

Provided herein is a method of producing an sesquiterpene alcohol comprising:

i) contacting a terpene of Formula I:

Formula I

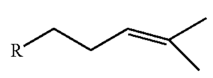

with a polypeptide having an amino acid sequence having at least, or at least about, 45% of sequence identify to a polypeptide selected from the group consisting of SEQ ID NO: 2, SEQ ID NO: 4, SEQ ID NO: 6, SEQ ID NO: 8, SEQ ID NO: 28, SEQ ID NO: 30, SEQ ID NO: 32, SEQ ID NO: 34, SEQ ID NO: 36, SEQ ID NO: 38, SEQ ID NO: 40, SEQ ID NO: 42, SEQ ID NO: 44, SEQ ID NO: 50, SEQ ID NO: 52, SEQ ID NO: 54, SEQ ID NO: 58, SEQ ID NO: 60, SEQ ID NO: 62, SEQ ID NO: 64, SEQ ID NO: 66, SEQ ID NO: 68, SEQ ID NO: 71, SEQ ID NO: 73, SEQ ID NO: 79, and SEQ ID NO: 81; and ii) optionally isolating the alcohol wherein R is a saturated, mono-unsaturated or poly-unsaturated aliphatic group composed of 9 carbons and wherein R can be a branched chain or composed of one or more non-aromatic rings.

Further provided herein is a method of producing a sesquiterpene comprising α-sinensol, β-sinensol, α-santalol, β-santalol, α-trans-bergamotol, epi-β-santalol, lancelol and/or or mixtures thereof comprising:

i) contacting α-farnesene, β-farnesene, α-santalene, β-santalene, α-trans-bergamotene, epi-β-santalene, and/or β-bisabolene, with a polypeptide having an amino acid sequence having at least, or at least about, 45% of sequence identify to a polypeptide selected from the group consisting of SEQ ID NO: 2, SEQ ID NO: 4, SEQ ID NO: 6, SEQ ID NO: 8, SEQ ID NO: 28, SEQ ID NO: 30, SEQ ID NO: 32, SEQ ID NO: 34, SEQ ID NO: 36, SEQ ID NO: 38, SEQ ID NO: 40, SEQ ID NO: 42, SEQ ID NO: 44, SEQ ID NO: 50, SEQ ID NO: 52, SEQ ID NO: 54, SEQ ID NO: 58, SEQ ID NO: 60, SEQ ID NO: 62, SEQ ID NO: 64, SEQ ID NO: 66, SEQ ID NO: 68, SEQ ID NO: 71, SEQ ID NO: 73, SEQ ID NO: 79, and SEQ ID NO: 81 to produce the alcohol; and ii) optionally isolating the alcohol.

Also provided herein is a method of producing α-sinensol, β-sinensol, α-santalol, β-santalol, α-trans-bergamotol, epi-β-santalol, lancelol and/or mixtures thereof comprising contacting α-farnesene, β-farnesene, α-santalene, β-santalene, α-trans-bergamotene and/or epi-β-santalene, with a polypeptide having a P450 monooxygenase activity wherein the sesquiterpene alcohol produced comprises at least, or at least about, 36% of a cis isomer.

Further provided herein is an isolated polypeptide having monooxygenase activity comprising an amino acid sequence that is at least, or at least about 45%, 50%, 55%, 50%, 65%, 70%, 80%, 90%, 95%, 98% or more identical to an amino acid sequence selected from the group consisting of SEQ ID NO: 71, and SEQ ID NO:73.

Further provided herein is an isolated polypeptide having monooxygenase activity comprising an amino acid sequence that is at least, or at least about 45%, 50%, 55%, 50%, 65%, 70%, 80%, 90%, 95%, 98% or more identical to an amino acid sequence selected from the group consisting of SEQ ID NO: 79, and SEQ ID NO: 81.

Also provided herein is an isolated polypeptide having monooxygenase activity comprising an amino acid sequence selected from the group consisting of SEQ ID NO: SEQ ID NO:28, SEQ ID NO:30, SEQ ID NO:32, SEQ ID NO: 34, SEQ ID NO:36, SEQ ID NO:71, SEQ ID NO:73 SEQ ID NO: 79, and SEQ ID NO: 81.

Further provided herein is method of producing a sesquiterpene alcohol selected from the group consisting of α-sinensol, β-sinensol, α-santalol, β-santalol, α-trans-bergamotol, epi-β-santalol, and lancelol or mixtures thereof:

i) cultivating a cell under conditions suitable to produce a p450 polypeptide having monooxygenase activity wherein the cell: a) produces a acylic pyrophosphate terpene precursor; b) expresses a P450 reductase, c) expresses a polypeptide that has α-farnesene, β-farnesene, α-santalene, β-santalene, α-trans-bergamotene and/or epi-β-santalene, synthase activity and produces α-farnesene, β-farnesene, α-santalene, β-santalene, α-trans-bergamotene and/or epi-β-santalene and d) expresses a polypeptide with an amino acid sequence having at least, or at least about, 45% of sequence identify to a polypeptide selected from the group consisting of SEQ ID NO: 2, SEQ ID NO: 4, SEQ ID NO: 6, SEQ ID NO: 8, SEQ ID NO: 28, SEQ ID NO: 30, SEQ ID NO: 32, SEQ ID NO: 34, SEQ ID NO: 36, SEQ ID NO: 38, SEQ ID NO: 40, SEQ ID NO: 42, SEQ ID NO: 44, SEQ ID NO: 50, SEQ ID NO: 52, SEQ ID NO: 54, SEQ ID NO: 58, SEQ ID NO: 60, SEQ ID NO: 62, SEQ ID NO: 64, SEQ ID NO: 66, SEQ ID NO: 68, SEQ ID NO: 71, SEQ ID NO: 73 SEQ ID NO: 79, and SEQ ID NO: 81; and ii) optionally isolating the alcohol from the cell.

DETAILED DESCRIPTION OF THE DRAWINGS

FIG. 1. Amino acid sequence alignment of the N-terminal region of the different CYP71AV8 variants: CYP71AV8_wt (SEQ ID NO: 2), cyp71AV8-65188 (SEQ ID NO: 4), CYP71AV8-P2 (SEQ ID NO: 6), CYP71AV8-P20 (SEQ ID NO: 8).

FIG. 2A-D. Alignment of DNA sequences of the different CYP71AV8 variants: CYP71AV8 wt (SEQ ID NO: 1), cyp71AV8-65188 (SEQ ID NO: 3), CYP71AV8-P2 (SEQ ID NO: 5), CYP71AV8-P20 (SEQ ID NO: 6). The encoded amino acid sequences are shown below each sequence using the one-letter code.

FIG. 3. GCMS analysis of the conversion of sesquiterpenes by *E. Coli* cells expressing the CYP71AV8 and the CPRm proteins. A, Bioconversion of (+)-alpha-santalene. B, Bioconversion of a (+)-alpha-santalene/(−)-beta-santalene mixture.

FIG. 4. Organisation of the synthetic bi-cistronic operon containing a P450 and a CPR cDNA.

FIG. 5. Comparison of the bioconversion of (+)-α-santalene and the α/β-santalene mixture by *E. coli* cells transformed with different bi-cistronic operons composed of a P450 and a CPR cDNA. 1, CYP71AV8-65188 and aaCPR. 2, CYP71AV8-P2 and aaCPR. 3, CYP71AV8-P2O and aaCPR. 4, CYP71AV8-65188 and CPRm. 5, CYP71AV8-P2 and CPRm. 6, CYP71AV8-P2O and CPRm.

FIG. 6. GCMS analysis of the sesquiterpene molecules produced by *E. Coli* cells expressing CYP71AV8, CPRm, an alpha-santalene synthase (A) or a alpha-santalene/beta-santalene synthase (B), and mevalonate pathway enzymes. 1, (+)-α-santalene; 2 (−)-α-trans-bergamotene; 3, (+)-epi-β-santalene; 4, (−)-β-santalene.

FIG. 7. Oxidation of (+)-α-santalene by CYP71AV8 wild type (A) and mutant L-358 (B). GC-MS profiles of the sesquiterpene products generated by *E. Coli* KRX cells expressing CPRm, ClASS, the mevalonate pathway enzymes and CYP71AV8 (A) or CYP71AV8-L358F (B). The cultivations were performed in TB medium containing 3% glycerol as carbon source. The different products were identified as α-santalene (1), (E)-α-santalal (2), (Z)-α-santalol (4), and (E)-α-santalol (3).

FIG. 8. GC-MS profiles of the sesquiterpene products generated by *E. Coli* KRX cells expressing CPRm, SaSAS, the mevalonate pathway enzymes and CYP71AV8-L358F. The cultivations were performed in TB medium containing 3% glycerol as carbon source. The different products identified by their mass spectra are indicated.

FIG. 9. GCMS analysis of the conversion of (+)-α-santalene by *E. Coli* cells expressing the CYP71AV1 and the CPRm proteins.

FIG. 10: GC analysis of the in vivo conversion of (+)-α-santalene to (Z)-α-santalol by a P450-BM3 double-mutant (variant #17). Solvent extracts of cultures of recombinant *E. coli* cells co-expressing a *Clausena lansium* α-santalene synthase and either the wild-type P450-BM3 (A) or the P450-BM3 variant #17 (B) were analyzed as described in example 11. 1, (+)-α-santalene; 2, (−)-α-trans-bergamotene; 3, (Z)-α-santalol; The chromatograms are shown in selected ion mode (M/Z 93).

FIG. 11: GC analysis of the in vivo conversion of (+)-α-santalene, (−)-β-santalene, (−)-α-trans-bergamotene and (+)-epi-β-santalene by a P450-BM3 double-mutant. Solvent extracts of cultures of recombinant *E. coli* cells co-expressing an alpha-santalene/beta-santalene synthase from *Santalum album* and either the wild-type P450-BM3 (A) or the P450-BM3 variant #17 (B) were analyzed as described in example 11. 1, (+)-α-santalene; 2, (−)-α-trans-bergamotene; 3, (+)-epi-β-santalene; 4, (−)-β-santalene; 5, (Z)-α-santalol; 6, (Z)-α-trans-bergamotol; 7, (Z)-epi-β-santalol; 8, (Z)-β-santalol. The chromatograms are shown in selected ion (M/Z 93).

FIG. 12: GCMS analysis of the conversion of (+)-α-santalene by the recombinant SaCP816 enzyme. A. Control without the recombinant P450 enzyme. B. Assay with *E. coli* crude protein extract containing the recombinant SaCP816 protein. C. Sandalwood oil for comparison of the retention times. All assays were performed in-vitro as described in example 4. 1, (+)-α-santalene; 5, (Z)-α-santalol; 6, (Z)-α-trans-bergamotol; 7, (Z)-epi-β-santalol; 8, (Z)-β-santalol. The identity of the sequiterpene molecules were confirmed by matching of the mass spectra with authentic standards.

FIG. 13: GCMS analysis of the conversion of (+)-α-santalene, (−)-β-santalene, (−)-α-trans-bergamotene and (+)-epi-β-santalene by the recombinant SaCP816 enzyme. A. Control without the recombinant P450 enzyme. B. Assay with *E. coli* crude protein extract containing the recombinant SaCP816 protein. C. Sandalwood oil for comparison of the retention times. All assays were performed in-vitro as described in example 4. 1, (+)-α-santalene; 2, (−)-α-trans-bergamotene; 3, (+)-epi-β-santalene; 4, (−)-β-santalene; 5, (Z)-α-santalol; 6, (Z)-α-trans-bergamotol; 7, (Z)-epi-β-santalol; 8, (Z)-β-santalol. The identity of the sequiterpene molecules were confirmed by matching of the mass spectra with authentic standards.

FIG. 14: GCMS analysis of the molecules produced by *E. Coli* engineered to produced sesquiterpenes and expressing SaCP816, CPRm, an alpha-santalene synthase (CLASS) (A) or a alpha-santalene/beta-santalene synthase (SaSAS) (B). 1, (+)-α-santalene; 2, (−)-α-trans-bergamotene; 3, (+)-epi-β-santalene; 4, (−)-β-santalene; 5, (Z)-α-santalol; 6, (Z)-α-trans-bergamotol; 7, (Z)-epi-β-santalol; 8, (Z)-β-santalol (co-eluted with farnesol produced from an excess pool of farnesyl diphosphate). The identity of the sequiterpene molecules were confirmed by matching of the mass spectra with authentic standards.

FIG. 15: GCMS analysis of the conversion of (+)-α-santalene (21) by the recombinant SaCP10374 P450 enzyme. A. Control without the recombinant P450 enzyme. B. Assay with *E. coli* crude protein extract containing the recombinant SaCP10374 protein. The numbers indicated on the chromatograms refer to the structures presented in FIG. 27.

FIG. 16: GCMS analysis of the conversion of a mixture composed of (+)-α-santalene (21), (−)-α-trans-bergamotene (17); (+)-epi-β-santalene and (−)-β-santalene (25) (prepared using the SaTp8201 recombinant protein, example 4) by the recombinant SaCP10374 P450s enzymes. A. Control without the recombinant P450 enzyme. B. Assay with *E. coli* crude protein extract containing the recombinant SaCP10374 protein. The numbers indicated on the chromatograms refer to the structures presented in FIG. 27.

FIG. 17: GCMS analysis of the conversion of β-farnesene (1) by the recombinant *S. album* P450s enzymes. A. Control without the recombinant P450 enzyme. B. Assay with *E. coli* crude protein extract containing the recombinant SaCP10374 protein. C. Assay with *E. coli* crude protein extract containing the recombinant SaCP816 protein. The numbers indicated on the chromatograms refer to the structures presented in FIG. 27.

FIG. 18: GCMS analysis of the conversion of α-farnesene (5) by the recombinant *S. album* P450s enzymes. A. Control without the recombinant P450 enzyme. B. Assay with *E. coli* crude protein extract containing the recombinant SaCP10374 protein. C. Assay with *E. coli* crude protein extract containing the recombinant SaCP816 protein. The numbers indicated on the chromatograms refer to the structures presented in FIG. 27.

FIG. 19: GCMS analysis of the conversion of (−)-sesquisabinene B (9) by the recombinant *S. album* P450s enzymes. A. Control without the recombinant P450 enzyme. B. Assay with *E. coli* crude protein extract containing the recombinant SaCP10374 protein. C. Assay with *E. coli* crude protein extract containing the recombinant SaCP816 protein. The numbers indicated on the chromatograms refer to the structures presented in FIG. 27.

FIG. 20: GCMS analysis of the conversion of (−)-β-bisabolene (13) by the recombinant *S. album* P450s enzymes. A. Control without the recombinant P450 enzyme. B. Assay with *E. coli* crude protein extract containing the recombinant SaCP10374 protein. C. Assay with *E. coli* crude protein extract containing the recombinant SaCP816 protein. The numbers indicated on the chromatograms refer to the structures presented in FIG. 27.

FIG. 21: GCMS analysis of the conversion of (−)-α-bergamotene (17) by the recombinant *S. album* P450s enzymes. A. Control without the recombinant P450 enzyme. B. Assay with *E. coli* crude protein extract containing the recombinant SaCP10374 protein. C. Assay with *E. coli* crude protein extract containing the recombinant SaCP816 protein. The numbers indicated on the chromatograms refer to the structures presented in FIG. 27.

FIG. 22: GCMS analysis of the products generated in-vivo as described in example 23 by *E. Coli* KRX cells transformed with the plasmids pACYC-29258-4506 and the plasmid pD444-SR-AaBFS (A), SaCP10374-CPRm-AaBFS-pCWori (B), or SaCP816-CPRm-AaBFS-pCWori (C). The chromatograms show the formation of (E)-β-farnesene (1) as well as oxidized derivatives (2-3) (see FIG. 27 for corresponding structures).

FIG. 23: GCMS analysis of the products generated in-vivo as described in example 23 by *E. Coli* KRX cells transformed with the plasmids pACYC-29258-4506 and the plasmid pD444-SR-PaBAFS (A), SaCP10374-CPRm-PaAFS-pCWori (B), or SaCP816-CPRm-PaAFS-pCWori (C). The chromatograms show the formation of (E,E)-α-farnesene (5) as well as oxidized derivatives (6-8) (see FIG. 27 for corresponding structures). The peak of farnesol resulting from the hydrolysis of excess FPP is inducated on each chromatogram.

FIG. 24: GCMS analysis of the products generated in-vivo as described in example 23 by *E. Coli* KRX cells transformed with the plasmids pACYC-29258-4506 and the plasmid pETDuet-SaTps647 (A), SaCP10374-CPRm-SaTps647-pCWori (B), or SaCP816-CPRm-SaTPS647-pCWori(C). The chromatograms show the formation of (−)-sesquisabinene B (9) as well as oxidized derivatives (10-12) (see FIG. 27 for corresponding structures).

FIG. 25: GCMS analysis of the products generated in-vivo as described in example 23 by *E. Coli* KRX cells transformed with the plasmids pACYC-29258-4506 and the plasmid pETDuet-ClTps2 (A) or SaCP10374-CPRm-ClTps2-pCWori (B). The chromatograms show the formation of (+)-α-santalene (21) as well as oxidized derivatives (23-24) (see FIG. 27 for corresponding structures).

FIG. 26: GCMS analysis of the products generated in-vivo as described in example 23 by *E. Coli* KRX cells transformed with the plasmids pACYC-29258-4506 and the plasmid pETDuet-SaTps8201 (A) or SaCP10374-CPRm-SaTps8201-pCWori (B). The chromatograms show the formation of (+)-α-santalene (21), (−)-β-santalene (25) and (−)-trans-α-Bergamotene (17) as well as oxidized derivatives (19, 20, 23, 24, 27 and 28) (see FIG. 27 for corresponding structures).

FIG. 27A-B: Structure of the enzymes substrates and products discussed in the text.

DETAILED DESCRIPTION

In some embodiments, provided herein is a method of producing a sesquiterpene comprising α-sinensol, β-sinensol, α-santalol, β-santalol, α-trans-bergamotol, epi-β-santalol, and lancelol and/or mixtures thereof comprising contacting α-farnesene, β-farnesene, α-santalene, β-santalene, α-trans-bergamotene and/or epi-β-santalene, with a polypeptide comprising an amino acid sequence having at least, or at least about, 45%, 50%, 55%, 60%, 65%, 70%, 80%, 90%, 95%, or 98% % sequence identify to SEQ ID NO: 2. In a particular embodiment, the method comprises a cell that expresses the polypeptide.

In some embodiments, provided herein is a method of producing a α-sinensol, β-sinensol, α-santalol, β-santalol, α-trans-bergamotol, epi-β-santalol, lancelol and/or mixtures thereof comprising contacting α-farnesene, β-farnesene, α-santalene, β-santalene, α-trans-bergamotene and/or epi-β-santalene, with a polypeptide comprising an amino acid sequence having at least, or at least about, 45%, 50%, 55%, 60%, 65%, 70%, 80%, 90%, 95%, or 98% % sequence identify to SEQ ID NO: 4. In a particular embodiment, the method comprises a cell that expresses the polypeptide.

In some embodiments, provided herein is a method of producing α-sinensol, β-sinensol, α-santalol, β-santalol, α-trans-bergamotol, epi-β-santalol, lancelol and/or mixtures thereof comprising contacting α-farnesene, β-farnesene, α-santalene, β-santalene, α-trans-bergamotene and/or epi-β-santalene, with a polypeptide comprising an amino acid sequence having at least, or at least about, 45%, 50%, 55%, 60%, 65%, 70%, 80%, 90%, 95%, or 98% % sequence identify to SEQ ID NO: 6. In a particular embodiment, the method comprises a cell that expresses the polypeptide.

In some embodiments, provided herein is a method of producing α-sinensol, β-sinensol, α-santalol, β-santalol, α-trans-bergamotol, epi-β-santalol, lancelol and/or mixtures thereof comprising contacting α-farnesene, β-farnesene, α-santalene, β-santalene, α-trans-bergamotene and/or epi-β-santalene, with a polypeptide comprising an amino acid sequence having at least, or at least about, 45%, 50%, 55%, 60%, 65%, 70%, 80%, 90%, 95%, or 98% % sequence identify to SEQ ID NO: 8. In a particular embodiment, the method comprises a cell that expresses the polypeptide.

In some embodiments, provided herein is a method of producing α-sinensol, β-sinensol, α-santalol, β-santalol, α-trans-bergamotol, epi-β-santalol, lancelol and/or mixtures thereof comprising contacting α-farnesene, β-farnesene, α-santalene, β-santalene, α-trans-bergamotene and/or epi-β-santalene, with a polypeptide comprising an amino acid sequence having at least, or at least about, 45%, 50%, 55%, 60%, 65%, 70%, 80%, 90%, 95%, or 98% % sequence identify to SEQ ID NO: 28. In a particular embodiment, the method comprises a cell that expresses the polypeptide.

In some embodiments, provided herein is a method of producing α-sinensol, β-sinensol, α-santalol, β-santalol, α-trans-bergamotol, epi-β-santalol, lancelol and/or mixtures thereof comprising contacting α-farnesene, β-farnesene, α-santalene, β-santalene, α-trans-bergamotene and/or epi-β-santalene, with a polypeptide comprising an amino acid sequence having at least, or at least about, 45%, 50%, 55%, 60%, 65%, 70%, 80%, 90%, 95%, or 98% % sequence identify to SEQ ID NO: 30. In a particular embodiment, the method comprises a cell that expresses the polypeptide.

In some embodiments, provided herein is a method of producing α-sinensol, β-sinensol, α-santalol, β-santalol, α-trans-bergamotol, epi-β-santalol, lancelol and/or mixtures thereof comprising contacting α-farnesene, β-farnesene, α-santalene, β-santalene, α-trans-bergamotene and/or epi-β-santalene, with a polypeptide comprising an amino acid sequence having at least, or at least about, 45%, 50%, 55%, 60%, 65%, 70%, 80%, 90%, 95%, or 98% % sequence identify to SEQ ID NO: 32. In a particular embodiment, the method comprises a cell that expresses the polypeptide.

In some embodiments, provided herein is a method of producing α-sinensol, β-sinensol, α-santalol, β-santalol, α-trans-bergamotol, epi-β-santalol, lancelol and/or mixtures thereof comprising contacting α-farnesene, β-farnesene, α-santalene, β-santalene, α-trans-bergamotene and/or epi-β-santalene, with a polypeptide comprising an amino acid sequence having at least, or at least about, 45%, 50%, 55%, 60%, 65%, 70%, 80%, 90%, 95%, or 98% % sequence identify to SEQ ID NO: 34. In a particular embodiment, the method comprises a cell that expresses the polypeptide.

In some embodiments, provided herein is a method of producing α-sinensol, β-sinensol, α-santalol, β-santalol, α-trans-bergamotol, epi-β-santalol, lancelol and/or mixtures thereof comprising contacting α-farnesene, β-farnesene, α-santalene, β-santalene, α-trans-bergamotene and/or epi-β-santalene, with a polypeptide comprising an amino acid sequence having at least, or at least about, 45%, 50%, 55%, 60%, 65%, 70%, 80%, 90%, 95%, or 98% % sequence identify to SEQ ID NO: 36. In a particular embodiment, the method comprises a cell that expresses the polypeptide.

In some embodiments, provided herein is a method of producing α-sinensol, β-sinensol, α-santalol, β-santalol, α-trans-bergamotol, epi-β-santalol, lancelol and/or mixtures thereof comprising contacting α-farnesene, β-farnesene, α-santalene, β-santalene, α-trans-bergamotene and/or epi-β-santalene, with a polypeptide comprising an amino acid sequence having at least, or at least about, 45%, 50%, 55%, 60%, 65%, 70%, 80%, 90%, 95%, or 98% % sequence identify to SEQ ID NO: 38. In a particular embodiment, the method comprises a cell that expresses the polypeptide.

In some embodiments, provided herein is a method of producing α-sinensol, β-sinensol, α-santalol, β-santalol, α-trans-bergamotol, epi-β-santalol, lancelol and/or mixtures thereof comprising contacting α-farnesene, β-farnesene, α-santalene, β-santalene, α-trans-bergamotene and/or epi-β-santalene, with a polypeptide comprising an amino acid sequence having at least, or at least about, 45%, 50%, 55%, 60%, 65%, 70%, 80%, 90%, 95%, or 98% % sequence identify to SEQ ID NO: 40. In a particular embodiment, the method comprises a cell that expresses the polypeptide.

In some embodiments, provided herein is a method of producing α-sinensol, β-sinensol, α-santalol, β-santalol, α-trans-bergamotol, epi-β-santalol, lancelol and/or mixtures thereof comprising contacting α-farnesene, β-farnesene, α-santalene, β-santalene, α-trans-bergamotene and/or epi-β-santalene, with a polypeptide comprising an amino acid sequence having at least, or at least about, 45%, 50%, 55%, 60%, 65%, 70%, 80%, 90%, 95%, or 98% % sequence identify to SEQ ID NO: 42. In a particular embodiment, the method comprises a cell that expresses the polypeptide.

In some embodiments, provided herein is a method of producing α-sinensol, β-sinensol, α-santalol, β-santalol, α-trans-bergamotol, epi-β-santalol, lancelol and/or mixtures thereof comprising contacting α-farnesene, β-farnesene, α-santalene, β-santalene, α-trans-bergamotene and/or epi-β-santalene, with a polypeptide comprising an amino acid sequence having at least, or at least about, 45%, 50%, 55%, 60%, 65%, 70%, 80%, 90%, 95%, or 98% % sequence identify to SEQ ID NO: 44. In a particular embodiment, the method comprises a cell that expresses the polypeptide.

In some embodiments, provided herein is a method of producing α-sinensol, β-sinensol, α-santalol, β-santalol, α-trans-bergamotol, epi-β-santalol, lancelol and/or mixtures thereof comprising contacting α-farnesene, β-farnesene, α-santalene, β-santalene, α-trans-bergamotene and/or epi-β-santalene, with a polypeptide comprising an amino acid sequence having at least, or at least about, 45%, 50%, 55%, 60%, 65%, 70%, 80%, 90%, 95%, or 98% % sequence identify to SEQ ID NO: 50. In a particular embodiment, the method comprises a cell that expresses the polypeptide.

In some embodiments, provided herein is a method of producing α-sinensol, β-sinensol, α-santalol, β-santalol, α-trans-bergamotol, epi-β-santalol, lancelol and/or mixtures thereof comprising contacting α-farnesene, β-farnesene, α-santalene, β-santalene, α-trans-bergamotene and/or epi-β-santalene, with a polypeptide comprising an amino acid sequence having at least, or at least about, 45%, 50%, 55%, 60%, 65%, 70%, 80%, 90%, 95%, or 98% % sequence identify to SEQ ID NO: 52. In a particular embodiment, the method comprises a cell that expresses the polypeptide.

In some embodiments, provided herein is a method of producing α-sinensol, β-sinensol, α-santalol, β-santalol, α-trans-bergamotol, epi-β-santalol, lancelol and/or mixtures thereof comprising contacting α-farnesene, β-farnesene, α-santalene, β-santalene, α-trans-bergamotene and/or epi-β-santalene, with a polypeptide comprising an amino acid sequence having at least, or at least about, 45%, 50%, 55%, 60%, 65%, 70%, 80%, 90%, 95%, or 98% % sequence identify to SEQ ID NO: 54. In a particular embodiment, the method comprises a cell that expresses the polypeptide.

In some embodiments, provided herein is a method of producing α-sinensol, β-sinensol, α-santalol, β-santalol, α-trans-bergamotol, epi-β-santalol, lancelol and/or mixtures thereof comprising contacting α-farnesene, β-farnesene, α-santalene, β-santalene, α-trans-bergamotene and/or epi-β-santalene, with a polypeptide comprising an amino acid sequence having at least, or at least about, 45%, 50%, 55%, 60%, 65%, 70%, 80%, 90%, 95%, or 98% % sequence identify to SEQ ID NO: 58. In a particular embodiment, the method comprises a cell that expresses the polypeptide.

In some embodiments, provided herein is a method of producing α-sinensol, β-sinensol, α-santalol, β-santalol, α-trans-bergamotol, epi-β-santalol, lancelol and/or mixtures thereof comprising contacting α-farnesene, β-farnesene, α-santalene, β-santalene, α-trans-bergamotene and/or epi-β-santalene, with a polypeptide comprising an amino acid sequence having at least, or at least about, 45%, 50%, 55%, 60%, 65%, 70%, 80%, 90%, 95%, or 98% % sequence identify to SEQ ID NO:60. In a particular embodiment, the method comprises a cell that expresses the polypeptide.

In some embodiments, provided herein is a method of producing α-sinensol, β-sinensol, α-santalol, β-santalol, α-trans-bergamotol, epi-β-santalol, lancelol and/or mixtures thereof comprising contacting α-farnesene, β-farnesene, α-santalene, β-santalene, α-trans-bergamotene and/or epi-β-santalene, with a polypeptide comprising an amino acid sequence having at least, or at least about, 45%, 50%, 55%, 60%, 65%, 70%, 80%, 90%, 95%, or 98% % sequence identify to SEQ ID NO: 62. In a particular embodiment, the method comprises a cell that expresses the polypeptide.

In some embodiments, provided herein is a method of producing α-sinensol, β-sinensol, α-santalol, β-santalol, α-trans-bergamotol, epi-β-santalol, lancelol and/or mixtures thereof comprising contacting α-farnesene, β-farnesene, α-santalene, β-santalene, α-trans-bergamotene and/or epi-β-santalene, with a polypeptide comprising an amino acid sequence having at least, or at least about, 45%, 50%, 55%, 60%, 65%, 70%, 80%, 90%, 95%, or 98% % sequence identify to SEQ ID NO: 64. In a particular embodiment, the method comprises a cell that expresses the polypeptide.

In some embodiments, provided herein is a method of producing α-sinensol, β-sinensol, α-santalol, β-santalol, α-trans-bergamotol, epi-β-santalol, lancelol and/or mixtures thereof comprising contacting α-farnesene, β-farnesene, α-santalene, β-santalene, α-trans-bergamotene and/or epi-β-santalene, with a polypeptide comprising an amino acid sequence having at least, or at least about, 45%, 50%, 55%, 60%, 65%, 70%, 80%, 90%, 95%, or 98% % sequence identify to SEQ ID NO: 66. In a particular embodiment, the method comprises a cell that expresses the polypeptide.

In some embodiments, provided herein is a method of producing α-sinensol, β-sinensol, α-santalol, β-santalol, α-trans-bergamotol, epi-β-santalol, lancelol and/or mixtures thereof comprising contacting α-farnesene, β-farnesene, α-santalene, β-santalene, α-trans-bergamotene and/or epi-β-santalene, with a polypeptide comprising an amino acid sequence having at least, or at least about, 45%, 50%, 55%, 60%, 65%, 70%, 80%, 90%, 95%, or 98% % sequence identify to SEQ ID NO: 68. In a particular embodiment, the method comprises a cell that expresses the polypeptide.

In some embodiments, provided herein is a method of producing α-sinensol, β-sinensol, α-santalol, β-santalol, α-trans-bergamotol, epi-β-santalol, lancelol and/or mixtures thereof comprising contacting α-farnesene, β-farnesene, α-santalene, β-santalene, α-trans-bergamotene and/or epi-β-santalene, with a polypeptide comprising an amino acid sequence having at least, or at least about, 45%, 50%, 55%, 60%, 65%, 70%, 80%, 90%, 95%, or 98% % sequence identify to SEQ ID NO: 71. In a particular embodiment, the method comprises a cell that expresses the polypeptide.

In some embodiments, provided herein is a method of producing α-sinensol, β-sinensol, α-santalol, β-santalol, α-trans-bergamotol, epi-β-santalol, lancelol and/or mixtures thereof comprising contacting α-farnesene, β-farnesene, α-santalene, β-santalene, α-trans-bergamotene and/or epi-β-santalene, with a polypeptide comprising an amino acid sequence having at least, or at least about, 45%, 50%, 55%, 60%, 65%, 70%, 80%, 90%, 95%, or 98% % sequence identify to SEQ ID NO: 73. In a particular embodiment, the method comprises a cell that expresses the polypeptide.

In some embodiments, provided herein is a method of producing α-sinensol, β-sinensol, α-santalol, β-santalol, α-trans-bergamotol, epi-β-santalol, lancelol and/or mixtures thereof comprising contacting α-farnesene, β-farnesene, α-santalene, β-santalene, α-trans-bergamotene and/or epi-β-santalene, with a polypeptide comprising an amino acid sequence having at least, or at least about, 45%, 50%, 55%, 60%, 65%, 70%, 80%, 90%, 95%, or 98% % sequence identify to SEQ ID NO: 79. In a particular embodiment, the method comprises a cell that expresses the polypeptide.

In some embodiments, provided herein is a method of producing α-sinensol, β-sinensol, α-santalol, β-santalol, α-trans-bergamotol, epi-β-santalol, lancelol and/or mixtures thereof comprising contacting α-farnesene, β-farnesene, α-santalene, β-santalene, α-trans-bergamotene and/or epi-β-santalene, with a polypeptide comprising an amino acid sequence having at least, or at least about, 45%, 50%, 55%, 60%, 65%, 70%, 80%, 90%, 95%, or 98% % sequence identify to SEQ ID NO: 81. In a particular embodiment, the method comprises a cell that expresses the polypeptide.

The nucleotide sequences provided herein for producing a polypeptide for use in producing an alcohol have a nucleic acid sequence at least, or at least about 45%, 50%, 55%, 60%, 65%, 70%, 75%, 80%, 85%, 90%, 95% or 98% to a sequence selected from the group consisting of SEQ ID NO: 1, SEQ ID NO: 3, SEQ ID NO: 5, SEQ ID NO: 7, SEQ ID NO: 27, SEQ ID NO: 29, SEQ ID NO: 31, SEQ ID NO: 33, SEQ ID NO: 35, SEQ ID NO: 37, SEQ ID NO: 39, SEQ ID NO: 41, SEQ ID NO: 43, SEQ ID NO: 49, SEQ ID NO: 51, SEQ ID NO: 53, SEQ ID NO: 57, SEQ ID NO: 59, SEQ ID NO: 61, SEQ ID NO: 63, SEQ ID NO: 65, SEQ ID NO: 67, SEQ ID NO: 70 SEQ ID NO: 72, SEQ ID NO: 78 and SEQ ID NO: 80. The nucleotide sequences provided herein are heterologous in that they are not typically or normally produced by a cell in which it is expressed herein and is generally not endogenous to the cell into which it is introduced—it being typically obtained from another cell or could be made synthetically.

In another embodiment, provided herein is a method of producing a sesquiterpene alcohol comprising α-sinensol, β-sinensol, α-santalol, β-santalol, α-trans-bergamotol, epi-β-santalol, lancelol, and/or mixtures thereof comprising contacting trans-α-farnesene trans-β-farnesene, α-santalene, β-santalene, α-trans-bergamotene, epi-β-santalene, and/or β-bisabolene with a polypeptide having a P450 monoxygenase activity wherein the alcohol produced comprises at least, or at least about, 36%, of a cis isomer and wherein the polpeptide e comprises an amino acid sequence having at least or at least about 45%, 50%, 55%, 60%, 65%, 70%, 80%, 90%, 95%, or 98% % sequence identify to a polypeptide having an amino acid sequence selected from the group consisting of SEQ ID NO: 28, SEQ ID NO: 30, SEQ ID NO: 58, SEQ ID NO: 60, SEQ ID NO: 62, SEQ ID NO: 64, SEQ ID NO: 66, SEQ ID NO: 68, SEQ ID NO: 71, and SEQ ID NO: 73.

In another embodiment, provided herein is a method of producing a sesquiterpene alcohol comprising α-sinensol, β-sinensol, α-santalol, β-santalol, α-trans-bergamotol, epi-β-santalol, lancelol, and/or mixtures thereof comprising contacting trans-α-farnesene trans-β-farnesene, α-santalene, β-santalene, α-trans-bergamotene, epi-β-santalene, and/or β-bisabolene with a polypeptide having a P450 monoxygenase activity wherein the alcohol produced comprises at least, or at least about, 46%, of a cis isomer and wherein the polpeptide e comprises an amino acid sequence having at least or at least about 45%, 50%, 55%, 60%, 65%, 70%, 80%, 90%, 95%, or 98% % sequence identify to a polypeptide having an amino acid sequence selected from the group consisting of SEQ ID NO: 30, SEQ ID NO: 58, SEQ ID NO: 60, SEQ ID NO: 62, SEQ ID NO: 66, SEQ ID NO: 68, SEQ ID NO: 71, and SEQ ID NO: 73.

In another embodiment, provided herein is a method of producing a sesquiterpene alcohol comprising α-sinensol, β-sinensol, α-santalol, β-santalol, α-trans-bergamotol, epi-β-santalol, lancelol, and/or mixtures thereof comprising contacting trans-α-farnesene trans-β-farnesene, α-santalene, β-santalene, α-trans-bergamotene, epi-β-santalene, and/or β-bisabolene with a polypeptide having a P450 monoxygenase activity wherein the alcohol produced comprises at least, or at least about, 50%, of a cis isomer and wherein the polpeptide e comprises an amino acid sequence having at least or at least about 45%, 50%, 55%, 60%, 65%, 70%, 80%, 90%, 95%, or 98% % sequence identify to a polypeptide having an amino acid sequence selected from the group consisting of SEQ ID NO: 58, SEQ ID NO: 60, SEQ ID NO: 62, SEQ ID NO: 68, SEQ ID NO: 71, and SEQ ID NO: 73.

In another embodiment, provided herein is a method of producing a sesquiterpene alcohol comprising α-sinensol, β-sinensol, α-santalol, β-santalol, α-trans-bergamotol, epi-β-santalol, lancelol, and/or mixtures thereof comprising contacting trans-α-farnesene trans-β-farnesene, α-santalene, β-santalene, α-trans-bergamotene, epi-β-santalene, and/or β-bisabolene with a polypeptide having a P450 monoxygenase activity wherein the alcohol produced comprises at least, or at least about, 72%, of a cis isomer and wherein the polpeptide e comprises an amino acid sequence having at least or at least about 45%, 50%, 55%, 60%, 65%, 70%, 80%, 90%, 95%, or 98% % sequence identify to a polypeptide having an amino acid sequence selected from the group consisting of 45%, 50%, 55%, 60%, 65%, 70%, 80%, 90%, 95%, or 98% % sequence identify to a polypeptide having an amino acid sequence selected from the group consisting of SEQ ID NO: 58, SEQ ID NO: 60, SEQ ID NO: 62, SEQ ID NO: 68, SEQ ID NO: 71, and SEQ ID NO: 73.

In another embodiment, provided herein is a method of producing a sesquiterpene alcohol comprising α-sinensol, β-sinensol, α-santalol, β-santalol, α-trans-bergamotol, epi-β-santalol, lancelol, and/or mixtures thereof comprising contacting trans-α-farnesene trans-β-farnesene, α-santalene, β-santalene, α-trans-bergamotene, epi-β-santalene, and/or β-bisabolene with a polypeptide having a P450 monoxygenase activity wherein the alcohol produced comprises at least, or at least about, 96%, of a cis isomer and wherein the polpeptide e comprises an amino acid sequence having at least or at least about 45%, 50%, 55%, 60%, 65%, 70%, 80%, 90%, 95%, or 98% % sequence identify to a polypeptide having an amino acid sequence selected from the group consisting of ID NO: 68, SEQ ID NO: 71, and SEQ ID NO: 73.

In another embodiment, provided herein is a method of producing a sesquiterpene alcohol comprising α-sinensol, β-sinensol, α-santalol, β-santalol, α-trans-bergamotol, epi-β-santalol, lancelol, and/or mixtures thereof comprising contacting trans-α-farnesene trans-β-farnesene, α-santalene, β-santalene, α-trans-bergamotene, epi-β-santalene, and/or β-bisabolene with a polypeptide having a P450 monoxygenase activity wherein the alcohol produced comprises at least, or at least about, 100%, of a cis isomer and wherein the polpeptide e comprises an amino acid sequence having at least or at least about 45%, 50%, 55%, 60%, 65%, 70%, 80%, 90%, 95%, or 98% % sequence identify to a polypeptide having an amino acid sequence selected from the group consisting of SEQ ID NO: 71, and 73.

Provided herein is also an isolated nucleic acid molecule selected from the group consisting of: i) a nucleic acid having an nucleic acid sequence selected from the group consisting SEQ ID. NO: 70 and 72; and ii) a nucleic acid molecule that encodes a polypeptide having p450 monooxygenase activity wherein the polypeptide comprises an amino acid sequence that is at least, or at least about 45%, 50%, 55%, 50%, 65%, 70%, 80%, 90%, 95%, or 98% or more identical to an amino acid sequence selected from the group consisting of SEQ ID NOs: 71, and SEQ ID NO: 73. More particularly the polypeptide encoded has the sequence selected from the group consisting of SEQ ID NOs: 71, and SEQ ID NO: 73.

Provided herein is also an isolated nucleic acid molecule selected from the group consisting of: i) a nucleic acid having an nucleic acid sequence selected from the group consisting SEQ ID. NO: 78 and 80; and ii) a nucleic acid molecule that encodes a polypeptide having p450 monooxygenase activity wherein the polypeptide comprises an amino acid sequence that is at least, or at least about 45%, 50%, 55%, 50%, 65%, 70%, 80%, 90%, 95%, or 98% or more identical to an amino acid sequence selected from the group consisting of SEQ ID NOs: 79, and SEQ ID NO: 82. More particularly the polypeptide encoded has the sequence selected from the group consisting of SEQ ID NOs: 79, and SEQ ID NO: 82.

Also provided herein is an isolated nucleic acid molecule selected from the group consisting of: i) a nucleic acid having an nucleic acid sequence selected from the group consisting SEQ ID. NO: 27, 29, 31, 33, and 35; and ii) a nucleic acid molecule that encodes a polypeptide having p450 monooxygenase activity wherein the polypeptide has the sequence selected from the group consisting of SEQ ID NO: 28, SEQ ID NO: 30, SEQ ID NO: 32, SEQ ID NO: 34, SEQ ID NO: 36.

In another embodiment provided herein is a method for producing a polypeptide having P450 monoxygenase activity comprising the steps of transforming a host cell or non-human organism with a nucleic acid encoding a polypeptide having at least, or at least about, 45%, 50%, 55%, 50%, 65%, 70%, 80%, 90%, 95%, or 98% sequence identity to a polypeptide selected from the group consisting of SEQ ID NO: 71, and SEQ ID NO: 73 and culturing the host cell or organism under conditions that allow for the production of the polypeptide.

In a further embodiment provided here is a method for producing a polypeptide having P450 monoxygenase activity comprising the steps of transforming a host cell or non-human organism with a nucleic acid encoding a polypeptide having the sequence selected from the group consisting of SEQ ID NO: 71, and SEQ ID NO: 73 and culturing the host cell or organism under conditions that allow for the production of the polypeptide.

In another embodiment provided herein is a method for producing a polypeptide having P450 monoxygenase activity comprising the steps of transforming a host cell or non-human organism with a nucleic acid encoding a polypeptide having at least, or at least about, 45%, 50%, 55%, 50%, 65%, 70%, 80%, 90%, 95%, or 98% sequence identity to a polypeptide selected from the group consisting of SEQ ID NO: 79, and SEQ ID NO: 81 and culturing the host cell or organism under conditions that allow for the production of the polypeptide.

In a further embodiment provided here is a method for producing a polypeptide having P450 monoxygenase activity comprising the steps of transforming a host cell or non-human organism with a nucleic acid encoding a polypeptide having the sequence selected from the group consisting of SEQ ID NO: 79, and SEQ ID NO: 81 and culturing the host cell or organism under conditions that allow for the production of the polypeptide.

The alcohols can be converted to aldehydes or acids such as but not limited to sinensals, santalals, bergamotenals, and lanceals. The alcohols, aldehydes or acids can be further converted to derivatives such as, but not limited to esters, amides, glycosides, ethers or acetals.

Nucleic acid and polypeptides described herein may be isolated for example from *Cichorium intybus* L., *Bacillus megaterium, Santalum Album* and *Artemisia annua*. CYP71AV8, P450-BM3 (CYP102A1), and CYP71AV1 including variants are described herein.

CYP71AV8 from the plant *Cichorium intybus* L. was previously characterized as a P450 mono-oxygenase able to oxidize region-selectively (+)-valencene producing trans-nootkatol, cis-nootkatol and (+)-nootkatone. CYP71AV8 was also found to catalyse the oxidation of germacrene A and *amorpha*-4,11-diene in the C-12 position (Cankar et al, *FEBS Lett.* 585(1), 178-182 (2011)). The amino acid sequence of the wild type enzyme (NCBI accession No ADM86719.1, SEQ ID No 1 and 2) was used to design a cDNA sequence optimized for expression in *E. coli.*

In eukaryotes, the P450 monooxygenases are membrane-bound proteins and the N-terminal sequence of these proteins constitute a membrane anchor essential for the membrane localization of these enzymes. This part of the protein, usually delimited by a proline-rich domaine, is not essential for the control of the specificity of the enzymatic activity. This region can thus be modified by deletion, insertion or mutation without effect on the catalytic activity. However, specific modification of the N-terminal region of eukaryotic P450s, including plant P450s, have been shown to have a positive effect on the levels of functional recombinant proteins when expressed in microorganisms (Halkier et al (1995) *Arch. Biochem. Biophys.* 322, 369-377; Haudenschield et al (2000) *Arch. Biochem. Biophys.* 379, 127-136).

In P450 monooxygenases the recognition and binding of the substrate is controlled by several amino acid residues distributed in different regions along the protein amino acid sequences. These regions, defined as substrate recognition sites (SRS), can be localized in the amino acid sequence of any P450 by simple sequence alignment based for example on the work made by Gotoh (Gotoh O (1992) J. Biol. Chem. 267(1), 83-90). Thus residues in the CYP71AV8 protein that interact with the substrate and can influence the regioselectivity of the hydroxylation reaction are the amino acids Asn98 to Gly121, Thr198 to Leu205, Lys232 to Ile 240, Asn282 to Ala300, His355 to Arg367 and Thr469 to Val 476. The modification of one or more residues in these regions can potentially alter the substrate specificity, the stereochemistry of the reaction or its regioselectivity. One example of alteration of the regioselectivity of the reaction catalyzed by a P450 can be found in Schalk et al (2002) Proc. Natl. Acad. Sci. USA 97(22), 11948-11953. In this publication a single residue change in plant P450 enzymes led to a complete conversion to the regiospecificity of the enzymatique reaction.

A "sesquiterpene synthase" or a "polypeptide having a sesquiterpene synthase activity" is intended for the purpose of the present application as a polypeptide capable of catalyzing the synthesis of a sesquiterpene molecule or of a mixture of sesquiterpene molecules from a acyclic pyrophosphate terpene precursor selected from the group consisting of geranyl-pyrophosphate (GPP), farnesy-diphosphate (FPP) and geranylgeranyl-pyrophosphate (GGPP).

Alpha santalene, beta-santalene, alpha-trans-bergamotene, and/or epi-beta santalene may be prepared using the synthases described for example in U.S. Patent Publication No.: 2011-0008836, published Jan. 13, 20111 and in U.S. Patent Publication No.: 2011-0281257, published Nov. 27, 2011, both of which are incorporated herein in their entirety.

According to the present invention, polypeptides are also meant to include truncated polypeptides provided that they keep their P450 monooxygenase activity as defined in any of the above embodiments.

The percentage of identity between two peptidic or nucleotidic sequences is a function of the number of amino acids or nucleotide residues that are identical in the two sequences when an alignment of these two sequences has been generated. Identical residues are defined as residues that are the same in the two sequences in a given position of the alignment. The percentage of sequence identity, as used herein, is calculated from the optimal alignment by taking the number of residues identical between two sequences dividing it by the total number of residues in the shortest sequence and multiplying by 100. The optimal alignment is the alignment in which the percentage of identity is the highest possible. Gaps may be introduced into one or both sequences in one or more positions of the alignment to obtain the optimal alignment. These gaps are then taken into account as non-identical residues for the calculation of the percentage of sequence identity.

Alignment for the purpose of determining the percentage of amino acid or nucleic acid sequence identity can be achieved in various ways using computer programs and for instance publicly available computer programs available on the world wide web. Particularly, the BLAST program (Tatiana et al, *FEMS Microbiol Lett.,* 1999, 174:247-250, 1999) set to the default parameters, available from the National Center for Biotechnology Information (NCBI) at their webpage ncbi.nlm.nih.gov/BLAST/bl2seq/wblast2.cgi, can be used to obtain an optimal alignment of peptidic or nucleotidic sequences and to calculate the percentage of sequence identity.

A particular organism or cell is meant to be "capable of producing FPP" when it produces FPP naturally or when it does not produce FPP naturally but is transformed to produce FPP, either prior to the transformation with a nucleic acid as described herein or together with said nucleic acid. Organisms or cells transformed to produce a higher amount of FPP than the naturally occurring organism or cell are also encompassed by the "organisms or cells capable of producing FPP". Methods to transform organisms, for example microorganisms, so that they produce FPP are already known in the art. Such methods can for example be found in the literature, for example in the following publications: Martin, V. J., Pitera, D. J., Withers, S. T., Newman, J. D., and Keasling, J. D. Nat Biotechnol., 2003, 21(7), 796-802 (transformation of *E. coli*); Wu, S., Schalk, M., Clark, A., Miles, R. B., Coates, R., and Chappell, J., *Nat Biotechnol.,* 2006, 24(11), 1441-1447 (transformation of plants); Takahashi, S., Yeo, Y., Greenhagen, B. T., McMullin, T., Song, L., Maurina-Brunker, J., Rosson, R., Noel, J., Chappell, J, *Biotechnology and Bioengineering,* 2007, 97(1), 170-181 (transformation of yeast).

Non-human host organisms suitable to carry out the method described herein in vivo may be any non-human multicellular or unicellular organisms. In a particular embodiment, the non-human host organism used to carry out the invention in vivo is a plant, a prokaryote or a fungus. Any plant, prokaryote or fungus can be used. Particularly useful plants are those that naturally produce high amounts of terpenes. In a more particular embodiment, the plant is selected from the family of Solanaceae, Poaceae, Brassicaceae, Fabaceae, Malvaceae, Asteraceae or Lamiaceae. For example, the plant is selected from the genera *Nicotiana, Solanum, Sorghum, Arabidopsis, Brassica* (rape), *Medicago* (alfalfa), *Gossypium* (cotton), *Artemisia, Salvia* and *Mentha*. Particularly, the plant belongs to the species of *Nicotiana tabacum.*

In a more particular embodiment the non-human host organism used to carry out the method of the invention in vivo is a microorganism. Any microorganism can be used but according to an even more particular embodiment said microorganism is a bacteria or yeast. Most particularly, said bacteria is *E. coli* and said yeast is *Saccharomyces cerevisiae.*

Some of these organisms do not produce FPP naturally. To be suitable to carry out the method of the invention, these organisms have to be transformed to produce said precursor. They can be so transformed either before the modification with the nucleic acid described according to any of the above embodiments or simultaneously, as explained above.

Isolated higher eukaryotic cells can also be used, instead of complete organisms, as hosts to carry out the method of the invention in vivo. Suitable eukaryotic cells may be any non-human cell, but are particularly plant or fungal cells.

As used herein, the polypeptide is intended as a polypeptide or peptide fragment that encompasses the amino acid sequences identified herein, as well as truncated or variant polypeptides, provided that they keep their P450 monooxygenaseactivity as defined above and that they share at least the defined percentage of identity with the corresponding polypeptide.

Examples of variant polypeptides are naturally occurring proteins that result from alternate mRNA splicing events or from proteolytic cleavage of the polypeptides described herein. Variations attributable to proteolysis include, for example, differences in the N- or C-termini upon expression in different types of host cells, due to proteolytic removal of one or more terminal amino acids from the polypeptides of the invention. Polypeptides encoded by a nucleic acid obtained by natural or artificial mutation of a nucleic acid of the invention, as described thereafter, are also encompassed by the invention.

Polypeptide variants resulting from a fusion of additional peptide sequences at the amino and carboxyl terminal ends can also be used in the methods of the invention. In particular such a fusion can enhance expression of the polypeptides, be useful in the purification of the protein or improve the enzymatic activity of the polypeptide in a desired environment or expression system. Such additional peptide sequences may be signal peptides, for example. Accordingly, the present invention encompasses methods using variant polypeptides, such as those obtained by fusion with other oligo- or polypeptides and/or those which are linked to signal peptides. Polypeptides resulting from a fusion with another functional protein, such as another protein from the terpene biosynthesis pathway, can also be advantageously be used in the methods of the invention.

As used herein, the polypeptide is intended as a polypeptide or peptide fragment that encompasses the amino acid sequence identified herein, as well as truncated or variant polypeptides, provided that they keep their activity as defined above.

Examples of variant polypeptides are naturally occurring proteins that result from alternate mRNA splicing events or from proteolytic cleavage of the polypeptides described herein. Variations attributable to proteolysis include, for example, differences in the N- or C-termini upon expression in different types of host cells, due to proteolytic removal of one or more terminal amino acids from the polypeptides of the invention. Polypeptides encoded by a nucleic acid obtained by natural or artificial mutation of a nucleic acid of the invention, as described thereafter, are also encompassed by the invention.

Polypeptide variants resulting from a fusion of additional peptide sequences at the amino and carboxyl terminal ends are also encompassed by the polypeptides of the invention. In particular such a fusion can enhance expression of the polypeptides, be useful in the purification of the protein or improve the enzymatic activity of the polypeptide in a desired environment or expression system. Such additional peptide sequences may be signal peptides, for example. Accordingly, the present invention encompasses variants of the polypeptides of the invention, such as those obtained by fusion with other oligo- or polypeptides and/or those which are linked to signal peptides. Polypeptides resulting from a fusion with another functional protein, such as another protein from the terpene biosynthesis pathway, are also encompassed by the polypeptides of the invention.

The nucleic acid of the invention can be defined as including deoxyribonucleotide or ribonucleotide polymers in either single- or double-stranded form (DNA and/or RNA). The terms "nucleotide sequence" should also be understood as comprising a polynucleotide molecule or an oligonucleotide molecule in the form of a separate fragment or as a component of a larger nucleic acid. Nucleic acids of the invention also encompass certain isolated nucleotide sequences including those that are substantially free from contaminating endogenous material. The nucleic acid of the invention may be truncated, provided that it encodes a polypeptide encompassed by the present invention, as described above.

Another important tool for transforming host organisms or cells suitable to carry out the method of the invention in vivo is an expression vector comprising a nucleic acid according to any embodiment of the invention. Such a vector is therefore also an object of the present invention.

An "expression vector" as used herein includes any linear or circular recombinant vector including but not limited to viral vectors, bacteriophages and plasmids. The skilled person is capable of selecting a suitable vector according to the expression system. In one embodiment, the expression vector includes the nucleic acid of the invention operably linked to at least one regulatory sequence, which controls transcription, translation, initiation and termination, such as a transcriptional promoter, operator or enhancer, or an mRNA ribosomal binding site and, optionally, including at least one selection marker. Nucleotide sequences are "operably linked" when the regulatory sequence functionally relates to the nucleic acid of the invention.

The expression vectors of the present invention may be used in the methods for preparing a genetically transformed host organism and/or cell, in host organisms and/or cells harboring the nucleic acids of the invention and in the methods for making polypeptides having a P450 monooxygenase activity, as disclosed further below.

Recombinant non-human host organisms and cells transformed to harbor at least one nucleic acid of the invention so that it heterologously expresses or over-expresses at least one polypeptide of the invention are also very useful tools to carry out the method of the invention. Such non-human host organisms and cells are therefore another object of the present invention.

A nucleic acid according to any of the above-described embodiments can be used to transform the non-human host organisms and cells and the expressed polypeptide can be any of the above-described polypeptides.

Non-human host organisms of the invention may be any non-human multicellular or unicellular organisms. In a particular embodiment, the non-human host organism is a plant, a prokaryote or a fungus. Any plant, prokaryote or fungus is suitable to be transformed according to the present invention. Particularly useful plants are those that naturally produce high amounts of terpenes. In a more particular embodiment, the plant is selected from the family of Solanaceae, Poaceae, Brassicaceae, Fabaceae, Malvaceae, Asteraceae or Lamiaceae. For example, the plant is selected from the genera *Nicotiana, Solanum, Sorghum, Arabidopsis, Brassica* (rape), *Medicago* (alfalfa), *Gossypium* (cotton), *Artemisia, Salvia* and *Mentha*. Particularly, the plant belongs to the species of *Nicotiana tabacum.*

In a more particular embodiment the non-human host organism is a microorganism. Any microorganism is suitable for the present invention, but according to an even more particular embodiment said microorganism is a bacteria or yeast. Most particularly, said bacteria is *E. coli* and said yeast is *Saccharomyces cerevisiae.*

Isolated higher eukaryotic cells can also be transformed, instead of complete organisms. As higher eukaryotic cells, we mean here any non-human eukaryotic cell except yeast cells. Particular higher eukaryotic cells are plant cells or fungal cells.

The term "transformed" refers to the fact that the host was subjected to genetic engineering to comprise one, two or more copies of each of the nucleic acids required in any of the above-described embodiment. Particularly the term "transformed" relates to hosts heterologously expressing the polypeptides encoded by the nucleic acid with which they are transformed, as well as over-expressing said polypeptides. Accordingly, in an embodiment, the present invention provides a transformed organism, in which the polypeptides are expressed in higher quantity than in the same organism not so transformed.

There are several methods known in the art for the creation of transgenic host organisms or cells such as plants, fungi, prokaryotes, or cultures of higher eukaryotic cells. Appropriate cloning and expression vectors for use with bacterial, fungal, yeast, plant and mammalian cellular hosts are described, for example, in Pouwels et al., *Cloning Vectors: A Laboratory Manual,* 1985, Elsevier, New York and Sambrook et al., *Molecular Cloning: A Laboratory Manual,* 2nd edition, 1989, Cold Spring Harbor Laboratory Press. Cloning and expression vectors for higher plants and/or plant cells in particular are available to the skilled person. See for example Schardl et al. *Gene* 61: 1-11, 1987.

Methods for transforming host organisms or cells to harbor transgenic nucleic acids are familiar to the skilled person. For the creation of transgenic plants, for example, current methods include: electroporation of plant protoplasts, liposome-mediated transformation, *agrobacterium*-mediated transformation, polyethylene-glycol-mediated transformation, particle bombardement, microinjection of plant cells, and transformation using viruses.

In one embodiment, transformed DNA is integrated into a chromosome of a non-human host organism and/or cell such that a stable recombinant system results. Any chromosomal integration method known in the art may be used in the practice of the invention, including but not limited to recombinase-mediated cassette exchange (RMCE), viral site-specific chromosomal insertion, adenovirus and pronuclear injection.

A "polypeptide variant" as referred to herein means a polypeptide having the above described activity and being substantially homologous to the polypeptide according to any of the above embodiments, but having an amino acid sequence different from that encoded by any of the nucleic acid sequences of the invention because of one or more deletions, insertions or substitutions.

Variants can comprise conservatively substituted sequences, meaning that a given amino acid residue is replaced by a residue having similar physiochemical characteristics. Examples of conservative substitutions include substitution of one aliphatic residue for another, such as Ile, Val, Leu, or Ala for one another, or substitutions of one polar residue for another, such as between Lys and Arg; Glu and Asp; or Gln and Asn. See Zubay, *Biochemistry,* 1983, Addison-Wesley Pub. Co. The effects of such substitutions can be calculated using substitution score matrices such a PAM-120, PAM-200, and PAM-250 as discussed in Altschul, *J. Mol. Biol.,* 1991, 219, 555-565. Other such conservative substitutions, for example substitutions of entire regions having similar hydrophobicity characteristics, are well known.

Naturally occurring peptide variants are also encompassed by the invention. Examples of such variants are proteins that result from alternate mRNA splicing events or from proteolytic cleavage of the polypeptides described herein. Variations attributable to proteolysis include, for example, differences in the N- or C-termini upon expression in different types of host cells, due to proteolytic removal of one or more terminal amino acid from the polypeptides encoded by the sequences of the invention.

Variants of the polypeptides of the invention may be used to attain for example desired enhanced or reduced enzymatic activity, modified regiochemistry or stereochemistry, or altered substrate utilization or product distribution, increased affinity for the substrate, improved specificity for the production of one or more desired compounds, increased velocity of the enzyme reaction, higher activity or stability in a specific environment (pH, temperature, solvent, etc), or improved expression level in a desired expression system. A variant or site directed mutant may be made by any method known in the art. Variants and derivatives of native polypeptides can be obtained by isolating naturally-occurring variants, or the nucleotide sequence of variants, of other or same plant lines or species, for examples plants from the *Santalum* species, or by artificially programming mutations of nucleotide sequences coding for the polypeptides of the invention. Alterations of the native amino acid sequence can be accomplished by any of a number of conventional methods.

Polypeptide variants resulting from a fusion of additional peptide sequences at the amino and carboxyl terminal ends of the polypeptides of the invention can be used to enhance expression of the polypeptides, be useful in the purification of the protein or improve the enzymatic activity of the polypeptide in a desired environment or expression system. Such additional peptide sequences may be signal peptides, for example. Accordingly, the present invention encompasses variants of the polypeptides of the invention, such as those obtained by fusion with other oligo- or polypeptides and/or those which are linked to signal peptides. Fusion polypeptide encompassed by the invention also comprise fusion polypeptides resulting from a fusion of other functional proteins, such as other proteins from the terpene biosynthesis pathway.

The alcohols produced herein may be isolated by extraction for example using known methods to extract the alcohols generated in nature (e.g., extraction from Sandalwood). The alcohols produced herein have use as fragrant compounds that may be used in perfumery.

ABBREVIATIONS USED aaCPR *Arthemisia annua* Cytochrome P450 reductase
bp base pair
kb kilo base
DNA deoxyribonucleic acid
cDNA complementary DNA
ClASS *Clausena lansium* (+)-α-santalene synthase
CPRm *Mentha piperita* Cytochrome P450 reductase
DTT dithiothreitol
EDTA ethylene-diamine-tetraacetic acid
FPP farnesyl pyrophosphate
GC gaseous chromatograph
IPTG isopropyl-D-thiogalacto-pyranoside
LB lysogeny broth
MS mass spectrometer
MTBE methyl tert-buthyl ether
PCR polymerase chain reaction
RMCE recombinase-mediated cassette exchange
RNA ribonucleic acid
mRNA messenger ribonucleic acid
SaSAS *Santalum album* (+)-α-santalene/(−)-β-santalene synthase The following examples are illustrative only and are not meant to limit the scope of invention as set forth in the Summary, Description or in the Claims.

EXAMPLES

Example 1

Optimization of the CYP71AV8 cDNA Sequence for Expression in Bacteria

The membrane anchor region of CYP71AV8 was redesigned to introduce the modifications detailed bellow.

In the optimized CYP71AV8 sequences the 5'-end was modified to replace the first amino acids of the membrane anchor region with a peptide sequence shown to improve the heterologous expression of membrane-bound P450s in bacterial cells (Alkier, B. A. et al. *Arch. Biochem. Biophys.* 322, 369-377 (1995), Haudenschield, et al *Arch. Biochem. Biophys.* 379, 127-136 (2000)). In addition, for the entire cDNA, the codon usage was adapted to match the *E. Coli* codon usage. Thus, several cDNA were designed for CYP71AV8 with different 3'-end modifications and optimizations:

CYP71AV8-65188: in this construct the 22 first codons were replaced by a sequence coding for the MALLLAVFWSALIILV peptide (SEQ ID NO 3 and 4).

CYP71AV8-P2: the entire anchor-encoding sequence was replaced by the anchor sequence of an optimized limonene-hydroxylase from mint (PM2 in Haudenschield, et al *Arch. Biochem. Biophys.* 379, 127-136 (2000)) (SEQ ID NO 5 and 6).

CYP71AV8-P20: this construct encodes for the same protein as the previous one but the membrane anchor region was further codon optimize (SEQ ID NO 7 and 8).

The FIG. 1 compares the amino acid sequences of the N-terminal regions of the different CYP71AV8 variants and FIG. 2 compares the DNA sequences of the 3 constructs. The three optimized CYP71AV8 cDNAs were synthesized in-vitro (DNA2.0, Menlo Park, Calif., USA) and cloned as NdeI-HindIII fragment into the pCWori+ expression plasmid (Barnes, H. J. *Method Enzymol.* 272, 3-14; (1996)).

Example 2

Functional Expression of CYP71AV8 in Bacterial Cells

For heterologous expression, the JM109 *E. coli* cells were transformed with the CYP71AV8 expression plasmids (example 1). Single colonies of transformants were used to inoculated cultures of 5 mL LB medium containing 50 μg/mL ampicillin. The cells are grown for 10 to 12 hours at 37° C. The cultures were then used to inoculate 250 mL TB Medium (Terrific Broth) supplemented with 50 μg/mL ampicillin and 1 mM Thiamine HCL. The cultures were incubated at 28° C. for 3-4 h with moderate shaking (200 rpm) before 75 mg/L δ-aminolevulinic acid (sigma) and 1 mM IPTG (Isopropyl β-D-1-thiogalactopyranoside) was added, and the cultures were maintained at 28° C. for 24-48 h with 200 rpm shaking.

The expression of the P450 enzymes can be evaluated qualitatively and quantitatively by measuring the CO-binding spectrum (Omura, T. & Sato, R. (1964) *J. Biol. Chem.* 239, 2379-2387) in the *E. coli* protein fractions. For protein extraction, the cells are centrifuged (10 min, 5000 g, 4° C.) and resuspended in 35 mL ice-cold buffer 1 (100 mM Tris-HCl pH 7.5, 20% glycerol, 0.5 mM EDTA). One volume of 0.3 mg/ml lysozyme (Sigma-Aldrich) in water was added and the suspension left 10-15 min at 4° C. with agitation. The suspension is centrifuged 10 min at 7000 g and 4° C. and the pellet is resuspended in 20 mL buffer 2 (25 mM $KPO_4$ pH 7.4, 0.1 mM EDTA, 0.1 mM DTT, 20% glycerol). The suspension is subject to one cycle of freeze-thaw at −80° C., 0.5 mM PMSF (phenylmethylsulfonyl fluoride, Sigma-Aldrich) is added and the suspension is sonicated 3 times for 20 sec. The suspension is centrifuged 10 min at 10000 g (to remove cell debris) and the supernatant is recovered and centrifuged 2 hours at 100,000 g. The pellet (membrane protein fraction) is resuspended in 2-3 ml of buffer 3 (50 mM Tris-HCl pH 7.4, 1 mM EDTA, 20% glycerol). To measure the CO-spectrum, the protein fraction is diluted (1/10) in buffer 3 to a final volume of 2 mL. Some crystals of sodium dithionite ($Na_2S_2O_4$) are added, the sample is divided into two cuvettes and the baseline recorded between 370 and 500 nm. The sample cuvette is then saturated with carbon monoxide and the difference spectrum is recorded. The concentration of P450 enzyme can be estimated from the amplitude of the peak at 450 nm using the extension coefficient for the reduced CO complex of 91 $mM^{-1}\cdot cm^{-1}$ (Omura, T. & Sato, R. (1964) *J. Biol. Chem.* 239, 2379-2387).

Following this procedure, typical CO-spectra with a maximum absorbance at 450 nm were measured for the recombinant CYP71AV8, attesting for a proper folding into functional P450 enzymes.

Example 3

Co-Expression of CYP71AV8 and a P450-Reductase in Bacteria

To reconstitute the activity of plant P450s, the presence of a second membrane protein is essential. This protein, the P450-reductase (CPR), is involved in the transfer of electrons from the cofactor NADPH (reduced Nicotinamide adenine dinucleotide phosphate) to the P450 active site. It has been shown that a CPR from one plant can complement the activity of P450 enzyme from another plant (Jensen and Moller (2010) *Phytochemsitry* 71, 132-141). Several CPR-encoding DNA sequences have been reported from different plant sources. We first selected a CPR previously isolated from *Mentha piperita* (CPRm, unpublished data, SEQ ID NO 10), optimized the codon usage of the full-length cDNA (SEQ ID No 9) and cloned it into the NcoI and HindIII restriction sites of the pACYCDuet-1 expression plasmid (Novagen) providing the plasmid pACYC-CPRm.

CYP71AV8 and CPRm were co-expressed in *E. Coli* cells using the two plasmids pCWori-CYP71AV8-65188 and pACYCDuet-CPRm. BL21 Star™ (DE3) *E. coli* cells (Invitrogen, Carlsbad, Calif.) were co-transformed with these two plasmids. Transformed cells were selected on carbenicillin (50 μg/ml) and chloramphenicol (34 μg/ml) LB-agarose plates. Single colonies were used to inoculate 5 mL liquid LB medium supplemented with the same antibiotics. The culture was incubated overnight at 37° C. The next day, 2 to 250 mL of TB medium supplemented with the same antibiotics were inoculated with 0.2 to 2 mL of the overnight culture. After 6 hours incubation at 37° C., the culture was cooled down to 28° C. and 1 mM IPTG and 75 mg/L δ-aminolevulinic acid were added. After 16 to 24 hours, the cells were harvested in exponential growing phase, centrifuged and resuspended in 0.5 volume of potassium phosphate buffer 50 mM pH 7.0 supplemented with 5% glycerol or 3% glucose. These cells were used for evaluation of the enzymatic activities of the P450 enzymes.

Example 4

Bioconversion of (+)-α-santalene, (−)-β-santalene, (−)-α-trans-bergamotene and (+)-epi-β-santalene Using *E coli* Cells Expressing CYP71AV8

The different sequiterpene hydrocarbons used as substrates in the bioconversion assays were prepared as described previously using *E. coli* cells engineered to produced farnesyl diphosphate (FPP) from an heterologous mevalonate pathway and expressing a plant derived sesquiterpene synthase. The engineering and use of the *E. coli* host cells was described in patent WO2013064411 or in Schalk et al (2013) *J. Am. Chem. Soc.* 134, 18900-18903. Briefly, an expression plasmid was prepared containing two operons composed of the genes encoding the enzymes for a complete mevalonate pathway. A first synthetic operon consisting of an *E. coli* acetoacetyl-CoA thiolase (atoB), a *Staphylococcus aureus* HMG-CoA synthase (mvaS), a *Staphylococcus aureus* HMG-CoA reductase (mvaA) and a *Saccharomyces cerevisiae* FPP synthase (ERG20) genes was synthetized in-vitro (DNA2.0, Menlo Park, Calif., USA) and ligated into the NcoI-BamHI digested pACYCDuet-1 vector (Invitrogen) yielding pACYC-29258. A second operon containing a mevalonate kinase (MvaK1), a phosphomevalonate kinase (MvaK2), a mevalonate diphosphate decarboxylase (MvaD), and an isopentenyl diphosphate isomerase (idi) was amplified from genomic DNA of *Streptococcus pneumoniae* (ATCC BAA-334) and ligated into the second multicloning site of pACYC-29258 providing the plasmid pACYC-29258-4506. This plasmid thus contains the genes encoding all enzymes of the biosynthetic pathway leading from acetyl-coenzyme A to FPP. *E. coli* cells (BL21 Star™ (DE3), Invitrogen) were co-transformed with the plasmid pACYC-29258-4506 and either the plasmid pET101-Cont2_1 (containing a cDNA encoding for the *Clausena lansium* (+)-α-santalene synthase (CLASS), WO2009109597) or the plasmid pETDuet-SCH10-Tps8201-opt (containing a cDNA encoding for a *Santalum album* (+)-α-santalene/(−)-β-santalene synthase (SaSAS), WO2010067309) and this cells were used to produce and purify (+)-α-santalene or a mixture of (+)-α-santalene, (−)-β-santalene, (−)-α-trans-bergamotene and (+)-epi-β-santalene.

The enzymatic activity of CYP71AV8 was evaluated by bioconversion in *E. coli* cells using the sesquiterpene molecules listed above as substrates. BL21 Star™ (DE3) *E. coli* cells (Invitrogen) transformed with the plasmids pACYC-Duet-CPRm and pCWori-CYP71AV8-65188 were cultivated and harvested as described in example 3. The substrates (sesquiterpene hydrocarbons) were added to the cell suspension to a final concentration of 0.5 mg/ml as mixture composed of 10 mg Tween® 20 (sigma-Aldrich), 10 mg antifoam (Erol D F, PMC Ouvrie, Lesquin, France), 20 mg sesquiterpene and 1 ml water. The conversion was allowed to proceed for 24 hours at 20° C. with moderate shaking. The media were extracted with 2 volumes of MTBE (Methyl tert-buthyl ether, Sigma) and the extracts were analyzed by GCMS on an Agilent 6890 Series GC system connected to an Agilent 5975 mass detector. The GC was equipped with 0.25 mm inner diameter by 30 m SPB-1 capillary column (Supelco, Bellefonte, Pa.). The carrier gas was He at a constant flow of 1 mL/min. The initial oven temperature was 80° C. (1 min hold) followed by a gradient of 10° C./min to 300° C. The identification of the products was based on the comparison of the mass spectra and retention indices with authentic standards and internal databases.

In these conditions, oxidation of (+)-α-santalene was observed. The primary product of the conversion was (E)-α-santalol. Other products derived from the conversion of (E)-α-santalol by *E. Coli* endogenous enzymes were detected: (E)-α-santalal (produced by an alcohol dehydrogenase) and (E)-α-dihydrosantalol (produced by an enoate reductase) (FIG. 3A). Similarly, using a mixture of (+)-α-santalene, (−)-β-santalene, (−)-α-trans-bergamotene and (+)-epi-β-santalene as substrate the formation of (E)-α-santalol, (E)-β-santalol, (E)-α-trans-bergamotol and (E)-epi- β-santalol was observed as well as further metabolized products were obtained (FIG. 3B). This example shows that CYP71AV8 can be used for the terminal oxidation of (+)-α-santalene, (−)-β-santalene, and structurally similar molecules.

Example 5

Construction of Synthetic Operons to Co-Express CYP71AV8 and a CPR from a Single Plasmid Several bicistronic operons were designed to express the P450 enzyme and a CPR from a single plasmid and under the control of a unique promoter. The three variants of optimized CYP71AV8 cDNAs (example 1) were combined with 2 CPR cDNAs: the codon optimized CPRm cDNA (example 2) and a codon optimized cDNA (Seq ID No 11) encoding for an *Artemisia annua* CPR (NCBI accession No. ABM88789.1, SEQ ID No 12). Thus, six constructs were designed (Seq ID No 13-18), each containing a P450 cDNA followed by a linker sequence including a ribosome binding site (RBS) and a CPR cDNA (FIG. 4). This constructs were prepared by PCR: the P450 and CPR cDNAs were amplified separately and with 5' and 3' overhangs suitable for the cloning using the In-Fusion® procedure (Clontech) in the NdeI-HindIII sites of the pCWori+ plasmid.

To evaluate the effect of the different N-terminal modification made on the P450s and the coupling with the CPRs, the 6 plasmids were transferred into *E. Coli* BL21 Star™ (DE3) cells and the recombinant cells were used in bioconversion assays as described in example 4. The (+)-α-santalene and the (+)-α-santalene, (−)-β-santalene, (−)-α-trans-bergamotene and (+)-epi-β-santalene mixture were used as substrates and quantities of total oxygenated sesquiterpene products were evaluated. The results presented in FIG. 5 show that all recombinant bacterial cells transformed with one of the 6 plasmids described above can be used for the oxidation of (+)-α-santalene, (−)-β-santalene and the structurally similar molecules. The highest titer was obtained with the operon combining the CYP71AV8-P2O cDNA and the CPRm cDNA. This construct (plasmid pCWori-CYP71AV8-P2O-CPRm) was used for further experiments.

Example 6

In-Vivo Production of Oxygenated Sesquiterpenes in Engineered Cells

The oxidized products of (+)-α-santalene and the (+)-α-santalene, (−)-β-santalene, (−)-α-trans-bergamotene, (+)-epi-β-santalene or other structurally similar molecules can also be produced directly in *E. Coli* cells engineered to produce sesquiterpenes from a carbon source such as glucose or glycerol. Plasmids were prepared consisting of the pCWori+ plasmid (Barnes H. J (1996) *Method Enzymol.* 272, 3-14) containing a synthetic operon composed of a P450, a CPR and the terpene synthase. For the P450, the CYP71AV8-P2 or CYP71AV8-P2O cDNA was used and for the terpene synthase, the *Clausena lansium* (+)-α-santalene synthase cDNA (ClASS) (WO2009109597) or a cDNA encoding for a *Santalum album* (+)-α-santalene/(−)-β-santalene synthase (SaSAS) (WO2010067309) was used. Four plasmids were thus constructed using the following procedure. A codon optimized version of the ClASS cDNA (SEQ ID NO 19-20) was designed and synthesized (DNA 2.0) and cloned in the NdeI-KpnI sites of the pETDUET-1 plasmid (Novagen) providing the plasmid pETDuet-Tps2opt. For SaSAS an optimized full-length cDNA was designed (SEQ ID NO 21-22), synthesized and cloned in the pJexpress414 plasmid (DNA2.0) providing the plasmid pJ414-SaTps8201-1-FLopt. For each constructs primer were designed for cloning using the In-Fusion® technique (Clontech, Takara Bio Europe). The optimized ClASS cDNA and the optimized SaSAS cDNA were amplified using these primers and the pETDuet-Tps2opt and pJ414-SaTps8201-1-FLopt plasmids as template, respectively. The two PCR products were ligated in the plasmids pCWori-CYP71AV8-P2-CPRm or pCWori-CYP71AV8-P20-CPRm digested with the HindIII restriction enzyme and using the In-Fusion® Dry-Down PCR Cloning Kit (Clontech, Takara Bio Europe), providing four new plasmids: pCWori-CYP71AV8-P2-CPRm-ClASS, pCWori-CYP71AV8-P2-CPRm-SaSAS, pCWori-CYP71AV8-P20-CPRm-ClASS, and pCWori-CYP71AV8-P2O-CPRm-SaSAS (SEQ ID NO 23-26).

The evaluation of the performance of these operons was performed in the *E. coli* BL21 Star™ (DE3) (Invitrogen) cells co-transformed with either of the 4 plasmids and with the plasmid pACYC-29258-4506 carrying a complete mevalonate pathway (example 4). Transformed cells were selected on carbenicillin (50 μg/ml) and chloramphenicol (34 μg/ml) LB-agarose plates. Single colonies were used to inoculate 5 mL of LB medium supplemented with appropriate antibiotics. Cultures were incubated overnight at 37° C. and 250 rpm. The next day 2 mL of TB medium in glass culture tubes containing 100 μg/L carbenicilin and 17 μg/L chloramphenicol, were inoculated with 200 μl of the LB pre-culture and incubated at 37° C. and 250 rpm. After 6 hours of cultivation (or when the optical density at 600 nm of the culture reach a value of 3), the culture were cooled down to 20° C. and the expression of the proteins was induced with 0.1 mM IPTG (Isopropyl β-D-1-thiogalactopyranoside), and 75 μg/L δ-aminolevulinic acid (sigma) and 2% (v/v) of decane were added. After 48 h incubation with 250 rpm shaking, the whole culture broth was extracted with 1 volume of MTBE and analyzed by GCMS as described in example 4.

All resulting strains produced the sesquiterpene hydrocarbons as well as the corresponding oxygenated products also observed in the bioconversion experiments (FIG. 6). This experiment shows that using engineered cells expressing CYP71AV8, the sesquiterpenes (E)-α-santalol, (E)-β-santalol and other structurally similar molecules can be produced.

Example 7

Production of (E)-α-santalol and (E)-β-santalol Using CYP71AV8 Variants

In previous examples we showed that CYP71AV8 is highly selective for the 'terminal trans carbon' of (+)-α-santalene and (−)-β-santalene and produced exclusively (E)-α-santalol, (E)-β-santalol. In this example, we describe a site directed mutagenesis approach to modify the CYP71AV8 enzyme activity in order to produce (Z)-α-santalol and (Z)-β-santalol. L358 was first selected as an active site residue controlling the enzyme activity. A series of variant of CYP71AV8 were generated by replacing the codon encoding for L358 by codons encoding for other amino acids. The mutation was introduced in a two-step PCR procedure using a combination of degenerated oligonucleotide (containing the NBT (N=A,C,G,T; B=C,G,T) codon in place of L358 encoding codon) and specific oligonucleotides. This combination of oligonucleotides allow to change the L358 encoding codon with codons encoding for 12 other residues including all the amino acids with a hydrophobic side chain. A first PCR was performed to amplify the 5' portion of the cDNA using the mutagenesis reverse primer AV8-L358-rev (5'-CACGCGGCATCACCA-GCGGAVNCGGCGGATGCAGGCGCAGGGTTTCTT-TAAT C-3') (SEQ ID NO: 93) and the primer AV8-pcw-fw (5'-CATCGATGCTTAGGAGGTCATATGGCTCTGTT-ATTAGCAG-3') (SEQ ID NO: 94). A second PCR product was amplified using the primer AV8-L358-fw (5'-TC-CGCTGGTGATGCCGCGTGAGTGC-3') (SEQ ID NO: 95) and AV8-CPR-rev (5'-ATATATCTCCTTCTTAAAGT-TAGTCGACTCATTAGGTG-3') (SEQ ID NO: 96). For both amplifications the pCWori-CYP71AV8-P2-CPRm-ClASS was use for the template. A second round of amplification was performed using the two above PCR products as template and the primers AV8-L358-fw+AV8-CPR-rev and allowed to amplify the full-length CYP71AV8 variant cDNAs. All the PCR reactions were performed using the PfuUltra II fusion HS DNA polymerase (Stratagene) following the manufacturer instruction. The modified cDNA were ligated into the NdeI-SalI digested pCWori-CYP71AV8-P2-CPRm-ClASS using the Gibson Assembly Master Mix (New England Biolabs). The final constructions were controlled by sequencing and one plasmid clone was selected for each desired CYP71AV8 variant. Twelve variants were thus generated by replacing Leu358 by Ala, Phe, Thr, Ser, Val, Gly, Ile, Met, Pro, Tyr, Trp, and Arg (SEQ ID NO 27 to 50).

The evaluation of each CYP71AV8 variant was performed using the in-vivo sesquiterpene production method described in example 6. Briefly, the pCWori+ plasmid containing one of the CYP71AV8 variant cDNA, the CPRm cDNA and the ClASS cDNA was co-transformed with the pACYC-29258 plasmid into KRX *E. Coli* cells (Promega). The transformed cells were selected, cultivated and the production of sesquiterpenes was evaluated as described in example 6. As shown in FIG. 7, compared to the wild type P450 enzyme, with some of the variants (Z)-α-santalol was produced in addition to the trans oxidation products. For each variant, the ratio of cis to trans oxidation was calculated by dividing the total amount of (Z)-α-santalol produced by the total amount of oxygenated α-santalene derivatives. The results of these calculations for each variants is presented in Table 1 below:

TABLE 1

Regio-selectivity of the CYP71AV8 wild-type enzyme and active site variants for the oxidation of α-santalene.

| CYp71AV8 variants | Titer [mg/L] sesquiterpenes | Titer [mg/L] Oxygenated products | % (Z)-α-santalol of total santalol content |
|---|---|---|---|
| CYP71AV8 wt | 97.7 ± 2.8 | 78.1 ± 3.5 | 0% |
| L358A | 28 ± 1.5 | 40.3 ± 2.8 | 36% |
| L358F | 88.4 ± 3.9 | 40.7 ± 0.4 | 46% |
| L358T | 90.9 ± 5.6 | 33.8 ± 1.5 | 5% |
| L358S | 43.4 ± 1.8 | 15.3 ± 0.8 | 17% |
| L358V | 56.1 ± 3.5 | 66.1 ± 1.1 | 1% |
| L358G | 84.3 ± 2.8 | 85 ± 2.2 | 0% |
| L358I | 71.2 ± 3.7 | 41 ± 0.3 | 0% |
| L358M | 84 ± 4.5 | 2.3 ± 0.3 | 0% |
| L358P | 71.6 ± 2.0 | 21 ± 1.1 | 0% |
| L358Y | 71.6 ± 2.9 | 0 ± 0 | 0% |
| L358W | 78.2 ± 0.6 | 0 ± 0 | 0% |
| L358R | 76 ± 1.1 | 2.3 ± 0.3 | 0% |

The data presented in Table 1 above show that CYP71AV8 can be engineered and used to produce the (Z)-α-santalol. Particularly, the L358T, L358S, L358A and L358F variants can be used for the terminal oxidation of (+)-α-santalene with a selectivity up to 46% for the cis terminal carbon.

In a similar approach the variants of CYP71AV8 were evaluated for the production of (Z)-β-santalol. New plasmids were prepared by replacing the ClASS cDNA in the above plasmid by the SaSAS cDNA. Thus the plasmid pCW-CYP71AV8-L358F-CPRm-ClASS was digested with the restriction enzymes HindIII and EcoRI to remove the ClASS cDNA. In parallel, the pCWori-CYP71AV8-P2-CPRm-SaSAS was digested with the same enzymes to recover the SaSAS cDNA with the compatible cohesive ends. The linearized vector and the digested insert were ligated using the T4 DNA ligase (New England Biolabs). The plasmid thus obtained was used for in-vivo production of oxygenated sesquiterpenes in *E. coli* cells in the same condition as described above. The FIG. 8 present the GCMS profile of the analysis of the products formed by CYP71AV8-L358F and shows that modified CYP71AV8 enzymes can also be used to produce (Z)-β-santalol.

Example 8

Evaluation of Other Members of CYP71AV Family

CYP71AV1 (NCBI accession No ABB82944.1) was evaluated for the oxidation of sesquiterpenes with the santalene skeleton. A plasmid was prepared with a configuration similar to the plasmids described in example 5: a bi-cistronic operon containing an optimized cDNA encoding for an N-terminal modified CYP71AV1 protein (SEQ ID NO 53 and 54) and the aaCPR cDNA (example 5) was designed, synthesized in-vitro (DNA2.0) and cloned as a bi-cistronic operon into the pCWori+ plasmid. The plasmid was used to transform KRX *E. Coli* cells (Promega). The transformed cells were cultivated and protein expression was induced as described in example 3. A bioconversion experiment using (+)-α-santalene as substrate was conducted as described in example 4. As shown in FIG. 9 the same products as with CYP71AV8 were obtained (i.e. (E)-α-santalol and (E)-α-santalal) showing that other members of the CYP71AV P450 family can be use for the terminal oxidation of santalenes.

Using CYP71AV1, a synthetic operon containing the CYP71AV1 cDNA, the aaCPR and the (+)-α-santalene synthase cDNA (ClASS) was prepared. The pCWori+ plasmid containing the CYP71AV8-P2-CPRm-ClASS operon (example 6) was digested with NdeI and HindIII to cut out the P450 encoding cDNA. In parallel, the CYP71AV1 cDNA was recovered from the bi-cistronic operon described in the previous paragraph by digestion with the same enzymes and ligated, using the T4 DNA ligase (New England Biolabs), into the digested pCWori plasmid described above yielding the plasmid pCWori-CYP71AV1-CPRm-ClASS. This plasmid together with the plasmid pACYC-29258-4506 were used to co-transform *E coli* BL21 Star™ (DE3) (Invitrogen) cells. The recombinant cells were cultivated in conditions allowing the production of sesquiterpene molecules as described in example 6. The GCMS analysis of the sesquiterpene produced revealed the formation of the same product as in the bio-conversion experiments. This experiment shows that CYP71AV1 can also be used oxidize santalene molecules and to produce santalols (FIG. 9).

Example 9

Construction of a P450-BM3 (CYP102A1) Mutant Library

A P450-BM3 mutant library of 24 variants was constructed by systematically combining five hydrophobic amino-acids (alanine, valine, phenylalanine, leucine and isoleucine) in two positions located close to the centre of the heme group of P450-BM3. Altering the side chain size of these two amino acids has been shown to drastically change the shape of the substrate binding cavity in close proximity of the heme group (*Appl Microbiol Biotechnol* 2006, 70:53; *Adv Synth Catal* 2006, 348:763). The first hot spot (Phe 87) is known to alter substrate specificity and regioselectivity while the second position (Ala 328) has been predicted to interact with all substrates during oxidation (*ChemBiochem* 2009, 10:853). The P450-BM3 variants were either generated using the QuickChange™ site-directed mutagenesis kit (Invitrogen, Carlsbad, Calif.) or were chemically synthetized by DNA2.0 (Menlo Park, Calif.). The P450-BM3 variants and wild-type were subcloned into the bacteria expression plasmids pET22b, pET28+, pETDuet-1 and pCDFDuet-1 (Novagen, Madison, Wis.) and were transformed in *Escherichia coli* BL21(DE3) or BL21Star™ (DE3) (Invitrogen, Carlsbad, Calif.).

Example 10

Alpha-Santalene: In Vitro Screening of the P450-BM3 Library

The 24 P450-BM3 mutants and the wild-type version of the enzyme were heterologously expressed in *E. coli* BL21 (DE3) cells as reported previously (*Adv. Synth. Catal.* 2003, 345:802). In brief, a single colony of transformed cells was used to inoculate 2 ml of Luria-Bertani (LB) medium supplemented with 30 μg/ml kanamycin and grown at 37° C. with orbital shaking (150 rpm) until $OD_{578}$ reaches a value of 0.6 to 1.0. This pre-culture was used to inoculate 200 ml of LB medium containing 30 μg/ml kanamycin. The cells were grown at 37° C. with orbital shaking at 160 rpm to an $OD_{578}$ of 0.8. Expression of the protein was then induced by the addition of 0.35 mM isopropyl β-D-1-thiogalactopyranoside (IPTG). After 6 hours of growth at 30° C. under agitation, the cells were harvested by centrifugation and lysed by sonication.

The alpha-santalene used as substrate in the bioconversion assays was prepared as described in Example 4. The conversions were carried out in 1 ml of 50 mM potassium phosphate buffer containing ~0.5 μM CYP enzyme, 2% (v/v) DMSO, and 0.2 mM μ-santalene substrate. Reaction was started by adding 0.1 mM NADPH and was carried out for 22 h at room temperature with moderate shaking.

Samples were then analyzed on a GC/MS QP-2010 instrument (Shimadzu, Japan) equipped with a FS-Supreme-5 column (30 m×0.25 mm×0.25 μm), helium as carrier gas (flow rate: 0.68 ml/min; linear velocity: 30 cm/s). Mass spectra were collected using electrospray ionization. The injector temperature was set at 250° C. The column oven was set at 50° C. for 1 min, then raised to 170° C. at 30° C./min, then raised to 185° C. at 5° C./min, held isotherm for 3 min, then raised to 200° C. at 5° C./min, then raised to 300° C. at 30° C./min, and finally held isotherm for 1 min.

Example 11

Alpha-Santalene In Vivo Screening of the P450-BM3 Library

The P450-BM3 mutant library was also screened in vivo using a bacteria strain engineered to produce (+)-α-santalene from a simple carbon source. To this end, the FPP-overproducing strain described in Example 4 was transformed with a pETDuet-1 plasmid containing a codon-optimized version of a (+)-α-santalene synthase from *Clausena lansium* (CLASS) (WO2009109597) (SEQ ID No 19 and 20) and each of the P450-BM3 variants cloned into the first and second multiple cloning sites (MCS) of the vector, respectively. Alternatively, the (+)-α-santalene synthase cDNA was cloned into the pET101expression plasmid (Novagen) and each of the P450-BM3 mutants from the library into the pCDFDuet-1 vector (Novagen). The resulting recombinant vectors were co-transformed in the FPP-overproducing strain.

Single colonies of transformed cells were used to inoculate 5 mL of LB medium supplemented with the appropriate antibiotics. Cultures were then incubated overnight at 37° C. and 250 rpm. The following day, 2 mL of Terrific Broth (TB) medium supplemented with 3% glycerol, 1 mM thiamine-HCl (Sigma-Aldrich, St Louis, Mich.) and 75 μg/L δ-aminolevulinic acid (Sigma-Aldrich) were inoculated with 200 μl of the overnight culture and incubated at 37° C. and 250 rpm. After 4 to 6 hours of cultivation (or when the optical density at 600 nm of the culture reach a value of 2 to 3), the cultures were cooled down to 28° C. and the protein expression was induced with 0.1 mM IPTG. At that time, 10% (v/v) of dodecane were added to the growth media. After 48 h incubation with orbital shaking (250 rpm), the cell culture was extracted twice with one volume of methyl tert-butyl ether (MTBE) and the solvent extract analyzed by GC/MS. GC/MS was performed on an Agilent 6890 series GC system equipped with a DB1 column (30 m×0.25 mm×0.25 mm film thickness; Agilent) and coupled with a 5975 series mass spectrometer. The carrier gas was helium at a constant flow of 1 ml/min. Injection was in split-less mode with the injector temperature set at 250° C. and the oven temperature was programmed from 50° C. to 225° C. at 10° C./min and to 320° C. at 20° C./min. The identities of the products were confirmed based on the concordance of the retention indices and mass spectra of authentic standards.

The in vitro (Example 10) and in vivo screening of the P450-BM3 mutant library gave comparable results that are summarized in Table 2. While P450-BM3 wild-type (SEQ ID No 55 and 56) did not show any detectable activity on (+)-α-santalene, 6 P450-BM3 variants were able to convert α-santalene to the desired α-santalol(s). These variants revealed between 45% to 96% preference for oxidation of the cis-terminal carbon of (+)-α-santalene. The single mutant #23 (A328V) (SEQ ID No 67 and 68) and the double mutants #7 (F87I/A328I) (SEQ ID No 57 and 58), #17 (F87V/A328I) (SEQ ID No 59 and 60) and #18 (F87V/A328L) (SEQ ID No 61 and 62) showed the highest regioselectivity ranging from 72% to 96% (Table 2 and FIG. 10). Two additional variants #19 (F87V/A328V) (SEQ ID No 63 and 64) and #20 (F87V/A328F) (SEQ ID No 65 and 66) were less selective for the cis-hydroxylation (in the range of 45%-50%) and generated additional oxidation products.

TABLE 2

Alpha-santalene conversion to alpha-santalol(s) by P450-BM3 variants

| P450-BM3 | | cis-α-santalol (%) | trans-α-santalol (%) | Additional oxydation products (%) | Conversion (%) |
|---|---|---|---|---|---|
| Wild-type | F87/A328 | | | | |
| Variant #7 | F87 I/A328 I | 87 | | 13 | 6 |
| Variant #17 | F87 V/A328 I | 78 | 11 | 11 | 16 |
| Variant #18 | F87 V/A328 L | 72 | 13 | 15 | 9 |
| Variant #19 | F87 V/A328 V | 45.5 | 4 | 50.5 | 8 |
| Variant #20 | F87 V/A328 F | 49 | 8 | 43 | 3 |
| Variant #23 | F87/A328 V | 96 | | 4 | 5 |

These results indicate that P450-BM3 active site mutations enable binding of the non-native substrate (+)-α-santalene. Selected P450-BM3 variants incorporating these mutations were shown to selectively hydroxylate the cis-terminal carbon of (+)-α-santalene to generate the olfactively important compound (Z)-α-santalol (FIG. 10).

Example 12

In Vivo Production of (Z)-α-santalol, (Z)-β-santalol, (Z)-α-trans-bergamotol and (Z)-epi-β-santalol Using a P450-BM3 Double Mutant One of the P450-BM3 variants identified in the α-santalene screen (variant #17; Table 2) was tested for its ability to oxidize a sandalwood oil-like mixture of sesquiterpene hydrocarbons consisting of (+)-α-santalene, (−)-β-santalene, (−)-α-trans-bergamotene and (+)-epi-β-santalene. To this end, the FPP-overproducing bacteria strain described in Example 4 was transformed with a recombinant pETDuet-1 expression vector containing a codon-optimized cDNA encoding for a *Santalum album* (+)-α-santalene/(−)-β-santalene synthase (WO2010067309) (SEQ ID No 21 and 22) into the first MCS and the P450-BM3 variant #17 in the second MCS. Cell growth, induction conditions, culture extraction and product analysis were performed essentially as described in Example 11.

As shown in FIG. 11, (+)-α-santalene, (−)-β-santalene, (−)-α-trans-bergamotene and (+)-epi-β-santalene were efficiently oxidized by the P450-BM3 double-mutant to yield (Z)-α-santalol, (Z)-β-santalol, (Z)-α-trans-bergamotol and (Z)-epi-β-santalol. Remarkably, only the desired cis-isomers of the sesquiterpene alcohols were detected under these experimental conditions. These data show that the *Bacillus megaterium* CYP102A1 (P450-BM3) can be efficiently engineer to selectively hydroxylate the cis-terminal carbon of (+)-α-santalene, (−)-β-santalene and structurally related terpenes such as bergamotane sesquiterpenes and to generate the key sesquiterpene alcohols found in Sandalwood oil.

Example 13

Isolation of a cDNA Encoding for SaCP816, a Cytochrome P450 from *Santalum Album*

The seeds of *S. album* were obtained from B&T World Seeds (Aigues-Vives, France) and from Sandeman Seeds (Lalongue, France). The seeds were first surface sterilised in 2.5% Hypochlorous acid (HClO) for 120 min, and rinsed 3 times in sterile ultrapure water. The seeds were then shelled and placed on MS basal medium (Murashige & Skoog, 1962, *Physiologia Plantarum* 15, 473-497) supplemented with 15 g/L sucrose and 7.8 g/L agar, pH 5.7. Germination was typically observed after 9 to 18 days with a yield of approximately 40%. Seedlings of *Santalum* album obtained from the aseptically germinated seeds were transferred to soil 5 to 10 weeks after germination. Since *santalum* species are root hemiparasites, the soil adaptation was made in close contact with 6-months to 1-year old citrus (*Citrus sinensis*) plants. The roots of the *santalum* plants were harvested, 2-3 years after the transfer to the soils and separated from the host plant roots. GC-MS analysis of an extract of these roots showed the presence of the sandalwood oil characteristic sesquiterpenes. Total RNA was extracted from the roots using the Concert Plant RNA Reagent (Invitrogen). From 12 grams of tissue, 640 micrograms of total RNA were isolated.

The whole transcriptome was sequenced using the Illumina Total RNA-Seq technique and the Illumina HiSeq 2000 sequencer. A total of 108.7 millions of paired-reads of 2100 bp were generated. The reads were assembled using the De Novo Assembly application of CLC-Bio Genomic Workbench (CLCBo, Denmark). A total 82,479 of contigs with an average size of 683 bp were assembled. The contigs were search using the tBlastn algorithm (Altschul et al, J. Mol. Biol. 215, 403-410, 1990) and using as query sequence known P450 amino acid sequences such as the sequence of CYP71AV1 (NCBI accession No ABB82944.1). This approach allowed identifying several contigs encoding for proteins with characteristic cytochrome P450 motifs. One selected contig, SCH37-Ct816 (SED ID NO 69), contained a 1503 bp length open reading frame (ORF) (SEQ ID NO 70) encoding for a 500 amino acid protein, SaCP816 (SEQ ID NO 71). This amino acid showed homology with know cytochrome P450 sequences the closest sequence being a P450 from *Vitis vinifera*, CYP71D10 (NCBI accession No AAB94588.1) sharing 62% amino acid sequence identity.

Example 14

Heterologous Expression of SaCP816 in Bacterial Cells

For functional characterization of the protein encoded by SCH37-Ct816, the protein was heterologously expressed in *E. coli* cells. The ORF sequence was modified to for improved expression in *E. Coli*: the first 17 codons were replaced by the codons encoding for the MALLLAVFWSALIILV peptide (first 17 amino acids of SEQ ID NO: 73) and the codon usage of the whole ORF sequence was modified to match the *E. coli* codon usage. This cDNA (SaCP120293 (SEQ ID NO: 72) encoding for the modified SaCP816 (SEQ ID NO: 73) was synthesized in-vitro (DNA2.0) and cloned in the pJExpress404 plasmid (DNA2.0). The heterologous expression was performed as described in example 2.

Example 15

Co-Expression of SaCP816 and a P450-Reductase in Bacteria

A bicistronic operons was designed to express the P450 enzyme and a CPR from a single plasmid and under the control of a unique promoter. The optimized SaCP120293 cDNA was combined with the CPRm cDNA (SEQ ID No 9, Example 3) to prepare a bicistronic construct (SEQ ID NO 74) containing successively the P450 cDNA a linker sequence including a ribosome binding site (RBS) and the CPRm cDNA. This construct was prepared by PCR by amplifying the P450 and CPR cDNAs separately and with 5' and 3' overhangs suitable for the cloning using the In-Fusion® procedure (Clotech) in the NdeI-HindIII sites of the pCWori+ plasmid (Barnes H. J (1996) *Method Enzymol.* 272, 3-14) providing the plasmid SaCP816-CPRm-pCWori (SEQ ID NO 74).

The JM109 *E. coli* cells were transformed with the SaCP816-CPRm-pCWori expression plasmid. The transformed cells were grown and the cell-free extract containing the recombinant proteins were prepared as described in example 2. This protein fraction was used for the evaluation the enzymatique conversion of sesquiterpene molecules (example 16).

Example 16

In-Vitro Conversion of (+)-α-santalene, (−)-β-santalene, (−)-α-trans-bergamotene and (+)-epi-β-santalene Using the Recombinant SaCP816 P450 Enzyme The different sequiterpene hydrocarbons used as substrates in the bioconversion assays were prepared as described in example 4.

The crude protein extract from *E. coli* cells expressing the recombinant SaCP816 and CPRm proteins (example 15) was used for the in-vitro oxidation of these sesquiterpene molecules. The assays were performed in 1 mL of 100 mM Tris-HCL pH 7.4 buffer containing 20 to 50 microL protein extract, 500 microM NADPH (reduced Nicotinamide adenine dinucleotide phosphate), 5 microM FAD (Flavine adenine dinucleotide), 5 microM FMN (flavine mononucleotide), and 300 microM of sesquiterpenes (either (α)-santalene or a mixture of (+)-α-santalene, (−)-β-santalene, (−)-α-trans-bergamotene and (+)-epi-β-santalene). After 2 hours of incubation in Teflon sealed glass tubes with gentle agitation, the reaction was stopped on ice and extraction with 1 volume of MTBE (Methyl tert-buthyl ether, Sigma). The extracts were analyzed by GCMS as described in example 4.

In these conditions, oxidation of (+)-α-santalene, (−)-β-santalene, (−)-α-trans-bergamotene and (+)-epi-β-santalene was observed. FIG. 12 shows that the oxidation of (+)-α-santalene by SaCP816 provides (Z)-α-santalol. FIG. 13 shows that (+)-α-santalene, (−)-β-santalene, (−)-α-trans-bergamotene and (+)-epi-β-santalene were oxidized by SaCP816 to forme (Z)-α-santalol, (Z)-β-santalol, (Z)-α-trans-bergamotol and (Z)-epi-β-santalol. In all assays, no detectable amounts of the corresponding trans-isomers of the sesquiterpene alcohols was observed (the trans and cis isomers of each sesquiterpene alcohol are easily separated in the chromatographic conditions used in these assays).

This experiments show that the cytochrome P450 enzymes, SaCP816, isolated from *Santalum album* can be used for the selective hydroxylates the cis-terminal carbon of (+)-α-santalene, (−)-β-santalene and similar sesquiterpene structures.

Example 17

In-Vivo Production of Oxygenated Sesquiterpenes in Engineered Cells Using the Recombinant SaCP816 P450 Enzyme The oxidized products of (+)-α-santalene and the (+)-α-santalene, (−)-β-santalene, (−)-α-trans-bergamotene, (+)-epi-β-santalene or other structurally similar molecules can also be produced directly in *E. Coli* cells engineered to produce sesquiterpenes from a carbon source such as glucose or glycerol. Plasmids were prepared consisting of the pCWori+ plasmid containing a synthetic operon composed of the SaCP120293 cDNA (SEQ ID No 72), the CPRm cDNA (SEQ ID No 9) and a terpene synthase encoding cDNA. For the terpene synthase, the *Clausena lansium* (+)-α-santalene synthase cDNA (ClASS) (WO2009109597) or a cDNA encoding for a *Santalum album* (+)-α-santalene/(−)-β-santalene synthase (SaSAS) (WO2010067309) was used.

Two plasmids were thus constructed using a procedure similar to the procedure described in example 6. The codon optimized (+)-α-santalene synthase cDNA (SEQ ID NO 19) and the (+)-α-santalene/(−)-β-santalene synthase cDNA (SEQ ID NO 21) were amplified as described in example 6 and ligated using the In-Fusion® Dry-Down PCR Cloning Kit (Clontech, Takara Bio Europe) in the plasmids SaCP816-CPRm-pCWori digested with the HindIII restriction enzyme providing the two new plasmids SaCP816-CPRm-ClASS-pCWori (SEQ ID NO 75) and SaCP816-CPRm-SaSAS-pCWori (SEQ ID NO 76).

The evaluation of the performance of these operons was performed in the *E. coli* XRX cells (Promega) co-transformed with either of these 2 plasmids and with the plasmid pACYC-29258-4506 carrying a complete mevalonate pathway (example 4). Transformed cells were selected on carbenicillin (50 μg/ml) and chloramphenicol (34 μg/ml) LB-agarose plates. Single colonies were used to inoculate 5 mL of LB medium supplemented with appropriate antibiotics. Cultures were incubated overnight at 37° C. and 250 rpm. The next day 2 mL of TB medium in glass culture tubes containing 100 μg/L carbenicilin and 17 μg/L chloramphenicol, were inoculated with 200 μl of the LB pre-culture and incubated at 37° C. and 250 rpm. After 6 hours of cultivation (or when the optical density at 600 nm of the culture reach a value of 3), the culture were cooled down to 20° C. and the expression of the proteins was induced with 0.1 mM IPTG (Isopropyl β-D-1-thiogalactopyranoside) and 0.1% Rhamnose, and 75 μg/δ-aminolevulinic acid (sigma) and 2% (v/v) of decane were added. After 48 h incubation with 250 rpm shaking, the whole culture broth was extracted with 1 volume of MTBE and analyzed by GCMS as described in example 4.

All resulting strains produced the sesquiterpene hydrocarbons as well as the corresponding oxygenated products also observed in the in-vitro experiments (FIG. 14). This experiment shows that using engineered cells expressing SaCP816, the sesquiterpenes (Z)-α-santalol, (Z)-β-santalol and other structurally similar molecules can be produced.

Example 18

Isolation of a cDNA Encoding SaCP10374, a Cytochrome P450 from *Santalum Album*

As described in example 13, several P450-encoding contig sequences were identified in the transcriptome from *Santalum album* roots. Beside SCH37-Ct816, another contig was selected: SCH37-Ctl0374 (SED ID NO 77), contained a 1533 bp length ORF (SEQ ID NO 78) encoding for a protein composed of 510 amino acids, SaCP10374 (SEQ ID NO 79), showing homology with know cytochrome P450 sequences and 58% identity with CYP71D10 from *Vitis vinifera*, CYP71D10.

Example 19

Heterologous Expression of SaCP10374 in Bacterial Cells and Co-Expression with a P450-Reductase in Bacteria For functional characterization of the enzymes encoded by SCH37-Ct10374, the protein was heterologously expressed in *E. coli* cells. The ORFs sequence were modified to improve the expression in *E. Coli*: the 18 first codons were replaced by the codons encoding for the MALLLAVFWSA-LII peptide and the codon usage of the whole ORF sequence was optimized. The new cDNA, SaCP120292 (SEQ ID NO 80), encoding for the modified SaCP10374 (SEQ ID NO 81) was synthesized in-vitro (DNA2.0) and cloned in the pJExpress404 plasmid (DNA2.0).

The heterologous expression was performed as described in example 2. Following this procedure, typical CO-spectra with a maximum absorbance at 450 nm was measured for this new recombinant *S. abum P*450, attesting for a proper folding into functional P450 enzymes.

To reconstitute the activity of this P450 enzyme, a P450 reductase (CPR) was coexpressed. For this purpose, a bicistronic operons was designed similarly as described in example 15 to express SaCP10374 and CPRm (a mint P450 reductase) from a single plasmid and under the control of a unique promoter. The optimized SaCP12092 cDNA was combined with the CPRm cDNA to prepare the bicistronic constructs (SEQ ID NO 82) containing successively the P450 cDNA a linker sequence including a ribosome binding site (RBS) and the CPRm cDNA. This construct was prepared by PCR as described in example 15. and cloned in the pCWori+ plasmid (Barnes H. J (1996) *Method Enzymol.* 272, 3-14) providing the plasmid SaCP10374-CPRm-pCWori.

The JM109 *E. coli* cells were transformed with these bicistronic expression plasmid. The transformed cells were grown and the cell-free extract containing the recombinant proteins were prepared as described in example 2. The membrane protein fractions were used for the evaluation the enzymatique conversion of sesquiterpene molecules (example 21)

Example 21

In-Vitro Conversion of (+)-α-santalene, (−)-β-santalene and (−)-α-trans-bergamotene Using the Recombinant SaCP10374 P450 Enzyme The different sequiterpene hydrocarbons (either (a)-santalene or a mixture of (+)-α-santalene, (−)-β-santalene, (−)-α-trans-bergamotene and (+)-epi-β-santalene) used as substrates in this example of bioconversion assays were prepared as described in example 4.

The crude protein extract from *E. coli* cells expressing the recombinant SaCP10374 and CPRm proteins (example 20) was used for the in-vitro oxidation of these sesquiterpene molecules and the assays were performed as described in example 16. After 2 hours of incubation in Teflon sealed glass tubes with gentle agitation, the reaction was stopped on ice and extraction with 1 volume of MTBE (Methyl tert-buthyl ether, Sigma). The extracts were analyzed by GCMS as described in example 4.

In these conditions, oxidation of (+)-α-santalene, (−)-β-santalene, (−)-α-trans-bergamotene and (+)-epi-β-santalene by SaCP10374 was observed. FIGS. 15 and 16 show that (+)-α-santalene, (−)-β-santalene, (−)-α-trans-bergamotene and (+)-epi-β-santalene were oxidized by SaCP10374 to form (E)-α-santalol, (E)-β-santalol, (E)-α-trans-bergamotol and (E)-epi-β-santalol. In all assays, no detectable amounts of the corresponding cis-isomers of the sesquiterpene alcohols was observed (the trans and cis isomers of each sesquiterpene alcohol are easily separated in the chromatographic conditions used in these assays).

This experiments show that the cytochrome P450 enzyme SaCP10374, isolated from *Santalum album*, can be used for the selective hydroxylation of the trans-terminal carbon of (+)-α-santalene, (−)-β-santalene and structurally similar sesquiterpene molecules.

Example 22

In-Vitro Conversion of (E)-β-farnesene, (E)-α-farnesene, (−)-Sesquisabinene B, (−)-β-Bisabolene and (−)-α-trans-bergamotene Using the Recombinant SaCP816 and SaCP10374 P450s Enzyme Using the method described in example 4, several sequiterpene hydrocarbons structurally similar to the santalenes were prepared. The (−)-sesquisabinene B and (−)-β-bisabolene were produced using the pETDuet expression plasmid containing either a cDNA encoding for SaTps647, a *Santalum album* (−)-sesquisabinene B synthase (NCBI accession No. ADP37190.1) or a cDNA encoding for SaTps30, a *Santalum album* (−)-β-bisabolene synthase (NCBI accession No. ADP37189.1), in combination with the pACYC-29258-4506 plasmid described in example 4. The β-farnesene was obtained from Bedoukian (Dambury, Ct, USA), α-farnesene was from Treatt (Suffolk, UK) and (−)-α-trans-bergamotene was purified from citrus oil.

The crude protein extracts from *E. coli* cells expressing the recombinant SaCP816 or SaCP10374 together with CPRm proteins (example 15 and 20) were used for the in-vitro oxidation of these sesquiterpene molecules. The assays and product identification by GCMS analysis was performed as described in example 16.

In these conditions oxidation of (E)-β-farnesene, (E)-α-farnesene, (−)-sesquisabinene B, (−)-β-bisabolene and (−)-α-trans-bergamotene, was observed (FIGS. 17 to 21). For all these compounds, the two *S. album* P450s are regioselective for one of the two carbons of the terminal gem-dimethyl group (R1 or R2 in FIG. 27): SaCP816 catalyzes the selective oxidation of the carbon atom of the methyl in cis position relative to the terminal double bond (R1 in FIG. 27), whereas SaCP10374 catalyzes the oxidation of the same substrates exclusively on the carbon atom of the methyl group in trans relative to the terminal double bond (R2 in FIG. 27). The trans and cis isomers of each sesquiterpene alcohol are easily separated in the chromatographic conditions used in these assays. The formation of the corresponding aldehyde when the trans-methyl group is oxidyzes is attributed to *E. coli* endogenous alcohol dehydrogenase activity.

This experiments show that the cytochrome P450 enzymes, SaCP816 and SaCP10374, isolated from *Santalum album* can be used for the selective hydroxylation of the cis-terminal and trans-terminal carbon, respectively, of various sesquiterpene molecules have structure similarities with β-farnesene, α-farnesene, (+)-α-santalene, (−)-β-santalene, (−)-α-trans-bergamotene, (−)-sesquisabinene B or (−)-β-bisabolene.

Example 23

In-Vivo Production of Various Oxygenated Sesquiterpenes in Engineered Cells Using the Recombinant SaCP816 or SaCP10374 P450s Enzyme The oxidized sesquiterpene molecules described in example 21 and 22 can also be produced directly using whole cells, such as for example *E. coli* cells engineered to produce sesquiterpenes from a carbon source such as glucose or glycerol. Plasmids were prepared consisting of the pCWori+ plasmid containing a synthetic operon composed of the SaCP120293 cDNA (SEQ ID No 72), or the SaCP120292 (SEQ ID No 80), the CPRm cDNA (SEQ ID No 9) and a terpene synthase encoding cDNA (encoding either for an *Artemisia annua* β-farnesene synthase cDNA (NCBI accession No AAX39387.1.1), a *Picea abies* α-farnesene synthase (NCBI accession No AAS47697.1), a *S. album* (−)-Sesquisabinene B (NCBI accession No ADP37190.1), a *S. album* (−)-β-Bisabolene synthase (NCBI accession No ADP37189.1), a *Clausena lansium* α-santalene synthase (NCBI accession No ADR71055.1) or a *S. album* α-/β-santalene synthase (NCBI accession No ADP30867.1)).

The plasmids carrying the different combinations of synthetic operons were prepared using the following procedure. The plasmid pD444-SR-AaBFS (containing an optimized cDNA encoding for AaBFS, an *Artemisia annua* (E)-β-farnesene synthase (NCBI accession No AAX39387.1), the plasmid pD444-SR-PaAFS (containing an optimized cDNA encoding for PaAFS, a *Picea abies* (E)-α-farnesene synthase (NCBI accession No. AAS47697.1) were used to amplify by PCR the (E)-β-farnesene synthase and (E)-α-farnesene synthase cDNAs, respectively. The plasmids pETDuet-SaTps647 and pETDuet-SaTps30 (example 22) were used as template to amplify by PCR the sesquisabinene B synthase and the bisabolene synthase cDNAs, respectively. For each constructs primer were designed for the cloning using the In-Fusion® technique (Clontech, Takara Bio Europe). The AaBFS cDNA was amplified using the forward primer CPRm_aaBFS_Inf1 (TTACCTGCGTGATGTGTGG-TAATAAAAGCTTAGGAGGTAAAAATGTCTACCC TGCCAATTTCTTC) (SEQ ID NO: 97) and the reverse primer AaBFS_Inf2 (ATGTTTGACAGCTTATCATCGA-TAAGCTGAATTCTTACACAACCATCGGGTG CACAAAGAATG) (SEQ ID NO: 98). The PaAFS cDNA was amplified using the forward primer CPRm_PaAFS_Inf1 (TTACCTGCGTGATGTGTGGTAATAAAAGCTTAG-GAGGTAAAAATGGATCTGG CAGTGGAAATCGC) (SEQ ID NO: 99) and the reverse primer PaAFS_Inf2 (CTCATGTTTGACAGCTTATCATCGATAAGCTGAAT-TCTTACATCGGGACCGGC TCCAGGACGGTGC) (SEQ ID NO: 100). The SaTps647 cDNA was amplified using the primer forward CPRm_Tps647_inf1(5'GCGTGATGTGTG-GTAATAAAAGCTTAGGAGGTAAAAAT GGCGAC-CGTTGTGGATGATTCT-3') (SEQ ID NO: 101) and the primer reverse Tps647_Inf2 (GCTTATCATCGATAAGCT-GAATTCTTACTCTTCATCCAGGGTAATCGGGTGG) (SEQ ID NO: 102). The SaTps30 cDNA was amplified using the primer forward CPRm_Tps30_Inf1-(GCGTGATGT-GTGGTAATAAAAGCTTAGGAGGTAAAAATGGACG-CATTCGCA ACGAGCC) (SEQ ID NO: 103) and the primer reverse Tps30_Inf2(GTGATGTGTGG-TAATAAAAAGCTGAATTCTTAGTCCTCTTCATTCA GCGGGATCGGGTG) (SEQ ID NO: 104).

The PCR products were ligated in the plasmids SaCP816-CPRm-pCWori (SEQ ID No 74) or SaCP10374-CPRm-pCWOri (SEQ ID NO 82) digested with the HindIII restriction enzyme and using the In-Fusion® Dry-Down PCR Cloning Kit (Clontech, Takara Bio Europe), providing the new plasmids SaCP816-CPRm-SaTPS647-pCWori (SEQ ID NO 83), SaCP10374-CPRm-SaTPS647-pCWori (SEQ ID NO 84), SaCP816-CPRm-SaTPS30-pCWori (SEQ ID NO 85), SaCP10374-CPRm-SaTPS30-pCWori (SEQ ID NO 86), SaCP816-CPRm-AaBFS-pCWori (SEQ ID NO 87), SaCP10374-CPRm-AaBFS-pCWori (SEQ ID NO 88), SaCP816-CPRm-PaAFS-pCWori (SEQ ID NO 89), SaCP10374-CPRm-PaAFS-pCWori (SEQ ID NO 90), SaCP10374-CPRm-ClTps2-pCWori (SEQ ID NO 91), and SaCP10374-CPRm-SaTps8201-pCWori (SEQ ID NO 92).

The in-vivo production of oxygenated sesquiterpenes in *E coli* cells using the above plasmids was performed as described in example 17. All recombinant bacteria cells transformed with these plasmids produced the expected sesquiterpene hydrocarbons as well as the corresponding oxygenated products also observed in the in-vitro experiments (FIGS. 22 to 26).

What is claimed is:

1. An isolated polypeptide having monooxygenase activity comprising an amino acid sequence having at least 90% sequence identity to a polypeptide having an amino acid sequence SEQ ID NO: 73, wherein the amino acid sequence MALLLAVFWSALIILV corresponding to amino acid positions 1 to 16 of SEQ ID NO: 73 is not modified and wherein at least one amino acid at positions 17 to 499 of SEQ ID NO: 73 is modified.

2. A vector comprising a nucleic acid molecule that encodes the polypeptide of claim 1.

3. The vector of claim 2, wherein the vector is a prokaryotic vector, viral vector or a eukaryotic vector.

4. The vector of claim 2, wherein the vector is an expression vector.

5. A host cell or non-human organism comprising the nucleic acid molecule encoding the amino acid sequence of claim 1.

6. The isolated polypeptide of claim 1 having at least 95% sequence identity to SEQ ID NO: 73.

* * * * *

SEQUENCE LISTING

```
<160> NUMBER OF SEQ ID NOS: 104

<210> SEQ ID NO 1
<211> LENGTH: 1500
<212> TYPE: DNA
<213> ORGANISM: Cichorium intybus

<400> SEQUENCE: 1

atggagattt ctatccccac taccettggc cttgccgtca tcatcttcat cattttcaag     60

ttgctaacgc gtaccacatc aaagaaaaac ctactcccag agccatggag actaccaata    120

atcggacaca tgcatcatct gataggtacg atgccacatc gtggtgtcat ggaactagcc    180

aggaagcatg gatctctcat gcatctacaa cttggagaag tgtccactat tgtggtctca    240

tccccacgtt gggcaaaaga ggttctgaca acgtacgata ttacgtttgc aaacagaccg    300

gagactttaa ccggtgagat tgttgcatat cacaataccg atattgtcct tgctccgtat    360

ggtgaatact ggaggcagtt gcgaaagctt tgcaccttgg agcttttaag caacaagaaa    420
```

```
gtgaagtcgt ttcagtccct tcgtgaggag gaatgttgga atctggttaa agacattcga    480

tcaactgggc agggatcccc aatcaatctt tcagaaaaca ttttcaagat gattgccacc    540

atacttagta gggcagcatt cggaaaggga atcaaagacc aaatgaaatt tacagaatta    600

gtaaaagaaa tactaaggct tacgggaggt tttgatgtgg cggacatctt tccttctaaa    660

aagttacttc accatctttc aggcaagaga gctaagttaa ccaacataca caataagctt    720

gacaatttga tcaacaatat catcgctgag caccctggaa accgtacaag ctcatcacag    780

gagactctac ttgatgttct gttaagactg aaagaaagcg cagagtttcc attgacagca    840

gacaatgtca aagcagtcat tttggatatg tttggagctg gcacggatac ttcgtcagcc    900

acaattgaat gggcaatctc agaattgata aggtgtccga gagccatgga gaaagttcaa    960

acagaattaa ggcaagcact aaatggaaag gaaaggatcc aagaagaaga tctacaggaa   1020

ctaaattacc taaagctagt gatcaaagaa acattgaggt tgcatccacc actaccgttg   1080

gttatgccta gagagtgtag ggagccatgt gtgttggggg gatacgatat acccagcaag   1140

acgaaactta ttgtcaacgt gtttgccata aacagggatc ctgaatactg gaaagatgct   1200

gaaactttca tgccagagag atttgaaaac agccccatca ctgtaatggg ttcagagtat   1260

gagtatctcc cgtttggtgc aggaagaaga atgtgtccag gcgctgccct tggtttagcc   1320

aacgtggaac ttcctcttgc tcatatactt tactacttca attggaagct cccaaatgga   1380

aaaacatttg aagacttgga catgactgag agctttggag ccactgtcca aagaaagacg   1440

gagttgttac tagttccaac ggatttccaa acacttacgg catctactta atgactcgag   1500


<210> SEQ ID NO 2
<211> LENGTH: 496
<212> TYPE: PRT
<213> ORGANISM: Cichorium intybus

<400> SEQUENCE: 2

Met Glu Ile Ser Ile Pro Thr Thr Leu Gly Leu Ala Val Ile Ile Phe
1               5                   10                  15

Ile Ile Phe Lys Leu Leu Thr Arg Thr Thr Ser Lys Lys Asn Leu Leu
            20                  25                  30

Pro Glu Pro Trp Arg Leu Pro Ile Ile Gly His Met His His Leu Ile
        35                  40                  45

Gly Thr Met Pro His Arg Gly Val Met Glu Leu Ala Arg Lys His Gly
    50                  55                  60

Ser Leu Met His Leu Gln Leu Gly Glu Val Ser Thr Ile Val Val Ser
65                  70                  75                  80

Ser Pro Arg Trp Ala Lys Glu Val Leu Thr Thr Tyr Asp Ile Thr Phe
                85                  90                  95

Ala Asn Arg Pro Glu Thr Leu Thr Gly Glu Ile Val Ala Tyr His Asn
            100                 105                 110

Thr Asp Ile Val Leu Ala Pro Tyr Gly Glu Tyr Trp Arg Gln Leu Arg
        115                 120                 125

Lys Leu Cys Thr Leu Glu Leu Leu Ser Asn Lys Lys Val Lys Ser Phe
    130                 135                 140

Gln Ser Leu Arg Glu Glu Glu Cys Trp Asn Leu Val Lys Asp Ile Arg
145                 150                 155                 160

Ser Thr Gly Gln Gly Ser Pro Ile Asn Leu Ser Glu Asn Ile Phe Lys
                165                 170                 175

Met Ile Ala Thr Ile Leu Ser Arg Ala Ala Phe Gly Lys Gly Ile Lys
```

-continued

```
            180                 185                 190

Asp Gln Met Lys Phe Thr Glu Leu Val Lys Glu Ile Leu Arg Leu Thr
        195                 200                 205

Gly Gly Phe Asp Val Ala Asp Ile Phe Pro Ser Lys Lys Leu Leu His
    210                 215                 220

His Leu Ser Gly Lys Arg Ala Lys Leu Thr Asn Ile His Asn Lys Leu
225                 230                 235                 240

Asp Asn Leu Ile Asn Asn Ile Ile Ala Glu His Pro Gly Asn Arg Thr
                245                 250                 255

Ser Ser Ser Gln Glu Thr Leu Leu Asp Val Leu Leu Arg Leu Lys Glu
            260                 265                 270

Ser Ala Glu Phe Pro Leu Thr Ala Asp Asn Val Lys Ala Val Ile Leu
        275                 280                 285

Asp Met Phe Gly Ala Gly Thr Asp Thr Ser Ser Ala Thr Ile Glu Trp
    290                 295                 300

Ala Ile Ser Glu Leu Ile Arg Cys Pro Arg Ala Met Glu Lys Val Gln
305                 310                 315                 320

Thr Glu Leu Arg Gln Ala Leu Asn Gly Lys Glu Arg Ile Gln Glu Glu
                325                 330                 335

Asp Leu Gln Glu Leu Asn Tyr Leu Lys Leu Val Ile Lys Glu Thr Leu
            340                 345                 350

Arg Leu His Pro Pro Leu Pro Leu Val Met Pro Arg Glu Cys Arg Glu
        355                 360                 365

Pro Cys Val Leu Gly Gly Tyr Asp Ile Pro Ser Lys Thr Lys Leu Ile
    370                 375                 380

Val Asn Val Phe Ala Ile Asn Arg Asp Pro Glu Tyr Trp Lys Asp Ala
385                 390                 395                 400

Glu Thr Phe Met Pro Glu Arg Phe Glu Asn Ser Pro Ile Thr Val Met
                405                 410                 415

Gly Ser Glu Tyr Glu Tyr Leu Pro Phe Gly Ala Gly Arg Arg Met Cys
            420                 425                 430

Pro Gly Ala Ala Leu Gly Leu Ala Asn Val Glu Leu Pro Leu Ala His
        435                 440                 445

Ile Leu Tyr Tyr Phe Asn Trp Lys Leu Pro Asn Gly Lys Thr Phe Glu
    450                 455                 460

Asp Leu Asp Met Thr Glu Ser Phe Gly Ala Thr Val Gln Arg Lys Thr
465                 470                 475                 480

Glu Leu Leu Leu Val Pro Thr Asp Phe Gln Thr Leu Thr Ala Ser Thr
                485                 490                 495
```

<210> SEQ ID NO 3
<211> LENGTH: 1473
<212> TYPE: DNA
<213> ORGANISM: Artificial Sequence
<220> FEATURE:
<223> OTHER INFORMATION: CYP71AV8-65188 DNA sequence

<400> SEQUENCE: 3

```
atggcactct tactggcagt attctggtcc gccctgatca ttcttgtaac ccgcacgact      60

agcaaaaaga atctgttgcc ggagccatgg cgtctgccga ttatcggtca catgcaccat     120

ttgatcggca ccatgccgca tcgtggtgtt atggaactgg cccgtaagca tggcagcctg     180

atgcacctgc aactgggtga agtctctacg attgttgtca gcagcccgcg ttgggcgaaa     240

gaggtcttga ccacctatga tatcaccttc gccaatcgcc cggaaaccct gactggcgag     300
```

-continued

```
atcgtcgcat accacaacac ggatatcgtc ctggcgccgt atggtgagta ttggcgtcaa    360

ctgcgtaaac tgtgcacgct ggagctgctg agcaacaaga aagtgaagag cttccagagc    420

ctgcgcgaag aagagtgttg gaacctggtc aaggacatcc gcagcaccgg ccaaggtagc    480

ccaatcaatc tgtcggagaa cattttcaag atgattgcga cgattctgag ccgtgctgcg    540

ttcggtaagg gtattaagga tcaaatgaag tttaccgaac tggtgaaaga aatcctgcgt    600

ctgaccggcg gttttgatgt cgctgacatc ttccctagca agaagttgct gcaccacctg    660

agcggcaagc gtgcaaaact gaccaatatc cataacaagc tggataatct gatcaataac    720

atcatcgcag agcacccggg caaccgtacc tcgtcctccc aggaaacgct gctggacgtt    780

ctgctgcgcc tgaaagagtc tgcggagttt ccgctgaccg ccgacaacgt taaagcagtg    840

atcctggata tgttcggcgc tggtacggat accagcagcg cgacgatcga gtgggcgatt    900

agcgagctga ttcgctgccc tcgcgcgatg gagaaagtgc agacggaatt gcgtcaggca    960

ctgaatggca aagagcgtat tcaggaagag gatttgcagg agctgaatta tctgaagctg   1020

gtgattaaag aaaccctgcg cctgcatccg ccgttgccgc tggtgatgcc gcgtgagtgc   1080

cgtgaaccgt gtgttttggg cggttacgac attccgagca aaacgaagct gatcgttaat   1140

gttttcgcga ttaaccgtga cccggaatac tggaaagacg cggaaacgtt tatgccggag   1200

cgttttgaga atagcccgat taccgttatg ggttccgagt acgaatacct gccatttggt   1260

gctggtcgtc gtatgtgtcc tggtgcagcg ctgggtctgg ccaacgtgga actgccgctg   1320

gcgcacattc tgtactattt caactggaaa ctgccgaacg gcaagacctt cgaagatttg   1380

gacatgaccg agagctttgg tgccactgtg cagcgcaaaa ccgagctgct gctggttccg   1440

accgactttc aaacgctgac tgcgagcacc taa                                1473
```

<210> SEQ ID NO 4
<211> LENGTH: 490
<212> TYPE: PRT
<213> ORGANISM: Artificial Sequence
<220> FEATURE:
<223> OTHER INFORMATION: CYP71AV8-65188 amino acid sequence

<400> SEQUENCE: 4

```
Met Ala Leu Leu Leu Ala Val Phe Trp Ser Ala Leu Ile Ile Leu Val
1               5                   10                  15

Thr Arg Thr Thr Ser Lys Lys Asn Leu Leu Pro Glu Pro Trp Arg Leu
            20                  25                  30

Pro Ile Ile Gly His Met His His Leu Ile Gly Thr Met Pro His Arg
        35                  40                  45

Gly Val Met Glu Leu Ala Arg Lys His Gly Ser Leu Met His Leu Gln
    50                  55                  60

Leu Gly Glu Val Ser Thr Ile Val Val Ser Ser Pro Arg Trp Ala Lys
65                  70                  75                  80

Glu Val Leu Thr Thr Tyr Asp Ile Thr Phe Ala Asn Arg Pro Glu Thr
                85                  90                  95

Leu Thr Gly Glu Ile Val Ala Tyr His Asn Thr Asp Ile Val Leu Ala
            100                 105                 110

Pro Tyr Gly Glu Tyr Trp Arg Gln Leu Arg Lys Leu Cys Thr Leu Glu
        115                 120                 125

Leu Leu Ser Asn Lys Lys Val Lys Ser Phe Gln Ser Leu Arg Glu Glu
    130                 135                 140

Glu Cys Trp Asn Leu Val Lys Asp Ile Arg Ser Thr Gly Gln Gly Ser
145                 150                 155                 160
```

```
Pro Ile Asn Leu Ser Glu Asn Ile Phe Lys Met Ile Ala Thr Ile Leu
                165                 170                 175

Ser Arg Ala Ala Phe Gly Lys Gly Ile Lys Asp Gln Met Lys Phe Thr
            180                 185                 190

Glu Leu Val Lys Glu Ile Leu Arg Leu Thr Gly Gly Phe Asp Val Ala
        195                 200                 205

Asp Ile Phe Pro Ser Lys Lys Leu Leu His His Leu Ser Gly Lys Arg
    210                 215                 220

Ala Lys Leu Thr Asn Ile His Asn Lys Leu Asp Asn Leu Ile Asn Asn
225                 230                 235                 240

Ile Ile Ala Glu His Pro Gly Asn Arg Thr Ser Ser Ser Gln Glu Thr
                245                 250                 255

Leu Leu Asp Val Leu Leu Arg Leu Lys Glu Ser Ala Glu Phe Pro Leu
            260                 265                 270

Thr Ala Asp Asn Val Lys Ala Val Ile Leu Asp Met Phe Gly Ala Gly
        275                 280                 285

Thr Asp Thr Ser Ser Ala Thr Ile Glu Trp Ala Ile Ser Glu Leu Ile
    290                 295                 300

Arg Cys Pro Arg Ala Met Glu Lys Val Gln Thr Glu Leu Arg Gln Ala
305                 310                 315                 320

Leu Asn Gly Lys Glu Arg Ile Gln Glu Glu Asp Leu Gln Glu Leu Asn
                325                 330                 335

Tyr Leu Lys Leu Val Ile Lys Glu Thr Leu Arg Leu His Pro Pro Leu
            340                 345                 350

Pro Leu Val Met Pro Arg Glu Cys Arg Glu Pro Cys Val Leu Gly Gly
        355                 360                 365

Tyr Asp Ile Pro Ser Lys Thr Lys Leu Ile Val Asn Val Phe Ala Ile
    370                 375                 380

Asn Arg Asp Pro Glu Tyr Trp Lys Asp Ala Glu Thr Phe Met Pro Glu
385                 390                 395                 400

Arg Phe Glu Asn Ser Pro Ile Thr Val Met Gly Ser Glu Tyr Glu Tyr
                405                 410                 415

Leu Pro Phe Gly Ala Gly Arg Arg Met Cys Pro Gly Ala Ala Leu Gly
            420                 425                 430

Leu Ala Asn Val Glu Leu Pro Leu Ala His Ile Leu Tyr Tyr Phe Asn
        435                 440                 445

Trp Lys Leu Pro Asn Gly Lys Thr Phe Glu Asp Leu Asp Met Thr Glu
    450                 455                 460

Ser Phe Gly Ala Thr Val Gln Arg Lys Thr Glu Leu Leu Leu Val Pro
465                 470                 475                 480

Thr Asp Phe Gln Thr Leu Thr Ala Ser Thr
                485                 490
```

<210> SEQ ID NO 5
<211> LENGTH: 1509
<212> TYPE: DNA
<213> ORGANISM: Artificial Sequence
<220> FEATURE:
<223> OTHER INFORMATION: CYP71AV8-P2 DNA sequence

<400> SEQUENCE: 5

```
atggctctgt tattagcagt tttttggtcg gcgcttataa tcctcgtagt aacctacacc      60

atatccctcc taatcaacca atggcgaaaa ccgaaacccc aagggaagtt ccccccgggc     120

ccatggcgtc tgccgattat cggtcacatg caccatttga tcggcaccat gccgcatcgt     180
```

-continued

```
ggtgttatgg aactggcccg taagcatggc agcctgatgc acctgcaact gggtgaagtc    240
tctacgattg ttgtcagcag cccgcgttgg gcgaaagagg tcttgaccac ctatgatatc    300
accttcgcca atcgcccgga aaccctgact ggcgagatcg tcgcatacca caacacggat    360
atcgtcctgg cgccgtatgg tgagtattgg cgtcaactgc gtaaactgtg cacgctggag    420
ctgctgagca acaagaaagt gaagagcttc cagagcctgc gcgaagaaga gtgttggaac    480
ctggtcaagg acatccgcag caccggccaa ggtagcccaa tcaatctgtc ggagaacatt    540
ttcaagatga ttgcgacgat tctgagccgt gctgcgttcg gtaagggtat taaggatcaa    600
atgaagttta ccgaactggt gaaagaaatc ctgcgtctga ccggcggttt tgatgtcgct    660
gacatcttcc ctagcaagaa gttgctgcac cacctgagcg gcaagcgtgc aaaactgacc    720
aatatccata acaagctgga taatctgatc aataacatca tcgcagagca cccgggcaac    780
cgtacctcgt cctcccagga aacgctgctg gacgttctgc tgcgcctgaa agagtctgcg    840
gagtttccgc tgaccgccga caacgttaaa gcagtgatcc tggatatgtt cggcgctggt    900
acggatacca gcagcgcgac gatcgagtgg gcgattagcg agctgattcg ctgccctcgc    960
gcgatggaga aagtgcagac ggaattgcgt caggcactga atggcaaaga gcgtattcag   1020
gaagaggatt tgcaggagct gaattatctg aagctggtga ttaaagaaac cctgcgcctg   1080
catccgccgt tgccgctggt gatgccgcgt gagtgccgtg aaccgtgtgt tttgggcggt   1140
tacgacattc cgagcaaaac gaagctgatc gttaatgttt tcgcgattaa ccgtgacccg   1200
gaatactgga aagacgcgga aacgtttatg ccggagcgtt ttgagaatag cccgattacc   1260
gttatgggtt ccgagtacga atacctgcca tttggtgctg gtcgtcgtat gtgtcctggt   1320
gcagcgctgg gtctggccaa cgtggaactg ccgctggcgc acattctgta ctatttcaac   1380
tggaaactgc cgaacggcaa gaccttcgaa gatttggaca tgaccgagag ctttggtgcc   1440
actgtgcagc gcaaaaccga gctgctgctg gttccgaccg actttcaaac gctgactgcg   1500
agcaccctaa                                                          1509
```

<210> SEQ ID NO 6
<211> LENGTH: 502
<212> TYPE: PRT
<213> ORGANISM: Artificial Sequence
<220> FEATURE:
<223> OTHER INFORMATION: CYP71AV8-P2 amino acid sequence

<400> SEQUENCE: 6

```
Met Ala Leu Leu Leu Ala Val Phe Trp Ser Ala Leu Ile Ile Leu Val
1               5                   10                  15

Val Thr Tyr Thr Ile Ser Leu Leu Ile Asn Gln Trp Arg Lys Pro Lys
            20                  25                  30

Pro Gln Gly Lys Phe Pro Pro Gly Pro Trp Arg Leu Pro Ile Ile Gly
        35                  40                  45

His Met His His Leu Ile Gly Thr Met Pro His Arg Gly Val Met Glu
    50                  55                  60

Leu Ala Arg Lys His Gly Ser Leu Met His Leu Gln Leu Gly Glu Val
65                  70                  75                  80

Ser Thr Ile Val Val Ser Ser Pro Arg Trp Ala Lys Glu Val Leu Thr
                85                  90                  95

Thr Tyr Asp Ile Thr Phe Ala Asn Arg Pro Glu Thr Leu Thr Gly Glu
            100                 105                 110

Ile Val Ala Tyr His Asn Thr Asp Ile Val Leu Ala Pro Tyr Gly Glu
```

-continued

```
        115                 120                 125

Tyr Trp Arg Gln Leu Arg Lys Leu Cys Thr Leu Glu Leu Leu Ser Asn
    130                 135                 140

Lys Lys Val Lys Ser Phe Gln Ser Leu Arg Glu Glu Glu Cys Trp Asn
145                 150                 155                 160

Leu Val Lys Asp Ile Arg Ser Thr Gly Gln Gly Ser Pro Ile Asn Leu
                165                 170                 175

Ser Glu Asn Ile Phe Lys Met Ile Ala Thr Ile Leu Ser Arg Ala Ala
            180                 185                 190

Phe Gly Lys Gly Ile Lys Asp Gln Met Lys Phe Thr Glu Leu Val Lys
        195                 200                 205

Glu Ile Leu Arg Leu Thr Gly Gly Phe Asp Val Ala Asp Ile Phe Pro
    210                 215                 220

Ser Lys Lys Leu Leu His His Leu Ser Gly Lys Arg Ala Lys Leu Thr
225                 230                 235                 240

Asn Ile His Asn Lys Leu Asp Asn Leu Ile Asn Asn Ile Ile Ala Glu
                245                 250                 255

His Pro Gly Asn Arg Thr Ser Ser Ser Gln Glu Thr Leu Leu Asp Val
            260                 265                 270

Leu Leu Arg Leu Lys Glu Ser Ala Glu Phe Pro Leu Thr Ala Asp Asn
        275                 280                 285

Val Lys Ala Val Ile Leu Asp Met Phe Gly Ala Gly Thr Asp Thr Ser
    290                 295                 300

Ser Ala Thr Ile Glu Trp Ala Ile Ser Glu Leu Ile Arg Cys Pro Arg
305                 310                 315                 320

Ala Met Glu Lys Val Gln Thr Glu Leu Arg Gln Ala Leu Asn Gly Lys
                325                 330                 335

Glu Arg Ile Gln Glu Glu Asp Leu Gln Glu Leu Asn Tyr Leu Lys Leu
            340                 345                 350

Val Ile Lys Glu Thr Leu Arg Leu His Pro Pro Leu Pro Leu Val Met
        355                 360                 365

Pro Arg Glu Cys Arg Glu Pro Cys Val Leu Gly Gly Tyr Asp Ile Pro
    370                 375                 380

Ser Lys Thr Lys Leu Ile Val Asn Val Phe Ala Ile Asn Arg Asp Pro
385                 390                 395                 400

Glu Tyr Trp Lys Asp Ala Glu Thr Phe Met Pro Glu Arg Phe Glu Asn
                405                 410                 415

Ser Pro Ile Thr Val Met Gly Ser Glu Tyr Glu Tyr Leu Pro Phe Gly
            420                 425                 430

Ala Gly Arg Arg Met Cys Pro Gly Ala Ala Leu Gly Leu Ala Asn Val
        435                 440                 445

Glu Leu Pro Leu Ala His Ile Leu Tyr Tyr Phe Asn Trp Lys Leu Pro
    450                 455                 460

Asn Gly Lys Thr Phe Glu Asp Leu Asp Met Thr Glu Ser Phe Gly Ala
465                 470                 475                 480

Thr Val Gln Arg Lys Thr Glu Leu Leu Leu Val Pro Thr Asp Phe Gln
                485                 490                 495

Thr Leu Thr Ala Ser Thr
            500
```

<210> SEQ ID NO 7
<211> LENGTH: 1509
<212> TYPE: DNA
<213> ORGANISM: Artificial Sequence -continued
<220> FEATURE:
<223> OTHER INFORMATION: CYP71AV8-P2O DNA sequence

<400> SEQUENCE: 7
atggcactgt tgctggctgt cttttggtct gctctgatta ttttggtggt tacctacacc 60
atctccctgc tgattaacca gtggcgtaaa ccgaaaccac agggtaaatt cccgccgggt 120
ccgtggcgtc tgccgattat cggtcacatg caccatttga tcggcaccat gccgcatcgt 180
ggtgttatgg aactggcccg taagcatggc agcctgatgc acctgcaact gggtgaagtc 240
tctacgattg ttgtcagcag cccgcgttgg gcgaaagagg tcttgaccac ctatgatatc 300
accttcgcca atcgcccgga aaccctgact ggcgagatcg tcgcatacca caacacggat 360
atcgtcctgg cgccgtatgg tgagtattgg cgtcaactgc gtaaactgtg cacgctggag 420
ctgctgagca acaagaaagt gaagagcttc cagagcctgc gcgaagaaga gtgttggaac 480
ctggtcaagg acatccgcag caccggccaa ggtagcccaa tcaatctgtc ggagaacatt 540
ttcaagatga ttgcgacgat tctgagccgt gctgcgttcg gtaagggtat taaggatcaa 600
atgaagttta ccgaactggt gaaagaaatc ctgcgtctga ccggcggttt tgatgtcgct 660
gacatcttcc ctagcaagaa gttgctgcac cacctgagcg gcaagcgtgc aaaactgacc 720
aatatccata acaagctgga taatctgatc aataacatca tcgcagagca cccgggcaac 780
cgtacctcgt cctcccagga aacgctgctg gacgttctgc tgcgcctgaa agagtctgcg 840
gagtttccgc tgaccgccga caacgttaaa gcagtgatcc tggatatgtt cggcgctggt 900
acggatacca gcagcgcgac gatcgagtgg gcgattagcg agctgattcg ctgccctcgc 960
gcgatggaga aagtgcagac ggaattgcgt caggcactga atggcaaaga gcgtattcag 1020
gaagaggatt tgcaggagct gaattatctg aagctggtga ttaaagaaac cctgcgcctg 1080
catccgccgt tgccgctggt gatgccgcgt gagtgccgtg aaccgtgtgt tttgggcggt 1140
tacgacattc cgagcaaaac gaagctgatc gttaatgttt tcgcgattaa ccgtgacccg 1200
gaatactgga aagacgcgga aacgtttatg ccggagcgtt ttgagaatag cccgattacc 1260
gttatgggtt ccgagtacga atacctgcca tttggtgctg gtcgtcgtat gtgtcctggt 1320
gcagcgctgg gtctggccaa cgtggaactg ccgctggcgc acattctgta ctatttcaac 1380
tggaaactgc cgaacggcaa gaccttcgaa gatttggaca tgaccgagag ctttggtgcc 1440
actgtgcagc gcaaaaccga gctgctgctg gttccgaccg actttcaaac gctgactgcg 1500
agcacctaa 1509

<210> SEQ ID NO 8
<211> LENGTH: 502
<212> TYPE: PRT
<213> ORGANISM: Artificial Sequence
<220> FEATURE:
<223> OTHER INFORMATION: CYP71AV8-P2O amino acid sequence

<400> SEQUENCE: 8

Met Ala Leu Leu Leu Ala Val Phe Trp Ser Ala Leu Ile Ile Leu Val
1 5 10 15

Val Thr Tyr Thr Ile Ser Leu Leu Ile Asn Gln Trp Arg Lys Pro Lys
20 25 30

Pro Gln Gly Lys Phe Pro Pro Gly Pro Trp Arg Leu Pro Ile Ile Gly
35 40 45

His Met His His Leu Ile Gly Thr Met Pro His Arg Gly Val Met Glu
50 55 60

-continued

```
Leu Ala Arg Lys His Gly Ser Leu Met His Leu Gln Leu Gly Glu Val
65                  70                  75                  80

Ser Thr Ile Val Val Ser Ser Pro Arg Trp Ala Lys Glu Val Leu Thr
                85                  90                  95

Thr Tyr Asp Ile Thr Phe Ala Asn Arg Pro Glu Thr Leu Thr Gly Glu
            100                 105                 110

Ile Val Ala Tyr His Asn Thr Asp Ile Val Leu Ala Pro Tyr Gly Glu
        115                 120                 125

Tyr Trp Arg Gln Leu Arg Lys Leu Cys Thr Leu Glu Leu Leu Ser Asn
    130                 135                 140

Lys Lys Val Lys Ser Phe Gln Ser Leu Arg Glu Glu Glu Cys Trp Asn
145                 150                 155                 160

Leu Val Lys Asp Ile Arg Ser Thr Gly Gln Gly Ser Pro Ile Asn Leu
                165                 170                 175

Ser Glu Asn Ile Phe Lys Met Ile Ala Thr Ile Leu Ser Arg Ala Ala
            180                 185                 190

Phe Gly Lys Gly Ile Lys Asp Gln Met Lys Phe Thr Glu Leu Val Lys
        195                 200                 205

Glu Ile Leu Arg Leu Thr Gly Gly Phe Asp Val Ala Asp Ile Phe Pro
    210                 215                 220

Ser Lys Lys Leu Leu His His Leu Ser Gly Lys Arg Ala Lys Leu Thr
225                 230                 235                 240

Asn Ile His Asn Lys Leu Asp Asn Leu Ile Asn Asn Ile Ile Ala Glu
                245                 250                 255

His Pro Gly Asn Arg Thr Ser Ser Ser Gln Glu Thr Leu Leu Asp Val
            260                 265                 270

Leu Leu Arg Leu Lys Glu Ser Ala Glu Phe Pro Leu Thr Ala Asp Asn
        275                 280                 285

Val Lys Ala Val Ile Leu Asp Met Phe Gly Ala Gly Thr Asp Thr Ser
    290                 295                 300

Ser Ala Thr Ile Glu Trp Ala Ile Ser Glu Leu Ile Arg Cys Pro Arg
305                 310                 315                 320

Ala Met Glu Lys Val Gln Thr Glu Leu Arg Gln Ala Leu Asn Gly Lys
                325                 330                 335

Glu Arg Ile Gln Glu Glu Asp Leu Gln Glu Leu Asn Tyr Leu Lys Leu
            340                 345                 350

Val Ile Lys Glu Thr Leu Arg Leu His Pro Pro Leu Pro Leu Val Met
        355                 360                 365

Pro Arg Glu Cys Arg Glu Pro Cys Val Leu Gly Gly Tyr Asp Ile Pro
    370                 375                 380

Ser Lys Thr Lys Leu Ile Val Asn Val Phe Ala Ile Asn Arg Asp Pro
385                 390                 395                 400

Glu Tyr Trp Lys Asp Ala Glu Thr Phe Met Pro Glu Arg Phe Glu Asn
                405                 410                 415

Ser Pro Ile Thr Val Met Gly Ser Glu Tyr Glu Tyr Leu Pro Phe Gly
            420                 425                 430

Ala Gly Arg Arg Met Cys Pro Gly Ala Ala Leu Gly Leu Ala Asn Val
        435                 440                 445

Glu Leu Pro Leu Ala His Ile Leu Tyr Tyr Phe Asn Trp Lys Leu Pro
    450                 455                 460

Asn Gly Lys Thr Phe Glu Asp Leu Asp Met Thr Glu Ser Phe Gly Ala
465                 470                 475                 480

Thr Val Gln Arg Lys Thr Glu Leu Leu Leu Val Pro Thr Asp Phe Gln
```

-continued

```
            485                 490                 495

Thr Leu Thr Ala Ser Thr
            500


<210> SEQ ID NO 9
<211> LENGTH: 2133
<212> TYPE: DNA
<213> ORGANISM: Mentha piperita

<400> SEQUENCE: 9

atggaaccta gctctcagaa actgtctccg ttggaatttg ttgctgctat cctgaagggc      60

gactacagca gcggtcaggt tgaaggtggt ccaccgccag gtctggcagc tatgttgatg     120

gaaaataagg atttggtgat ggttctgacg acgtccgtgg cagtcctgat cggctgtgtc     180

gtggtcctgg catggcgtcg tgcggcaggt agcggtaagt acaagcaacc tgaactgcct     240

aaactggtgg tcccgaaagc agccgaaccg gaggaggcag aggatgataa aaccaagatc     300

agcgtgtttt tcggcaccca aaccggtacg gcagaaggtt tcgcgaaggc ttttgttgaa     360

gaggccaagg cgcgttatca gcaggcccgt ttcaaagtta tcgacctgga cgactatgcg     420

gcagacgatg acgagtacga agagaaactg aagaaggaaa acttggcatt cttcttcttg     480

gcgtcctacg gtgacggcga gccgacggac aacgcggcac gcttttacaa atggtttacg     540

gagggtaagg accgtggtga atggctgaac aatctgcagt acggcgtttt tggtctgggt     600

aaccgtcaat atgagcattt caataagatc gccattgtcg tcgatgatct gatcttcgag     660

caaggtggca agaagctggt tccggtgggt ctgggtgacg atgaccagtg cattgaggat     720

gattttgcgg cgtggcgtga actggtctgg ccggaactgg ataaactgct gcgtaacgaa     780

gacgacgcta ccgtggcaac cccgtacagc gccgctgtgc tgcaataccg cgtggttttc     840

cacgatcaca ttgacggcct gattagcgaa aacggtagcc cgaacggtca tgctaatggc     900

aataccgtgt acgatgcgca acacccgtgc cgtagcaacg tcgcggtcaa gaaggaattg     960

catactccgg cgagcgatcg cagctgcacc cacctggaat ttaacattag cggtaccggc    1020

ctgatgtacg agacgggtga ccacgtcggt gtgtattgcg agaacctgtt ggaaaccgtg    1080

gaggaggccg agaagttgtt gaacctgagc ccgcagacgt acttctccgt tcacaccgac    1140

aacgaggacg gtacgccgtt gagcggcagc agcctgccgc caccgtttcc gccgtgcacc    1200

ttgcgcacgg cattgaccaa atacgcagac ttgacttctg caccgaaaaa gtcggtgctg    1260

gtggcgctgg ccgagtacgc atctgaccag ggtgaagcgg atcgtttgcg tttcttggcg    1320

agcccgagcg gcaaagagga atatgcacag tacatcttgg caagccagcg cacgctgctg    1380

gaggtcatgg cggagttccc gtcggcgaaa ccgccgctgg gtgtcttttt cgcgggtgtc    1440

gctccgcgcc tgcagccgcg tttctattcc attagctcta gcccgaagat cgcaccgttc    1500

cgtattcacg tgacctgcgc cctggtttat gacaaatccc ctaccggtcg cgttcataag    1560

ggcatctgta gcacgtggat gaaaaatgcg gtcccgctgg aagaaagcaa cgattgttcc    1620

tgggctccga tcttcgtccg caacagcaac ttcaagctgc cgaccgaccc gaaggttccg    1680

attatcatga ttggtccggg taccggtctg gccccttttc gtggcttttt gcaagagcgc    1740

ttggcgttga aagagagcgg tgctgaattg ggtccggcga tcttgttctt tggttgccgt    1800

aaccgtaaaa tggactttat ttacgaggat gaactgaatg atttcgtcaa agcgggcgtt    1860

gtcagcgagc tgatcgtcgc ttttagccgc gaaggcccga tgaaagaata cgtgcaacac    1920

aaaatgagcc aacgtgcctc cgatgtgtgg aacatcatta gcgacggtgg ttatgtttat    1980
```

-continued

```
gtttgcggtg acgcgaaggg tatggctcgt gatgttcacc gtaccctgca taccatcgca   2040

caggagcaag gtagcatgtc cagctcggag gccgaaggta tggtcaaaaa cctgcaaacc   2100

accggtcgtt acctgcgtga tgtgtggtaa taa                                2133


<210> SEQ ID NO 10
<211> LENGTH: 709
<212> TYPE: PRT
<213> ORGANISM: Mentha piperita

<400> SEQUENCE: 10

Met Glu Pro Ser Ser Gln Lys Leu Ser Pro Leu Glu Phe Val Ala Ala
1               5                   10                  15

Ile Leu Lys Gly Asp Tyr Ser Ser Gly Gln Val Glu Gly Gly Pro Pro
            20                  25                  30

Pro Gly Leu Ala Ala Met Leu Met Glu Asn Lys Asp Leu Val Met Val
        35                  40                  45

Leu Thr Thr Ser Val Ala Val Leu Ile Gly Cys Val Val Val Leu Ala
    50                  55                  60

Trp Arg Arg Ala Ala Gly Ser Gly Lys Tyr Lys Gln Pro Glu Leu Pro
65                  70                  75                  80

Lys Leu Val Val Pro Lys Ala Ala Glu Pro Glu Glu Ala Glu Asp Asp
                85                  90                  95

Lys Thr Lys Ile Ser Val Phe Phe Gly Thr Gln Thr Gly Thr Ala Glu
            100                 105                 110

Gly Phe Ala Lys Ala Phe Val Glu Glu Ala Lys Ala Arg Tyr Gln Gln
        115                 120                 125

Ala Arg Phe Lys Val Ile Asp Leu Asp Asp Tyr Ala Ala Asp Asp Asp
    130                 135                 140

Glu Tyr Glu Glu Lys Leu Lys Lys Glu Asn Leu Ala Phe Phe Phe Leu
145                 150                 155                 160

Ala Ser Tyr Gly Asp Gly Glu Pro Thr Asp Asn Ala Ala Arg Phe Tyr
                165                 170                 175

Lys Trp Phe Thr Glu Gly Lys Asp Arg Gly Glu Trp Leu Asn Asn Leu
            180                 185                 190

Gln Tyr Gly Val Phe Gly Leu Gly Asn Arg Gln Tyr Glu His Phe Asn
        195                 200                 205

Lys Ile Ala Ile Val Val Asp Asp Leu Ile Phe Glu Gln Gly Gly Lys
    210                 215                 220

Lys Leu Val Pro Val Gly Leu Gly Asp Asp Asp Gln Cys Ile Glu Asp
225                 230                 235                 240

Asp Phe Ala Ala Trp Arg Glu Leu Val Trp Pro Glu Leu Asp Lys Leu
                245                 250                 255

Leu Arg Asn Glu Asp Asp Ala Thr Val Ala Thr Pro Tyr Ser Ala Ala
            260                 265                 270

Val Leu Gln Tyr Arg Val Val Phe His Asp His Ile Asp Gly Leu Ile
        275                 280                 285

Ser Glu Asn Gly Ser Pro Asn Gly His Ala Asn Gly Asn Thr Val Tyr
    290                 295                 300

Asp Ala Gln His Pro Cys Arg Ser Asn Val Ala Val Lys Lys Glu Leu
305                 310                 315                 320

His Thr Pro Ala Ser Asp Arg Ser Cys Thr His Leu Glu Phe Asn Ile
                325                 330                 335

Ser Gly Thr Gly Leu Met Tyr Glu Thr Gly Asp His Val Gly Val Tyr
            340                 345                 350
```

```
Cys Glu Asn Leu Leu Glu Thr Val Glu Glu Ala Glu Lys Leu Leu Asn
        355                 360                 365

Leu Ser Pro Gln Thr Tyr Phe Ser Val His Thr Asp Asn Glu Asp Gly
    370                 375                 380

Thr Pro Leu Ser Gly Ser Ser Leu Pro Pro Pro Phe Pro Pro Cys Thr
385                 390                 395                 400

Leu Arg Thr Ala Leu Thr Lys Tyr Ala Asp Leu Thr Ser Ala Pro Lys
                405                 410                 415

Lys Ser Val Leu Val Ala Leu Ala Glu Tyr Ala Ser Asp Gln Gly Glu
            420                 425                 430

Ala Asp Arg Leu Arg Phe Leu Ala Ser Pro Ser Gly Lys Glu Glu Tyr
        435                 440                 445

Ala Gln Tyr Ile Leu Ala Ser Gln Arg Thr Leu Leu Glu Val Met Ala
    450                 455                 460

Glu Phe Pro Ser Ala Lys Pro Pro Leu Gly Val Phe Phe Ala Gly Val
465                 470                 475                 480

Ala Pro Arg Leu Gln Pro Arg Phe Tyr Ser Ile Ser Ser Ser Pro Lys
                485                 490                 495

Ile Ala Pro Phe Arg Ile His Val Thr Cys Ala Leu Val Tyr Asp Lys
            500                 505                 510

Ser Pro Thr Gly Arg Val His Lys Gly Ile Cys Ser Thr Trp Met Lys
        515                 520                 525

Asn Ala Val Pro Leu Glu Glu Ser Asn Asp Cys Ser Trp Ala Pro Ile
    530                 535                 540

Phe Val Arg Asn Ser Asn Phe Lys Leu Pro Thr Asp Pro Lys Val Pro
545                 550                 555                 560

Ile Ile Met Ile Gly Pro Gly Thr Gly Leu Ala Pro Phe Arg Gly Phe
                565                 570                 575

Leu Gln Glu Arg Leu Ala Leu Lys Glu Ser Gly Ala Glu Leu Gly Pro
            580                 585                 590

Ala Ile Leu Phe Phe Gly Cys Arg Asn Arg Lys Met Asp Phe Ile Tyr
        595                 600                 605

Glu Asp Glu Leu Asn Asp Phe Val Lys Ala Gly Val Val Ser Glu Leu
    610                 615                 620

Ile Val Ala Phe Ser Arg Glu Gly Pro Met Lys Glu Tyr Val Gln His
625                 630                 635                 640

Lys Met Ser Gln Arg Ala Ser Asp Val Trp Asn Ile Ile Ser Asp Gly
                645                 650                 655

Gly Tyr Val Tyr Val Cys Gly Asp Ala Lys Gly Met Ala Arg Asp Val
            660                 665                 670

His Arg Thr Leu His Thr Ile Ala Gln Glu Gln Gly Ser Met Ser Ser
        675                 680                 685

Ser Glu Ala Glu Gly Met Val Lys Asn Leu Gln Thr Thr Gly Arg Tyr
    690                 695                 700

Leu Arg Asp Val Trp
705
```

<210> SEQ ID NO 11
<211> LENGTH: 1992
<212> TYPE: DNA
<213> ORGANISM: Artemisia annua

<400> SEQUENCE: 11
atggcactgg acaaactgga cctgtacgta atcatcacct tagtcgtcgc cgtggccgcg     60

```
tattttgcga aaaatcgccg ctcgtctagc gcagccaaga aagccgcgga gagcccggtt    120

attgtcgtcc cgaagaaggt tacggaggac gaagtggacg acggtcgtaa aaaggtcacg    180

gtgttcttcg gcacgcagac tggtaccgct gaaggtttcg cgaaggcgct ggttgaagaa    240

gcaaaggcgc gctatgaaaa ggcagtgttc aaggttatcg atctggacga ttacgccgca    300

gaggacgacg aatacgagga gaagttgaaa aaggagtccc tcgccttctt cttcctggcg    360

acgtacggcg atggtgagcc gaccgataac gcagctcgtt tctacaagtg gttcaccgag    420

ggtgaggaga agggtgagtg gctggataaa ctgcaatatg cggtctttgg tctgggcaac    480

cgccaatatg agcacttcaa taagatcgca aaggttgtgg atgagaaact ggtcgagcag    540

ggtgccaagc gcctggtgcc ggttggcatg ggtgatgacg atcagtgcat cgaggatgac    600

ttcaccgcct ggaaggagct ggtgtggccg gagctggacc aactgttgcg cgacgaagat    660

gacaccagcg ttgcgacgcc gtataccgcg gcagttggcg aatatcgtgt tgtttttcat    720

gataagccgg aaacctacga tcaggatcaa ctgaccaatg gtcatgctgt gcatgacgcg    780

cagcacccgt gcagaagcaa tgttgctgtt aagaaagaat tgcactctcc gctgtccgat    840

cgcagctgca cccacctgga atttgacatc agcaataccg gtttgagcta cgaaacgggc    900

gatcacgtcg gtgtgtatgt ggaaaatctg agcgaagttg tcgatgaggc tgagaagctg    960

atcggtttac caccgcacac ctacttcagc gtgcatactg acaatgagga tggcacccca   1020

ctgggcggtg ctagcctgcc accgcctttc ccgccttgca ccctgcgcaa agccctcgct   1080

agctacgctg atgtgctgag cagcccgaag aagagcgcac tgctggcact ggcagcacac   1140

gctaccgatt ccaccgaagc cgatcgcctg aagtttttcg ctagcccggc aggcaaggac   1200

gagtatgcgc agtggattgt cgcgagccac cgtagcctgc tggaagtgat ggaggcgttc   1260

ccgagcgcga agcctccgct cggcgtcttt ttcgcatcgg ttgcgcctcg cctgcaaccg   1320

cgttattact caatcagcag ctctccgaaa ttcgcgccga atcgtattca cgttacttgc   1380

gcgctggttt atgagcaaac tccgagcggt cgtgttcaca agggcgtttg ctctacctgg   1440

atgaaaaacg cggttcctat gacggagagc caagactgta gctgggctcc gatttatgtt   1500

cgcacgtcta actttcgcct gcctagcgac ccgaaggtgc cagtgattat gattggtccg   1560

ggtaccggtc tggcaccgtt ccgcggtttc ctgcaagaac gtctggcaca gaaagaagct   1620

ggtacggaat tgggcaccgc aattctgttc tttggttgtc gtaatcgtaa agtggacttt   1680

atctatgagg atgaactgaa caacttcgtg gaaaccggtg ccctgagcga attggtgacg   1740

gctttttctc gtgagggtgc gaccaaagaa tacgtgcagc acaagatgac gcagaaagca   1800

agcgacattt ggaatctgct gtccgaaggt gcgtacctgt atgtctgtgg cgacgcgaag   1860

ggcatggcaa aagacgttca ccgtaccctg cacaccattg tgcaggagca aggtagcctg   1920

gactcttcga aggcggaatt gtacgtcaaa aacctgcaaa tggccggtcg ttatctgcgt   1980

gacgtttggt aa                                                        1992
```

<210> SEQ ID NO 12
<211> LENGTH: 663
<212> TYPE: PRT
<213> ORGANISM: Artemisia annua

<400> SEQUENCE: 12

```
Met Ala Leu Asp Lys Leu Asp Leu Tyr Val Ile Ile Thr Leu Val Val
1               5                   10                  15

Ala Val Ala Ala Tyr Phe Ala Lys Asn Arg Arg Ser Ser Ser Ala Ala
```

-continued

```
            20                  25                  30

Lys Lys Ala Ala Glu Ser Pro Val Ile Val Val Pro Lys Lys Val Thr
        35                  40                  45

Glu Asp Glu Val Asp Asp Gly Arg Lys Lys Val Thr Val Phe Phe Gly
    50                  55                  60

Thr Gln Thr Gly Thr Ala Glu Gly Phe Ala Lys Ala Leu Val Glu Glu
65                  70                  75                  80

Ala Lys Ala Arg Tyr Glu Lys Ala Val Phe Lys Val Ile Asp Leu Asp
                85                  90                  95

Asp Tyr Ala Ala Glu Asp Asp Glu Tyr Glu Glu Lys Leu Lys Lys Glu
            100                 105                 110

Ser Leu Ala Phe Phe Phe Leu Ala Thr Tyr Gly Asp Gly Glu Pro Thr
        115                 120                 125

Asp Asn Ala Ala Arg Phe Tyr Lys Trp Phe Thr Glu Gly Glu Glu Lys
    130                 135                 140

Gly Glu Trp Leu Asp Lys Leu Gln Tyr Ala Val Phe Gly Leu Gly Asn
145                 150                 155                 160

Arg Gln Tyr Glu His Phe Asn Lys Ile Ala Lys Val Val Asp Glu Lys
                165                 170                 175

Leu Val Glu Gln Gly Ala Lys Arg Leu Val Pro Val Gly Met Gly Asp
            180                 185                 190

Asp Asp Gln Cys Ile Glu Asp Asp Phe Thr Ala Trp Lys Glu Leu Val
        195                 200                 205

Trp Pro Glu Leu Asp Gln Leu Leu Arg Asp Glu Asp Asp Thr Ser Val
    210                 215                 220

Ala Thr Pro Tyr Thr Ala Ala Val Gly Glu Tyr Arg Val Val Phe His
225                 230                 235                 240

Asp Lys Pro Glu Thr Tyr Asp Gln Asp Gln Leu Thr Asn Gly His Ala
                245                 250                 255

Val His Asp Ala Gln His Pro Cys Arg Ser Asn Val Ala Val Lys Lys
            260                 265                 270

Glu Leu His Ser Pro Leu Ser Asp Arg Ser Cys Thr His Leu Glu Phe
        275                 280                 285

Asp Ile Ser Asn Thr Gly Leu Ser Tyr Glu Thr Gly Asp His Val Gly
    290                 295                 300

Val Tyr Val Glu Asn Leu Ser Glu Val Val Asp Glu Ala Glu Lys Leu
305                 310                 315                 320

Ile Gly Leu Pro Pro His Thr Tyr Phe Ser Val His Thr Asp Asn Glu
                325                 330                 335

Asp Gly Thr Pro Leu Gly Gly Ala Ser Leu Pro Pro Pro Phe Pro Pro
            340                 345                 350

Cys Thr Leu Arg Lys Ala Leu Ala Ser Tyr Ala Asp Val Leu Ser Ser
        355                 360                 365

Pro Lys Lys Ser Ala Leu Leu Ala Leu Ala Ala His Ala Thr Asp Ser
    370                 375                 380

Thr Glu Ala Asp Arg Leu Lys Phe Phe Ala Ser Pro Ala Gly Lys Asp
385                 390                 395                 400

Glu Tyr Ala Gln Trp Ile Val Ala Ser His Arg Ser Leu Leu Glu Val
                405                 410                 415

Met Glu Ala Phe Pro Ser Ala Lys Pro Pro Leu Gly Val Phe Phe Ala
            420                 425                 430

Ser Val Ala Pro Arg Leu Gln Pro Arg Tyr Tyr Ser Ile Ser Ser Ser
        435                 440                 445
```

```
Pro Lys Phe Ala Pro Asn Arg Ile His Val Thr Cys Ala Leu Val Tyr
    450                 455                 460

Glu Gln Thr Pro Ser Gly Arg Val His Lys Gly Val Cys Ser Thr Trp
465                 470                 475                 480

Met Lys Asn Ala Val Pro Met Thr Glu Ser Gln Asp Cys Ser Trp Ala
                485                 490                 495

Pro Ile Tyr Val Arg Thr Ser Asn Phe Arg Leu Pro Ser Asp Pro Lys
            500                 505                 510

Val Pro Val Ile Met Ile Gly Pro Gly Thr Gly Leu Ala Pro Phe Arg
        515                 520                 525

Gly Phe Leu Gln Glu Arg Leu Ala Gln Lys Glu Ala Gly Thr Glu Leu
    530                 535                 540

Gly Thr Ala Ile Leu Phe Phe Gly Cys Arg Asn Arg Lys Val Asp Phe
545                 550                 555                 560

Ile Tyr Glu Asp Glu Leu Asn Asn Phe Val Glu Thr Gly Ala Leu Ser
                565                 570                 575

Glu Leu Val Thr Ala Phe Ser Arg Glu Gly Ala Thr Lys Glu Tyr Val
            580                 585                 590

Gln His Lys Met Thr Gln Lys Ala Ser Asp Ile Trp Asn Leu Leu Ser
        595                 600                 605

Glu Gly Ala Tyr Leu Tyr Val Cys Gly Asp Ala Lys Gly Met Ala Lys
    610                 615                 620

Asp Val His Arg Thr Leu His Thr Ile Val Gln Glu Gln Gly Ser Leu
625                 630                 635                 640

Asp Ser Ser Lys Ala Glu Leu Tyr Val Lys Asn Leu Gln Met Ala Gly
                645                 650                 655

Arg Tyr Leu Arg Asp Val Trp
            660


<210> SEQ ID NO 13
<211> LENGTH: 3534
<212> TYPE: DNA
<213> ORGANISM: Artificial Sequence
<220> FEATURE:
<223> OTHER INFORMATION: pCWori-CYP71AV8-P2-aaCPR insert DNA sequence

<400> SEQUENCE: 13

catatggctc tgttattagc agtttttgg tcggcgctta taatcctcgt agtaacctac     60

accatatccc tcctaatcaa ccaatggcga aaaccgaaac cccaagggaa gttccccccg    120

ggcccatggc gtctgccgat tatcggtcac atgcaccatt tgatcggcac catgccgcat    180

cgtggtgtta tggaactggc ccgtaagcat ggcagcctga tgcacctgca actgggtgaa    240

gtctctacga ttgttgtcag cagcccgcgt tgggcgaaag aggtcttgac cacctatgat    300

atcaccttcg ccaatcgccc ggaaaccctg actggcgaga tcgtcgcata ccacaacacg    360

gatatcgtcc tggcgccgta tggtgagtat tggcgtcaac tgcgtaaact gtgcacgctg    420

gagctgctga gcaacaagaa agtgaagagc ttccagagcc tgcgcgaaga agagtgttgg    480

aacctggtca aggacatccg cagcaccggc caaggtagcc caatcaatct gtcggagaac    540

attttcaaga tgattgcgac gattctgagc cgtgctgcgt tcggtaaggg tattaaggat    600

caaatgaagt ttaccgaact ggtgaaagaa atcctgcgtc tgaccggcgg ttttgatgtc    660

gctgacatct tccctagcaa gaagttgctg caccacctga gcggcaagcg tgcaaaactg    720

accaatatcc ataacaagct ggataatctg atcaataaca tcatcgcaga gcacccgggc    780
```

-continued

```
aaccgtacct cgtcctccca ggaaacgctg ctggacgttc tgctgcgcct gaaagagtct    840
gcggagtttc cgctgaccgc cgacaacgtt aaagcagtga tcctggatat gttcggcgct    900
ggtacggata ccagcagcgc gacgatcgag tgggcgatta gcgagctgat tcgctgccct    960
cgcgcgatgg agaaagtgca gacggaattg cgtcaggcac tgaatggcaa agagcgtatt   1020
caggaagagg atttgcagga gctgaattat ctgaagctgg tgattaaaga aaccctgcgc   1080
ctgcatccgc cgttgccgct ggtgatgccg cgtgagtgcc gtgaaccgtg tgttttgggc   1140
ggttacgaca ttccgagcaa aacgaagctg atcgttaatg ttttcgcgat taaccgtgac   1200
ccggaatact ggaaagacgc ggaaacgttt atgccggagc gttttgagaa tagcccgatt   1260
accgttatgg gttccgagta cgaatacctg ccatttggtg ctggtcgtcg tatgtgtcct   1320
ggtgcagcgc tgggtctggc caacgtggaa ctgccgctgg cgcacattct gtactatttc   1380
aactggaaac tgccgaacgg caagaccttc gaagatttgg acatgaccga gagctttggt   1440
gccactgtgc agcgcaaaac cgagctgctg ctggttccga ccgactttca aacgctgact   1500
gcgagcacct aatgagtcga cagaggaaga tataccatgg cactggacaa actggacctg   1560
tacgtaatca tcaccttagt cgtcgccgtg gccgcgtatt ttgcgaaaaa tcgccgctcg   1620
tctagcgcag ccaagaaagc cgcggagagc ccggttattg tcgtcccgaa gaaggttacg   1680
gaggacgaag tggacgacgg tcgtaaaaag gtcacggtgt tcttcggcac gcagactggt   1740
accgctgaag gtttcgcgaa ggcgctggtt gaagaagcaa aggcgcgcta tgaaaaggca   1800
gtgttcaagg ttatcgatct ggacgattac gccgcagagg acgacgaata cgaggagaag   1860
ttgaaaaagg agtccctcgc cttcttcttc ctggcgacgt acggcgatgg tgagccgacc   1920
gataacgcag ctcgtttcta caagtggttc accgagggtg aggagaaggg tgagtggctg   1980
gataaactgc aatatgcggt ctttggtctg ggcaaccgcc aatatgagca cttcaataag   2040
atcgcaaagg ttgtggatga gaaactggtc gagcagggtg ccaagcgcct ggtgccggtt   2100
ggcatgggtg atgacgatca gtgcatcgag gatgacttca ccgcctggaa ggagctggtg   2160
tggccggagc tggaccaact gttgcgcgac gaagatgaca ccagcgttgc gacgccgtat   2220
accgcggcag ttggcgaata tcgtgttgtt tttcatgata agccggaaac ctacgatcag   2280
gatcaactga ccaatggtca tgctgtgcat gacgcgcagc acccgtgcag aagcaatgtt   2340
gctgttaaga aagaattgca ctctccgctg tccgatcgca gctgcaccca cctggaattt   2400
gacatcagca ataccggttt gagctacgaa acgggcgatc acgtcggtgt gtatgtggaa   2460
aatctgagcg aagttgtcga tgaggctgag aagctgatcg gtttaccacc gcacacctac   2520
ttcagcgtgc atactgacaa tgaggatggc accccactgg gcggtgctag cctgccaccg   2580
cctttcccgc cttgcaccct gcgcaaagcc ctcgctagct acgctgatgt gctgagcagc   2640
ccgaagaaga gcgcactgct ggcactggca gcacacgcta ccgattccac cgaagccgat   2700
cgcctgaagt ttttcgctag cccggcaggc aaggacgagt atgcgcagtg gattgtcgcg   2760
agccaccgta gcctgctgga agtgatggag gcgttcccga gcgcgaagcc tccgctcggc   2820
gtctttttcg catcggttgc gcctcgcctg caaccgcgtt attactcaat cagcagctct   2880
ccgaaattcg cgccgaatcg tattcacgtt acttgcgcgc tggtttatga gcaaactccg   2940
agcggtcgtg ttcacaaggg cgtttgctct acctggatga aaaacgcggt tcctatgacg   3000
gagagccaag actgtagctg ggctccgatt tatgttcgca cgtctaactt tcgcctgcct   3060
agcgacccga aggtgccagt gattatgatt ggtccgggta ccggtctggc accgttccgc   3120
ggtttcctgc aagaacgtct ggcacagaaa gaagctggta cggaattggg caccgcaatt   3180
```

ctgttctttg gttgtcgtaa tcgtaaagtg gactttatct atgaggatga actgaacaac 3240
ttcgtggaaa ccggtgccct gagcgaattg gtgacggctt tttctcgtga gggtgcgacc 3300
aaagaatacg tgcagcacaa gatgacgcag aaagcaagcg acatttggaa tctgctgtcc 3360
gaaggtgcgt acctgtatgt ctgtggcgac gcgaagggca tggcaaaaga cgttcaccgt 3420
accctgcaca ccattgtgca ggagcaaggt agcctggact cttcgaaggc ggaattgtac 3480
gtcaaaaacc tgcaaatggc cggtcgttat ctgcgtgacg tttggtaaaa gctt 3534

<210> SEQ ID NO 14
<211> LENGTH: 3534
<212> TYPE: DNA
<213> ORGANISM: Artificial Sequence
<220> FEATURE:
<223> OTHER INFORMATION: pCWori-CYP71AV8-P2O-aaCPR insert DNA sequence

<400> SEQUENCE: 14
catatggcac tgttgctggc tgtcttttgg tctgctctga ttattttggt ggttacctac 60
accatctccc tgctgattaa ccagtggcgt aaaccgaaac cacagggtaa attcccgccg 120
ggtccgtggc gtctgccgat tatcggtcac atgcaccatt tgatcggcac catgccgcat 180
cgtggtgtta tggaactggc ccgtaagcat ggcagcctga tgcacctgca actgggtgaa 240
gtctctacga ttgttgtcag cagcccgcgt tgggcgaaag aggtcttgac cacctatgat 300
atcaccttcg ccaatcgccc ggaaaccctg actggcgaga tcgtcgcata ccacaacacg 360
gatatcgtcc tggcgccgta tggtgagtat tggcgtcaac tgcgtaaact gtgcacgctg 420
gagctgctga gcaacaagaa agtgaagagc ttccagagcc tgcgcgaaga agagtgttgg 480
aacctggtca aggacatccg cagcaccggc caaggtagcc caatcaatct gtcggagaac 540
attttcaaga tgattgcgac gattctgagc cgtgctgcgt tcggtaaggg tattaaggat 600
caaatgaagt ttaccgaact ggtgaaagaa atcctgcgtc tgaccggcgg ttttgatgtc 660
gctgacatct tccctagcaa gaagttgctg caccacctga gcggcaagcg tgcaaaactg 720
accaatatcc ataacaagct ggataatctg atcaataaca tcatcgcaga gcacccgggc 780
aaccgtacct cgtcctccca ggaaacgctg ctggacgttc tgctgcgcct gaaagagtct 840
gcggagtttc cgctgaccgc cgacaacgtt aaagcagtga tcctggatat gttcggcgct 900
ggtacggata ccagcagcgc gacgatcgag tgggcgatta gcgagctgat tcgctgccct 960
cgcgcgatgg agaaagtgca gacggaattg cgtcaggcac tgaatggcaa agagcgtatt 1020
caggaagagg atttgcagga gctgaattat ctgaagctgg tgattaaaga aaccctgcgc 1080
ctgcatccgc cgttgccgct ggtgatgccg cgtgagtgcc gtgaaccgtg tgttttgggc 1140
ggttacgaca ttccgagcaa aacgaagctg atcgttaatg ttttcgcgat taaccgtgac 1200
ccggaatact ggaaagacgc ggaaacgttt atgccggagc gttttgagaa tagcccgatt 1260
accgttatgg gttccgagta cgaatacctg ccatttggtg ctggtcgtcg tatgtgtcct 1320
ggtgcagcgc tgggtctggc caacgtggaa ctgccgctgg cgcacattct gtactatttc 1380
aactggaaac tgccgaacgg caagaccttc gaagatttgg acatgaccga gagctttggt 1440
gccactgtgc agcgcaaaac cgagctgctg ctggttccga ccgactttca aacgctgact 1500
gcgagcacct aatgagtcga cagaggaaga tataccatgg cactggacaa actggacctg 1560
tacgtaatca tcaccttagt cgtcgccgtg gccgcgtatt ttgcgaaaaa tcgccgctcg 1620
tctagcgcag ccaagaaagc cgcggagagc ccggttattg tcgtcccgaa gaaggttacg 1680

-continued gaggacgaag tggacgacgg tcgtaaaaag gtcacggtgt tcttcggcac gcagactggt 1740
accgctgaag gtttcgcgaa ggcgctggtt gaagaagcaa aggcgcgcta tgaaaaggca 1800
gtgttcaagg ttatcgatct ggacgattac gccgcagagg acgacgaata cgaggagaag 1860
ttgaaaaagg agtccctcgc cttcttcttc ctggcgacgt acggcgatgg tgagccgacc 1920
gataacgcag ctcgtttcta caagtggttc accgagggtg aggagaaggg tgagtggctg 1980
gataaactgc aatatgcggt ctttggtctg ggcaaccgcc aatatgagca cttcaataag 2040
atcgcaaagg ttgtggatga gaaactggtc gagcagggtg ccaagcgcct ggtgccggtt 2100
ggcatgggtg atgacgatca gtgcatcgag gatgacttca ccgcctggaa ggagctggtg 2160
tggccggagc tggaccaact gttgcgcgac gaagatgaca ccagcgttgc gacgccgtat 2220
accgcggcag ttggcgaata tcgtgttgtt tttcatgata agccggaaac ctacgatcag 2280
gatcaactga ccaatggtca tgctgtgcat gacgcgcagc acccgtgcag aagcaatgtt 2340
gctgttaaga aagaattgca ctctccgctg tccgatcgca gctgcaccca cctggaattt 2400
gacatcagca ataccggttt gagctacgaa acgggcgatc acgtcggtgt gtatgtggaa 2460
aatctgagcg aagttgtcga tgaggctgag aagctgatcg gtttaccacc gcacacctac 2520
ttcagcgtgc atactgacaa tgaggatggc accccactgg gcggtgctag cctgccaccg 2580
cctttcccgc cttgcaccct gcgcaaagcc ctcgctagct acgctgatgt gctgagcagc 2640
ccgaagaaga gcgcactgct ggcactggca gcacacgcta ccgattccac cgaagccgat 2700
cgcctgaagt ttttcgctag cccggcaggc aaggacgagt atgcgcagtg gattgtcgcg 2760
agccaccgta gcctgctgga agtgatggag gcgttcccga gcgcgaagcc tccgctcggc 2820 gtcttttttcg catcggttgc gcctcgcctg caaccgcgtt attactcaat cagcagctct 2880
ccgaaattcg cgccgaatcg tattcacgtt acttgcgcgc tggtttatga gcaaactccg 2940
agcggtcgtg ttcacaaggg cgtttgctct acctggatga aaaacgcggt tcctatgacg 3000
gagagccaag actgtagctg ggctccgatt tatgttcgca cgtctaactt tcgcctgcct 3060
agcgacccga aggtgccagt gattatgatt ggtccgggta ccggtctggc accgttccgc 3120
ggtttcctgc aagaacgtct ggcacagaaa gaagctggta cggaattggg caccgcaatt 3180
ctgttctttg gttgtcgtaa tcgtaaagtg gactttatct atgaggatga actgaacaac 3240
ttcgtggaaa ccggtgccct gagcgaattg gtgacggctt tttctcgtga gggtgcgacc 3300
aaagaatacg tgcagcacaa gatgacgcag aaagcaagcg acatttggaa tctgctgtcc 3360
gaaggtgcgt acctgtatgt ctgtggcgac gcgaagggca tggcaaaaga cgttcaccgt 3420
accctgcaca ccattgtgca ggagcaaggt agcctggact cttcgaaggc ggaattgtac 3480
gtcaaaaacc tgcaaatggc cggtcgttat ctgcgtgacg tttggtaaaa gctt 3534

<210> SEQ ID NO 15
<211> LENGTH: 3684
<212> TYPE: DNA
<213> ORGANISM: Artificial Sequence
<220> FEATURE:
<223> OTHER INFORMATION: pCWori-CYP71AV8-P2-CPRm insert DNA sequence

<400> SEQUENCE: 15
catatggctc tgttattagc agttttttgg tcggcgctta taatcctcgt agtaacctac 60
accatatccc tcctaatcaa ccaatggcga aaaccgaaac cccaagggaa gttccccccg 120
ggcccatggc gtctgccgat tatcggtcac atgcaccatt tgatcggcac catgccgcat 180
cgtggtgtta tggaactggc ccgtaagcat ggcagcctga tgcacctgca actgggtgaa 240

```
gtctctacga ttgttgtcag cagcccgcgt tgggcgaaag aggtcttgac cacctatgat    300
atcaccttcg ccaatcgccc ggaaaccctg actggcgaga tcgtcgcata ccacaacacg    360
gatatcgtcc tggcgccgta tggtgagtat tggcgtcaac tgcgtaaact gtgcacgctg    420
gagctgctga gcaacaagaa agtgaagagc ttccagagcc tgcgcgaaga agagtgttgg    480
aacctggtca aggacatccg cagcaccggc caaggtagcc caatcaatct gtcggagaac    540
attttcaaga tgattgcgac gattctgagc cgtgctgcgt tcggtaaggg tattaaggat    600
caaatgaagt ttaccgaact ggtgaaagaa atcctgcgtc tgaccggcgg ttttgatgtc    660
gctgacatct tccctagcaa gaagttgctg caccacctga gcggcaagcg tgcaaaactg    720
accaatatcc ataacaagct ggataatctg atcaataaca tcatcgcaga gcacccgggc    780
aaccgtacct cgtcctccca ggaaacgctg ctggacgttc tgctgcgcct gaaagagtct    840
gcggagtttc cgctgaccgc cgacaacgtt aaagcagtga tcctggatat gttcggcgct    900
ggtacggata ccagcagcgc gacgatcgag tgggcgatta gcgagctgat tcgctgccct    960
cgcgcgatgg agaaagtgca gacggaattg cgtcaggcac tgaatggcaa agagcgtatt   1020
caggaagagg atttgcagga gctgaattat ctgaagctgg tgattaaaga aaccctgcgc   1080
ctgcatccgc cgttgccgct ggtgatgccg cgtgagtgcc gtgaaccgtg tgttttgggc   1140
ggttacgaca ttccgagcaa aacgaagctg atcgttaatg ttttcgcgat taaccgtgac   1200
ccggaatact ggaaagacgc ggaaacgttt atgccggagc gttttgagaa tagcccgatt   1260
accgttatgg gttccgagta cgaatacctg ccatttggtg ctggtcgtcg tatgtgtcct   1320
ggtgcagcgc tgggtctggc caacgtggaa ctgccgctgg cgcacattct gtactatttc   1380
aactggaaac tgccgaacgg caagaccttc gaagatttgg acatgaccga gagctttggt   1440
gccactgtgc agcgcaaaac cgagctgctg ctggttccga ccgactttca aaccctgact   1500
gcgagcacct aatgagtcga ctaactttaa gaaggagata tatccatgga acctagctct   1560
cagaaactgt ctccgttgga atttgttgct gctatcctga agggcgacta cagcagcggt   1620
caggttgaag gtggtccacc gccaggtctg gcagctatgt tgatggaaaa taaggatttg   1680
gtgatggttc tgacgacgtc cgtggcagtc ctgatcggct gtgtcgtggt cctggcatgg   1740
cgtcgtgcgg caggtagcgg taagtacaag caacctgaac tgcctaaact ggtggtcccg   1800
aaagcagccg aaccggagga ggcagaggat gataaaacca agatcagcgt gtttttcggc   1860
acccaaaccg gtacggcaga aggtttcgcg aaggcttttg ttgaagaggc caaggcgcgt   1920
tatcagcagg cccgtttcaa agttatcgac ctggacgact atgcggcaga cgatgacgag   1980
tacgaagaga aactgaagaa ggaaaacttg gcattcttct tcttggcgtc ctacggtgac   2040
ggcgagccga cggacaacgc ggcacgcttt tacaaatggt ttacggaggg taaggaccgt   2100
ggtgaatggc tgaacaatct gcagtacggc gtttttggtc tgggtaaccg tcaatatgag   2160
catttcaata agatcgccat tgtcgtcgat gatctgatct tcgagcaagg tggcaagaag   2220
ctggttccgg tgggtctggg tgacgatgac cagtgcattg aggatgattt tgcggcgtgg   2280
cgtgaactgg tctggccgga actggataaa ctgctgcgta acgaagacga cgctaccgtg   2340
gcaaccccgt acagcgccgc tgtgctgcaa taccgcgtgg ttttccacga tcacattgac   2400
ggcctgatta gcgaaaacgg tagcccgaac ggtcatgcta atggcaatac cgtgtacgat   2460
gcgcaacacc cgtgccgtag caacgtcgcg gtcaagaagg aattgcatac tccggcgagc   2520
gatcgcagct gcacccacct ggaatttaac attagcggta ccggcctgat gtacgagacg   2580
```

-continued

```
ggtgaccacg tcggtgtgta ttgcgagaac ctgttggaaa ccgtggagga ggccgagaag   2640

ttgttgaacc tgagcccgca gacgtacttc tccgttcaca ccgacaacga ggacggtacg   2700

ccgttgagcg gcagcagcct gccgccaccg tttccgccgt gcaccttgcg cacggcattg   2760

accaaatacg cagacttgac ttctgcaccg aaaaagtcgg tgctggtggc gctggccgag   2820

tacgcatctg accagggtga agcggatcgt ttgcgtttct tggcgagccc gagcggcaaa   2880

gaggaatatg cacagtacat cttggcaagc cagcgcacgc tgctggaggt catggcggag   2940

ttcccgtcgg cgaaaccgcc gctgggtgtc tttttcgcgg gtgtcgctcc gcgcctgcag   3000

ccgcgtttct attccattag ctctagcccg aagatcgcac cgttccgtat tcacgtgacc   3060

tgcgccctgg tttatgacaa atcccctacc ggtcgcgttc ataagggcat ctgtagcacg   3120

tggatgaaaa atgcggtccc gctggaagaa agcaacgatt gttcctgggc tccgatcttc   3180

gtccgcaaca gcaacttcaa gctgccgacc gacccgaagg ttccgattat catgattggt   3240

ccgggtaccg gtctggcccc ttttcgtggc tttttgcaag agcgcttggc gttgaaagag   3300

agcggtgctg aattgggtcc ggcgatcttg ttctttggtt gccgtaaccg taaaatggac   3360

tttatttacg aggatgaact gaatgatttc gtcaaagcgg gcgttgtcag cgagctgatc   3420

gtcgctttta gccgcgaagg cccgatgaaa gaatacgtgc aacacaaaat gagccaacgt   3480

gcctccgatg tgtggaacat cattagcgac ggtggttatg tttatgtttg cggtgacgcg   3540

aagggtatgg ctcgtgatgt tcaccgtacc ctgcatacca tcgcacagga gcaaggtagc   3600

atgtccagct cggaggccga aggtatggtc aaaaacctgc aaaccaccgg tcgttacctg   3660

cgtgatgtgt ggtaataaaa gctt                                          3684
```

<210> SEQ ID NO 16
<211> LENGTH: 3684
<212> TYPE: DNA
<213> ORGANISM: Artificial Sequence
<220> FEATURE:
<223> OTHER INFORMATION: pCWori-CYP71AV8-P2O-CPRm insert DNA sequence

<400> SEQUENCE: 16

```
catatggcac tgttgctggc tgtcttttgg tctgctctga ttattttggt ggttacctac     60

accatctccc tgctgattaa ccagtggcgt aaaccgaaac cacagggtaa attcccgccg    120

ggtccgtggc gtctgccgat tatcggtcac atgcaccatt tgatcggcac catgccgcat    180

cgtggtgtta tggaactggc ccgtaagcat ggcagcctga tgcacctgca actgggtgaa    240

gtctctacga ttgttgtcag cagcccgcgt tgggcgaaag aggtcttgac cacctatgat    300

atcaccttcg ccaatcgccc ggaaaccctg actggcgaga tcgtcgcata ccacaacacg    360

gatatcgtcc tggcgccgta tggtgagtat tggcgtcaac tgcgtaaact gtgcacgctg    420

gagctgctga gcaacaagaa agtgaagagc ttccagagcc tgcgcgaaga agagtgttgg    480

aacctggtca aggacatccg cagcaccggc caaggtagcc caatcaatct gtcggagaac    540

attttcaaga tgattgcgac gattctgagc cgtgctgcgt tcggtaaggg tattaaggat    600

caaatgaagt ttaccgaact ggtgaaagaa atcctgcgtc tgaccggcgg ttttgatgtc    660

gctgacatct tccctagcaa gaagttgctg caccacctga gcggcaagcg tgcaaaactg    720

accaatatcc ataacaagct ggataatctg atcaataaca tcatcgcaga gcacccgggc    780

aaccgtacct cgtcctccca ggaaacgctg ctggacgttc tgctgcgcct gaaagagtct    840

gcggagtttc cgctgaccgc cgacaacgtt aaagcagtga tcctggatat gttcggcgct    900

ggtacggata ccagcagcgc gacgatcgag tgggcgatta gcgagctgat tcgctgccct    960
```

```
cgcgcgatgg agaaagtgca gacggaattg cgtcaggcac tgaatggcaa agagcgtatt   1020
caggaagagg atttgcagga gctgaattat ctgaagctgg tgattaaaga aaccctgcgc   1080
ctgcatccgc cgttgccgct ggtgatgccg cgtgagtgcc gtgaaccgtg tgttttgggc   1140
ggttacgaca ttccgagcaa aacgaagctg atcgttaatg ttttcgcgat taaccgtgac   1200
ccggaatact ggaaagacgc ggaaacgttt atgccggagc gttttgagaa tagcccgatt   1260
accgttatgg gttccgagta cgaatacctg ccatttggtg ctggtcgtcg tatgtgtcct   1320
ggtgcagcgc tgggtctggc caacgtggaa ctgccgctgg cgcacattct gtactatttc   1380
aactggaaac tgccgaacgg caagaccttc gaagatttgg acatgaccga gagctttggt   1440
gccactgtgc agcgcaaaac cgagctgctg ctggttccga ccgactttca aacgctgact   1500
gcgagcacct aatgagtcga ctaactttaa gaaggagata tatccatgga acctagctct   1560
cagaaactgt ctccgttgga atttgttgct gctatcctga agggcgacta cagcagcggt   1620
caggttgaag gtggtccacc gccaggtctg gcagctatgt tgatggaaaa taaggatttg   1680
gtgatggttc tgacgacgtc cgtggcagtc ctgatcggct gtgtcgtggt cctggcatgg   1740
cgtcgtgcgg caggtagcgg taagtacaag caacctgaac tgcctaaact ggtggtcccg   1800
aaagcagccg aaccggagga ggcagaggat gataaaacca agatcagcgt gtttttcggc   1860
acccaaaccg gtacggcaga aggtttcgcg aaggcttttg ttgaagaggc caaggcgcgt   1920
tatcagcagg cccgtttcaa agttatcgac ctggacgact atgcggcaga cgatgacgag   1980
tacgaagaga aactgaagaa ggaaaacttg gcattcttct tcttggcgtc ctacggtgac   2040
ggcgagccga cggacaacgc ggcacgcttt tacaaatggt ttacggaggg taaggaccgt   2100
ggtgaatggc tgaacaatct gcagtacggc gtttttggtc tgggtaaccg tcaatatgag   2160
catttcaata agatcgccat tgtcgtcgat gatctgatct tcgagcaagg tggcaagaag   2220
ctggttccgg tgggtctggg tgacgatgac cagtgcattg aggatgattt tgcggcgtgg   2280
cgtgaactgg tctggccgga actggataaa ctgctgcgta acgaagacga cgctaccgtg   2340
gcaaccccgt acagcgccgc tgtgctgcaa taccgcgtgg ttttccacga tcacattgac   2400
ggcctgatta gcgaaaacgg tagcccgaac ggtcatgcta atggcaatac cgtgtacgat   2460
gcgcaacacc cgtgccgtag caacgtcgcg gtcaagaagg aattgcatac tccggcgagc   2520
gatcgcagct gcacccacct ggaatttaac attagcggta ccggcctgat gtacgagacg   2580
ggtgaccacg tcggtgtgta ttgcgagaac ctgttggaaa ccgtggagga ggccgagaag   2640
ttgttgaacc tgagcccgca gacgtacttc tccgttcaca ccgacaacga ggacggtacg   2700
ccgttgagcg gcagcagcct gccgccaccg tttccgccgt gcaccttgcg cacggcattg   2760
accaaatacg cagacttgac ttctgcaccg aaaaagtcgg tgctggtggc gctggccgag   2820
tacgcatctg accagggtga agcggatcgt ttgcgtttct tggcgagccc gagcggcaaa   2880
gaggaatatg cacagtacat cttggcaagc cagcgcacgc tgctggaggt catggcggag   2940
ttcccgtcgg cgaaaccgcc gctgggtgtc tttttcgcgg gtgtcgctcc gcgcctgcag   3000
ccgcgtttct attccattag ctctagcccg aagatcgcac cgttccgtat tcacgtgacc   3060
tgcgccctgg tttatgacaa atcccctacc ggtcgcgttc ataagggcat ctgtagcacg   3120
tggatgaaaa atgcggtccc gctggaagaa agcaacgatt gttcctgggc tccgatcttc   3180
gtccgcaaca gcaacttcaa gctgccgacc gacccgaagg ttccgattat catgattggt   3240
ccgggtaccg gtctggcccc ttttcgtggc tttttgcaag agcgcttggc gttgaaagag   3300
```

-continued agcggtgctg aattgggtcc ggcgatcttg ttctttggtt gccgtaaccg taaaatggac 3360
tttatttacg aggatgaact gaatgatttc gtcaaagcgg gcgttgtcag cgagctgatc 3420
gtcgctttta gccgcgaagg cccgatgaaa gaatacgtgc aacacaaaat gagccaacgt 3480
gcctccgatg tgtggaacat cattagcgac ggtggttatg tttatgtttg cggtgacgcg 3540
aagggtatgg ctcgtgatgt tcaccgtacc ctgcatacca tcgcacagga gcaaggtagc 3600
atgtccagct cggaggccga aggtatggtc aaaaacctgc aaaccaccgg tcgttacctg 3660
cgtgatgtgt ggtaataaaa gctt 3684

<210> SEQ ID NO 17
<211> LENGTH: 3498
<212> TYPE: DNA
<213> ORGANISM: Artificial Sequence
<220> FEATURE:
<223> OTHER INFORMATION: pCWori-CYP71AV8-65188-aaCPR insert DNA sequence

<400> SEQUENCE: 17
catatggcac tcttactggc agtattctgg tccgccctga tcattcttgt aacccgcacg 60
actagcaaaa agaatctgtt gccggagcca tggcgtctgc cgattatcgg tcacatgcac 120
catttgatcg gcaccatgcc gcatcgtggt gttatggaac tggcccgtaa gcatggcagc 180
ctgatgcacc tgcaactggg tgaagtctct acgattgttg tcagcagccc gcgttgggcg 240
aaagaggtct tgaccaccta tgatatcacc ttcgccaatc gcccggaaac cctgactggc 300
gagatcgtcg cataccacaa cacggatatc gtcctggcgc cgtatggtga gtattggcgt 360
caactgcgta aactgtgcac gctggagctg ctgagcaaca agaaagtgaa gagcttccag 420
agcctgcgcg aagaagagtg ttggaacctg gtcaaggaca tccgcagcac cggccaaggt 480
agcccaatca atctgtcgga gaacattttc aagatgattg cgacgattct gagccgtgct 540
gcgttcggta agggtattaa ggatcaaatg aagtttaccg aactggtgaa agaaatcctg 600
cgtctgaccg gcggttttga tgtcgctgac atcttcccta gcaagaagtt gctgcaccac 660
ctgagcggca agcgtgcaaa actgaccaat atccataaca agctggataa tctgatcaat 720
aacatcatcg cagagcaccc gggcaaccgt acctcgtcct cccaggaaac gctgctggac 780
gttctgctgc gcctgaaaga gtctgcggag tttccgctga ccgccgacaa cgttaaagca 840
gtgatcctgg atatgttcgg cgctggtacg gataccagca gcgcgacgat cgagtgggcg 900
attagcgagc tgattcgctg ccctcgcgcg atggagaaag tgcagacgga attgcgtcag 960
gcactgaatg gcaaagagcg tattcaggaa gaggatttgc aggagctgaa ttatctgaag 1020
ctggtgatta aagaaaccct gcgcctgcat ccgccgttgc cgctggtgat gccgcgtgag 1080
tgccgtgaac cgtgtgtttt gggcggttac gacattccga gcaaaacgaa gctgatcgtt 1140
aatgttttcg cgattaaccg tgacccggaa tactggaaag acgcggaaac gtttatgccg 1200
gagcgttttg agaatagccc gattaccgtt atgggttccg agtacgaata cctgccattt 1260
ggtgctggtc gtcgtatgtg tcctggtgca gcgctgggtc tggccaacgt ggaactgccg 1320
ctggcgcaca ttctgtacta tttcaactgg aaactgccga acggcaagac cttcgaagat 1380
ttggacatga ccgagagctt tggtgccact gtgcagcgca aaaccgagct gctgctggtt 1440
ccgaccgact ttcaaacgct gactgcgagc acctaatgag tcgacagagg aagatatacc 1500
atggcactgg acaaactgga cctgtacgta atcatcacct tagtcgtcgc cgtggccgcg 1560
tattttgcga aaaatcgccg ctcgtctagc gcagccaaga aagccgcgga gagcccggtt 1620
attgtcgtcc cgaagaaggt tacggaggac gaagtggacg acggtcgtaa aaaggtcacg 1680

```
gtgttcttcg gcacgcagac tggtaccgct gaaggtttcg cgaaggcgct ggttgaagaa   1740
gcaaaggcgc gctatgaaaa ggcagtgttc aaggttatcg atctggacga ttacgccgca   1800
gaggacgacg aatacgagga gaagttgaaa aaggagtccc tcgccttctt cttcctggcg   1860
acgtacggcg atggtgagcc gaccgataac gcagctcgtt tctacaagtg gttcaccgag   1920
ggtgaggaga agggtgagtg gctggataaa ctgcaatatg cggtctttgg tctgggcaac   1980
cgccaatatg agcacttcaa taagatcgca aaggttgtgg atgagaaact ggtcgagcag   2040
ggtgccaagc gcctggtgcc ggttggcatg ggtgatgacg atcagtgcat cgaggatgac   2100
ttcaccgcct ggaaggagct ggtgtggccg gagctggacc aactgttgcg cgacgaagat   2160
gacaccagcg ttgcgacgcc gtataccgcg gcagttggcg aatatcgtgt tgtttttcat   2220
gataagccgg aaacctacga tcaggatcaa ctgaccaatg gtcatgctgt gcatgacgcg   2280
cagcacccgt gcagaagcaa tgttgctgtt aagaaagaat tgcactctcc gctgtccgat   2340
cgcagctgca cccacctgga atttgacatc agcaataccg gtttgagcta cgaaacgggc   2400
gatcacgtcg gtgtgtatgt ggaaaatctg agcgaagttg tcgatgaggc tgagaagctg   2460
atcggtttac caccgcacac ctacttcagc gtgcatactg acaatgagga tggcacccca   2520
ctgggcggtg ctagcctgcc accgcctttc ccgccttgca ccctgcgcaa agccctcgct   2580
agctacgctg atgtgctgag cagcccgaag aagagcgcac tgctggcact ggcagcacac   2640
gctaccgatt ccaccgaagc cgatcgcctg aagtttttcg ctagcccggc aggcaaggac   2700
gagtatgcgc agtggattgt cgcgagccac cgtagcctgc tggaagtgat ggaggcgttc   2760
ccgagcgcga agcctccgct cggcgtcttt ttcgcatcgg ttgcgcctcg cctgcaaccg   2820
cgttattact caatcagcag ctctccgaaa ttcgcgccga atcgtattca cgttacttgc   2880
gcgctggttt atgagcaaac tccgagcggt cgtgttcaca agggcgtttg ctctacctgg   2940
atgaaaaacg cggttcctat gacggagagc caagactgta gctgggctcc gatttatgtt   3000
cgcacgtcta actttcgcct gcctagcgac ccgaaggtgc cagtgattat gattggtccg   3060
ggtaccggtc tggcaccgtt ccgcggtttc ctgcaagaac gtctggcaca gaaagaagct   3120
ggtacggaat tgggcaccgc aattctgttc tttggttgtc gtaatcgtaa agtggacttt   3180
atctatgagg atgaactgaa caacttcgtg gaaaccggtg ccctgagcga attggtgacg   3240
gctttttctc gtgagggtgc gaccaaagaa tacgtgcagc acaagatgac gcagaaagca   3300
agcgacattt ggaatctgct gtccgaaggt gcgtacctgt atgtctgtgg cgacgcgaag   3360
ggcatggcaa aagacgttca ccgtaccctg cacaccattg tgcaggagca aggtagcctg   3420
gactcttcga aggcggaatt gtacgtcaaa aacctgcaaa tggccggtcg ttatctgcgt   3480
gacgtttggt aaaagctt                                                 3498
```

<210> SEQ ID NO 18
<211> LENGTH: 3648
<212> TYPE: DNA
<213> ORGANISM: Artificial Sequence
<220> FEATURE:
<223> OTHER INFORMATION: pCWori-CYP71AV8-65188-CPRm insert DNA sequence

<400> SEQUENCE: 18

```
catatggcac tcttactggc agtattctgg tccgccctga tcattcttgt aacccgcacg     60
actagcaaaa agaatctgtt gccggagcca tggcgtctgc cgattatcgg tcacatgcac    120
catttgatcg gcaccatgcc gcatcgtggt gttatggaac tggcccgtaa gcatggcagc    180
```

-continued

```
ctgatgcacc tgcaactggg tgaagtctct acgattgttg tcagcagccc gcgttgggcg    240
aaagaggtct tgaccaccta tgatatcacc ttcgccaatc gcccggaaac cctgactggc    300
gagatcgtcg cataccacaa cacggatatc gtcctggcgc cgtatggtga gtattggcgt    360
caactgcgta aactgtgcac gctggagctg ctgagcaaca agaaagtgaa gagcttccag    420
agcctgcgcg aagaagagtg ttggaacctg gtcaaggaca tccgcagcac cggccaaggt    480
agcccaatca atctgtcgga gaacatttc aagatgattg cgacgattct gagccgtgct     540
gcgttcggta agggtattaa ggatcaaatg aagtttaccg aactggtgaa agaaatcctg    600
cgtctgaccg gcggttttga tgtcgctgac atcttcccta gcaagaagtt gctgcaccac    660
ctgagcggca agcgtgcaaa actgaccaat atccataaca agctggataa tctgatcaat    720
aacatcatcg cagagcaccc gggcaaccgt acctcgtcct cccaggaaac gctgctggac    780
gttctgctgc gcctgaaaga gtctgcggag tttccgctga ccgccgacaa cgttaaagca    840
gtgatcctgg atatgttcgg cgctggtacg gataccagca gcgcgacgat cgagtgggcg    900
attagcgagc tgattcgctg ccctcgcgcg atggagaaag tgcagacgga attgcgtcag    960
gcactgaatg gcaaagagcg tattcaggaa gaggatttgc aggagctgaa ttatctgaag   1020
ctggtgatta aagaaaccct gcgcctgcat ccgccgttgc cgctggtgat gccgcgtgag   1080
tgccgtgaac cgtgtgtttt gggcggttac gacattccga gcaaaacgaa gctgatcgtt   1140
aatgttttcg cgattaaccg tgacccggaa tactggaaag acgcggaaac gtttatgccg   1200
gagcgttttg agaatagccc gattaccgtt atgggttccg agtacgaata cctgccattt   1260
ggtgctggtc gtcgtatgtg tcctggtgca gcgctgggtc tggccaacgt ggaactgccg   1320
ctggcgcaca ttctgtacta tttcaactgg aaactgccga acggcaagac cttcgaagat   1380
ttggacatga ccgagagctt tggtgccact gtgcagcgca aaaccgagct gctgctggtt   1440
ccgaccgact ttcaaacgct gactgcgagc acctaatgag tcgactaact ttaagaagga   1500
gatatatcca tggaacctag ctctcagaaa ctgtctccgt tggaatttgt tgctgctatc   1560
ctgaagggcg actacagcag cggtcaggtt gaaggtggtc caccgccagg tctggcagct   1620
atgttgatgg aaaataagga tttggtgatg gttctgacga cgtccgtggc agtcctgatc   1680
ggctgtgtcg tggtcctggc atggcgtcgt gcggcaggta gcggtaagta caagcaacct   1740
gaactgccta aactggtggt cccgaaagca gccgaaccgg aggaggcaga ggatgataaa   1800
accaagatca gcgtgttttt cggcacccaa accggtacgg cagaaggttt cgcgaaggct   1860
tttgttgaag aggccaaggc gcgttatcag caggcccgtt tcaaagttat cgacctggac   1920
gactatgcgg cagacgatga cgagtacgaa gagaaactga agaaggaaaa cttggcattc   1980
ttcttcttgg cgtcctacgg tgacggcgag ccgacggaca acgcggcacg cttttacaaa   2040
tggtttacgg agggtaagga ccgtggtgaa tggctgaaca atctgcagta cggcgttttt   2100
ggtctgggta accgtcaata tgagcatttc aataagatcg ccattgtcgt cgatgatctg   2160
atcttcgagc aaggtggcaa gaagctggtt ccggtgggtc tgggtgacga tgaccagtgc   2220
attgaggatg attttgcggc gtggcgtgaa ctggtctggc cggaactgga taaactgctg   2280
cgtaacgaag acgacgctac cgtggcaacc ccgtacagcg ccgctgtgct gcaataccgc   2340
gtggttttcc acgatcacat tgacggcctg attagcgaaa acggtagccc gaacggtcat   2400
gctaatggca ataccgtgta cgatgcgcaa cacccgtgcc gtagcaacgt cgcggtcaag   2460
aaggaattgc atactccggc gagcgatcgc agctgcaccc acctggaatt taacattagc   2520
ggtaccggcc tgatgtacga gacgggtgac cacgtcggtg tgtattgcga gaacctgttg   2580
```

```
gaaaccgtgg aggaggccga gaagttgttg aacctgagcc cgcagacgta cttctccgtt   2640

cacaccgaca acgaggacgg tacgccgttg agcggcagca gcctgccgcc accgtttccg   2700

ccgtgcacct tgcgcacggc attgaccaaa tacgcagact tgacttctgc accgaaaaag   2760

tcggtgctgg tggcgctggc cgagtacgca tctgaccagg gtgaagcgga tcgtttgcgt   2820

ttcttggcga gcccgagcgg caaagaggaa tatgcacagt acatcttggc aagccagcgc   2880

acgctgctgg aggtcatggc ggagttcccg tcggcgaaac cgccgctggg tgtctttttc   2940

gcgggtgtcg ctccgcgcct gcagccgcgt ttctattcca ttagctctag cccgaagatc   3000

gcaccgttcc gtattcacgt gacctgcgcc ctggtttatg acaaatcccc taccggtcgc   3060

gttcataagg gcatctgtag cacgtggatg aaaaatgcgg tcccgctgga agaaagcaac   3120

gattgttcct gggctccgat cttcgtccgc aacagcaact tcaagctgcc gaccgacccg   3180

aaggttccga ttatcatgat tggtccgggt accggtctgg ccccttttcg tggcttttttg   3240

caagagcgct tggcgttgaa agagagcggt gctgaattgg gtccggcgat cttgttcttt   3300

ggttgccgta accgtaaaat ggactttatt tacgaggatg aactgaatga tttcgtcaaa   3360

gcgggcgttg tcagcgagct gatcgtcgct tttagccgcg aaggcccgat gaaagaatac   3420

gtgcaacaca aaatgagcca acgtgcctcc gatgtgtgga acatcattag cgacggtggt   3480

tatgtttatg tttgcggtga cgcgaagggt atggctcgtg atgttcaccg taccctgcat   3540

accatcgcac aggagcaagg tagcatgtcc agctcggagg ccgaaggtat ggtcaaaaac   3600

ctgcaaacca ccggtcgtta cctgcgtgat gtgtggtaat aaaagctt                3648
```

<210> SEQ ID NO 19
<211> LENGTH: 1665
<212> TYPE: DNA
<213> ORGANISM: Artificial Sequence
<220> FEATURE:
<223> OTHER INFORMATION: alpha-santalene synthase optimized cDNA sequence

<400> SEQUENCE: 19

```
atggaccaca tgtctaccca gcaggttagc tccgagaata tcgttcgcaa cgcggcgaac     60

ttccacccga atatctgggg taatcatttc ttgacgtgtc caagccagac gatcgattct    120

tggacgcaac aacaccataa agagctgaaa gaagaggtcc gcaagatgat ggtgagcgac    180

gcaaacaaac cggcacaacg tctgcgtctg attgacaccg ttcaacgttt gggcgtggcg    240

tatcatttcg aaaaagaaat cgatgacgct ctggaaaaga tcggtcacga tccgtttgac    300

gataaggatg acctgtatat cgttagcctg tgttttcgcc tgctgcgtca gcatggcatc    360

aagattagct gcgatgtttt tgagaagttc aaagacgacg atggcaagtt taaggcttcc    420

ctgatgaatg atgtccaagg tatgctgtcg ttgtatgaag cggcccacct ggcaattcat    480

ggcgaggaca tcctggatga ggctattgtc tttacgacca cccacctgaa gagcaccgtt    540

tctaactccc cggtcaattc cacctttgcg gaacagattc gccacagcct gcgtgtgccg    600

ctgcgtaagg cagtcccgcg tttggagagc cgctacttcc tggatatcta tagccgtgac    660

gacctgcacg acaagactct gctgaacttt gccaaactgg acttcaacat cctgcaggcg    720

atgcaccaga aagaggcaag cgagatgacc cgttggtggc gtgatttcga tttcctgaag    780

aagctgccgt acattcgtga tcgcgtggtt gaactgtact tttggatttt ggtcggtgtg    840

agctaccaac cgaaattcag cacgggtcgt atctttttga gcaagattat ctgtctggaa    900

accctggtgg acgacacgtt tgatgcgtac ggtactttcg acgaactggc cattttcacc    960
```

```
gaggccgtta cgcgttggga cctgggtcat cgcgacgcgc tgcctgagta catgaaattc   1020

attttcaaga ccctgattga tgtgtacagc gaggcggaac aagagctggc aaaagagggc   1080

cgctcctata gcattcacta tgcgatccgt agcttccagg agttggtcat gaagtacttt   1140

tgcgaggcga aatggctgaa taagggttat gttccgagcc tggatgacta caagagcgtc   1200

agcctgcgca gcatcggctt cctgccgatc gccgtggctt cttttgtttt catgggcgac   1260

attgctacga aagaggtttt tgagtgggaa atgaataacc cgaaaatcat catcgcagcc   1320

gaaaccattt tccgctttct ggatgacatt gcaggtcatc gcttcgaaca aaaacgtgag   1380

cacagcccga gcgcaatcga gtgctacaaa aaccaacatg gtgtctcgga agaagaggca   1440

gtgaaagcgc tgagcttgga ggtcgccaat tcgtggaaag acattaacga agagctgctg   1500

ctgaacccta tggcaattcc actgccgttg ctgcaggtga tcctggattt gagccgtagc   1560

gcggacttca tgtacggtaa tgcgcaggac cgtttcacgc actccaccat gatgaaagat   1620

caagttgacc tggttctgaa agatccggtg aaactggacg attaa                  1665
```

<210> SEQ ID NO 20
<211> LENGTH: 554
<212> TYPE: PRT
<213> ORGANISM: Artificial Sequence
<220> FEATURE:
<223> OTHER INFORMATION: alpha-santalene synthase amino acid sequence

<400> SEQUENCE: 20

```
Met Asp His Met Ser Thr Gln Gln Val Ser Ser Glu Asn Ile Val Arg
1               5                   10                  15

Asn Ala Ala Asn Phe His Pro Asn Ile Trp Gly Asn His Phe Leu Thr
            20                  25                  30

Cys Pro Ser Gln Thr Ile Asp Ser Trp Thr Gln Gln His His Lys Glu
        35                  40                  45

Leu Lys Glu Glu Val Arg Lys Met Met Val Ser Asp Ala Asn Lys Pro
    50                  55                  60

Ala Gln Arg Leu Arg Leu Ile Asp Thr Val Gln Arg Leu Gly Val Ala
65                  70                  75                  80

Tyr His Phe Glu Lys Glu Ile Asp Asp Ala Leu Glu Lys Ile Gly His
                85                  90                  95

Asp Pro Phe Asp Asp Lys Asp Asp Leu Tyr Ile Val Ser Leu Cys Phe
            100                 105                 110

Arg Leu Leu Arg Gln His Gly Ile Lys Ile Ser Cys Asp Val Phe Glu
        115                 120                 125

Lys Phe Lys Asp Asp Asp Gly Lys Phe Lys Ala Ser Leu Met Asn Asp
    130                 135                 140

Val Gln Gly Met Leu Ser Leu Tyr Glu Ala Ala His Leu Ala Ile His
145                 150                 155                 160

Gly Glu Asp Ile Leu Asp Glu Ala Ile Val Phe Thr Thr Thr His Leu
                165                 170                 175

Lys Ser Thr Val Ser Asn Ser Pro Val Asn Ser Thr Phe Ala Glu Gln
            180                 185                 190

Ile Arg His Ser Leu Arg Val Pro Leu Arg Lys Ala Val Pro Arg Leu
        195                 200                 205

Glu Ser Arg Tyr Phe Leu Asp Ile Tyr Ser Arg Asp Asp Leu His Asp
    210                 215                 220

Lys Thr Leu Leu Asn Phe Ala Lys Leu Asp Phe Asn Ile Leu Gln Ala
225                 230                 235                 240
```

```
Met His Gln Lys Glu Ala Ser Glu Met Thr Arg Trp Trp Arg Asp Phe
                245                 250                 255

Asp Phe Leu Lys Lys Leu Pro Tyr Ile Arg Asp Arg Val Val Glu Leu
            260                 265                 270

Tyr Phe Trp Ile Leu Val Gly Val Ser Tyr Gln Pro Lys Phe Ser Thr
        275                 280                 285

Gly Arg Ile Phe Leu Ser Lys Ile Ile Cys Leu Glu Thr Leu Val Asp
    290                 295                 300

Asp Thr Phe Asp Ala Tyr Gly Thr Phe Asp Glu Leu Ala Ile Phe Thr
305                 310                 315                 320

Glu Ala Val Thr Arg Trp Asp Leu Gly His Arg Asp Ala Leu Pro Glu
                325                 330                 335

Tyr Met Lys Phe Ile Phe Lys Thr Leu Ile Asp Val Tyr Ser Glu Ala
            340                 345                 350

Glu Gln Glu Leu Ala Lys Glu Gly Arg Ser Tyr Ser Ile His Tyr Ala
        355                 360                 365

Ile Arg Ser Phe Gln Glu Leu Val Met Lys Tyr Phe Cys Glu Ala Lys
    370                 375                 380

Trp Leu Asn Lys Gly Tyr Val Pro Ser Leu Asp Asp Tyr Lys Ser Val
385                 390                 395                 400

Ser Leu Arg Ser Ile Gly Phe Leu Pro Ile Ala Val Ala Ser Phe Val
                405                 410                 415

Phe Met Gly Asp Ile Ala Thr Lys Glu Val Phe Glu Trp Glu Met Asn
            420                 425                 430

Asn Pro Lys Ile Ile Ile Ala Ala Glu Thr Ile Phe Arg Phe Leu Asp
        435                 440                 445

Asp Ile Ala Gly His Arg Phe Glu Gln Lys Arg Glu His Ser Pro Ser
    450                 455                 460

Ala Ile Glu Cys Tyr Lys Asn Gln His Gly Val Ser Glu Glu Glu Ala
465                 470                 475                 480

Val Lys Ala Leu Ser Leu Glu Val Ala Asn Ser Trp Lys Asp Ile Asn
                485                 490                 495

Glu Glu Leu Leu Leu Asn Pro Met Ala Ile Pro Leu Pro Leu Leu Gln
            500                 505                 510

Val Ile Leu Asp Leu Ser Arg Ser Ala Asp Phe Met Tyr Gly Asn Ala
        515                 520                 525

Gln Asp Arg Phe Thr His Ser Thr Met Met Lys Asp Gln Val Asp Leu
    530                 535                 540

Val Leu Lys Asp Pro Val Lys Leu Asp Asp
545                 550
```

<210> SEQ ID NO 21
<211> LENGTH: 1728
<212> TYPE: DNA
<213> ORGANISM: Artificial Sequence
<220> FEATURE:
<223> OTHER INFORMATION: SaTps8201-1-FL_optEc (alpha/santalene synthase optimized full-length cDNA) including RBS region and restriction sites

<400> SEQUENCE: 21

```
aggaggtaaa acatatggac agcagcaccg ccaccgcaat gaccgcacca ttcatcgacc      60

cgacggatca tgtgaatctg aaaaccgaca cggatgcgag cgaaaatcgt cgtatgggta     120

actacaagcc gagcatttgg aactacgatt ttctgcagtc cctggcgacg caccacaaca     180
```

-continued

```
ttgttgaaga gcgtcacctg aagctggcag agaaactgaa aggtcaagtg aaattcatgt    240

tcggtgcgcc gatggagcca ttggctaagt tggagctggt tgatgtggtg caacgcttgg    300

gtctgaacca cctgttcgag actgaaatca aagaagctct gttcagcatc tacaaagatg    360

gcagcaatgg ctggtggttt ggccatctgc atgctacctc tttgcgcttc cgtctgttgc    420

gccaatgtgg cctgtttatc ccgcaggacg ttttcaaaac ctttcaaaac aagaccggtg    480

agtttgacat gaagctgtgg gacaacgtta agggcctgct gagcctgtac gaggcgagct    540

acctgggctg gaagggcgag aacatcttgg atgaagcaaa ggcgttcacg accaagtgcc    600

tgaagagcgc atgggagaac attagcgaga agtggctggc gaagcgtgtt aaacatgcgt    660

tggcgctgcc gctgcactgg cgtgttccgc gtattgaagc acgctggttt atcgaggtgt    720

acgaacaaga ggccaatatg aatccgacgc tgctgaaact ggcgaaactg gacttcaaca    780

tggtccaaag cattcaccag aaagaaatcg gtgaactggc ccgctggtgg gttactaccg    840

gcctggacaa gctggatttc gcacgcaaca atctgttgca gtcttatatg tggagctgcg    900

ccatcgcgtc cgacccgaaa ttcaaactgg cgcgtgaaac cattgtcgag atcggttccg    960

tgttgacggt tgtcgacgac ggctatgatg tgtacggttc tatggatgag ctggacctgt   1020

acaccagctc ggtggagcgt tggtcctgtg tcaaaattga caagctgcct aatacgctga   1080

agctgatctt tatgtctatg ttcaacaaaa ccaacgaggt gggtctgcgt gttcaacacg   1140

agcgtggtta caatagcatc ccgaccttca ttaaggcgtg ggtggaacag tgtaagagct   1200

atcaaaaaga ggcgcgttgg tttcatggtg gtcacacgcc tccgctggaa gaatacagcc   1260

tgaacggtct ggtcagcatt ggttttccgc tgttgctgat caccggctat gttgcgattg   1320

ctgagaatga agcagccctg gataaagtcc acccgctgcc ggacctgctg cattattcca   1380

gcttgctgag ccgtctgatt aatgatatcg gcactagccc ggatgaaatg gcgcgtggtg   1440

acaatctgaa gagcattcac tgctatatga atgaaaccgg tgccagcgaa gaggtcgcac   1500

gcgagcacat caaaggcgtc atcgaagaga attggaaaat tctgaaccag tgttgctttg   1560

accagtccca gttccaggag ccgttcatca cgtttaacct gaacagcgtg cgcggctcgc   1620

atttcttcta tgaatttggt gatggttttg gtgttaccga cagctggacc aaggtggata   1680

tgaaaagcgt cctgattgat ccgattccgc tgggtgaaga gtaagctt                1728
```

```
<210> SEQ ID NO 22
<211> LENGTH: 569
<212> TYPE: PRT
<213> ORGANISM: Artificial Sequence
<220> FEATURE:
<223> OTHER INFORMATION: SaTps8201-1-FL (alpha/beta santalene synthase
      full-length) amino acid sequence

<400> SEQUENCE: 22

Met Asp Ser Ser Thr Ala Thr Ala Met Thr Ala Pro Phe Ile Asp Pro
1               5                   10                  15

Thr Asp His Val Asn Leu Lys Thr Asp Thr Asp Ala Ser Glu Asn Arg
            20                  25                  30

Arg Met Gly Asn Tyr Lys Pro Ser Ile Trp Asn Tyr Asp Phe Leu Gln
        35                  40                  45

Ser Leu Ala Thr His His Asn Ile Val Glu Glu Arg His Leu Lys Leu
    50                  55                  60

Ala Glu Lys Leu Lys Gly Gln Val Lys Phe Met Phe Gly Ala Pro Met
65                  70                  75                  80

Glu Pro Leu Ala Lys Leu Glu Leu Val Asp Val Val Gln Arg Leu Gly
```

-continued

```
                85                  90                  95

Leu Asn His Leu Phe Glu Thr Glu Ile Lys Glu Ala Leu Phe Ser Ile
            100                 105                 110

Tyr Lys Asp Gly Ser Asn Gly Trp Trp Phe Gly His Leu His Ala Thr
        115                 120                 125

Ser Leu Arg Phe Arg Leu Leu Arg Gln Cys Gly Leu Phe Ile Pro Gln
    130                 135                 140

Asp Val Phe Lys Thr Phe Gln Asn Lys Thr Gly Glu Phe Asp Met Lys
145                 150                 155                 160

Leu Trp Asp Asn Val Lys Gly Leu Leu Ser Leu Tyr Glu Ala Ser Tyr
                165                 170                 175

Leu Gly Trp Lys Gly Glu Asn Ile Leu Asp Glu Ala Lys Ala Phe Thr
            180                 185                 190

Thr Lys Cys Leu Lys Ser Ala Trp Glu Asn Ile Ser Glu Lys Trp Leu
        195                 200                 205

Ala Lys Arg Val Lys His Ala Leu Ala Leu Pro Leu His Trp Arg Val
    210                 215                 220

Pro Arg Ile Glu Ala Arg Trp Phe Ile Glu Val Tyr Glu Gln Glu Ala
225                 230                 235                 240

Asn Met Asn Pro Thr Leu Leu Lys Leu Ala Lys Leu Asp Phe Asn Met
                245                 250                 255

Val Gln Ser Ile His Gln Lys Glu Ile Gly Glu Leu Ala Arg Trp Trp
            260                 265                 270

Val Thr Thr Gly Leu Asp Lys Leu Asp Phe Ala Arg Asn Asn Leu Leu
        275                 280                 285

Gln Ser Tyr Met Trp Ser Cys Ala Ile Ala Ser Asp Pro Lys Phe Lys
    290                 295                 300

Leu Ala Arg Glu Thr Ile Val Glu Ile Gly Ser Val Leu Thr Val Val
305                 310                 315                 320

Asp Asp Gly Tyr Asp Val Tyr Gly Ser Met Asp Glu Leu Asp Leu Tyr
                325                 330                 335

Thr Ser Ser Val Glu Arg Trp Ser Cys Val Lys Ile Asp Lys Leu Pro
            340                 345                 350

Asn Thr Leu Lys Leu Ile Phe Met Ser Met Phe Asn Lys Thr Asn Glu
        355                 360                 365

Val Gly Leu Arg Val Gln His Glu Arg Gly Tyr Asn Ser Ile Pro Thr
    370                 375                 380

Phe Ile Lys Ala Trp Val Glu Gln Cys Lys Ser Tyr Gln Lys Glu Ala
385                 390                 395                 400

Arg Trp Phe His Gly Gly His Thr Pro Pro Leu Glu Glu Tyr Ser Leu
                405                 410                 415

Asn Gly Leu Val Ser Ile Gly Phe Pro Leu Leu Leu Ile Thr Gly Tyr
            420                 425                 430

Val Ala Ile Ala Glu Asn Glu Ala Ala Leu Asp Lys Val His Pro Leu
        435                 440                 445

Pro Asp Leu Leu His Tyr Ser Ser Leu Leu Ser Arg Leu Ile Asn Asp
    450                 455                 460

Ile Gly Thr Ser Pro Asp Glu Met Ala Arg Gly Asp Asn Leu Lys Ser
465                 470                 475                 480

Ile His Cys Tyr Met Asn Glu Thr Gly Ala Ser Glu Glu Val Ala Arg
                485                 490                 495

Glu His Ile Lys Gly Val Ile Glu Glu Asn Trp Lys Ile Leu Asn Gln
            500                 505                 510
```

```
Cys Cys Phe Asp Gln Ser Gln Phe Gln Glu Pro Phe Ile Thr Phe Asn
        515                 520                 525

Leu Asn Ser Val Arg Gly Ser His Phe Phe Tyr Glu Phe Gly Asp Gly
    530                 535                 540

Phe Gly Val Thr Asp Ser Trp Thr Lys Val Asp Met Lys Ser Val Leu
545                 550                 555                 560

Ile Asp Pro Ile Pro Leu Gly Glu Glu
                565
```

<210> SEQ ID NO 23
<211> LENGTH: 5361
<212> TYPE: DNA
<213> ORGANISM: Artificial Sequence
<220> FEATURE:
<223> OTHER INFORMATION: DNA sequence of the synthetic operon containing CYP71AV-P2, CPRm, and ClASS including the NdeI and HindIII restriction sites in 3' and 5' ends

<400> SEQUENCE: 23

```
catatggctc tgttattagc agttttttgg tcggcgctta taatcctcgt agtaacctac     60

accatatccc tcctaatcaa ccaatggcga aaaccgaaac cccaagggaa gttccccccg    120

ggcccatggc gtctgccgat tatcggtcac atgcaccatt tgatcggcac catgccgcat    180

cgtggtgtta tggaactggc ccgtaagcat ggcagcctga tgcacctgca actgggtgaa    240

gtctctacga ttgttgtcag cagcccgcgt tgggcgaaag aggtcttgac cacctatgat    300

atcaccttcg ccaatcgccc ggaaaccctg actggcgaga tcgtcgcata ccacaacacg    360

gatatcgtcc tggcgccgta tggtgagtat tggcgtcaac tgcgtaaact gtgcacgctg    420

gagctgctga gcaacaagaa agtgaagagc ttccagagcc tgcgcgaaga agagtgttgg    480

aacctggtca aggacatccg cagcaccggc caaggtagcc caatcaatct gtcggagaac    540

attttcaaga tgattgcgac gattctgagc cgtgctgcgt tcggtaaggg tattaaggat    600

caaatgaagt ttaccgaact ggtgaaagaa atcctgcgtc tgaccggcgg ttttgatgtc    660

gctgacatct tccctagcaa gaagttgctg caccacctga gcggcaagcg tgcaaaactg    720

accaatatcc ataacaagct ggataatctg atcaataaca tcatcgcaga gcacccgggc    780

aaccgtacct cgtcctccca ggaaacgctg ctggacgttc tgctgcgcct gaaagagtct    840

gcggagtttc cgctgaccgc cgacaacgtt aaagcagtga tcctggatat gttcggcgct    900

ggtacggata ccagcagcgc gacgatcgag tgggcgatta gcgagctgat tcgctgccct    960

cgcgcgatgg agaaagtgca gacggaattg cgtcaggcac tgaatggcaa agagcgtatt   1020

caggaagagg atttgcagga gctgaattat ctgaagctgg tgattaaaga aaccctgcgc   1080

ctgcatccgc cgttgccgct ggtgatgccg cgtgagtgcc gtgaaccgtg tgttttgggc   1140

ggttacgaca ttccgagcaa aacgaagctg atcgttaatg ttttcgcgat taaccgtgac   1200

ccggaatact ggaaagacgc ggaaacgttt atgccggagc gttttgagaa tagcccgatt   1260

accgttatgg gttccgagta cgaatacctg ccatttggtg ctggtcgtcg tatgtgtcct   1320

ggtgcagcgc tgggtctggc caacgtggaa ctgccgctgg cgcacattct gtactatttc   1380

aactggaaac tgccgaacgg caagaccttc gaagatttgg acatgaccga gagctttggt   1440

gccactgtgc agcgcaaaac cgagctgctg ctggttccga ccgactttca aacgctgact   1500

gcgagcacct aatgagtcga ctaactttaa gaaggagata tatccatgga acctagctct   1560

cagaaactgt ctccgttgga atttgttgct gctatcctga agggcgacta cagcagcggt   1620
```

-continued

```
caggttgaag gtggtccacc gccaggtctg gcagctatgt tgatggaaaa taaggatttg   1680
gtgatggttc tgacgacgtc cgtggcagtc ctgatcggct gtgtcgtggt cctggcatgg   1740
cgtcgtgcgg caggtagcgg taagtacaag caacctgaac tgcctaaact ggtggtcccg   1800
aaagcagccg aaccggagga ggcagaggat gataaaacca agatcagcgt gtttttcggc   1860
acccaaaccg gtacggcaga aggtttcgcg aaggcttttg ttgaagaggc caaggcgcgt   1920
tatcagcagg cccgtttcaa agttatcgac ctggacgact atgcggcaga cgatgacgag   1980
tacgaagaga aactgaagaa ggaaaacttg gcattcttct tcttggcgtc ctacggtgac   2040
ggcgagccga cggacaacgc ggcacgcttt tacaaatggt ttacggaggg taaggaccgt   2100
ggtgaatggc tgaacaatct gcagtacggc gtttttggtc tgggtaaccg tcaatatgag   2160
catttcaata agatcgccat tgtcgtcgat gatctgatct tcgagcaagg tggcaagaag   2220
ctggttccgg tgggtctggg tgacgatgac cagtgcattg aggatgattt tgcggcgtgg   2280
cgtgaactgg tctggccgga actggataaa ctgctgcgta acgaagacga cgctaccgtg   2340
gcaaccccgt acagcgccgc tgtgctgcaa taccgcgtgg ttttccacga tcacattgac   2400
ggcctgatta gcgaaaacgg tagcccgaac ggtcatgcta atggcaatac cgtgtacgat   2460
gcgcaacacc cgtgccgtag caacgtcgcg gtcaagaagg aattgcatac tccggcgagc   2520
gatcgcagct gcacccacct ggaatttaac attagcggta ccggcctgat gtacgagacg   2580
ggtgaccacg tcggtgtgta ttgcgagaac ctgttggaaa ccgtggagga ggccgagaag   2640
ttgttgaacc tgagcccgca gacgtacttc tccgttcaca ccgacaacga ggacggtacg   2700
ccgttgagcg gcagcagcct gccgccaccg tttccgccgt gcaccttgcg cacggcattg   2760
accaaatacg cagacttgac ttctgcaccg aaaaagtcgg tgctggtggc gctggccgag   2820
tacgcatctg accagggtga agcggatcgt ttgcgtttct tggcgagccc gagcggcaaa   2880
gaggaatatg cacagtacat cttggcaagc cagcgcacgc tgctggaggt catggcggag   2940
ttcccgtcgg cgaaaccgcc gctgggtgtc tttttcgcgg gtgtcgctcc gcgcctgcag   3000
ccgcgtttct attccattag ctctagcccg aagatcgcac cgttccgtat tcacgtgacc   3060
tgcgccctgg tttatgacaa atcccctacc ggtcgcgttc ataagggcat ctgtagcacg   3120
tggatgaaaa atgcggtccc gctggaagaa agcaacgatt gttcctgggc tccgatcttc   3180
gtccgcaaca gcaacttcaa gctgccgacc gacccgaagg ttccgattat catgattggt   3240
ccgggtaccg gtctggcccc ttttcgtggc tttttgcaag agcgcttggc gttgaaagag   3300
agcggtgctg aattgggtcc ggcgatcttg ttctttggtt gccgtaaccg taaaatggac   3360
tttatttacg aggatgaact gaatgatttc gtcaaagcgg gcgttgtcag cgagctgatc   3420
gtcgctttta gccgcgaagg cccgatgaaa gaatacgtgc aacacaaaat gagccaacgt   3480
gcctccgatg tgtggaacat cattagcgac ggtggttatg tttatgtttg cggtgacgcg   3540
aagggtatgg ctcgtgatgt tcaccgtacc ctgcatacca tcgcacagga gcaaggtagc   3600
atgtccagct cggaggccga aggtatggtc aaaaacctgc aaaccaccgg tcgttacctg   3660
cgtgatgtgt ggtaataaaa gcttgaagga gatatactaa tgtctaccca gcaggttagc   3720
tccgagaata tcgttcgcaa cgcggcgaac ttccacccga atatctgggg taatcatttc   3780
ttgacgtgtc caagccagac gatcgattct tggacgcaac aacaccataa agagctgaaa   3840
gaagaggtcc gcaagatgat ggtgagcgac gcaaacaaac cggcacaacg tctgcgtctg   3900
attgacaccg ttcaacgttt gggcgtggcg tatcatttcg aaaaagaaat cgatgacgct   3960
ctggaaaaga tcggtcacga tccgtttgac gataaggatg acctgtatat cgttagcctg   4020
```

```
tgttttcgcc tgctgcgtca gcatggcatc aagattagct gcgatgtttt tgagaagttc   4080
aaagacgacg atggcaagtt taaggcttcc ctgatgaatg atgtccaagg tatgctgtcg   4140
ttgtatgaag cggcccacct ggcaattcat ggcgaggaca tcctggatga ggctattgtc   4200
tttacgacca cccacctgaa gagcaccgtt tctaactccc cggtcaattc cacctttgcg   4260
gaacagattc gccacagcct gcgtgtgccg ctgcgtaagg cagtcccgcg tttggagagc   4320
cgctacttcc tggatatcta tagccgtgac gacctgcacg acaagactct gctgaacttt   4380
gccaaactgg acttcaacat cctgcaggcg atgcaccaga aagaggcaag cgagatgacc   4440
cgttggtggc gtgatttcga tttcctgaag aagctgccgt acattcgtga tcgcgtggtt   4500
gaactgtact tttggatttt ggtcggtgtg agctaccaac cgaaattcag cacgggtcgt   4560
atctttttga gcaagattat ctgtctggaa accctggtgg acgacacgtt tgatgcgtac   4620
ggtactttcg acgaactggc cattttcacc gaggccgtta cgcgttggga cctgggtcat   4680
cgcgacgcgc tgcctgagta catgaaattc attttcaaga ccctgattga tgtgtacagc   4740
gaggcggaac aagagctggc aaaagagggc cgctcctata gcattcacta tgcgatccgt   4800
agcttccagg agttggtcat gaagtacttt tgcgaggcga aatggctgaa taagggttat   4860
gttccgagcc tggatgacta caagagcgtc agcctgcgca gcatcggctt cctgccgatc   4920
gccgtggctt cttttgtttt catgggcgac attgctacga aagaggtttt tgagtgggaa   4980
atgaataacc cgaaaatcat catcgcagcc gaaaccattt tccgctttct ggatgacatt   5040
gcaggtcatc gcttcgaaca aaaacgtgag cacagcccga gcgcaatcga gtgctacaaa   5100
aaccaacatg gtgtctcgga agaagaggca gtgaaagcgc tgagcttgga ggtcgccaat   5160
tcgtggaaag acattaacga agagctgctg ctgaacccta tggcaattcc actgccgttg   5220
ctgcaggtga tcctggattt gagccgtagc gcggacttca tgtacggtaa tgcgcaggac   5280
cgtttcacgc actccaccat gatgaaagat caagttgacc tggttctgaa agatccggtg   5340
aaactggacg attaagaatt c                                             5361
```

<210> SEQ ID NO 24
<211> LENGTH: 5414
<212> TYPE: DNA
<213> ORGANISM: Artificial Sequence
<220> FEATURE:
<223> OTHER INFORMATION: DNA sequence of the synthetic operon containing CYP71AV-P2, CPRm, and SaSAS including the NdeI and HindIII restriction sites in 3' and 5' ends

<400> SEQUENCE: 24

```
catatggctc tgttattagc agtttttgg tcggcgctta taatcctcgt agtaacctac      60
accatatccc tcctaatcaa ccaatggcga aaaccgaaac cccaagggaa gttccccccg    120
ggcccatggc gtctgccgat tatcggtcac atgcaccatt tgatcggcac catgccgcat    180
cgtggtgtta tggaactggc ccgtaagcat ggcagcctga tgcacctgca actgggtgaa    240
gtctctacga ttgttgtcag cagcccgcgt tgggcgaaag aggtcttgac cacctatgat    300
atcaccttcg ccaatcgccc ggaaaccctg actggcgaga tcgtcgcata ccacaacacg    360
gatatcgtcc tggcgccgta tggtgagtat tggcgtcaac tgcgtaaact gtgcacgctg    420
gagctgctga gcaacaagaa agtgaagagc ttccagagcc tgcgcgaaga agagtgttgg    480
aacctggtca aggacatccg cagcaccggc caaggtagcc caatcaatct gtcggagaac    540
attttcaaga tgattgcgac gattctgagc cgtgctgcgt tcggtaaggg tattaaggat    600
```

-continued

```
caaatgaagt ttaccgaact ggtgaaagaa atcctgcgtc tgaccggcgg ttttgatgtc    660
gctgacatct tccctagcaa gaagttgctg caccacctga gcggcaagcg tgcaaaactg    720
accaatatcc ataacaagct ggataatctg atcaataaca tcatcgcaga gcacccgggc    780
aaccgtacct cgtcctccca ggaaacgctg ctggacgttc tgctgcgcct gaaagagtct    840
gcggagtttc cgctgaccgc cgacaacgtt aaagcagtga tcctggatat gttcggcgct    900
ggtacggata ccagcagcgc gacgatcgag tgggcgatta gcgagctgat tcgctgccct    960
cgcgcgatgg agaaagtgca gacggaattg cgtcaggcac tgaatggcaa agagcgtatt   1020
caggaagagg atttgcagga gctgaattat ctgaagctgg tgattaaaga aaccctgcgc   1080
ctgcatccgc cgttgccgct ggtgatgccg cgtgagtgcc gtgaaccgtg tgttttgggc   1140
ggttacgaca ttccgagcaa aacgaagctg atcgttaatg ttttcgcgat taaccgtgac   1200
ccggaatact ggaaagacgc ggaaacgttt atgccggagc gttttgagaa tagcccgatt   1260
accgttatgg gttccgagta cgaatacctg ccatttggtg ctggtcgtcg tatgtgtcct   1320
ggtgcagcgc tgggtctggc caacgtggaa ctgccgctgg cgcacattct gtactatttc   1380
aactggaaac tgccgaacgg caagaccttc gaagatttgg acatgaccga gagctttggt   1440
gccactgtgc agcgcaaaac cgagctgctg ctggttccga ccgactttca aaccctgact   1500
gcaagcacct aatgagtcga ctaactttaa gaaggagata tatccatgga acctagctct   1560
cagaaactgt ctccgttgga atttgttgct gctatcctga agggcgacta cagcagcggt   1620
caggttgaag gtggtccacc gccaggtctg gcagctatgt tgatggaaaa taaggatttg   1680
gtgatggttc tgacgacgtc cgtggcagtc ctgatcggct gtgtcgtggt cctggcatgg   1740
cgtcgtgcgg caggtagcgg taagtacaag caacctgaac tgcctaaact ggtggtcccg   1800
aaagcagccg aaccggagga ggcagaggat gataaaacca agatcagcgt gtttttcggc   1860
acccaaaccg gtacggcaga aggtttcgcg aaggcttttg ttgaagaggc caaggcgcgt   1920
tatcagcagg cccgtttcaa agttatcgac ctggacgact atgcggcaga cgatgacgag   1980
tacgaagaga aactgaagaa ggaaaacttg gcattcttct tcttggcgtc ctacggtgac   2040
ggcgagccga cggacaacgc ggcacgcttt tacaaatggt ttacggaggg taaggaccgt   2100
ggtgaatggc tgaacaatct gcagtacggc gtttttggtc tgggtaaccg tcaatatgag   2160
catttcaata agatcgccat tgtcgtcgat gatctgatct tcgagcaagg tggcaagaag   2220
ctggttccgg tgggtctggg tgacgatgac cagtgcattg aggatgattt tgcggcgtgg   2280
cgtgaactgg tctggccgga actggataaa ctgctgcgta acgaagacga cgctaccgtg   2340
gcaaccccgt acagcgccgc tgtgctgcaa taccgcgtgg ttttccacga tcacattgac   2400
ggcctgatta gcgaaaacgg tagcccgaac ggtcatgcta atggcaatac cgtgtacgat   2460
gcgcaacacc cgtgccgtag caacgtcgcg gtcaagaagg aattgcatac tccggcgagc   2520
gatcgcagct gcacccacct ggaatttaac attagcggta ccggcctgat gtacgagacg   2580
ggtgaccacg tcggtgtgta ttgcgagaac ctgttggaaa ccgtggagga ggccgagaag   2640
ttgttgaacc tgagcccgca gacgtacttc tccgttcaca ccgacaacga ggacggtacg   2700
ccgttgagcg gcagcagcct gccgccaccg tttccgccgt gcaccttgcg cacggcattg   2760
accaaatacg cagacttgac ttctgcaccg aaaaagtcgg tgctggtggc gctggccgag   2820
tacgcatctg accagggtga agcggatcgt ttgcgtttct tggcgagccc gagcggcaaa   2880
gaggaatatg cacagtacat cttggcaagc cagcgcacgc tgctggaggt catggcggag   2940
ttcccgtcgg cgaaaccgcc gctgggtgtc tttttcgcgg gtgtcgctcc gcgcctgcag   3000
```

-continued

```
ccgcgtttct attccattag ctctagcccg aagatcgcac cgttccgtat tcacgtgacc   3060
tgcgccctgg tttatgacaa atcccctacc ggtcgcgttc ataagggcat ctgtagcacg   3120
tggatgaaaa atgcggtccc gctggaagaa agcaacgatt gttcctgggc tccgatcttc   3180
gtccgcaaca gcaacttcaa gctgccgacc gacccgaagg ttccgattat catgattggt   3240
ccgggtaccg gtctggcccc ttttcgtggc tttttgcaag agcgcttggc gttgaaagag   3300
agcggtgctg aattgggtcc ggcgatcttg ttctttggtt gccgtaaccg taaaatggac   3360
tttatttacg aggatgaact gaatgatttc gtcaaagcgg gcgttgtcag cgagctgatc   3420
gtcgctttta gccgcgaagg cccgatgaaa gaatacgtgc aacacaaaat gagccaacgt   3480
gcctccgatg tgtggaacat cattagcgac ggtggttatg tttatgtttg cggtgacgcg   3540
aagggtatgg ctcgtgatgt tcaccgtacc ctgcatacca tcgcacagga gcaaggtagc   3600
atgtccagct cggaggccga aggtatggtc aaaaacctgc aaaccaccgg tcgttacctg   3660
cgtgatgtgt ggtaataaaa gcttaggagg taaaacatat ggacagcagc accgccaccg   3720
caatgaccgc accattcatc gacccgacgg atcatgtgaa tctgaaaacc gacacggatg   3780
cgagcgaaaa tcgtcgtatg ggtaactaca agccgagcat ttggaactac gattttctgc   3840
agtccctggc gacgcaccac aacattgttg aagagcgtca cctgaagctg gcagagaaac   3900
tgaaaggtca agtgaaattc atgttcggtg cgccgatgga gccattggct aagttggagc   3960
tggttgatgt ggtgcaacgc ttgggtctga accacctgtt cgagactgaa atcaaagaag   4020
ctctgttcag catctacaaa gatggcagca atggctggtg gtttggccat ctgcatgcta   4080
cctctttgcg cttccgtctg ttgcgccaat gtggcctgtt tatcccgcag gacgttttca   4140
aaacctttca aaacaagacc ggtgagtttg acatgaagct gtgggacaac gttaagggcc   4200
tgctgagcct gtacgaggcg agctacctgg gctggaaggg cgagaacatc ttggatgaag   4260
caaaggcgtt cacgaccaag tgcctgaaga gcgcatggga gaacattagc gagaagtggc   4320
tggcgaagcg tgttaaacat gcgttggcgc tgccgctgca ctggcgtgtt ccgcgtattg   4380
aagcacgctg gtttatcgag gtgtacgaac aagaggccaa tatgaatccg acgctgctga   4440
aactggcgaa actggacttc aacatggtcc aaagcattca ccagaaagaa atcggtgaac   4500
tggcccgctg gtgggttact accggcctgg acaagctgga tttcgcacgc aacaatctgt   4560
tgcagtctta tatgtggagc tgcgccatcg cgtccgaccc gaaattcaaa ctggcgcgtg   4620
aaaccattgt cgagatcggt tccgtgttga cggttgtcga cgacggctat gatgtgtacg   4680
gttctatgga tgagctggac ctgtacacca gctcggtgga gcgttggtcc tgtgtcaaaa   4740
ttgacaagct gcctaatacg ctgaagctga tctttatgtc tatgttcaac aaaaccaacg   4800
aggtgggtct gcgtgttcaa cacgagcgtg gttacaatag catcccgacc ttcattaagg   4860
cgtgggtgga acagtgtaag agctatcaaa aagaggcgcg ttggtttcat ggtggtcaca   4920
cgcctccgct ggaagaatac agcctgaacg gtctggtcag cattggtttt ccgctgttgc   4980
tgatcaccgg ctatgttgcg attgctgaga atgaagcagc cctggataaa gtccacccgc   5040
tgccggacct gctgcattat tccagcttgc tgagccgtct gattaatgat atcggcacta   5100
gcccggatga aatggcgcgt ggtgacaatc tgaagagcat tcactgctat atgaatgaaa   5160
ccggtgccag cgaagaggtc gcacgcgagc acatcaaagg cgtcatcgaa gagaattgga   5220
aaattctgaa ccagtgttgc tttgaccagt cccagttcca ggagccgttc atcacgttta   5280
acctgaacag cgtgcgcggc tcgcatttct tctatgaatt tggtgatggt tttggtgtta   5340
```

ccgacagctg gaccaaggtg gatatgaaaa gcgtcctgat tgatccgatt ccgctgggtg 5400
aagagtaagc ttgc 5414

<210> SEQ ID NO 25
<211> LENGTH: 5361
<212> TYPE: DNA
<213> ORGANISM: Artificial Sequence
<220> FEATURE:
<223> OTHER INFORMATION: DNA sequence of the synthetic operon containing CYP71AV-P20, CPRm, and ClASS including the NdeI and HindIII restriction sites in 3' and 5' ends

<400> SEQUENCE: 25
catatggcac tgttgctggc tgtcttttgg tctgctctga ttattttggt ggttacctac 60
accatctccc tgctgattaa ccagtggcgt aaaccgaaac cacagggtaa attcccgccg 120
ggtccgtggc gtctgccgat tatcggtcac atgcaccatt tgatcggcac catgccgcat 180
cgtggtgtta tggaactggc ccgtaagcat ggcagcctga tgcacctgca actgggtgaa 240
gtctctacga ttgttgtcag cagcccgcgt tgggcgaaag aggtcttgac cacctatgat 300
atcaccttcg ccaatcgccc ggaaaccctg actggcgaga tcgtcgcata ccacaacacg 360
gatatcgtcc tggcgccgta tggtgagtat tggcgtcaac tgcgtaaact gtgcacgctg 420
gagctgctga gcaacaagaa agtgaagagc ttccagagcc tgcgcgaaga agagtgttgg 480
aacctggtca aggacatccg cagcaccggc caaggtagcc caatcaatct gtcggagaac 540
attttcaaga tgattgcgac gattctgagc cgtgctgcgt tcggtaaggg tattaaggat 600
caaatgaagt ttaccgaact ggtgaaagaa atcctgcgtc tgaccggcgg ttttgatgtc 660
gctgacatct tccctagcaa gaagttgctg caccacctga gcggcaagcg tgcaaaactg 720
accaatatcc ataacaagct ggataatctg atcaataaca tcatcgcaga gcacccgggc 780
aaccgtacct cgtcctccca ggaaacgctg ctggacgttc tgctgcgcct gaaagagtct 840
gcggagtttc cgctgaccgc cgacaacgtt aaagcagtga tcctggatat gttcggcgct 900
ggtacggata ccagcagcgc gacgatcgag tgggcgatta gcgagctgat tcgctgccct 960
cgcgcgatgg agaaagtgca gacggaattg cgtcaggcac tgaatggcaa agagcgtatt 1020
caggaagagg atttgcagga gctgaattat ctgaagctgg tgattaaaga aaccctgcgc 1080
ctgcatccgc cgttgccgct ggtgatgccg cgtgagtgcc gtgaaccgtg tgttttgggc 1140
ggttacgaca ttccgagcaa aacgaagctg atcgttaatg ttttcgcgat taaccgtgac 1200
ccggaatact ggaaagacgc ggaaacgttt atgccggagc gttttgagaa tagcccgatt 1260
accgttatgg gttccgagta cgaatacctg ccatttggtg ctggtcgtcg tatgtgtcct 1320
ggtgcagcgc tgggtctggc caacgtggaa ctgccgctgg cgcacattct gtactatttc 1380
aactggaaac tgccgaacgg caagaccttc gaagatttgg acatgaccga gagctttggt 1440
gccactgtgc agcgcaaaac cgagctgctg ctggttccga ccgactttca aacgctgact 1500
gcgagcacct aatgagtcga ctaactttaa gaaggagata tatccatgga acctagctct 1560
cagaaactgt ctccgttgga atttgttgct gctatcctga agggcgacta cagcagcggt 1620
caggttgaag gtggtccacc gccaggtctg gcagctatgt tgatggaaaa taaggatttg 1680
gtgatggttc tgacgacgtc cgtggcagtc ctgatcggct gtgtcgtggt cctggcatgg 1740
cgtcgtgcgg caggtagcgg taagtacaag caacctgaac tgcctaaact ggtggtcccg 1800
aaagcagccg aaccggagga ggcagaggat gataaaacca agatcagcgt gtttttcggc 1860
acccaaaccg gtacggcaga aggtttcgcg aaggcttttg ttgaagaggc caaggcgcgt 1920
tatcagcagg cccgtttcaa agttatcgac ctggacgact atgcggcaga cgatgacgag 1980
tacgaagaga aactgaagaa ggaaaacttg gcattcttct tcttggcgtc ctacggtgac 2040
ggcgagccga cggacaacgc ggcacgcttt tacaaatggt ttacggaggg taaggaccgt 2100
ggtgaatggc tgaacaatct gcagtacggc gtttttggtc tgggtaaccg tcaatatgag 2160
catttcaata agatcgccat tgtcgtcgat gatctgatct tcgagcaagg tggcaagaag 2220
ctggttccgg tgggtctggg tgacgatgac cagtgcattg aggatgattt tgcggcgtgg 2280
cgtgaactgg tctggccgga actggataaa ctgctgcgta acgaagacga cgctaccgtg 2340
gcaaccccgt acagcgccgc tgtgctgcaa taccgcgtgg ttttccacga tcacattgac 2400
ggcctgatta gcgaaaacgg tagcccgaac ggtcatgcta atggcaatac cgtgtacgat 2460
gcgcaacacc cgtgccgtag caacgtcgcg gtcaagaagg aattgcatac tccggcgagc 2520
gatcgcagct gcacccacct ggaatttaac attagcggta ccggcctgat gtacgagacg 2580
ggtgaccacg tcggtgtgta ttgcgagaac ctgttggaaa ccgtggagga ggccgagaag 2640
ttgttgaacc tgagcccgca gacgtacttc tccgttcaca ccgacaacga ggacggtacg 2700
ccgttgagcg gcagcagcct gccgccaccg tttccgccgt gcaccttgcg cacggcattg 2760
accaaatacg cagacttgac ttctgcaccg aaaaagtcgg tgctggtggc gctggccgag 2820
tacgcatctg accagggtga agcggatcgt ttgcgtttct tggcgagccc gagcggcaaa 2880
gaggaatatg cacagtacat cttggcaagc cagcgcacgc tgctggaggt catggcggag 2940
ttcccgtcgg cgaaaccgcc gctgggtgtc tttttcgcgg gtgtcgctcc gcgcctgcag 3000
ccgcgtttct attccattag ctctagcccg aagatcgcac cgttccgtat tcacgtgacc 3060
tgcgccctgg tttatgacaa atcccctacc ggtcgcgttc ataagggcat ctgtagcacg 3120
tggatgaaaa atgcggtccc gctggaagaa agcaacgatt gttcctgggc tccgatcttc 3180
gtccgcaaca gcaacttcaa gctgccgacc gacccgaagg ttccgattat catgattggt 3240
ccgggtaccg gtctggcccc ttttcgtggc tttttgcaag agcgcttggc gttgaaagag 3300
agcggtgctg aattgggtcc ggcgatcttg ttctttggtt gccgtaaccg taaaatggac 3360
tttatttacg aggatgaact gaatgatttc gtcaaagcgg gcgttgtcag cgagctgatc 3420
gtcgctttta gccgcgaagg cccgatgaaa gaatacgtgc aacacaaaat gagccaacgt 3480
gcctccgatg tgtggaacat cattagcgac ggtggttatg tttatgtttg cggtgacgcg 3540
aagggtatgg ctcgtgatgt tcaccgtacc ctgcatacca tcgcacagga gcaaggtagc 3600
atgtccagct cggaggccga aggtatggtc aaaaacctgc aaaccaccgg tcgttacctg 3660
cgtgatgtgt ggtaataaaa gcttgaagga gatatactaa tgtctaccca gcaggttagc 3720
tccgagaata tcgttcgcaa cgcggcgaac ttccacccga atatctgggg taatcatttc 3780
ttgacgtgtc caagccagac gatcgattct tggacgcaac aacaccataa agagctgaaa 3840
gaagaggtcc gcaagatgat ggtgagcgac gcaaacaaac cggcacaacg tctgcgtctg 3900
attgacaccg ttcaacgttt gggcgtggcg tatcatttcg aaaaagaaat cgatgacgct 3960
ctggaaaaga tcggtcacga tccgtttgac gataaggatg acctgtatat cgttagcctg 4020
tgttttcgcc tgctgcgtca gcatggcatc aagattagct gcgatgtttt tgagaagttc 4080
aaagacgacg atggcaagtt taaggcttcc ctgatgaatg atgtccaagg tatgctgtcg 4140
ttgtatgaag cggcccacct ggcaattcat ggcgaggaca tcctggatga ggctattgtc 4200
tttacgacca cccacctgaa gagcaccgtt tctaactccc cggtcaattc cacctttgcg 4260

-continued gaacagattc gccacagcct gcgtgtgccg ctgcgtaagg cagtcccgcg tttggagagc 4320
cgctacttcc tggatatcta tagccgtgac gacctgcacg acaagactct gctgaacttt 4380
gccaaactgg acttcaacat cctgcaggcg atgcaccaga aagaggcaag cgagatgacc 4440
cgttggtggc gtgatttcga tttcctgaag aagctgccgt acattcgtga tcgcgtggtt 4500
gaactgtact tttggatttt ggtcggtgtg agctaccaac cgaaattcag cacgggtcgt 4560
atctttttga gcaagattat ctgtctggaa accctggtgg acgacacgtt tgatgcgtac 4620
ggtactttcg acgaactggc cattttcacc gaggccgtta cgcgttggga cctgggtcat 4680
cgcgacgcgc tgcctgagta catgaaattc attttcaaga ccctgattga tgtgtacagc 4740
gaggcggaac aagagctggc aaaagagggc cgctcctata gcattcacta tgcgatccgt 4800
agcttccagg agttggtcat gaagtacttt tgcgaggcga aatggctgaa taagggttat 4860
gttccgagcc tggatgacta caagagcgtc agcctgcgca gcatcggctt cctgccgatc 4920
gccgtggctt cttttgtttt catgggcgac attgctacga aagaggtttt tgagtgggaa 4980
atgaataacc cgaaaatcat catcgcagcc gaaaccattt tccgctttct ggatgacatt 5040
gcaggtcatc gcttcgaaca aaaacgtgag cacagcccga gcgcaatcga gtgctacaaa 5100
aaccaacatg gtgtctcgga agaagaggca gtgaaagcgc tgagcttgga ggtcgccaat 5160
tcgtggaaag acattaacga agagctgctg ctgaacccta tggcaattcc actgccgttg 5220
ctgcaggtga tcctggattt gagccgtagc gcggacttca tgtacggtaa tgcgcaggac 5280
cgtttcacgc actccaccat gatgaaagat caagttgacc tggttctgaa agatccggtg 5340
aaactggacg attaagaatt c 5361

<210> SEQ ID NO 26
<211> LENGTH: 5414
<212> TYPE: DNA
<213> ORGANISM: Artificial Sequence
<220> FEATURE:
<223> OTHER INFORMATION: DNA sequence of the synthetic operon containing CYP71AV-P2O, CPRm, and SaSAS including the NdeI and HindIII restriction sites in 3' and 5' ends

<400> SEQUENCE: 26
catatggcac tgttgctggc tgtcttttgg tctgctctga ttattttggt ggttacctac 60
accatctccc tgctgattaa ccagtggcgt aaaccgaaac cacagggtaa attcccgccg 120
ggtccgtggc gtctgccgat tatcggtcac atgcaccatt tgatcggcac catgccgcat 180
cgtggtgtta tggaactggc ccgtaagcat ggcagcctga tgcacctgca actgggtgaa 240
gtctctacga ttgttgtcag cagcccgcgt tgggcgaaag aggtcttgac cacctatgat 300
atcaccttcg ccaatcgccc ggaaaccctg actggcgaga tcgtcgcata ccacaacacg 360
gatatcgtcc tggcgccgta tggtgagtat tggcgtcaac tgcgtaaact gtgcacgctg 420
gagctgctga gcaacaagaa agtgaagagc ttccagagcc tgcgcgaaga agagtgttgg 480
aacctggtca aggacatccg cagcaccggc caaggtagcc caatcaatct gtcggagaac 540
attttcaaga tgattgcgac gattctgagc cgtgctgcgt tcggtaaggg tattaaggat 600
caaatgaagt ttaccgaact ggtgaaagaa atcctgcgtc tgaccggcgg ttttgatgtc 660
gctgacatct tccctagcaa gaagttgctg caccacctga gcggcaagcg tgcaaaactg 720
accaatatcc ataacaagct ggataatctg atcaataaca tcatcgcaga gcacccgggc 780
aaccgtacct cgtcctccca ggaaacgctg ctggacgttc tgctgcgcct gaaagagtct 840
gcggagtttc cgctgaccgc cgacaacgtt aaagcagtga tcctggatat gttcggcgct 900

```
ggtacggata ccagcagcgc gacgatcgag tgggcgatta gcgagctgat tcgctgccct    960
cgcgcgatgg agaaagtgca gacggaattg cgtcaggcac tgaatggcaa agagcgtatt   1020
caggaagagg atttgcagga gctgaattat ctgaagctgg tgattaaaga aaccctgcgc   1080
ctgcatccgc cgttgccgct ggtgatgccg cgtgagtgcc gtgaaccgtg tgttttgggc   1140
ggttacgaca ttccgagcaa aacgaagctg atcgttaatg ttttcgcgat taaccgtgac   1200
ccggaatact ggaaagacgc ggaaacgttt atgccggagc gttttgagaa tagcccgatt   1260
accgttatgg gttccgagta cgaatacctg ccatttggtg ctggtcgtcg tatgtgtcct   1320
ggtgcagcgc tgggtctggc caacgtggaa ctgccgctgg cgcacattct gtactatttc   1380
aactggaaac tgccgaacgg caagaccttc gaagatttgg acatgaccga gagctttggt   1440
gccactgtgc agcgcaaaac cgagctgctg ctggttccga ccgactttca aacgctgact   1500
gcgagcacct aatgagtcga ctaactttaa gaaggagata tatccatgga acctagctct   1560
cagaaactgt ctccgttgga atttgttgct gctatcctga agggcgacta cagcagcggt   1620
caggttgaag gtggtccacc gccaggtctg gcagctatgt tgatggaaaa taaggatttg   1680
gtgatggttc tgacgacgtc cgtggcagtc ctgatcggct gtgtcgtggt cctggcatgg   1740
cgtcgtgcgg caggtagcgg taagtacaag caacctgaac tgcctaaact ggtggtcccg   1800
aaagcagccg aaccggagga ggcagaggat gataaaacca agatcagcgt gtttttcggc   1860
acccaaaccg gtacggcaga aggtttcgcg aaggcttttg ttgaagaggc caaggcgcgt   1920
tatcagcagg cccgtttcaa agttatcgac ctggacgact atgcggcaga cgatgacgag   1980
tacgaagaga aactgaagaa ggaaaacttg gcattcttct tcttggcgtc ctacggtgac   2040
ggcgagccga cggacaacgc ggcacgcttt tacaaatggt ttacggaggg taaggaccgt   2100
ggtgaatggc tgaacaatct gcagtacggc gtttttggtc tgggtaaccg tcaatatgag   2160
catttcaata agatcgccat tgtcgtcgat gatctgatct tcgagcaagg tggcaagaag   2220
ctggttccgg tgggtctggg tgacgatgac cagtgcattg aggatgattt tgcggcgtgg   2280
cgtgaactgg tctggccgga actggataaa ctgctgcgta acgaagacga cgctaccgtg   2340
gcaaccccgt acagcgccgc tgtgctgcaa taccgcgtgg ttttccacga tcacattgac   2400
ggcctgatta gcgaaaacgg tagcccgaac ggtcatgcta atggcaatac cgtgtacgat   2460
gcgcaacacc cgtgccgtag caacgtcgcg gtcaagaagg aattgcatac tccggcgagc   2520
gatcgcagct gcacccacct ggaatttaac attagcggta ccggcctgat gtacgagacg   2580
ggtgaccacg tcggtgtgta ttgcgagaac ctgttggaaa ccgtggagga ggccgagaag   2640
ttgttgaacc tgagcccgca gacgtacttc tccgttcaca ccgacaacga ggacggtacg   2700
ccgttgagcg gcagcagcct gccgccaccg tttccgccgt gcaccttgcg cacggcattg   2760
accaaatacg cagacttgac ttctgcaccg aaaaagtcgg tgctggtggc gctggccgag   2820
tacgcatctg accagggtga agcggatcgt ttgcgtttct tggcgagccc gagcggcaaa   2880
gaggaatatg cacagtacat cttggcaagc cagcgcacgc tgctggaggt catggcggag   2940
ttcccgtcgg cgaaaccgcc gctgggtgtc tttttcgcgg gtgtcgctcc gcgcctgcag   3000
ccgcgtttct attccattag ctctagcccg aagatcgcac cgttccgtat tcacgtgacc   3060
tgcgccctgg tttatgacaa atcccctacc ggtcgcgttc ataagggcat ctgtagcacg   3120
tggatgaaaa atgcggtccc gctggaagaa agcaacgatt gttcctgggc tccgatcttc   3180
gtccgcaaca gcaacttcaa gctgccgacc gacccgaagg ttccgattat catgattggt   3240
```

-continued

```
ccgggtaccg gtctggcccc ttttcgtggc tttttgcaag agcgcttggc gttgaaagag   3300
agcggtgctg aattgggtcc ggcgatcttg ttctttggtt gccgtaaccg taaaatggac   3360
tttatttacg aggatgaact gaatgatttc gtcaaagcgg gcgttgtcag cgagctgatc   3420
gtcgctttta gccgcgaagg cccgatgaaa gaatacgtgc aacacaaaat gagccaacgt   3480
gcctccgatg tgtggaacat cattagcgac ggtggttatg tttatgtttg cggtgacgcg   3540
aagggtatgg ctcgtgatgt tcaccgtacc ctgcatacca tcgcacagga gcaaggtagc   3600
atgtccagct cggaggccga aggtatggtc aaaaacctgc aaaccaccgg tcgttacctg   3660
cgtgatgtgt ggtaataaaa gcttaggagg taaaacatat ggacagcagc accgccaccg   3720
caatgaccgc accattcatc gacccgacgg atcatgtgaa tctgaaaacc gacacggatg   3780
cgagcgaaaa tcgtcgtatg ggtaactaca agccgagcat ttggaactac gattttctgc   3840
agtccctggc gacgcaccac aacattgttg aagagcgtca cctgaagctg gcagagaaac   3900
tgaaaggtca agtgaaattc atgttcggtg cgccgatgga gccattggct aagttggagc   3960
tggttgatgt ggtgcaacgc ttgggtctga accacctgtt cgagactgaa atcaaagaag   4020
ctctgttcag catctacaaa gatggcagca atggctggtg gtttggccat ctgcatgcta   4080
cctctttgcg cttccgtctg ttgcgccaat gtggcctgtt tatcccgcag gacgttttca   4140
aaacctttca aaacaagacc ggtgagtttg acatgaagct gtgggacaac gttaagggcc   4200
tgctgagcct gtacgaggcg agctacctgg gctggaaggg cgagaacatc ttggatgaag   4260
caaaggcgtt cacgaccaag tgcctgaaga gcgcatggga gaacattagc gagaagtggc   4320
tggcgaagcg tgttaaacat gcgttggcgc tgccgctgca ctggcgtgtt ccgcgtattg   4380
aagcacgctg gtttatcgag gtgtacgaac aagaggccaa tatgaatccg acgctgctga   4440
aactggcgaa actggacttc aacatggtcc aaagcattca ccagaaagaa atcggtgaac   4500
tggcccgctg gtgggttact accggcctgg acaagctgga tttcgcacgc aacaatctgt   4560
tgcagtctta tatgtggagc tgcgccatcg cgtccgaccc gaaattcaaa ctggcgcgtg   4620
aaaccattgt cgagatcggt tccgtgttga cggttgtcga cgacggctat gatgtgtacg   4680
gttctatgga tgagctggac ctgtacacca gctcggtgga gcgttggtcc tgtgtcaaaa   4740
ttgacaagct gcctaatacg ctgaagctga tctttatgtc tatgttcaac aaaaccaacg   4800
aggtgggtct gcgtgttcaa cacgagcgtg gttacaatag catcccgacc ttcattaagg   4860
cgtgggtgga acagtgtaag agctatcaaa aagaggcgcg ttggtttcat ggtggtcaca   4920
cgcctccgct ggaagaatac agcctgaacg gtctggtcag cattggtttt ccgctgttgc   4980
tgatcaccgg ctatgttgcg attgctgaga atgaagcagc cctggataaa gtccacccgc   5040
tgccggacct gctgcattat tccagcttgc tgagccgtct gattaatgat atcggcacta   5100
gcccggatga aatggcgcgt ggtgacaatc tgaagagcat tcactgctat atgaatgaaa   5160
ccggtgccag cgaagaggtc gcacgcgagc acatcaaagg cgtcatcgaa gagaattgga   5220
aaattctgaa ccagtgttgc tttgaccagt cccagttcca ggagccgttc atcacgttta   5280
acctgaacag cgtgcgcggc tcgcatttct tctatgaatt tggtgatggt tttggtgtta   5340
ccgacagctg gaccaaggtg gatatgaaaa gcgtcctgat tgatccgatt ccgctgggtg   5400
aagagtaagc ttgc                                                     5414
```

<210> SEQ ID NO 27
<211> LENGTH: 1512
<212> TYPE: DNA
<213> ORGANISM: Artificial Sequence
<220> FEATURE:
<223> OTHER INFORMATION: CYP71AV8-L358A DNA sequence

<400> SEQUENCE: 27
atggctctgt tattagcagt tttttggtcg gcgcttataa tcctcgtagt aacctacacc 60
atatccctcc taatcaacca atggcgaaaa ccgaaacccc aagggaagtt ccccccgggc 120
ccatggcgtc tgccgattat cggtcacatg caccatttga tcggcaccat gccgcatcgt 180
ggtgttatgg aactggcccg taagcatggc agcctgatgc acctgcaact gggtgaagtc 240
tctacgattg ttgtcagcag cccgcgttgg gcgaaagagg tcttgaccac ctatgatatc 300
accttcgcca atcgcccgga aaccctgact ggcgagatcg tcgcatacca caacacggat 360
atcgtcctgg cgccgtatgg tgagtattgg cgtcaactgc gtaaactgtg cacgctggag 420
ctgctgagca acaagaaagt gaagagcttc cagagcctgc gcgaagaaga gtgttggaac 480
ctggtcaagg acatccgcag caccggccaa ggtagcccaa tcaatctgtc ggagaacatt 540
ttcaagatga ttgcgacgat tctgagccgt gctgcgttcg gtaagggtat taaggatcaa 600
atgaagttta ccgaactggt gaaagaaatc ctgcgtctga ccggcggttt tgatgtcgct 660
gacatcttcc ctagcaagaa gttgctgcac cacctgagcg gcaagcgtgc aaaactgacc 720
aatatccata acaagctgga taatctgatc aataacatca tcgcagagca cccgggcaac 780
cgtacctcgt cctcccagga aacgctgctg gacgttctgc tgcgcctgaa agagtctgcg 840
gagtttccgc tgaccgccga caacgttaaa gcagtgatcc tggatatgtt cggcgctggt 900
acggatacca gcagcgcgac gatcgagtgg gcgattagcg agctgattcg ctgccctcgc 960
gcgatggaga aagtgcagac ggaattgcgt caggcactga atggcaaaga gcgtattcag 1020
gaagaggatt tgcaggagct gaattatctg aagctggtga ttaaagaaac cctgcgcctg 1080
catccgccgg ctccgctggt gatgccgcgt gagtgccgtg aaccgtgtgt tttgggcggt 1140
tacgacattc cgagcaaaac gaagctgatc gttaatgttt tcgcgattaa ccgtgacccg 1200
gaatactgga aagacgcgga aacgtttatg ccggagcgtt ttgagaatag cccgattacc 1260
gttatgggtt ccgagtacga atacctgcca tttggtgctg gtcgtcgtat gtgtcctggt 1320
gcagcgctgg gtctggccaa cgtggaactg ccgctggcgc acattctgta ctatttcaac 1380
tggaaactgc cgaacggcaa gaccttcgaa gatttggaca tgaccgagag ctttggtgcc 1440
actgtgcagc gcaaaaccga gctgctgctg gttccgaccg actttcaaac cctgactgcg 1500
agcacctaat ga 1512

<210> SEQ ID NO 28
<211> LENGTH: 502
<212> TYPE: PRT
<213> ORGANISM: Artificial Sequence
<220> FEATURE:
<223> OTHER INFORMATION: CYP71AV8-L358A amino acid sequence

<400> SEQUENCE: 28

Met Ala Leu Leu Leu Ala Val Phe Trp Ser Ala Leu Ile Ile Leu Val
1 5 10 15

Val Thr Tyr Thr Ile Ser Leu Leu Ile Asn Gln Trp Arg Lys Pro Lys
20 25 30

Pro Gln Gly Lys Phe Pro Pro Gly Pro Trp Arg Leu Pro Ile Ile Gly
35 40 45

His Met His His Leu Ile Gly Thr Met Pro His Arg Gly Val Met Glu
50 55 60

-continued

```
Leu Ala Arg Lys His Gly Ser Leu Met His Leu Gln Leu Gly Glu Val
65                  70                  75                  80

Ser Thr Ile Val Val Ser Ser Pro Arg Trp Ala Lys Glu Val Leu Thr
                85                  90                  95

Thr Tyr Asp Ile Thr Phe Ala Asn Arg Pro Glu Thr Leu Thr Gly Glu
            100                 105                 110

Ile Val Ala Tyr His Asn Thr Asp Ile Val Leu Ala Pro Tyr Gly Glu
        115                 120                 125

Tyr Trp Arg Gln Leu Arg Lys Leu Cys Thr Leu Glu Leu Leu Ser Asn
    130                 135                 140

Lys Lys Val Lys Ser Phe Gln Ser Leu Arg Glu Glu Glu Cys Trp Asn
145                 150                 155                 160

Leu Val Lys Asp Ile Arg Ser Thr Gly Gln Gly Ser Pro Ile Asn Leu
                165                 170                 175

Ser Glu Asn Ile Phe Lys Met Ile Ala Thr Ile Leu Ser Arg Ala Ala
            180                 185                 190

Phe Gly Lys Gly Ile Lys Asp Gln Met Lys Phe Thr Glu Leu Val Lys
        195                 200                 205

Glu Ile Leu Arg Leu Thr Gly Gly Phe Asp Val Ala Asp Ile Phe Pro
    210                 215                 220

Ser Lys Lys Leu Leu His His Leu Ser Gly Lys Arg Ala Lys Leu Thr
225                 230                 235                 240

Asn Ile His Asn Lys Leu Asp Asn Leu Ile Asn Asn Ile Ile Ala Glu
                245                 250                 255

His Pro Gly Asn Arg Thr Ser Ser Ser Gln Glu Thr Leu Leu Asp Val
            260                 265                 270

Leu Leu Arg Leu Lys Glu Ser Ala Glu Phe Pro Leu Thr Ala Asp Asn
        275                 280                 285

Val Lys Ala Val Ile Leu Asp Met Phe Gly Ala Gly Thr Asp Thr Ser
    290                 295                 300

Ser Ala Thr Ile Glu Trp Ala Ile Ser Glu Leu Ile Arg Cys Pro Arg
305                 310                 315                 320

Ala Met Glu Lys Val Gln Thr Glu Leu Arg Gln Ala Leu Asn Gly Lys
                325                 330                 335

Glu Arg Ile Gln Glu Glu Asp Leu Gln Glu Leu Asn Tyr Leu Lys Leu
            340                 345                 350

Val Ile Lys Glu Thr Leu Arg Leu His Pro Pro Ala Pro Leu Val Met
        355                 360                 365

Pro Arg Glu Cys Arg Glu Pro Cys Val Leu Gly Gly Tyr Asp Ile Pro
    370                 375                 380

Ser Lys Thr Lys Leu Ile Val Asn Val Phe Ala Ile Asn Arg Asp Pro
385                 390                 395                 400

Glu Tyr Trp Lys Asp Ala Glu Thr Phe Met Pro Glu Arg Phe Glu Asn
                405                 410                 415

Ser Pro Ile Thr Val Met Gly Ser Glu Tyr Glu Tyr Leu Pro Phe Gly
            420                 425                 430

Ala Gly Arg Arg Met Cys Pro Gly Ala Ala Leu Gly Leu Ala Asn Val
        435                 440                 445

Glu Leu Pro Leu Ala His Ile Leu Tyr Tyr Phe Asn Trp Lys Leu Pro
    450                 455                 460

Asn Gly Lys Thr Phe Glu Asp Leu Asp Met Thr Glu Ser Phe Gly Ala
465                 470                 475                 480

Thr Val Gln Arg Lys Thr Glu Leu Leu Leu Val Pro Thr Asp Phe Gln
```

-continued

```
            485                 490                 495

Thr Leu Thr Ala Ser Thr
            500


<210> SEQ ID NO 29
<211> LENGTH: 1512
<212> TYPE: DNA
<213> ORGANISM: Artificial Sequence
<220> FEATURE:
<223> OTHER INFORMATION: CYP71AV8-L358F DNA sequence

<400> SEQUENCE: 29

atggctctgt tattagcagt tttttggtcg gcgcttataa tcctcgtagt aacctacacc      60

atatccctcc taatcaacca atggcgaaaa ccgaaacccc aagggaagtt ccccccgggc     120

ccatggcgtc tgccgattat cggtcacatg caccatttga tcggcaccat gccgcatcgt     180

ggtgttatgg aactggcccg taagcatggc agcctgatgc acctgcaact gggtgaagtc     240

tctacgattg ttgtcagcag cccgcgttgg gcgaaagagg tcttgaccac ctatgatatc     300

accttcgcca atcgcccgga aaccctgact ggcgagatcg tcgcatacca caacacggat     360

atcgtcctgg cgccgtatgg tgagtattgg cgtcaactgc gtaaactgtg cacgctggag     420

ctgctgagca acaagaaagt gaagagcttc cagagcctgc gcgaagaaga gtgttggaac     480

ctggtcaagg acatccgcag caccggccaa ggtagcccaa tcaatctgtc ggagaacatt     540

ttcaagatga ttgcgacgat tctgagccgt gctgcgttcg gtaagggtat taaggatcaa     600

atgaagttta ccgaactggt gaaagaaatc ctgcgtctga ccggcggttt tgatgtcgct     660

gacatcttcc ctagcaagaa gttgctgcac cacctgagcg gcaagcgtgc aaaactgacc     720

aatatccata acaagctgga taatctgatc aataacatca tcgcagagca cccgggcaac     780

cgtacctcgt cctcccagga aacgctgctg gacgttctgc tgcgcctgaa agagtctgcg     840

gagtttccgc tgaccgccga caacgttaaa gcagtgatcc tggatatgtt cggcgctggt     900

acggatacca gcagcgcgac gatcgagtgg gcgattagcg agctgattcg ctgccctcgc     960

gcgatggaga aagtgcagac ggaattgcgt caggcactga atggcaaaga gcgtattcag    1020

gaagaggatt tgcaggagct gaattatctg aagctggtga ttaaagaaac cctgcgcctg    1080

catccgccgt ttccgctggt gatgccgcgt gagtgccgtg aaccgtgtgt tttgggcggt    1140

tacgacattc cgagcaaaac gaagctgatc gttaatgttt tcgcgattaa ccgtgacccg    1200

gaatactgga aagacgcgga aacgtttatg ccggagcgtt ttgagaatag cccgattacc    1260

gttatgggtt ccgagtacga atacctgcca tttggtgctg gtcgtcgtat gtgtcctggt    1320

gcagcgctgg gtctggccaa cgtggaactg ccgctggcgc acattctgta ctatttcaac    1380

tggaaactgc cgaacggcaa gaccttcgaa gatttggaca tgaccgagag ctttggtgcc    1440

actgtgcagc gcaaaaccga gctgctgctg gttccgaccg actttcaaac gctgactgcg    1500

agcacctaat ga                                                        1512


<210> SEQ ID NO 30
<211> LENGTH: 502
<212> TYPE: PRT
<213> ORGANISM: Artificial Sequence
<220> FEATURE:
<223> OTHER INFORMATION: CYP71AV8-L358F amino acid sequence

<400> SEQUENCE: 30

Met Ala Leu Leu Leu Ala Val Phe Trp Ser Ala Leu Ile Ile Leu Val
1               5                   10                  15
```

```
Val Thr Tyr Thr Ile Ser Leu Leu Ile Asn Gln Trp Arg Lys Pro Lys
            20                  25                  30

Pro Gln Gly Lys Phe Pro Pro Gly Pro Trp Arg Leu Pro Ile Ile Gly
        35                  40                  45

His Met His His Leu Ile Gly Thr Met Pro His Arg Gly Val Met Glu
    50                  55                  60

Leu Ala Arg Lys His Gly Ser Leu Met His Leu Gln Leu Gly Glu Val
65                  70                  75                  80

Ser Thr Ile Val Val Ser Ser Pro Arg Trp Ala Lys Glu Val Leu Thr
                85                  90                  95

Thr Tyr Asp Ile Thr Phe Ala Asn Arg Pro Glu Thr Leu Thr Gly Glu
            100                 105                 110

Ile Val Ala Tyr His Asn Thr Asp Ile Val Leu Ala Pro Tyr Gly Glu
        115                 120                 125

Tyr Trp Arg Gln Leu Arg Lys Leu Cys Thr Leu Glu Leu Leu Ser Asn
    130                 135                 140

Lys Lys Val Lys Ser Phe Gln Ser Leu Arg Glu Glu Glu Cys Trp Asn
145                 150                 155                 160

Leu Val Lys Asp Ile Arg Ser Thr Gly Gln Gly Ser Pro Ile Asn Leu
                165                 170                 175

Ser Glu Asn Ile Phe Lys Met Ile Ala Thr Ile Leu Ser Arg Ala Ala
            180                 185                 190

Phe Gly Lys Gly Ile Lys Asp Gln Met Lys Phe Thr Glu Leu Val Lys
        195                 200                 205

Glu Ile Leu Arg Leu Thr Gly Gly Phe Asp Val Ala Asp Ile Phe Pro
    210                 215                 220

Ser Lys Lys Leu Leu His His Leu Ser Gly Lys Arg Ala Lys Leu Thr
225                 230                 235                 240

Asn Ile His Asn Lys Leu Asp Asn Leu Ile Asn Asn Ile Ile Ala Glu
                245                 250                 255

His Pro Gly Asn Arg Thr Ser Ser Ser Gln Glu Thr Leu Leu Asp Val
            260                 265                 270

Leu Leu Arg Leu Lys Glu Ser Ala Glu Phe Pro Leu Thr Ala Asp Asn
        275                 280                 285

Val Lys Ala Val Ile Leu Asp Met Phe Gly Ala Gly Thr Asp Thr Ser
    290                 295                 300

Ser Ala Thr Ile Glu Trp Ala Ile Ser Glu Leu Ile Arg Cys Pro Arg
305                 310                 315                 320

Ala Met Glu Lys Val Gln Thr Glu Leu Arg Gln Ala Leu Asn Gly Lys
                325                 330                 335

Glu Arg Ile Gln Glu Glu Asp Leu Gln Glu Leu Asn Tyr Leu Lys Leu
            340                 345                 350

Val Ile Lys Glu Thr Leu Arg Leu His Pro Pro Phe Pro Leu Val Met
        355                 360                 365

Pro Arg Glu Cys Arg Glu Pro Cys Val Leu Gly Gly Tyr Asp Ile Pro
    370                 375                 380

Ser Lys Thr Lys Leu Ile Val Asn Val Phe Ala Ile Asn Arg Asp Pro
385                 390                 395                 400

Glu Tyr Trp Lys Asp Ala Glu Thr Phe Met Pro Glu Arg Phe Glu Asn
                405                 410                 415

Ser Pro Ile Thr Val Met Gly Ser Glu Tyr Glu Tyr Leu Pro Phe Gly
            420                 425                 430
```

```
Ala Gly Arg Arg Met Cys Pro Gly Ala Ala Leu Gly Leu Ala Asn Val
        435                 440                 445

Glu Leu Pro Leu Ala His Ile Leu Tyr Tyr Phe Asn Trp Lys Leu Pro
    450                 455                 460

Asn Gly Lys Thr Phe Glu Asp Leu Asp Met Thr Glu Ser Phe Gly Ala
465                 470                 475                 480

Thr Val Gln Arg Lys Thr Glu Leu Leu Leu Val Pro Thr Asp Phe Gln
                485                 490                 495

Thr Leu Thr Ala Ser Thr
            500


<210> SEQ ID NO 31
<211> LENGTH: 1512
<212> TYPE: DNA
<213> ORGANISM: Artificial Sequence
<220> FEATURE:
<223> OTHER INFORMATION: CYP71AV8-L358T DNA Sequence

<400> SEQUENCE: 31

atggctctgt tattagcagt tttttggtcg gcgcttataa tcctcgtagt aacctacacc     60

atatccctcc taatcaacca atggcgaaaa ccgaaacccc aagggaagtt ccccccgggc    120

ccatggcgtc tgccgattat cggtcacatg caccatttga tcggcaccat gccgcatcgt    180

ggtgttatgg aactggcccg taagcatggc agcctgatgc acctgcaact gggtgaagtc    240

tctacgattg ttgtcagcag cccgcgttgg gcgaaagagg tcttgaccac ctatgatatc    300

accttcgcca atcgcccgga aaccctgact ggcgagatcg tcgcatacca caacacggat    360

atcgtcctgg cgccgtatgg tgagtattgg cgtcaactgc gtaaactgtg cacgctggag    420

ctgctgagca acaagaaagt gaagagcttc cagagcctgc gcgaagaaga gtgttggaac    480

ctggtcaagg acatccgcag caccggccaa ggtagcccaa tcaatctgtc ggagaacatt    540

ttcaagatga ttgcgacgat tctgagccgt gctgcgttcg gtaagggtat taaggatcaa    600

atgaagttta ccgaactggt gaaagaaatc ctgcgtctga ccggcggttt tgatgtcgct    660

gacatcttcc ctagcaagaa gttgctgcac cacctgagcg gcaagcgtgc aaaactgacc    720

aatatccata acaagctgga taatctgatc aataacatca tcgcagagca cccgggcaac    780

cgtacctcgt cctcccagga aacgctgctg gacgttctgc tgcgcctgaa agagtctgcg    840

gagtttccgc tgaccgccga caacgttaaa gcagtgatcc tggatatgtt cggcgctggt    900

acggatacca gcagcgcgac gatcgagtgg gcgattagcg agctgattcg ctgccctcgc    960

gcgatggaga aagtgcagac ggaattgcgt caggcactga atggcaaaga gcgtattcag   1020

gaagaggatt tgcaggagct gaattatctg aagctggtga ttaaagaaac cctgcgcctg   1080

catccgccga ctccgctggt gatgccgcgt gagtgccgtg aaccgtgtgt tttgggcggt   1140

tacgacattc cgagcaaaac gaagctgatc gttaatgttt tcgcgattaa ccgtgacccg   1200

gaatactgga aagacgcgga aacgtttatg ccggagcgtt ttgagaatag cccgattacc   1260

gttatgggtt ccgagtacga atacctgcca tttggtgctg gtcgtcgtat gtgtcctggt   1320

gcagcgctgg gtctggccaa cgtggaactg ccgctggcgc acattctgta ctatttcaac   1380

tggaaactgc cgaacggcaa gaccttcgaa gatttggaca tgaccgagag ctttggtgcc   1440

actgtgcagc gcaaaaccga gctgctgctg gttccgaccg actttcaaac cctgactgcg   1500

agcacctaat ga                                                       1512


<210> SEQ ID NO 32
```

<211> LENGTH: 502
<212> TYPE: PRT
<213> ORGANISM: Artificial Sequence
<220> FEATURE:
<223> OTHER INFORMATION: CYP71AV8-L358T amino acid sequence

<400> SEQUENCE: 32

```
Met Ala Leu Leu Leu Ala Val Phe Trp Ser Ala Leu Ile Ile Leu Val
1               5                   10                  15

Val Thr Tyr Thr Ile Ser Leu Leu Ile Asn Gln Trp Arg Lys Pro Lys
            20                  25                  30

Pro Gln Gly Lys Phe Pro Pro Gly Pro Trp Arg Leu Pro Ile Ile Gly
        35                  40                  45

His Met His His Leu Ile Gly Thr Met Pro His Arg Gly Val Met Glu
    50                  55                  60

Leu Ala Arg Lys His Gly Ser Leu Met His Leu Gln Leu Gly Glu Val
65                  70                  75                  80

Ser Thr Ile Val Val Ser Ser Pro Arg Trp Ala Lys Glu Val Leu Thr
                85                  90                  95

Thr Tyr Asp Ile Thr Phe Ala Asn Arg Pro Glu Thr Leu Thr Gly Glu
            100                 105                 110

Ile Val Ala Tyr His Asn Thr Asp Ile Val Leu Ala Pro Tyr Gly Glu
        115                 120                 125

Tyr Trp Arg Gln Leu Arg Lys Leu Cys Thr Leu Glu Leu Leu Ser Asn
    130                 135                 140

Lys Lys Val Lys Ser Phe Gln Ser Leu Arg Glu Glu Glu Cys Trp Asn
145                 150                 155                 160

Leu Val Lys Asp Ile Arg Ser Thr Gly Gln Gly Ser Pro Ile Asn Leu
                165                 170                 175

Ser Glu Asn Ile Phe Lys Met Ile Ala Thr Ile Leu Ser Arg Ala Ala
            180                 185                 190

Phe Gly Lys Gly Ile Lys Asp Gln Met Lys Phe Thr Glu Leu Val Lys
        195                 200                 205

Glu Ile Leu Arg Leu Thr Gly Gly Phe Asp Val Ala Asp Ile Phe Pro
    210                 215                 220

Ser Lys Lys Leu Leu His His Leu Ser Gly Lys Arg Ala Lys Leu Thr
225                 230                 235                 240

Asn Ile His Asn Lys Leu Asp Asn Leu Ile Asn Asn Ile Ile Ala Glu
                245                 250                 255

His Pro Gly Asn Arg Thr Ser Ser Ser Gln Glu Thr Leu Leu Asp Val
            260                 265                 270

Leu Leu Arg Leu Lys Glu Ser Ala Glu Phe Pro Leu Thr Ala Asp Asn
        275                 280                 285

Val Lys Ala Val Ile Leu Asp Met Phe Gly Ala Gly Thr Asp Thr Ser
    290                 295                 300

Ser Ala Thr Ile Glu Trp Ala Ile Ser Glu Leu Ile Arg Cys Pro Arg
305                 310                 315                 320

Ala Met Glu Lys Val Gln Thr Glu Leu Arg Gln Ala Leu Asn Gly Lys
                325                 330                 335

Glu Arg Ile Gln Glu Glu Asp Leu Gln Glu Leu Asn Tyr Leu Lys Leu
            340                 345                 350

Val Ile Lys Glu Thr Leu Arg Leu His Pro Pro Thr Pro Leu Val Met
        355                 360                 365

Pro Arg Glu Cys Arg Glu Pro Cys Val Leu Gly Gly Tyr Asp Ile Pro
    370                 375                 380
```

```
Ser Lys Thr Lys Leu Ile Val Asn Val Phe Ala Ile Asn Arg Asp Pro
385                 390                 395                 400

Glu Tyr Trp Lys Asp Ala Glu Thr Phe Met Pro Glu Arg Phe Glu Asn
                405                 410                 415

Ser Pro Ile Thr Val Met Gly Ser Glu Tyr Glu Tyr Leu Pro Phe Gly
            420                 425                 430

Ala Gly Arg Arg Met Cys Pro Gly Ala Ala Leu Gly Leu Ala Asn Val
        435                 440                 445

Glu Leu Pro Leu Ala His Ile Leu Tyr Tyr Phe Asn Trp Lys Leu Pro
    450                 455                 460

Asn Gly Lys Thr Phe Glu Asp Leu Asp Met Thr Glu Ser Phe Gly Ala
465                 470                 475                 480

Thr Val Gln Arg Lys Thr Glu Leu Leu Leu Val Pro Thr Asp Phe Gln
                485                 490                 495

Thr Leu Thr Ala Ser Thr
            500


<210> SEQ ID NO 33
<211> LENGTH: 1512
<212> TYPE: DNA
<213> ORGANISM: Artificial Sequence
<220> FEATURE:
<223> OTHER INFORMATION: CYP71AV8-L358S DNA sequence

<400> SEQUENCE: 33

atggctctgt tattagcagt tttttggtcg gcgcttataa tcctcgtagt aacctacacc      60

atatccctcc taatcaacca atggcgaaaa ccgaaacccc aagggaagtt cccccccgggc    120

ccatggcgtc tgccgattat cggtcacatg caccatttga tcggcaccat gccgcatcgt     180

ggtgttatgg aactggcccg taagcatggc agcctgatgc acctgcaact gggtgaagtc     240

tctacgattg ttgtcagcag cccgcgttgg gcgaaagagg tcttgaccac ctatgatatc     300

accttcgcca atcgcccgga aaccctgact ggcgagatcg tcgcatacca caacacggat     360

atcgtcctgg cgccgtatgg tgagtattgg cgtcaactgc gtaaactgtg cacgctggag     420

ctgctgagca acaagaaagt gaagagcttc cagagcctgc gcgaagaaga gtgttggaac     480

ctggtcaagg acatccgcag caccggccaa ggtagcccaa tcaatctgtc ggagaacatt     540

ttcaagatga ttgcgacgat tctgagccgt gctgcgttcg gtaagggtat taaggatcaa     600

atgaagttta ccgaactggt gaaagaaatc ctgcgtctga ccggcggttt tgatgtcgct     660

gacatcttcc ctagcaagaa gttgctgcac cacctgagcg gcaagcgtgc aaaactgacc     720

aatatccata acaagctgga taatctgatc aataacatca tcgcagagca cccgggcaac     780

cgtacctcgt cctcccagga aacgctgctg gacgttctgc tgcgcctgaa agagtctgcg     840

gagtttccgc tgaccgccga caacgttaaa gcagtgatcc tggatatgtt cggcgctggt     900

acggatacca gcagcgcgac gatcgagtgg gcgattagcg agctgattcg ctgccctcgc     960

gcgatggaga aagtgcagac ggaattgcgt caggcactga atggcaaaga gcgtattcag    1020

gaagaggatt tgcaggagct gaattatctg aagctggtga ttaaagaaac cctgcgcctg    1080

catccgccgt ctccgctggt gatgccgcgt gagtgccgtg aaccgtgtgt tttgggcggt    1140

tacgacattc cgagcaaaac gaagctgatc gttaatgttt tcgcgattaa ccgtgacccg    1200

gaatactgga aagacgcgga aacgtttatg ccggagcgtt ttgagaatag cccgattacc    1260

gttatgggtt ccgagtacga atacctgcca tttggtgctg gtcgtcgtat gtgtcctggt    1320
```

```
gcagcgctgg gtctggccaa cgtggaactg ccgctggcgc acattctgta ctatttcaac   1380

tggaaactgc cgaacggcaa gaccttcgaa gatttggaca tgaccgagag ctttggtgcc   1440

actgtgcagc gcaaaaccga gctgctgctg gttccgaccg actttcaaac cctgactgcg   1500

agcacctaat ga                                                       1512


<210> SEQ ID NO 34
<211> LENGTH: 502
<212> TYPE: PRT
<213> ORGANISM: Artificial Sequence
<220> FEATURE:
<223> OTHER INFORMATION: CYP71AV8-L358S amino acid sequence

<400> SEQUENCE: 34

Met Ala Leu Leu Leu Ala Val Phe Trp Ser Ala Leu Ile Ile Leu Val
1               5                   10                  15

Val Thr Tyr Thr Ile Ser Leu Leu Ile Asn Gln Trp Arg Lys Pro Lys
            20                  25                  30

Pro Gln Gly Lys Phe Pro Pro Gly Pro Trp Arg Leu Pro Ile Ile Gly
        35                  40                  45

His Met His His Leu Ile Gly Thr Met Pro His Arg Gly Val Met Glu
    50                  55                  60

Leu Ala Arg Lys His Gly Ser Leu Met His Leu Gln Leu Gly Glu Val
65                  70                  75                  80

Ser Thr Ile Val Val Ser Ser Pro Arg Trp Ala Lys Glu Val Leu Thr
                85                  90                  95

Thr Tyr Asp Ile Thr Phe Ala Asn Arg Pro Glu Thr Leu Thr Gly Glu
            100                 105                 110

Ile Val Ala Tyr His Asn Thr Asp Ile Val Leu Ala Pro Tyr Gly Glu
        115                 120                 125

Tyr Trp Arg Gln Leu Arg Lys Leu Cys Thr Leu Glu Leu Leu Ser Asn
    130                 135                 140

Lys Lys Val Lys Ser Phe Gln Ser Leu Arg Glu Glu Glu Cys Trp Asn
145                 150                 155                 160

Leu Val Lys Asp Ile Arg Ser Thr Gly Gln Gly Ser Pro Ile Asn Leu
                165                 170                 175

Ser Glu Asn Ile Phe Lys Met Ile Ala Thr Ile Leu Ser Arg Ala Ala
            180                 185                 190

Phe Gly Lys Gly Ile Lys Asp Gln Met Lys Phe Thr Glu Leu Val Lys
        195                 200                 205

Glu Ile Leu Arg Leu Thr Gly Gly Phe Asp Val Ala Asp Ile Phe Pro
    210                 215                 220

Ser Lys Lys Leu Leu His His Leu Ser Gly Lys Arg Ala Lys Leu Thr
225                 230                 235                 240

Asn Ile His Asn Lys Leu Asp Asn Leu Ile Asn Asn Ile Ile Ala Glu
                245                 250                 255

His Pro Gly Asn Arg Thr Ser Ser Ser Gln Glu Thr Leu Leu Asp Val
            260                 265                 270

Leu Leu Arg Leu Lys Glu Ser Ala Glu Phe Pro Leu Thr Ala Asp Asn
        275                 280                 285

Val Lys Ala Val Ile Leu Asp Met Phe Gly Ala Gly Thr Asp Thr Ser
    290                 295                 300

Ser Ala Thr Ile Glu Trp Ala Ile Ser Glu Leu Ile Arg Cys Pro Arg
305                 310                 315                 320

Ala Met Glu Lys Val Gln Thr Glu Leu Arg Gln Ala Leu Asn Gly Lys
```

```
                325                 330                 335

Glu Arg Ile Gln Glu Glu Asp Leu Gln Glu Leu Asn Tyr Leu Lys Leu
            340                 345                 350

Val Ile Lys Glu Thr Leu Arg Leu His Pro Pro Ser Pro Leu Val Met
        355                 360                 365

Pro Arg Glu Cys Arg Glu Pro Cys Val Leu Gly Gly Tyr Asp Ile Pro
    370                 375                 380

Ser Lys Thr Lys Leu Ile Val Asn Val Phe Ala Ile Asn Arg Asp Pro
385                 390                 395                 400

Glu Tyr Trp Lys Asp Ala Glu Thr Phe Met Pro Glu Arg Phe Glu Asn
                405                 410                 415

Ser Pro Ile Thr Val Met Gly Ser Glu Tyr Glu Tyr Leu Pro Phe Gly
            420                 425                 430

Ala Gly Arg Arg Met Cys Pro Gly Ala Ala Leu Gly Leu Ala Asn Val
        435                 440                 445

Glu Leu Pro Leu Ala His Ile Leu Tyr Tyr Phe Asn Trp Lys Leu Pro
    450                 455                 460

Asn Gly Lys Thr Phe Glu Asp Leu Asp Met Thr Glu Ser Phe Gly Ala
465                 470                 475                 480

Thr Val Gln Arg Lys Thr Glu Leu Leu Leu Val Pro Thr Asp Phe Gln
                485                 490                 495

Thr Leu Thr Ala Ser Thr
            500


<210> SEQ ID NO 35
<211> LENGTH: 1512
<212> TYPE: DNA
<213> ORGANISM: Artificial Sequence
<220> FEATURE:
<223> OTHER INFORMATION: CYP71AV8-L358V DNA sequence

<400> SEQUENCE: 35

atggctctgt tattagcagt tttttggtcg gcgcttataa tcctcgtagt aacctacacc     60

atatccctcc taatcaacca atggcgaaaa ccgaaacccc aagggaagtt ccccccgggc    120

ccatggcgtc tgccgattat cggtcacatg caccatttga tcggcaccat gccgcatcgt    180

ggtgttatgg aactggcccg taagcatggc agcctgatgc acctgcaact gggtgaagtc    240

tctacgattg ttgtcagcag cccgcgttgg gcgaaagagg tcttgaccac ctatgatatc    300

accttcgcca atcgcccgga aaccctgact ggcgagatcg tcgcatacca caacacggat    360

atcgtcctgg cgccgtatgg tgagtattgg cgtcaactgc gtaaactgtg cacgctggag    420

ctgctgagca acaagaaagt gaagagcttc cagagcctgc gcgaagaaga gtgttggaac    480

ctggtcaagg acatccgcag caccggccaa ggtagcccaa tcaatctgtc ggagaacatt    540

ttcaagatga ttgcgacgat tctgagccgt gctgcgttcg gtaagggtat taaggatcaa    600

atgaagttta ccgaactggt gaaagaaatc ctgcgtctga ccggcggttt tgatgtcgct    660

gacatcttcc ctagcaagaa gttgctgcac cacctgagcg gcaagcgtgc aaaactgacc    720

aatatccata acaagctgga taatctgatc aataacatca tcgcagagca cccgggcaac    780

cgtacctcgt cctcccagga aacgctgctg gacgttctgc tgcgcctgaa agagtctgcg    840

gagtttccgc tgaccgccga caacgttaaa gcagtgatcc tggatatgtt cggcgctggt    900

acggatacca gcagcgcgac gatcgagtgg gcgattagcg agctgattcg ctgccctcgc    960

gcgatggaga aagtgcagac ggaattgcgt caggcactga atggcaaaga gcgtattcag   1020
```

gaagaggatt tgcaggagct gaattatctg aagctggtga ttaaagaaac cctgcgcctg 1080
catccgccgg ttccgctggt gatgccgcgt gagtgccgtg aaccgtgtgt tttgggcggt 1140
tacgacattc cgagcaaaac gaagctgatc gttaatgttt tcgcgattaa ccgtgacccg 1200
gaatactgga aagacgcgga aacgtttatg ccggagcgtt ttgagaatag cccgattacc 1260
gttatgggtt ccgagtacga atacctgcca tttggtgctg gtcgtcgtat gtgtcctggt 1320
gcagcgctgg gtctggccaa cgtggaactg ccgctggcgc acattctgta ctatttcaac 1380
tggaaactgc cgaacggcaa gaccttcgaa gatttggaca tgaccgagag ctttggtgcc 1440
actgtgcagc gcaaaaccga gctgctgctg gttccgaccg actttcaaac cctgactgcg 1500
agcacctaat ga 1512

<210> SEQ ID NO 36
<211> LENGTH: 502
<212> TYPE: PRT
<213> ORGANISM: Artificial Sequence
<220> FEATURE:
<223> OTHER INFORMATION: CYP71AV8-L358V amino acid sequence

<400> SEQUENCE: 36

Met Ala Leu Leu Leu Ala Val Phe Trp Ser Ala Leu Ile Ile Leu Val
1 5 10 15

Val Thr Tyr Thr Ile Ser Leu Leu Ile Asn Gln Trp Arg Lys Pro Lys
20 25 30

Pro Gln Gly Lys Phe Pro Pro Gly Pro Trp Arg Leu Pro Ile Ile Gly
35 40 45

His Met His His Leu Ile Gly Thr Met Pro His Arg Gly Val Met Glu
50 55 60

Leu Ala Arg Lys His Gly Ser Leu Met His Leu Gln Leu Gly Glu Val
65 70 75 80

Ser Thr Ile Val Val Ser Ser Pro Arg Trp Ala Lys Glu Val Leu Thr
85 90 95

Thr Tyr Asp Ile Thr Phe Ala Asn Arg Pro Glu Thr Leu Thr Gly Glu
100 105 110

Ile Val Ala Tyr His Asn Thr Asp Ile Val Leu Ala Pro Tyr Gly Glu
115 120 125

Tyr Trp Arg Gln Leu Arg Lys Leu Cys Thr Leu Glu Leu Leu Ser Asn
130 135 140

Lys Lys Val Lys Ser Phe Gln Ser Leu Arg Glu Glu Glu Cys Trp Asn
145 150 155 160

Leu Val Lys Asp Ile Arg Ser Thr Gly Gln Gly Ser Pro Ile Asn Leu
165 170 175

Ser Glu Asn Ile Phe Lys Met Ile Ala Thr Ile Leu Ser Arg Ala Ala
180 185 190

Phe Gly Lys Gly Ile Lys Asp Gln Met Lys Phe Thr Glu Leu Val Lys
195 200 205

Glu Ile Leu Arg Leu Thr Gly Gly Phe Asp Val Ala Asp Ile Phe Pro
210 215 220

Ser Lys Lys Leu Leu His His Leu Ser Gly Lys Arg Ala Lys Leu Thr
225 230 235 240

Asn Ile His Asn Lys Leu Asp Asn Leu Ile Asn Asn Ile Ile Ala Glu
245 250 255

His Pro Gly Asn Arg Thr Ser Ser Ser Gln Glu Thr Leu Leu Asp Val
260 265 270

```
Leu Leu Arg Leu Lys Glu Ser Ala Glu Phe Pro Leu Thr Ala Asp Asn
        275                 280                 285

Val Lys Ala Val Ile Leu Asp Met Phe Gly Ala Gly Thr Asp Thr Ser
    290                 295                 300

Ser Ala Thr Ile Glu Trp Ala Ile Ser Glu Leu Ile Arg Cys Pro Arg
305                 310                 315                 320

Ala Met Glu Lys Val Gln Thr Glu Leu Arg Gln Ala Leu Asn Gly Lys
                325                 330                 335

Glu Arg Ile Gln Glu Glu Asp Leu Gln Glu Leu Asn Tyr Leu Lys Leu
            340                 345                 350

Val Ile Lys Glu Thr Leu Arg Leu His Pro Pro Val Pro Leu Val Met
        355                 360                 365

Pro Arg Glu Cys Arg Glu Pro Cys Val Leu Gly Gly Tyr Asp Ile Pro
    370                 375                 380

Ser Lys Thr Lys Leu Ile Val Asn Val Phe Ala Ile Asn Arg Asp Pro
385                 390                 395                 400

Glu Tyr Trp Lys Asp Ala Glu Thr Phe Met Pro Glu Arg Phe Glu Asn
                405                 410                 415

Ser Pro Ile Thr Val Met Gly Ser Glu Tyr Glu Tyr Leu Pro Phe Gly
            420                 425                 430

Ala Gly Arg Arg Met Cys Pro Gly Ala Ala Leu Gly Leu Ala Asn Val
        435                 440                 445

Glu Leu Pro Leu Ala His Ile Leu Tyr Tyr Phe Asn Trp Lys Leu Pro
    450                 455                 460

Asn Gly Lys Thr Phe Glu Asp Leu Asp Met Thr Glu Ser Phe Gly Ala
465                 470                 475                 480

Thr Val Gln Arg Lys Thr Glu Leu Leu Leu Val Pro Thr Asp Phe Gln
                485                 490                 495

Thr Leu Thr Ala Ser Thr
            500


<210> SEQ ID NO 37
<211> LENGTH: 1512
<212> TYPE: DNA
<213> ORGANISM: Artificial Sequence
<220> FEATURE:
<223> OTHER INFORMATION: CYP71AV8-L358G DNA sequence

<400> SEQUENCE: 37

atggctctgt tattagcagt tttttggtcg gcgcttataa tcctcgtagt aacctacacc      60

atatccctcc taatcaacca atggcgaaaa ccgaaacccc aagggaagtt ccccccgggc     120

ccatggcgtc tgccgattat cggtcacatg caccatttga tcggcaccat gccgcatcgt     180

ggtgttatgg aactggcccg taagcatggc agcctgatgc acctgcaact gggtgaagtc     240

tctacgattg ttgtcagcag cccgcgttgg gcgaaagagg tcttgaccac ctatgatatc     300

accttcgcca atcgcccgga aaccctgact ggcgagatcg tcgcatacca caacacggat     360

atcgtcctgg cgccgtatgg tgagtattgg cgtcaactgc gtaaactgtg cacgctggag     420

ctgctgagca acaagaaagt gaagagcttc cagagcctgc gcgaagaaga gtgttggaac     480

ctggtcaagg acatccgcag caccggccaa ggtagcccaa tcaatctgtc ggagaacatt     540

ttcaagatga ttgcgacgat tctgagccgt gctgcgttcg gtaagggtat taaggatcaa     600

atgaagttta ccgaactggt gaaagaaatc ctgcgtctga ccggcggttt tgatgtcgct     660

gacatcttcc ctagcaagaa gttgctgcac cacctgagcg gcaagcgtgc aaaactgacc     720
```

-continued aatatccata acaagctgga taatctgatc aataacatca tcgcagagca cccgggcaac 780
cgtacctcgt cctcccagga aacgctgctg gacgttctgc tgcgcctgaa agagtctgcg 840
gagtttccgc tgaccgccga caacgttaaa gcagtgatcc tggatatgtt cggcgctggt 900
acggatacca gcagcgcgac gatcgagtgg gcgattagcg agctgattcg ctgccctcgc 960
gcgatggaga aagtgcagac ggaattgcgt caggcactga atggcaaaga gcgtattcag 1020
gaagaggatt tgcaggagct gaattatctg aagctggtga ttaaagaaac cctgcgcctg 1080
catccgccgg ggccgctggt gatgccgcgt gagtgccgtg aaccgtgtgt tttgggcggt 1140
tacgacattc cgagcaaaac gaagctgatc gttaatgttt tcgcgattaa ccgtgacccg 1200
gaatactgga aagacgcgga aacgtttatg ccggagcgtt ttgagaatag cccgattacc 1260
gttatgggtt ccgagtacga atacctgcca tttggtgctg gtcgtcgtat gtgtcctggt 1320
gcagcgctgg gtctggccaa cgtggaactg ccgctggcgc acattctgta ctatttcaac 1380
tggaaactgc cgaacggcaa gaccttcgaa gatttggaca tgaccgagag ctttggtgcc 1440
actgtgcagc gcaaaaccga gctgctgctg gttccgaccg actttcaaac cctgactgcg 1500
agcacctaat ga 1512

<210> SEQ ID NO 38
<211> LENGTH: 502
<212> TYPE: PRT
<213> ORGANISM: Artificial Sequence
<220> FEATURE:
<223> OTHER INFORMATION: CYP71AV8-L358G amino acid sequence

<400> SEQUENCE: 38

Met Ala Leu Leu Leu Ala Val Phe Trp Ser Ala Leu Ile Ile Leu Val
1 5 10 15

Val Thr Tyr Thr Ile Ser Leu Leu Ile Asn Gln Trp Arg Lys Pro Lys
20 25 30

Pro Gln Gly Lys Phe Pro Pro Gly Pro Trp Arg Leu Pro Ile Ile Gly
35 40 45

His Met His His Leu Ile Gly Thr Met Pro His Arg Gly Val Met Glu
50 55 60

Leu Ala Arg Lys His Gly Ser Leu Met His Leu Gln Leu Gly Glu Val
65 70 75 80

Ser Thr Ile Val Val Ser Ser Pro Arg Trp Ala Lys Glu Val Leu Thr
85 90 95

Thr Tyr Asp Ile Thr Phe Ala Asn Arg Pro Glu Thr Leu Thr Gly Glu
100 105 110

Ile Val Ala Tyr His Asn Thr Asp Ile Val Leu Ala Pro Tyr Gly Glu
115 120 125

Tyr Trp Arg Gln Leu Arg Lys Leu Cys Thr Leu Glu Leu Leu Ser Asn
130 135 140

Lys Lys Val Lys Ser Phe Gln Ser Leu Arg Glu Glu Glu Cys Trp Asn
145 150 155 160

Leu Val Lys Asp Ile Arg Ser Thr Gly Gln Gly Ser Pro Ile Asn Leu
165 170 175

Ser Glu Asn Ile Phe Lys Met Ile Ala Thr Ile Leu Ser Arg Ala Ala
180 185 190

Phe Gly Lys Gly Ile Lys Asp Gln Met Lys Phe Thr Glu Leu Val Lys
195 200 205

Glu Ile Leu Arg Leu Thr Gly Gly Phe Asp Val Ala Asp Ile Phe Pro
210 215 220

```
Ser Lys Lys Leu Leu His His Leu Ser Gly Lys Arg Ala Lys Leu Thr
225                 230                 235                 240

Asn Ile His Asn Lys Leu Asp Asn Leu Ile Asn Asn Ile Ile Ala Glu
                245                 250                 255

His Pro Gly Asn Arg Thr Ser Ser Ser Gln Glu Thr Leu Leu Asp Val
            260                 265                 270

Leu Leu Arg Leu Lys Glu Ser Ala Glu Phe Pro Leu Thr Ala Asp Asn
        275                 280                 285

Val Lys Ala Val Ile Leu Asp Met Phe Gly Ala Gly Thr Asp Thr Ser
    290                 295                 300

Ser Ala Thr Ile Glu Trp Ala Ile Ser Glu Leu Ile Arg Cys Pro Arg
305                 310                 315                 320

Ala Met Glu Lys Val Gln Thr Glu Leu Arg Gln Ala Leu Asn Gly Lys
                325                 330                 335

Glu Arg Ile Gln Glu Glu Asp Leu Gln Glu Leu Asn Tyr Leu Lys Leu
            340                 345                 350

Val Ile Lys Glu Thr Leu Arg Leu His Pro Pro Gly Pro Leu Val Met
        355                 360                 365

Pro Arg Glu Cys Arg Glu Pro Cys Val Leu Gly Gly Tyr Asp Ile Pro
    370                 375                 380

Ser Lys Thr Lys Leu Ile Val Asn Val Phe Ala Ile Asn Arg Asp Pro
385                 390                 395                 400

Glu Tyr Trp Lys Asp Ala Glu Thr Phe Met Pro Glu Arg Phe Glu Asn
                405                 410                 415

Ser Pro Ile Thr Val Met Gly Ser Glu Tyr Glu Tyr Leu Pro Phe Gly
            420                 425                 430

Ala Gly Arg Arg Met Cys Pro Gly Ala Ala Leu Gly Leu Ala Asn Val
        435                 440                 445

Glu Leu Pro Leu Ala His Ile Leu Tyr Tyr Phe Asn Trp Lys Leu Pro
    450                 455                 460

Asn Gly Lys Thr Phe Glu Asp Leu Asp Met Thr Glu Ser Phe Gly Ala
465                 470                 475                 480

Thr Val Gln Arg Lys Thr Glu Leu Leu Leu Val Pro Thr Asp Phe Gln
                485                 490                 495

Thr Leu Thr Ala Ser Thr
            500
```

<210> SEQ ID NO 39
<211> LENGTH: 1512
<212> TYPE: DNA
<213> ORGANISM: Artificial Sequence
<220> FEATURE:
<223> OTHER INFORMATION: CYP71AV8-L358I DNA sequence

<400> SEQUENCE: 39

```
atggctctgt tattagcagt tttttggtcg gcgcttataa tcctcgtagt aacctacacc      60

atatccctcc taatcaacca atggcgaaaa ccgaaacccc aagggaagtt ccccccgggc     120

ccatggcgtc tgccgattat cggtcacatg caccatttga tcggcaccat gccgcatcgt     180

ggtgttatgg aactggcccg taagcatggc agcctgatgc acctgcaact gggtgaagtc     240

tctacgattg ttgtcagcag cccgcgttgg gcgaaagagg tcttgaccac ctatgatatc     300

accttcgcca atcgcccgga aaccctgact ggcgagatcg tcgcatacca caacacggat     360

atcgtcctgg cgccgtatgg tgagtattgg cgtcaactgc gtaaactgtg cacgctggag     420
```

-continued

```
ctgctgagca acaagaaagt gaagagcttc cagagcctgc gcgaagaaga gtgttggaac    480

ctggtcaagg acatccgcag caccggccaa ggtagcccaa tcaatctgtc ggagaacatt    540

ttcaagatga ttgcgacgat tctgagccgt gctgcgttcg gtaagggtat taaggatcaa    600

atgaagttta ccgaactggt gaaagaaatc ctgcgtctga ccggcggttt tgatgtcgct    660

gacatcttcc ctagcaagaa gttgctgcac cacctgagcg gcaagcgtgc aaaactgacc    720

aatatccata acaagctgga taatctgatc aataacatca tcgcagagca cccgggcaac    780

cgtacctcgt cctcccagga aacgctgctg gacgttctgc tgcgcctgaa agagtctgcg    840

gagtttccgc tgaccgccga caacgttaaa gcagtgatcc tggatatgtt cggcgctggt    900

acggatacca gcagcgcgac gatcgagtgg gcgattagcg agctgattcg ctgccctcgc    960

gcgatggaga aagtgcagac ggaattgcgt caggcactga atggcaaaga gcgtattcag   1020

gaagaggatt tgcaggagct gaattatctg aagctggtga ttaaagaaac cctgcgcctg   1080

catccgccga ttccgctggt gatgccgcgt gagtgccgtg aaccgtgtgt tttgggcggt   1140

tacgacattc cgagcaaaac gaagctgatc gttaatgttt tcgcgattaa ccgtgacccg   1200

gaatactgga aagacgcgga aacgtttatg ccggagcgtt ttgagaatag cccgattacc   1260

gttatgggtt ccgagtacga atacctgcca tttggtgctg gtcgtcgtat gtgtcctggt   1320

gcagcgctgg gtctggccaa cgtggaactg ccgctggcgc acattctgta ctatttcaac   1380

tggaaactgc cgaacggcaa gaccttcgaa gatttggaca tgaccgagag ctttggtgcc   1440

actgtgcagc gcaaaaccga gctgctgctg gttccgaccg actttcaaac cctgactgcg   1500

agcacctaat ga                                                      1512
```

<210> SEQ ID NO 40
<211> LENGTH: 502
<212> TYPE: PRT
<213> ORGANISM: Artificial Sequence
<220> FEATURE:
<223> OTHER INFORMATION: CYP71AV8-L358I amino acid sequence

<400> SEQUENCE: 40

```
Met Ala Leu Leu Leu Ala Val Phe Trp Ser Ala Leu Ile Ile Leu Val
1               5                   10                  15

Val Thr Tyr Thr Ile Ser Leu Leu Ile Asn Gln Trp Arg Lys Pro Lys
            20                  25                  30

Pro Gln Gly Lys Phe Pro Pro Gly Pro Trp Arg Leu Pro Ile Ile Gly
        35                  40                  45

His Met His His Leu Ile Gly Thr Met Pro His Arg Gly Val Met Glu
    50                  55                  60

Leu Ala Arg Lys His Gly Ser Leu Met His Leu Gln Leu Gly Glu Val
65                  70                  75                  80

Ser Thr Ile Val Val Ser Ser Pro Arg Trp Ala Lys Glu Val Leu Thr
                85                  90                  95

Thr Tyr Asp Ile Thr Phe Ala Asn Arg Pro Glu Thr Leu Thr Gly Glu
            100                 105                 110

Ile Val Ala Tyr His Asn Thr Asp Ile Val Leu Ala Pro Tyr Gly Glu
        115                 120                 125

Tyr Trp Arg Gln Leu Arg Lys Leu Cys Thr Leu Glu Leu Leu Ser Asn
    130                 135                 140

Lys Lys Val Lys Ser Phe Gln Ser Leu Arg Glu Glu Glu Cys Trp Asn
145                 150                 155                 160

Leu Val Lys Asp Ile Arg Ser Thr Gly Gln Gly Ser Pro Ile Asn Leu
```

-continued

```
                165                 170                 175

Ser Glu Asn Ile Phe Lys Met Ile Ala Thr Ile Leu Ser Arg Ala Ala
            180                 185                 190

Phe Gly Lys Gly Ile Lys Asp Gln Met Lys Phe Thr Glu Leu Val Lys
        195                 200                 205

Glu Ile Leu Arg Leu Thr Gly Gly Phe Asp Val Ala Asp Ile Phe Pro
    210                 215                 220

Ser Lys Lys Leu Leu His His Leu Ser Gly Lys Arg Ala Lys Leu Thr
225                 230                 235                 240

Asn Ile His Asn Lys Leu Asp Asn Leu Ile Asn Asn Ile Ile Ala Glu
                245                 250                 255

His Pro Gly Asn Arg Thr Ser Ser Ser Gln Glu Thr Leu Leu Asp Val
            260                 265                 270

Leu Leu Arg Leu Lys Glu Ser Ala Glu Phe Pro Leu Thr Ala Asp Asn
        275                 280                 285

Val Lys Ala Val Ile Leu Asp Met Phe Gly Ala Gly Thr Asp Thr Ser
    290                 295                 300

Ser Ala Thr Ile Glu Trp Ala Ile Ser Glu Leu Ile Arg Cys Pro Arg
305                 310                 315                 320

Ala Met Glu Lys Val Gln Thr Glu Leu Arg Gln Ala Leu Asn Gly Lys
                325                 330                 335

Glu Arg Ile Gln Glu Glu Asp Leu Gln Glu Leu Asn Tyr Leu Lys Leu
            340                 345                 350

Val Ile Lys Glu Thr Leu Arg Leu His Pro Pro Ile Pro Leu Val Met
        355                 360                 365

Pro Arg Glu Cys Arg Glu Pro Cys Val Leu Gly Gly Tyr Asp Ile Pro
    370                 375                 380

Ser Lys Thr Lys Leu Ile Val Asn Val Phe Ala Ile Asn Arg Asp Pro
385                 390                 395                 400

Glu Tyr Trp Lys Asp Ala Glu Thr Phe Met Pro Glu Arg Phe Glu Asn
                405                 410                 415

Ser Pro Ile Thr Val Met Gly Ser Glu Tyr Glu Tyr Leu Pro Phe Gly
            420                 425                 430

Ala Gly Arg Arg Met Cys Pro Gly Ala Ala Leu Gly Leu Ala Asn Val
        435                 440                 445

Glu Leu Pro Leu Ala His Ile Leu Tyr Tyr Phe Asn Trp Lys Leu Pro
    450                 455                 460

Asn Gly Lys Thr Phe Glu Asp Leu Asp Met Thr Glu Ser Phe Gly Ala
465                 470                 475                 480

Thr Val Gln Arg Lys Thr Glu Leu Leu Leu Val Pro Thr Asp Phe Gln
                485                 490                 495

Thr Leu Thr Ala Ser Thr
            500
```

<210> SEQ ID NO 41
<211> LENGTH: 1512
<212> TYPE: DNA
<213> ORGANISM: Artificial Sequence
<220> FEATURE:
<223> OTHER INFORMATION: CYP71AV8-L358M DNA sequence

<400> SEQUENCE: 41

```
atggctctgt tattagcagt tttttggtcg gcgcttataa tcctcgtagt aacctacacc      60

atatccctcc taatcaacca atggcgaaaa ccgaaacccc aagggaagtt ccccccgggc     120
```

-continued

```
ccatggcgtc tgccgattat cggtcacatg caccatttga tcggcaccat gccgcatcgt    180

ggtgttatgg aactggcccg taagcatggc agcctgatgc acctgcaact gggtgaagtc    240

tctacgattg ttgtcagcag cccgcgttgg gcgaaagagg tcttgaccac ctatgatatc    300

accttcgcca atcgcccgga aaccctgact ggcgagatcg tcgcatacca caacacggat    360

atcgtcctgg cgccgtatgg tgagtattgg cgtcaactgc gtaaactgtg cacgctggag    420

ctgctgagca acaagaaagt gaagagcttc cagagcctgc gcgaagaaga gtgttggaac    480

ctggtcaagg acatccgcag caccggccaa ggtagcccaa tcaatctgtc ggagaacatt    540

ttcaagatga ttgcgacgat tctgagccgt gctgcgttcg gtaagggtat taaggatcaa    600

atgaagttta ccgaactggt gaaagaaatc ctgcgtctga ccggcggttt tgatgtcgct    660

gacatcttcc ctagcaagaa gttgctgcac cacctgagcg gcaagcgtgc aaaactgacc    720

aatatccata acaagctgga taatctgatc aataacatca tcgcagagca cccgggcaac    780

cgtacctcgt cctcccagga aacgctgctg gacgttctgc tgcgcctgaa agagtctgcg    840

gagtttccgc tgaccgccga caacgttaaa gcagtgatcc tggatatgtt cggcgctggt    900

acggatacca gcagcgcgac gatcgagtgg gcgattagcg agctgattcg ctgccctcgc    960

gcgatggaga aagtgcagac ggaattgcgt caggcactga atggcaaaga gcgtattcag   1020

gaagaggatt tgcaggagct gaattatctg aagctggtga ttaaagaaac cctgcgcctg   1080

catccgccga tgccgctggt gatgccgcgt gagtgccgtg aaccgtgtgt tttgggcggt   1140

tacgacattc cgagcaaaac gaagctgatc gttaatgttt tcgcgattaa ccgtgacccg   1200

gaatactgga aagacgcgga aacgtttatg ccggagcgtt ttgagaatag cccgattacc   1260

gttatgggtt ccgagtacga atacctgcca tttggtgctg gtcgtcgtat gtgtcctggt   1320

gcagcgctgg gtctggccaa cgtggaactg ccgctggcgc acattctgta ctatttcaac   1380

tggaaactgc cgaacggcaa gaccttcgaa gatttggaca tgaccgagag ctttggtgcc   1440

actgtgcagc gcaaaaccga gctgctgctg gttccgaccg actttcaaac cctgactgcg   1500

agcacctaat ga                                                       1512
```

<210> SEQ ID NO 42
<211> LENGTH: 502
<212> TYPE: PRT
<213> ORGANISM: Artificial Sequence
<220> FEATURE:
<223> OTHER INFORMATION: CYP71AV8-L358M amino acid sequence

<400> SEQUENCE: 42

```
Met Ala Leu Leu Leu Ala Val Phe Trp Ser Ala Leu Ile Ile Leu Val
1               5                   10                  15

Val Thr Tyr Thr Ile Ser Leu Leu Ile Asn Gln Trp Arg Lys Pro Lys
            20                  25                  30

Pro Gln Gly Lys Phe Pro Pro Gly Pro Trp Arg Leu Pro Ile Ile Gly
        35                  40                  45

His Met His His Leu Ile Gly Thr Met Pro His Arg Gly Val Met Glu
    50                  55                  60

Leu Ala Arg Lys His Gly Ser Leu Met His Leu Gln Leu Gly Glu Val
65                  70                  75                  80

Ser Thr Ile Val Val Ser Ser Pro Arg Trp Ala Lys Glu Val Leu Thr
                85                  90                  95

Thr Tyr Asp Ile Thr Phe Ala Asn Arg Pro Glu Thr Leu Thr Gly Glu
            100                 105                 110
```

-continued

```
Ile Val Ala Tyr His Asn Thr Asp Ile Val Leu Ala Pro Tyr Gly Glu
        115                 120                 125

Tyr Trp Arg Gln Leu Arg Lys Leu Cys Thr Leu Glu Leu Leu Ser Asn
    130                 135                 140

Lys Lys Val Lys Ser Phe Gln Ser Leu Arg Glu Glu Glu Cys Trp Asn
145                 150                 155                 160

Leu Val Lys Asp Ile Arg Ser Thr Gly Gln Gly Ser Pro Ile Asn Leu
                165                 170                 175

Ser Glu Asn Ile Phe Lys Met Ile Ala Thr Ile Leu Ser Arg Ala Ala
            180                 185                 190

Phe Gly Lys Gly Ile Lys Asp Gln Met Lys Phe Thr Glu Leu Val Lys
        195                 200                 205

Glu Ile Leu Arg Leu Thr Gly Gly Phe Asp Val Ala Asp Ile Phe Pro
    210                 215                 220

Ser Lys Lys Leu Leu His His Leu Ser Gly Lys Arg Ala Lys Leu Thr
225                 230                 235                 240

Asn Ile His Asn Lys Leu Asp Asn Leu Ile Asn Asn Ile Ile Ala Glu
                245                 250                 255

His Pro Gly Asn Arg Thr Ser Ser Ser Gln Glu Thr Leu Leu Asp Val
            260                 265                 270

Leu Leu Arg Leu Lys Glu Ser Ala Glu Phe Pro Leu Thr Ala Asp Asn
        275                 280                 285

Val Lys Ala Val Ile Leu Asp Met Phe Gly Ala Gly Thr Asp Thr Ser
    290                 295                 300

Ser Ala Thr Ile Glu Trp Ala Ile Ser Glu Leu Ile Arg Cys Pro Arg
305                 310                 315                 320

Ala Met Glu Lys Val Gln Thr Glu Leu Arg Gln Ala Leu Asn Gly Lys
                325                 330                 335

Glu Arg Ile Gln Glu Glu Asp Leu Gln Glu Leu Asn Tyr Leu Lys Leu
            340                 345                 350

Val Ile Lys Glu Thr Leu Arg Leu His Pro Pro Met Pro Leu Val Met
        355                 360                 365

Pro Arg Glu Cys Arg Glu Pro Cys Val Leu Gly Gly Tyr Asp Ile Pro
    370                 375                 380

Ser Lys Thr Lys Leu Ile Val Asn Val Phe Ala Ile Asn Arg Asp Pro
385                 390                 395                 400

Glu Tyr Trp Lys Asp Ala Glu Thr Phe Met Pro Glu Arg Phe Glu Asn
                405                 410                 415

Ser Pro Ile Thr Val Met Gly Ser Glu Tyr Glu Tyr Leu Pro Phe Gly
            420                 425                 430

Ala Gly Arg Arg Met Cys Pro Gly Ala Ala Leu Gly Leu Ala Asn Val
        435                 440                 445

Glu Leu Pro Leu Ala His Ile Leu Tyr Tyr Phe Asn Trp Lys Leu Pro
    450                 455                 460

Asn Gly Lys Thr Phe Glu Asp Leu Asp Met Thr Glu Ser Phe Gly Ala
465                 470                 475                 480

Thr Val Gln Arg Lys Thr Glu Leu Leu Leu Val Pro Thr Asp Phe Gln
                485                 490                 495

Thr Leu Thr Ala Ser Thr
            500
```

<210> SEQ ID NO 43
<211> LENGTH: 1512
<212> TYPE: DNA

<213> ORGANISM: Artificial Sequence
<220> FEATURE:
<223> OTHER INFORMATION: CYP71AV8-L358P DNA sequence

<400> SEQUENCE: 43
atggctctgt tattagcagt tttttggtcg gcgcttataa tcctcgtagt aacctacacc 60
atatccctcc taatcaacca atggcgaaaa ccgaaacccc aagggaagtt ccccccgggc 120
ccatggcgtc tgccgattat cggtcacatg caccatttga tcggcaccat gccgcatcgt 180
ggtgttatgg aactggcccg taagcatggc agcctgatgc acctgcaact gggtgaagtc 240
tctacgattg ttgtcagcag cccgcgttgg gcgaaagagg tcttgaccac ctatgatatc 300
accttcgcca atcgcccgga aaccctgact ggcgagatcg tcgcatacca caacacggat 360
atcgtcctgg cgccgtatgg tgagtattgg cgtcaactgc gtaaactgtg cacgctggag 420
ctgctgagca acaagaaagt gaagagcttc cagagcctgc gcgaagaaga gtgttggaac 480
ctggtcaagg acatccgcag caccggccaa ggtagcccaa tcaatctgtc ggagaacatt 540
ttcaagatga ttgcgacgat tctgagccgt gctgcgttcg gtaagggtat taaggatcaa 600
atgaagttta ccgaactggt gaaagaaatc ctgcgtctga ccggcggttt tgatgtcgct 660
gacatcttcc ctagcaagaa gttgctgcac cacctgagcg gcaagcgtgc aaaactgacc 720
aatatccata acaagctgga taatctgatc aataacatca tcgcagagca cccgggcaac 780
cgtacctcgt cctcccagga aacgctgctg gacgttctgc tgcgcctgaa agagtctgcg 840
gagtttccgc tgaccgccga caacgttaaa gcagtgatcc tggatatgtt cggcgctggt 900
acggatacca gcagcgcgac gatcgagtgg gcgattagcg agctgattcg ctgccctcgc 960
gcgatggaga aagtgcagac ggaattgcgt caggcactga atggcaaaga gcgtattcag 1020
gaagaggatt tgcaggagct gaattatctg aagctggtga ttaaagaaac cctgcgcctg 1080
catccgccgc ctccgctggt gatgccgcgt gagtgccgtg aaccgtgtgt tttgggcggt 1140
tacgacattc cgagcaaaac gaagctgatc gttaatgttt tcgcgattaa ccgtgacccg 1200
gaatactgga aagacgcgga aacgtttatg ccggagcgtt ttgagaatag cccgattacc 1260
gttatgggtt ccgagtacga atacctgcca tttggtgctg gtcgtcgtat gtgtcctggt 1320
gcagcgctgg gtctggccaa cgtggaactg ccgctggcgc acattctgta ctatttcaac 1380
tggaaactgc cgaacggcaa gaccttcgaa gatttggaca tgaccgagag ctttggtgcc 1440
actgtgcagc gcaaaaccga gctgctgctg gttccgaccg actttcaaac cctgactgcg 1500
agcacctaat ga 1512

<210> SEQ ID NO 44
<211> LENGTH: 502
<212> TYPE: PRT
<213> ORGANISM: Artificial Sequence
<220> FEATURE:
<223> OTHER INFORMATION: CYP71AV8-L358P amino acid sequence

<400> SEQUENCE: 44

Met Ala Leu Leu Leu Ala Val Phe Trp Ser Ala Leu Ile Ile Leu Val
1               5                   10                  15

Val Thr Tyr Thr Ile Ser Leu Leu Ile Asn Gln Trp Arg Lys Pro Lys
            20                  25                  30

Pro Gln Gly Lys Phe Pro Pro Gly Pro Trp Arg Leu Pro Ile Ile Gly
        35                  40                  45

His Met His His Leu Ile Gly Thr Met Pro His Arg Gly Val Met Glu
    50                  55                  60

```
Leu Ala Arg Lys His Gly Ser Leu Met His Leu Gln Leu Gly Glu Val
65                  70                  75                  80

Ser Thr Ile Val Val Ser Ser Pro Arg Trp Ala Lys Glu Val Leu Thr
                85                  90                  95

Thr Tyr Asp Ile Thr Phe Ala Asn Arg Pro Glu Thr Leu Thr Gly Glu
            100                 105                 110

Ile Val Ala Tyr His Asn Thr Asp Ile Val Leu Ala Pro Tyr Gly Glu
        115                 120                 125

Tyr Trp Arg Gln Leu Arg Lys Leu Cys Thr Leu Glu Leu Leu Ser Asn
    130                 135                 140

Lys Lys Val Lys Ser Phe Gln Ser Leu Arg Glu Glu Glu Cys Trp Asn
145                 150                 155                 160

Leu Val Lys Asp Ile Arg Ser Thr Gly Gln Gly Ser Pro Ile Asn Leu
                165                 170                 175

Ser Glu Asn Ile Phe Lys Met Ile Ala Thr Ile Leu Ser Arg Ala Ala
            180                 185                 190

Phe Gly Lys Gly Ile Lys Asp Gln Met Lys Phe Thr Glu Leu Val Lys
        195                 200                 205

Glu Ile Leu Arg Leu Thr Gly Gly Phe Asp Val Ala Asp Ile Phe Pro
    210                 215                 220

Ser Lys Lys Leu Leu His His Leu Ser Gly Lys Arg Ala Lys Leu Thr
225                 230                 235                 240

Asn Ile His Asn Lys Leu Asp Asn Leu Ile Asn Asn Ile Ile Ala Glu
                245                 250                 255

His Pro Gly Asn Arg Thr Ser Ser Ser Gln Glu Thr Leu Leu Asp Val
            260                 265                 270

Leu Leu Arg Leu Lys Glu Ser Ala Glu Phe Pro Leu Thr Ala Asp Asn
        275                 280                 285

Val Lys Ala Val Ile Leu Asp Met Phe Gly Ala Gly Thr Asp Thr Ser
    290                 295                 300

Ser Ala Thr Ile Glu Trp Ala Ile Ser Glu Leu Ile Arg Cys Pro Arg
305                 310                 315                 320

Ala Met Glu Lys Val Gln Thr Glu Leu Arg Gln Ala Leu Asn Gly Lys
                325                 330                 335

Glu Arg Ile Gln Glu Glu Asp Leu Gln Glu Leu Asn Tyr Leu Lys Leu
            340                 345                 350

Val Ile Lys Glu Thr Leu Arg Leu His Pro Pro Pro Pro Leu Val Met
        355                 360                 365

Pro Arg Glu Cys Arg Glu Pro Cys Val Leu Gly Gly Tyr Asp Ile Pro
    370                 375                 380

Ser Lys Thr Lys Leu Ile Val Asn Val Phe Ala Ile Asn Arg Asp Pro
385                 390                 395                 400

Glu Tyr Trp Lys Asp Ala Glu Thr Phe Met Pro Glu Arg Phe Glu Asn
                405                 410                 415

Ser Pro Ile Thr Val Met Gly Ser Glu Tyr Glu Tyr Leu Pro Phe Gly
            420                 425                 430

Ala Gly Arg Arg Met Cys Pro Gly Ala Ala Leu Gly Leu Ala Asn Val
        435                 440                 445

Glu Leu Pro Leu Ala His Ile Leu Tyr Tyr Phe Asn Trp Lys Leu Pro
    450                 455                 460

Asn Gly Lys Thr Phe Glu Asp Leu Asp Met Thr Glu Ser Phe Gly Ala
465                 470                 475                 480
```

```
Thr Val Gln Arg Lys Thr Glu Leu Leu Leu Val Pro Thr Asp Phe Gln
                485                 490                 495

Thr Leu Thr Ala Ser Thr
            500
```

<210> SEQ ID NO 45
<211> LENGTH: 1512
<212> TYPE: DNA
<213> ORGANISM: Artificial Sequence
<220> FEATURE:
<223> OTHER INFORMATION: CYP71AV8-L358Y DNA sequence

<400> SEQUENCE: 45

```
atggctctgt tattagcagt tttttggtcg gcgcttataa tcctcgtagt aacctacacc     60

atatccctcc taatcaacca atggcgaaaa ccgaaacccc aagggaagtt ccccccgggc    120

ccatggcgtc tgccgattat cggtcacatg caccatttga tcggcaccat gccgcatcgt    180

ggtgttatgg aactggcccg taagcatggc agcctgatgc acctgcaact gggtgaagtc    240

tctacgattg ttgtcagcag cccgcgttgg gcgaaagagg tcttgaccac ctatgatatc    300

accttcgcca atcgcccgga aaccctgact ggcgagatcg tcgcatacca caacacggat    360

atcgtcctgg cgccgtatgg tgagtattgg cgtcaactgc gtaaactgtg cacgctggag    420

ctgctgagca acaagaaagt gaagagcttc cagagcctgc gcgaagaaga gtgttggaac    480

ctggtcaagg acatccgcag caccggccaa ggtagcccaa tcaatctgtc ggagaacatt    540

ttcaagatga ttgcgacgat tctgagccgt gctgcgttcg gtaagggtat taaggatcaa    600

atgaagttta ccgaactggt gaaagaaatc ctgcgtctga ccggcggttt tgatgtcgct    660

gacatcttcc ctagcaagaa gttgctgcac cacctgagcg gcaagcgtgc aaaactgacc    720

aatatccata acaagctgga taatctgatc aataacatca tcgcagagca cccgggcaac    780

cgtacctcgt cctcccagga aacgctgctg gacgttctgc tgcgcctgaa agagtctgcg    840

gagtttccgc tgaccgccga caacgttaaa gcagtgatcc tggatatgtt cggcgctggt    900

acggatacca gcagcgcgac gatcgagtgg gcgattagcg agctgattcg ctgccctcgc    960

gcgatggaga aagtgcagac ggaattgcgt caggcactga atggcaaaga gcgtattcag   1020

gaagaggatt tgcaggagct gaattatctg aagctggtga ttaaagaaac cctgcgcctg   1080

catccgccgt atccgctggt gatgccgcgt gagtgccgtg aaccgtgtgt tttgggcggt   1140

tacgacattc cgagcaaaac gaagctgatc gttaatgttt tcgcgattaa ccgtgacccg   1200

gaatactgga aagacgcgga aacgtttatg ccggagcgtt ttgagaatag cccgattacc   1260

gttatgggtt ccgagtacga atacctgcca tttggtgctg gtcgtcgtat gtgtcctggt   1320

gcagcgctgg gtctggccaa cgtggaactg ccgctggcgc acattctgta ctatttcaac   1380

tggaaactgc cgaacggcaa gaccttcgaa gatttggaca tgaccgagag ctttggtgcc   1440

actgtgcagc gcaaaaccga gctgctgctg gttccgaccg actttcaaac cctgactgcg   1500

agcacctaat ga                                                       1512
```

<210> SEQ ID NO 46
<211> LENGTH: 502
<212> TYPE: PRT
<213> ORGANISM: Artificial Sequence
<220> FEATURE:
<223> OTHER INFORMATION: CYP71AV8-L358Y amino acid sequence

<400> SEQUENCE: 46

```
Met Ala Leu Leu Leu Ala Val Phe Trp Ser Ala Leu Ile Ile Leu Val
```

-continued

```
1               5                   10                  15

Val Thr Tyr Thr Ile Ser Leu Leu Ile Asn Gln Trp Arg Lys Pro Lys
            20                  25                  30

Pro Gln Gly Lys Phe Pro Pro Gly Pro Trp Arg Leu Pro Ile Ile Gly
        35                  40                  45

His Met His His Leu Ile Gly Thr Met Pro His Arg Gly Val Met Glu
    50                  55                  60

Leu Ala Arg Lys His Gly Ser Leu Met His Leu Gln Leu Gly Glu Val
65                  70                  75                  80

Ser Thr Ile Val Val Ser Ser Pro Arg Trp Ala Lys Glu Val Leu Thr
                85                  90                  95

Thr Tyr Asp Ile Thr Phe Ala Asn Arg Pro Glu Thr Leu Thr Gly Glu
            100                 105                 110

Ile Val Ala Tyr His Asn Thr Asp Ile Val Leu Ala Pro Tyr Gly Glu
        115                 120                 125

Tyr Trp Arg Gln Leu Arg Lys Leu Cys Thr Leu Glu Leu Leu Ser Asn
    130                 135                 140

Lys Lys Val Lys Ser Phe Gln Ser Leu Arg Glu Glu Glu Cys Trp Asn
145                 150                 155                 160

Leu Val Lys Asp Ile Arg Ser Thr Gly Gln Gly Ser Pro Ile Asn Leu
                165                 170                 175

Ser Glu Asn Ile Phe Lys Met Ile Ala Thr Ile Leu Ser Arg Ala Ala
            180                 185                 190

Phe Gly Lys Gly Ile Lys Asp Gln Met Lys Phe Thr Glu Leu Val Lys
        195                 200                 205

Glu Ile Leu Arg Leu Thr Gly Gly Phe Asp Val Ala Asp Ile Phe Pro
    210                 215                 220

Ser Lys Lys Leu Leu His His Leu Ser Gly Lys Arg Ala Lys Leu Thr
225                 230                 235                 240

Asn Ile His Asn Lys Leu Asp Asn Leu Ile Asn Asn Ile Ile Ala Glu
                245                 250                 255

His Pro Gly Asn Arg Thr Ser Ser Ser Gln Glu Thr Leu Leu Asp Val
            260                 265                 270

Leu Leu Arg Leu Lys Glu Ser Ala Glu Phe Pro Leu Thr Ala Asp Asn
        275                 280                 285

Val Lys Ala Val Ile Leu Asp Met Phe Gly Ala Gly Thr Asp Thr Ser
    290                 295                 300

Ser Ala Thr Ile Glu Trp Ala Ile Ser Glu Leu Ile Arg Cys Pro Arg
305                 310                 315                 320

Ala Met Glu Lys Val Gln Thr Glu Leu Arg Gln Ala Leu Asn Gly Lys
                325                 330                 335

Glu Arg Ile Gln Glu Glu Asp Leu Gln Glu Leu Asn Tyr Leu Lys Leu
            340                 345                 350

Val Ile Lys Glu Thr Leu Arg Leu His Pro Pro Tyr Pro Leu Val Met
        355                 360                 365

Pro Arg Glu Cys Arg Glu Pro Cys Val Leu Gly Gly Tyr Asp Ile Pro
    370                 375                 380

Ser Lys Thr Lys Leu Ile Val Asn Val Phe Ala Ile Asn Arg Asp Pro
385                 390                 395                 400

Glu Tyr Trp Lys Asp Ala Glu Thr Phe Met Pro Glu Arg Phe Glu Asn
                405                 410                 415

Ser Pro Ile Thr Val Met Gly Ser Glu Tyr Glu Tyr Leu Pro Phe Gly
            420                 425                 430
```

-continued

```
Ala Gly Arg Arg Met Cys Pro Gly Ala Ala Leu Gly Leu Ala Asn Val
        435                 440                 445

Glu Leu Pro Leu Ala His Ile Leu Tyr Tyr Phe Asn Trp Lys Leu Pro
    450                 455                 460

Asn Gly Lys Thr Phe Glu Asp Leu Asp Met Thr Glu Ser Phe Gly Ala
465                 470                 475                 480

Thr Val Gln Arg Lys Thr Glu Leu Leu Leu Val Pro Thr Asp Phe Gln
                485                 490                 495

Thr Leu Thr Ala Ser Thr
            500
```

<210> SEQ ID NO 47
<211> LENGTH: 1512
<212> TYPE: DNA
<213> ORGANISM: Artificial Sequence
<220> FEATURE:
<223> OTHER INFORMATION: CYP71AV8-L358W DNA sequence

<400> SEQUENCE: 47

```
atggctctgt tattagcagt tttttggtcg gcgcttataa tcctcgtagt aacctacacc      60

atatccctcc taatcaacca atggcgaaaa ccgaaacccc aagggaagtt ccccccgggc     120

ccatggcgtc tgccgattat cggtcacatg caccatttga tcggcaccat gccgcatcgt     180

ggtgttatgg aactggcccg taagcatggc agcctgatgc acctgcaact gggtgaagtc     240

tctacgattg ttgtcagcag cccgcgttgg gcgaaagagg tcttgaccac ctatgatatc     300

accttcgcca atcgcccgga aaccctgact ggcgagatcg tcgcatacca caacacggat     360

atcgtcctgg cgccgtatgg tgagtattgg cgtcaactgc gtaaactgtg cacgctggag     420

ctgctgagca acaagaaagt gaagagcttc cagagcctgc gcgaagaaga gtgttggaac     480

ctggtcaagg acatccgcag caccggccaa ggtagcccaa tcaatctgtc ggagaacatt     540

ttcaagatga ttgcgacgat tctgagccgt gctgcgttcg gtaagggtat taaggatcaa     600

atgaagttta ccgaactggt gaaagaaatc ctgcgtctga ccggcggttt tgatgtcgct     660

gacatcttcc ctagcaagaa gttgctgcac cacctgagcg gcaagcgtgc aaaactgacc     720

aatatccata acaagctgga taatctgatc aataacatca tcgcagagca cccgggcaac     780

cgtacctcgt cctcccagga aacgctgctg gacgttctgc tgcgcctgaa agagtctgcg     840

gagtttccgc tgaccgccga caacgttaaa gcagtgatcc tggatatgtt cggcgctggt     900

acggatacca gcagcgcgac gatcgagtgg gcgattagcg agctgattcg ctgccctcgc     960

gcgatggaga aagtgcagac ggaattgcgt caggcactga atggcaaaga gcgtattcag    1020

gaagaggatt tgcaggagct gaattatctg aagctggtga ttaaagaaac cctgcgcctg    1080

catccgccgt ggccgctggt gatgccgcgt gagtgccgtg aaccgtgtgt tttgggcggt    1140

tacgacattc cgagcaaaac gaagctgatc gttaatgttt tcgcgattaa ccgtgacccg    1200

gaatactgga aagacgcgga aacgtttatg ccggagcgtt ttgagaatag cccgattacc    1260

gttatgggtt ccgagtacga atacctgcca tttggtgctg gtcgtcgtat gtgtcctggt    1320

gcagcgctgg gtctggccaa cgtggaactg ccgctggcgc acattctgta ctatttcaac    1380

tggaaactgc cgaacggcaa gaccttcgaa gatttggaca tgaccgagag ctttggtgcc    1440

actgtgcagc gcaaaaccga gctgctgctg gttccgaccg actttcaaac cctgactgcg    1500

agcacctaat ga                                                        1512
```

<210> SEQ ID NO 48
<211> LENGTH: 502
<212> TYPE: PRT
<213> ORGANISM: Artificial Sequence
<220> FEATURE:
<223> OTHER INFORMATION: CYP71AV8-L358W amino acid sequence

<400> SEQUENCE: 48

Met Ala Leu Leu Leu Ala Val Phe Trp Ser Ala Leu Ile Ile Leu Val
1 5 10 15

Val Thr Tyr Thr Ile Ser Leu Leu Ile Asn Gln Trp Arg Lys Pro Lys
20 25 30

Pro Gln Gly Lys Phe Pro Pro Gly Pro Trp Arg Leu Pro Ile Ile Gly
35 40 45

His Met His His Leu Ile Gly Thr Met Pro His Arg Gly Val Met Glu
50 55 60

Leu Ala Arg Lys His Gly Ser Leu Met His Leu Gln Leu Gly Glu Val
65 70 75 80

Ser Thr Ile Val Val Ser Ser Pro Arg Trp Ala Lys Glu Val Leu Thr
85 90 95

Thr Tyr Asp Ile Thr Phe Ala Asn Arg Pro Glu Thr Leu Thr Gly Glu
100 105 110

Ile Val Ala Tyr His Asn Thr Asp Ile Val Leu Ala Pro Tyr Gly Glu
115 120 125

Tyr Trp Arg Gln Leu Arg Lys Leu Cys Thr Leu Glu Leu Leu Ser Asn
130 135 140

Lys Lys Val Lys Ser Phe Gln Ser Leu Arg Glu Glu Glu Cys Trp Asn
145 150 155 160

Leu Val Lys Asp Ile Arg Ser Thr Gly Gln Gly Ser Pro Ile Asn Leu
165 170 175

Ser Glu Asn Ile Phe Lys Met Ile Ala Thr Ile Leu Ser Arg Ala Ala
180 185 190

Phe Gly Lys Gly Ile Lys Asp Gln Met Lys Phe Thr Glu Leu Val Lys
195 200 205

Glu Ile Leu Arg Leu Thr Gly Gly Phe Asp Val Ala Asp Ile Phe Pro
210 215 220

Ser Lys Lys Leu Leu His His Leu Ser Gly Lys Arg Ala Lys Leu Thr
225 230 235 240

Asn Ile His Asn Lys Leu Asp Asn Leu Ile Asn Asn Ile Ile Ala Glu
245 250 255

His Pro Gly Asn Arg Thr Ser Ser Ser Gln Glu Thr Leu Leu Asp Val
260 265 270

Leu Leu Arg Leu Lys Glu Ser Ala Glu Phe Pro Leu Thr Ala Asp Asn
275 280 285

Val Lys Ala Val Ile Leu Asp Met Phe Gly Ala Gly Thr Asp Thr Ser
290 295 300

Ser Ala Thr Ile Glu Trp Ala Ile Ser Glu Leu Ile Arg Cys Pro Arg
305 310 315 320

Ala Met Glu Lys Val Gln Thr Glu Leu Arg Gln Ala Leu Asn Gly Lys
325 330 335

Glu Arg Ile Gln Glu Glu Asp Leu Gln Glu Leu Asn Tyr Leu Lys Leu
340 345 350

Val Ile Lys Glu Thr Leu Arg Leu His Pro Pro Trp Pro Leu Val Met
355 360 365

Pro Arg Glu Cys Arg Glu Pro Cys Val Leu Gly Gly Tyr Asp Ile Pro

-continued

```
    370                 375                 380

Ser Lys Thr Lys Leu Ile Val Asn Val Phe Ala Ile Asn Arg Asp Pro
385                 390                 395                 400

Glu Tyr Trp Lys Asp Ala Glu Thr Phe Met Pro Glu Arg Phe Glu Asn
                405                 410                 415

Ser Pro Ile Thr Val Met Gly Ser Glu Tyr Glu Tyr Leu Pro Phe Gly
            420                 425                 430

Ala Gly Arg Arg Met Cys Pro Gly Ala Ala Leu Gly Leu Ala Asn Val
        435                 440                 445

Glu Leu Pro Leu Ala His Ile Leu Tyr Tyr Phe Asn Trp Lys Leu Pro
    450                 455                 460

Asn Gly Lys Thr Phe Glu Asp Leu Asp Met Thr Glu Ser Phe Gly Ala
465                 470                 475                 480

Thr Val Gln Arg Lys Thr Glu Leu Leu Leu Val Pro Thr Asp Phe Gln
                485                 490                 495

Thr Leu Thr Ala Ser Thr
            500


<210> SEQ ID NO 49
<211> LENGTH: 1512
<212> TYPE: DNA
<213> ORGANISM: Artificial Sequence
<220> FEATURE:
<223> OTHER INFORMATION: CYP71AV8-L358R DNA sequence

<400> SEQUENCE: 49

atggctctgt tattagcagt tttttggtcg gcgcttataa tcctcgtagt aacctacacc      60

atatccctcc taatcaacca atggcgaaaa ccgaaacccc aagggaagtt ccccccgggc     120

ccatggcgtc tgccgattat cggtcacatg caccatttga tcggcaccat gccgcatcgt     180

ggtgttatgg aactggcccg taagcatggc agcctgatgc acctgcaact gggtgaagtc     240

tctacgattg ttgtcagcag cccgcgttgg gcgaaagagg tcttgaccac ctatgatatc     300

accttcgcca atcgcccgga aaccctgact ggcgagatcg tcgcatacca caacacggat     360

atcgtcctgg cgccgtatgg tgagtattgg cgtcaactgc gtaaactgtg cacgctggag     420

ctgctgagca acaagaaagt gaagagcttc cagagcctgc gcgaagaaga gtgttggaac     480

ctggtcaagg acatccgcag caccggccaa ggtagcccaa tcaatctgtc ggagaacatt     540

ttcaagatga ttgcgacgat tctgagccgt gctgcgttcg gtaagggtat taaggatcaa     600

atgaagttta ccgaactggt gaaagaaatc ctgcgtctga ccggcggttt tgatgtcgct     660

gacatcttcc ctagcaagaa gttgctgcac cacctgagcg gcaagcgtgc aaaactgacc     720

aatatccata acaagctgga taatctgatc aataacatca tcgcagagca cccgggcaac     780

cgtacctcgt cctcccagga aacgctgctg gacgttctgc tgcgcctgaa agagtctgcg     840

gagtttccgc tgaccgccga caacgttaaa gcagtgatcc tggatatgtt cggcgctggt     900

acggatacca gcagcgcgac gatcgagtgg gcgattagcg agctgattcg ctgccctcgc     960

gcgatggaga aagtgcagac ggaattgcgt caggcactga atggcaaaga gcgtattcag    1020

gaagaggatt tgcaggagct gaattatctg aagctggtga ttaaagaaac cctgcgcctg    1080

catccgccgc gtccgctggt gatgccgcgt gagtgccgtg aaccgtgtgt tttgggcggt    1140

tacgacattc cgagcaaaac gaagctgatc gttaatgttt tcgcgattaa ccgtgacccg    1200

gaatactgga aagacgcgga aacgtttatg ccggagcgtt ttgagaatag cccgattacc    1260

gttatgggtt ccgagtacga atacctgcca tttggtgctg gtcgtcgtat gtgtcctggt    1320
```

```
gcagcgctgg gtctggccaa cgtggaactg ccgctggcgc acattctgta ctatttcaac   1380

tggaaactgc cgaacggcaa gaccttcgaa gatttggaca tgaccgagag ctttggtgcc   1440

actgtgcagc gcaaaaccga gctgctgctg gttccgaccg actttcaaac cctgactgcg   1500

agcacctaat ga                                                       1512
```

<210> SEQ ID NO 50
<211> LENGTH: 502
<212> TYPE: PRT
<213> ORGANISM: Artificial Sequence
<220> FEATURE:
<223> OTHER INFORMATION: CYP71AV8-L358R amino acid sequence

<400> SEQUENCE: 50

```
Met Ala Leu Leu Leu Ala Val Phe Trp Ser Ala Leu Ile Ile Leu Val
1               5                   10                  15

Val Thr Tyr Thr Ile Ser Leu Leu Ile Asn Gln Trp Arg Lys Pro Lys
            20                  25                  30

Pro Gln Gly Lys Phe Pro Pro Gly Pro Trp Arg Leu Pro Ile Ile Gly
        35                  40                  45

His Met His His Leu Ile Gly Thr Met Pro His Arg Gly Val Met Glu
    50                  55                  60

Leu Ala Arg Lys His Gly Ser Leu Met His Leu Gln Leu Gly Glu Val
65                  70                  75                  80

Ser Thr Ile Val Val Ser Ser Pro Arg Trp Ala Lys Glu Val Leu Thr
                85                  90                  95

Thr Tyr Asp Ile Thr Phe Ala Asn Arg Pro Glu Thr Leu Thr Gly Glu
            100                 105                 110

Ile Val Ala Tyr His Asn Thr Asp Ile Val Leu Ala Pro Tyr Gly Glu
        115                 120                 125

Tyr Trp Arg Gln Leu Arg Lys Leu Cys Thr Leu Glu Leu Leu Ser Asn
    130                 135                 140

Lys Lys Val Lys Ser Phe Gln Ser Leu Arg Glu Glu Glu Cys Trp Asn
145                 150                 155                 160

Leu Val Lys Asp Ile Arg Ser Thr Gly Gln Gly Ser Pro Ile Asn Leu
                165                 170                 175

Ser Glu Asn Ile Phe Lys Met Ile Ala Thr Ile Leu Ser Arg Ala Ala
            180                 185                 190

Phe Gly Lys Gly Ile Lys Asp Gln Met Lys Phe Thr Glu Leu Val Lys
        195                 200                 205

Glu Ile Leu Arg Leu Thr Gly Gly Phe Asp Val Ala Asp Ile Phe Pro
    210                 215                 220

Ser Lys Lys Leu Leu His His Leu Ser Gly Lys Arg Ala Lys Leu Thr
225                 230                 235                 240

Asn Ile His Asn Lys Leu Asp Asn Leu Ile Asn Asn Ile Ile Ala Glu
                245                 250                 255

His Pro Gly Asn Arg Thr Ser Ser Ser Gln Glu Thr Leu Leu Asp Val
            260                 265                 270

Leu Leu Arg Leu Lys Glu Ser Ala Glu Phe Pro Leu Thr Ala Asp Asn
        275                 280                 285

Val Lys Ala Val Ile Leu Asp Met Phe Gly Ala Gly Thr Asp Thr Ser
    290                 295                 300

Ser Ala Thr Ile Glu Trp Ala Ile Ser Glu Leu Ile Arg Cys Pro Arg
305                 310                 315                 320
```

-continued

```
Ala Met Glu Lys Val Gln Thr Glu Leu Arg Gln Ala Leu Asn Gly Lys
                325                 330                 335

Glu Arg Ile Gln Glu Glu Asp Leu Gln Glu Leu Asn Tyr Leu Lys Leu
            340                 345                 350

Val Ile Lys Glu Thr Leu Arg Leu His Pro Pro Arg Pro Leu Val Met
        355                 360                 365

Pro Arg Glu Cys Arg Glu Pro Cys Val Leu Gly Gly Tyr Asp Ile Pro
    370                 375                 380

Ser Lys Thr Lys Leu Ile Val Asn Val Phe Ala Ile Asn Arg Asp Pro
385                 390                 395                 400

Glu Tyr Trp Lys Asp Ala Glu Thr Phe Met Pro Glu Arg Phe Glu Asn
                405                 410                 415

Ser Pro Ile Thr Val Met Gly Ser Glu Tyr Glu Tyr Leu Pro Phe Gly
            420                 425                 430

Ala Gly Arg Arg Met Cys Pro Gly Ala Ala Leu Gly Leu Ala Asn Val
        435                 440                 445

Glu Leu Pro Leu Ala His Ile Leu Tyr Tyr Phe Asn Trp Lys Leu Pro
    450                 455                 460

Asn Gly Lys Thr Phe Glu Asp Leu Asp Met Thr Glu Ser Phe Gly Ala
465                 470                 475                 480

Thr Val Gln Arg Lys Thr Glu Leu Leu Leu Val Pro Thr Asp Phe Gln
                485                 490                 495

Thr Leu Thr Ala Ser Thr
            500
```

<210> SEQ ID NO 51
<211> LENGTH: 1488
<212> TYPE: DNA
<213> ORGANISM: Artemisia annua

<400> SEQUENCE: 51

```
atgaagagta tactaaaagc aatggcactc tcactgacca cttccattgc tcttgcaacg     60

atccttttgt tcgtttacaa gttcgctact cgttccaaat ccaccaaaaa aagccttcct    120

gagccatggc ggcttcccat tattggtcac atgcatcact tgattggtac aacgccacat    180

cgtggggtta gggatttagc cagaaagtat ggatctttga tgcatttaca gcttggtgaa    240

gttccaacaa tcgtggtgtc atctccgaaa tgggctaaag agattttgac aacgtacgac    300

attacctttg ctaacaggcc cgagacttta actggtgaga ttgttttata tcacaatacg    360

gatgttgttc ttgcacctta tggtgaatac tggaggcaat tacgtaaaat ttgcacattg    420

gagcttttga gtgttaagaa agtaaagtca tttcagtcac ttcgtgaaga ggagtgttgg    480

aatttggttc aagagattaa agcttcaggt tcagggagac cggttaacct ttcagagaat    540

gttttcaagt tgattgcaac gatacttagt agagccgcat ttgggaaagg gatcaaggac    600

cagaaagagt taacggagat tgtgaaagag atactgaggc aaactggtgg ttttgatgtg    660

gcagatatct ttccttcaaa gaaatttctt catcatcttt cgggcaagag agctcggtta    720

actagccttc gcaaaaagat cgataattta atcgataacc ttgtagctga gcatactgtt    780

aacacctcca gtaaaactaa cgagacactc ctcgatgttc ttttaaggct caaagacagt    840

gctgaattcc cattaacatc tgataacatt aaagccatca ttttggatat gtttggagca    900

ggcacagaca cttcctcatc cacaatcgaa tgggcgattt cggaactcat aaagtgtccg    960

aaagcaatgg agaaagtaca agcggaattg aggaaagcat tgaacggaaa agaaaagatc   1020

catgaggaag acattcaaga actaagctac ttgaacatgg taatcaaaga aacattgagg   1080
```

```
ttgcaccctc cactaccctt ggttctgcca agagagtgcc gccaaccagt caatttggct   1140

ggatacaaca tacccaataa gaccaaactt attgtcaacg tctttgcgat aaatagggac   1200

cctgaatatt ggaaagacgc tgaagctttc atccctgaac gatttgaaaa tagttctgca   1260

actgtcatgg gtgcagaata cgagtatctt ccgtttggag ctgggagaag gatgtgtcct   1320

ggagccgcac ttggtttagc taacgtgcag ctcccgctcg ctaatatact atatcatttc   1380

aactggaaac tccccaatgg tgtgagctat gaccagatcg acatgaccga gagctctgga   1440

gccacgatgc aaagaaagac tgagttgtta ctcgttccaa gtttctag               1488
```

<210> SEQ ID NO 52
<211> LENGTH: 495
<212> TYPE: PRT
<213> ORGANISM: Artemisia annua

<400> SEQUENCE: 52

```
Met Lys Ser Ile Leu Lys Ala Met Ala Leu Ser Leu Thr Thr Ser Ile
1               5                   10                  15

Ala Leu Ala Thr Ile Leu Leu Phe Val Tyr Lys Phe Ala Thr Arg Ser
            20                  25                  30

Lys Ser Thr Lys Lys Ser Leu Pro Glu Pro Trp Arg Leu Pro Ile Ile
        35                  40                  45

Gly His Met His His Leu Ile Gly Thr Thr Pro His Arg Gly Val Arg
    50                  55                  60

Asp Leu Ala Arg Lys Tyr Gly Ser Leu Met His Leu Gln Leu Gly Glu
65                  70                  75                  80

Val Pro Thr Ile Val Val Ser Ser Pro Lys Trp Ala Lys Glu Ile Leu
                85                  90                  95

Thr Thr Tyr Asp Ile Thr Phe Ala Asn Arg Pro Glu Thr Leu Thr Gly
            100                 105                 110

Glu Ile Val Leu Tyr His Asn Thr Asp Val Val Leu Ala Pro Tyr Gly
        115                 120                 125

Glu Tyr Trp Arg Gln Leu Arg Lys Ile Cys Thr Leu Glu Leu Leu Ser
    130                 135                 140

Val Lys Lys Val Lys Ser Phe Gln Ser Leu Arg Glu Glu Glu Cys Trp
145                 150                 155                 160

Asn Leu Val Gln Glu Ile Lys Ala Ser Gly Ser Gly Arg Pro Val Asn
                165                 170                 175

Leu Ser Glu Asn Val Phe Lys Leu Ile Ala Thr Ile Leu Ser Arg Ala
            180                 185                 190

Ala Phe Gly Lys Gly Ile Lys Asp Gln Lys Glu Leu Thr Glu Ile Val
        195                 200                 205

Lys Glu Ile Leu Arg Gln Thr Gly Gly Phe Asp Val Ala Asp Ile Phe
    210                 215                 220

Pro Ser Lys Lys Phe Leu His His Leu Ser Gly Lys Arg Ala Arg Leu
225                 230                 235                 240

Thr Ser Leu Arg Lys Lys Ile Asp Asn Leu Ile Asp Asn Leu Val Ala
                245                 250                 255

Glu His Thr Val Asn Thr Ser Ser Lys Thr Asn Glu Thr Leu Leu Asp
            260                 265                 270

Val Leu Leu Arg Leu Lys Asp Ser Ala Glu Phe Pro Leu Thr Ser Asp
        275                 280                 285

Asn Ile Lys Ala Ile Ile Leu Asp Met Phe Gly Ala Gly Thr Asp Thr
    290                 295                 300
```

```
Ser Ser Ser Thr Ile Glu Trp Ala Ile Ser Glu Leu Ile Lys Cys Pro
305                 310                 315                 320

Lys Ala Met Glu Lys Val Gln Ala Glu Leu Arg Lys Ala Leu Asn Gly
                325                 330                 335

Lys Glu Lys Ile His Glu Glu Asp Ile Gln Glu Leu Ser Tyr Leu Asn
            340                 345                 350

Met Val Ile Lys Glu Thr Leu Arg Leu His Pro Pro Leu Pro Leu Val
        355                 360                 365

Leu Pro Arg Glu Cys Arg Gln Pro Val Asn Leu Ala Gly Tyr Asn Ile
    370                 375                 380

Pro Asn Lys Thr Lys Leu Ile Val Asn Val Phe Ala Ile Asn Arg Asp
385                 390                 395                 400

Pro Glu Tyr Trp Lys Asp Ala Glu Ala Phe Ile Pro Glu Arg Phe Glu
                405                 410                 415

Asn Ser Ser Ala Thr Val Met Gly Ala Glu Tyr Glu Tyr Leu Pro Phe
            420                 425                 430

Gly Ala Gly Arg Arg Met Cys Pro Gly Ala Ala Leu Gly Leu Ala Asn
        435                 440                 445

Val Gln Leu Pro Leu Ala Asn Ile Leu Tyr His Phe Asn Trp Lys Leu
    450                 455                 460

Pro Asn Gly Val Ser Tyr Asp Gln Ile Asp Met Thr Glu Ser Ser Gly
465                 470                 475                 480

Ala Thr Met Gln Arg Lys Thr Glu Leu Leu Leu Val Pro Ser Phe
                485                 490                 495
```

<210> SEQ ID NO 53
<211> LENGTH: 1500
<212> TYPE: DNA
<213> ORGANISM: Artificial Sequence
<220> FEATURE:
<223> OTHER INFORMATION: CYP71AV1 codon optimized DNA sequence

<400> SEQUENCE: 53

```
atgaccgtac acgacatcat cgcaacgtac ttcactaaat ggtacgtaat tgtgccgctg      60

gcactgattg cgtatcgcgt gctggattat ttctacgcga cccgttctaa aagcactaag     120

aaatctctgc cggaaccgtg gcgtctgcca atcatcggtc acatgcacca cctgatcggc     180

accaccccgc accgtggcgt acgcgacctg gcgcgtaagt acggctctct gatgcatctg     240

cagctgggcg aggtacctac tatcgtcgtt tcctccccga agtgggccaa agaaatcctg     300

actacctatg acatcacttt cgccaaccgc ccggaaacgc tgaccggcga aattgtcctg     360

taccataaca cggatgtggt tctggccccg tacggtgagt actggcgcca gctgcgcaaa     420

atttgtactc tggaactgct gagcgttaaa aaggttaaat ccttccagag cctgcgtgaa     480

gaggaatgct ggaacctggt gcaggagatt aaagcgtctg gcagcggtcg tccagttaac     540

ctgtctgaga atgtttttaa actgatcgct actatcctgt ctcgcgcggc attcggtaaa     600

ggtatcaaag atcagaaaga actgaccgaa atcgttaagg aaatcctgcg ccagactggt     660

ggcttcgacg ttgcggacat cttcccgtcc aaaaagttcc tgcaccatct gtctggcaaa     720

cgcgctcgtc tgacctccct gcgtaagaaa attgataacc tgattgacaa cctggtcgct     780

gagcacactg tgaacacctc ttctaaaacc aacgaaaccc tgctggacgt actgctgcgc     840

ctgaaggact ctgccgaatt tccactgact agcgacaata tcaaagcaat catcctggac     900

atgttcggcg ccggtaccga tacgtcctct tccacgattg agtgggctat ttccgaactg     960
```

-continued

```
atcaaatgcc cgaaggcgat ggaaaaagtg caggcggaac tgcgtaaagc gctgaacggt   1020

aaagagaaaa ttcatgaaga ggacatccag gaactgtcct acctgaatat ggtaatcaaa   1080

gaaactctgc gtctgcatcc gccgctgcca ctggttctgc cgcgtgaatg ccgtcagccg   1140

gttaacctgg ccggctacaa cattccgaac aaaacgaagc tgatcgtcaa cgttttcgcg   1200

atcaaccgcg atcctgaata ctggaaagac gcggaagcgt tcattccgga acgctttgag   1260

aactcctctg ccaccgttat gggcgctgaa tacgagtacc tgccgttcgg tgcgggtcgc   1320

cgtatgtgcc cgggtgctgc actgggcctg gcgaacgttc aactgccact ggcgaacatc   1380

ctgtaccact tcaactggaa actgcctaac ggcgtatctt atgatcaaat cgacatgacc   1440

gaaagctccg gcgcgaccat gcagcgtaaa accgaactgc tgctggttcc gtccttttaa   1500
```

```
<210> SEQ ID NO 54
<211> LENGTH: 499
<212> TYPE: PRT
<213> ORGANISM: Artificial Sequence
<220> FEATURE:
<223> OTHER INFORMATION: CYP71AV1 codon optimized amino acid sequence

<400> SEQUENCE: 54

Met Thr Val His Asp Ile Ile Ala Thr Tyr Phe Thr Lys Trp Tyr Val
1               5                   10                  15

Ile Val Pro Leu Ala Leu Ile Ala Tyr Arg Val Leu Asp Tyr Phe Tyr
            20                  25                  30

Ala Thr Arg Ser Lys Ser Thr Lys Lys Ser Leu Pro Glu Pro Trp Arg
        35                  40                  45

Leu Pro Ile Ile Gly His Met His His Leu Ile Gly Thr Thr Pro His
    50                  55                  60

Arg Gly Val Arg Asp Leu Ala Arg Lys Tyr Gly Ser Leu Met His Leu
65                  70                  75                  80

Gln Leu Gly Glu Val Pro Thr Ile Val Val Ser Ser Pro Lys Trp Ala
                85                  90                  95

Lys Glu Ile Leu Thr Thr Tyr Asp Ile Thr Phe Ala Asn Arg Pro Glu
            100                 105                 110

Thr Leu Thr Gly Glu Ile Val Leu Tyr His Asn Thr Asp Val Val Leu
        115                 120                 125

Ala Pro Tyr Gly Glu Tyr Trp Arg Gln Leu Arg Lys Ile Cys Thr Leu
    130                 135                 140

Glu Leu Leu Ser Val Lys Lys Val Lys Ser Phe Gln Ser Leu Arg Glu
145                 150                 155                 160

Glu Glu Cys Trp Asn Leu Val Gln Glu Ile Lys Ala Ser Gly Ser Gly
                165                 170                 175

Arg Pro Val Asn Leu Ser Glu Asn Val Phe Lys Leu Ile Ala Thr Ile
            180                 185                 190

Leu Ser Arg Ala Ala Phe Gly Lys Gly Ile Lys Asp Gln Lys Glu Leu
        195                 200                 205

Thr Glu Ile Val Lys Glu Ile Leu Arg Gln Thr Gly Gly Phe Asp Val
    210                 215                 220

Ala Asp Ile Phe Pro Ser Lys Lys Phe Leu His His Leu Ser Gly Lys
225                 230                 235                 240

Arg Ala Arg Leu Thr Ser Leu Arg Lys Lys Ile Asp Asn Leu Ile Asp
                245                 250                 255

Asn Leu Val Ala Glu His Thr Val Asn Thr Ser Ser Lys Thr Asn Glu
            260                 265                 270
```

```
Thr Leu Leu Asp Val Leu Leu Arg Leu Lys Asp Ser Ala Glu Phe Pro
        275                 280                 285

Leu Thr Ser Asp Asn Ile Lys Ala Ile Ile Leu Asp Met Phe Gly Ala
    290                 295                 300

Gly Thr Asp Thr Ser Ser Ser Thr Ile Glu Trp Ala Ile Ser Glu Leu
305                 310                 315                 320

Ile Lys Cys Pro Lys Ala Met Glu Lys Val Gln Ala Glu Leu Arg Lys
                325                 330                 335

Ala Leu Asn Gly Lys Glu Lys Ile His Glu Glu Asp Ile Gln Glu Leu
            340                 345                 350

Ser Tyr Leu Asn Met Val Ile Lys Glu Thr Leu Arg Leu His Pro Pro
        355                 360                 365

Leu Pro Leu Val Leu Pro Arg Glu Cys Arg Gln Pro Val Asn Leu Ala
    370                 375                 380

Gly Tyr Asn Ile Pro Asn Lys Thr Lys Leu Ile Val Asn Val Phe Ala
385                 390                 395                 400

Ile Asn Arg Asp Pro Glu Tyr Trp Lys Asp Ala Glu Ala Phe Ile Pro
                405                 410                 415

Glu Arg Phe Glu Asn Ser Ser Ala Thr Val Met Gly Ala Glu Tyr Glu
            420                 425                 430

Tyr Leu Pro Phe Gly Ala Gly Arg Arg Met Cys Pro Gly Ala Ala Leu
        435                 440                 445

Gly Leu Ala Asn Val Gln Leu Pro Leu Ala Asn Ile Leu Tyr His Phe
    450                 455                 460

Asn Trp Lys Leu Pro Asn Gly Val Ser Tyr Asp Gln Ile Asp Met Thr
465                 470                 475                 480

Glu Ser Ser Gly Ala Thr Met Gln Arg Lys Thr Glu Leu Leu Leu Val
                485                 490                 495

Pro Ser Phe


<210> SEQ ID NO 55
<211> LENGTH: 3150
<212> TYPE: DNA
<213> ORGANISM: Bacillus megaterium

<400> SEQUENCE: 55

atgacaatta aagaaatgcc tcagccaaaa acgtttggag agcttaaaaa tttaccgtta      60

ttaaacacag ataaaccggt tcaagctttg atgaaaattg cggatgaatt aggagaaatc     120

tttaaattcg aggcgcctgg tcgtgtaacg cgctacttat caagtcagcg tctaattaaa     180

gaagcatgcg atgaatcacg ctttgataaa aacttaagtc aagcgcttaa atttgtacgt     240

gattttgcag gagacgggtt atttacaagc tggacgcatg aaaaaaattg gaaaaaagcg     300

cataatatct tacttccaag cttcagtcag caggcaatga aaggctatca tgcgatgatg     360

gtcgatatcg ccgtgcagct tgttcaaaag tgggagcgtc taaatgcaga tgagcatatt     420

gaagtaccgg aagacatgac acgtttaacg cttgatacaa ttggtctttg cggctttaac     480

tatcgcttta acagctttta ccgagatcag cctcatccat ttattacaag tatggtccgt     540

gcactggatg aagcaatgaa caagctgcag cgagcaaatc cagacgaccc agcttatgat     600

gaaaacaagc gccagtttca agaagatatc aaggtgatga acgacctagt agataaaatt     660

attgcagatc gcaaagcaag cggtgaacaa agcgatgatt tattaacgca catgctaaac     720

ggaaaagatc cagaaacggg tgagccgctt gatgacgaga acattcgcta tcaaattatt     780

acattcttaa ttgcgggaca cgaaacaaca agtggtcttt tatcatttgc gctgtatttc     840
```

-continued ttagtgaaaa atccacatgt attacaaaaa gcagcagaag aagcagcacg agttctagta 900
gatcctgttc caagctacaa acaagtcaaa cagcttaaat atgtcggcat ggtcttaaac 960
gaagcgctgc gcttatggcc aactgctcct gcgttttccc tatatgcaaa agaagatacg 1020
gtgcttggag gagaatatcc tttagaaaaa ggcgacgaac taatggttct gattcctcag 1080
cttcaccgtg ataaaacaat ttggggagac gatgtggaag agttccgtcc agagcgtttt 1140
gaaaatccaa gtgcgattcc gcagcatgcg tttaaaccgt ttggaaacgg tcagcgtgcg 1200
tgtatcggtc agcagttcgc tcttcatgaa gcaacgctgg tacttggtat gatgctaaaa 1260
cactttgact ttgaagatca tacaaactac gagctggata ttaaagaaac tttaacgtta 1320
aaacctgaag gctttgtggt aaaagcaaaa tcgaaaaaaa ttccgcttgg cggtattcct 1380
tcacctagca ctgaacagtc tgctaaaaaa gtacgcaaaa aggcagaaaa cgctcataat 1440
acgccgctgc ttgtgctata cggttcaaat atgggaacag ctgaaggaac ggcgcgtgat 1500
ttagcagata ttgcaatgag caaaggattt gcaccgcagg tcgcaacgct tgattcacac 1560
gccggaaatc ttccgcgcga aggagctgta ttaattgtaa cggcgtctta taacggtcat 1620
ccgcctgata acgcaaagca atttgtcgac tggttagacc aagcgtctgc tgatgaagta 1680
aaaggcgttc gctactccgt atttggatgc ggcgataaaa actgggctac tacgtatcaa 1740
aaagtgcctg cttttatcga tgaaacgctt gccgctaaag gggcagaaaa catcgctgac 1800
cgcggtgaag cagatgcaag cgacgacttt gaaggcacct atgaagaatg gcgtgaacac 1860
atgtggagtg acgtagcagc ctactttaac ctcgacattg aaaacagtga agataataaa 1920
tctactcttt cacttcaatt tgtcgacagc gccgcggata tgccgcttgc gaaaatgcac 1980
ggtgcgtttt caacgaacgt cgtagcaagc aaagaacttc aacagccagg cagtgcacga 2040
agcacgcgac atcttgaaat tgaacttcca aaagaagctt cttatcaaga aggagatcat 2100
ttaggtgtta ttcctcgcaa ctatgaagga atagtaaacc gtgtaacagc aaggttcggc 2160
ctagatgcat cacagcaaat ccgtctggaa gcagaagaag aaaaattagc tcatttgcca 2220
ctcgctaaaa cagtatccgt agaagagctt ctgcaatacg tggagcttca agatcctgtt 2280
acgcgcacgc agcttcgcgc aatggctgct aaaacggtct gcccgccgca taaagtagag 2340
cttgaagcct tgcttgaaaa gcaagcctac aaagaacaag tgctggcaaa acgtttaaca 2400
atgcttgaac tgcttgaaaa atacccggcg tgtgaaatga aattcagcga atttatcgcc 2460
cttctgccaa gcatacgccc gcgctattac tcgatttctt catcacctcg tgtcgatgaa 2520
aaacaagcaa gcatcacggt cagcgttgtc tcaggagaag cgtggagcgg atatggagaa 2580
tataaaggaa ttgcgtcgaa ctatcttgcc gagctgcaag aaggagatac gattacgtgc 2640
tttatttcca caccgcagtc agaatttacg ctgccaaaag accctgaaac gccgcttatc 2700
atggtcggac cgggaacagg cgtcgcgccg tttagaggct ttgtgcaggc gcgcaaacag 2760
ctaaaagaac aaggacagtc acttggagaa gcacatttat acttcggctg ccgttcacct 2820
catgaagact atctgtatca agaagagctt gaaaacgccc aaagcgaagg catcattacg 2880
cttcataccg ctttttctcg catgccaaat cagccgaaaa catacgttca gcacgtaatg 2940
gaacaagacg gcaagaaatt gattgaactt cttgatcaag gagcgcactt ctatatttgc 3000
ggagacggaa gccaaatggc acctgccgtt gaagcaacgc ttatgaaaag ctatgctgac 3060
gttcaccaag tgagtgaagc agacgctcgc ttatggctgc agcagctaga agaaaaaggc 3120
cgatacgcaa aagacgtgtg ggctgggtaa 3150

<210> SEQ ID NO 56
<211> LENGTH: 1049
<212> TYPE: PRT
<213> ORGANISM: Bacillus megaterium

<400> SEQUENCE: 56

Met Thr Ile Lys Glu Met Pro Gln Pro Lys Thr Phe Gly Glu Leu Lys
1 5 10 15

Asn Leu Pro Leu Leu Asn Thr Asp Lys Pro Val Gln Ala Leu Met Lys
20 25 30

Ile Ala Asp Glu Leu Gly Glu Ile Phe Lys Phe Glu Ala Pro Gly Arg
35 40 45

Val Thr Arg Tyr Leu Ser Ser Gln Arg Leu Ile Lys Glu Ala Cys Asp
50 55 60

Glu Ser Arg Phe Asp Lys Asn Leu Ser Gln Ala Leu Lys Phe Val Arg
65 70 75 80

Asp Phe Ala Gly Asp Gly Leu Phe Thr Ser Trp Thr His Glu Lys Asn
85 90 95

Trp Lys Lys Ala His Asn Ile Leu Leu Pro Ser Phe Ser Gln Gln Ala
100 105 110

Met Lys Gly Tyr His Ala Met Met Val Asp Ile Ala Val Gln Leu Val
115 120 125

Gln Lys Trp Glu Arg Leu Asn Ala Asp Glu His Ile Glu Val Pro Glu
130 135 140

Asp Met Thr Arg Leu Thr Leu Asp Thr Ile Gly Leu Cys Gly Phe Asn
145 150 155 160

Tyr Arg Phe Asn Ser Phe Tyr Arg Asp Gln Pro His Pro Phe Ile Thr
165 170 175

Ser Met Val Arg Ala Leu Asp Glu Ala Met Asn Lys Leu Gln Arg Ala
180 185 190

Asn Pro Asp Asp Pro Ala Tyr Asp Glu Asn Lys Arg Gln Phe Gln Glu
195 200 205

Asp Ile Lys Val Met Asn Asp Leu Val Asp Lys Ile Ile Ala Asp Arg
210 215 220

Lys Ala Ser Gly Glu Gln Ser Asp Asp Leu Leu Thr His Met Leu Asn
225 230 235 240

Gly Lys Asp Pro Glu Thr Gly Glu Pro Leu Asp Asp Glu Asn Ile Arg
245 250 255

Tyr Gln Ile Ile Thr Phe Leu Ile Ala Gly His Glu Thr Thr Ser Gly
260 265 270

Leu Leu Ser Phe Ala Leu Tyr Phe Leu Val Lys Asn Pro His Val Leu
275 280 285

Gln Lys Ala Ala Glu Glu Ala Ala Arg Val Leu Val Asp Pro Val Pro
290 295 300

Ser Tyr Lys Gln Val Lys Gln Leu Lys Tyr Val Gly Met Val Leu Asn
305 310 315 320

Glu Ala Leu Arg Leu Trp Pro Thr Ala Pro Ala Phe Ser Leu Tyr Ala
325 330 335

Lys Glu Asp Thr Val Leu Gly Gly Glu Tyr Pro Leu Glu Lys Gly Asp
340 345 350

Glu Leu Met Val Leu Ile Pro Gln Leu His Arg Asp Lys Thr Ile Trp
355 360 365

Gly Asp Asp Val Glu Glu Phe Arg Pro Glu Arg Phe Glu Asn Pro Ser
370 375 380

```
Ala Ile Pro Gln His Ala Phe Lys Pro Phe Gly Asn Gly Gln Arg Ala
385                 390                 395                 400

Cys Ile Gly Gln Gln Phe Ala Leu His Glu Ala Thr Leu Val Leu Gly
            405                 410                 415

Met Met Leu Lys His Phe Asp Phe Glu Asp His Thr Asn Tyr Glu Leu
            420                 425                 430

Asp Ile Lys Glu Thr Leu Thr Leu Lys Pro Glu Gly Phe Val Val Lys
        435                 440                 445

Ala Lys Ser Lys Lys Ile Pro Leu Gly Gly Ile Pro Ser Pro Ser Thr
    450                 455                 460

Glu Gln Ser Ala Lys Lys Val Arg Lys Lys Ala Glu Asn Ala His Asn
465                 470                 475                 480

Thr Pro Leu Leu Val Leu Tyr Gly Ser Asn Met Gly Thr Ala Glu Gly
            485                 490                 495

Thr Ala Arg Asp Leu Ala Asp Ile Ala Met Ser Lys Gly Phe Ala Pro
            500                 505                 510

Gln Val Ala Thr Leu Asp Ser His Ala Gly Asn Leu Pro Arg Glu Gly
        515                 520                 525

Ala Val Leu Ile Val Thr Ala Ser Tyr Asn Gly His Pro Pro Asp Asn
    530                 535                 540

Ala Lys Gln Phe Val Asp Trp Leu Asp Gln Ala Ser Ala Asp Glu Val
545                 550                 555                 560

Lys Gly Val Arg Tyr Ser Val Phe Gly Cys Gly Asp Lys Asn Trp Ala
            565                 570                 575

Thr Thr Tyr Gln Lys Val Pro Ala Phe Ile Asp Glu Thr Leu Ala Ala
            580                 585                 590

Lys Gly Ala Glu Asn Ile Ala Asp Arg Gly Glu Ala Asp Ala Ser Asp
        595                 600                 605

Asp Phe Glu Gly Thr Tyr Glu Glu Trp Arg Glu His Met Trp Ser Asp
    610                 615                 620

Val Ala Ala Tyr Phe Asn Leu Asp Ile Glu Asn Ser Glu Asp Asn Lys
625                 630                 635                 640

Ser Thr Leu Ser Leu Gln Phe Val Asp Ser Ala Ala Asp Met Pro Leu
            645                 650                 655

Ala Lys Met His Gly Ala Phe Ser Thr Asn Val Val Ala Ser Lys Glu
            660                 665                 670

Leu Gln Gln Pro Gly Ser Ala Arg Ser Thr Arg His Leu Glu Ile Glu
        675                 680                 685

Leu Pro Lys Glu Ala Ser Tyr Gln Glu Gly Asp His Leu Gly Val Ile
    690                 695                 700

Pro Arg Asn Tyr Glu Gly Ile Val Asn Arg Val Thr Ala Arg Phe Gly
705                 710                 715                 720

Leu Asp Ala Ser Gln Gln Ile Arg Leu Glu Ala Glu Glu Glu Lys Leu
            725                 730                 735

Ala His Leu Pro Leu Ala Lys Thr Val Ser Val Glu Glu Leu Leu Gln
            740                 745                 750

Tyr Val Glu Leu Gln Asp Pro Val Thr Arg Thr Gln Leu Arg Ala Met
        755                 760                 765

Ala Ala Lys Thr Val Cys Pro Pro His Lys Val Glu Leu Glu Ala Leu
    770                 775                 780

Leu Glu Lys Gln Ala Tyr Lys Glu Gln Val Leu Ala Lys Arg Leu Thr
785                 790                 795                 800
```

-continued

```
Met Leu Glu Leu Leu Glu Lys Tyr Pro Ala Cys Glu Met Lys Phe Ser
                805                 810                 815

Glu Phe Ile Ala Leu Leu Pro Ser Ile Arg Pro Arg Tyr Tyr Ser Ile
            820                 825                 830

Ser Ser Ser Pro Arg Val Asp Glu Lys Gln Ala Ser Ile Thr Val Ser
        835                 840                 845

Val Val Ser Gly Glu Ala Trp Ser Gly Tyr Gly Glu Tyr Lys Gly Ile
    850                 855                 860

Ala Ser Asn Tyr Leu Ala Glu Leu Gln Glu Gly Asp Thr Ile Thr Cys
865                 870                 875                 880

Phe Ile Ser Thr Pro Gln Ser Glu Phe Thr Leu Pro Lys Asp Pro Glu
                885                 890                 895

Thr Pro Leu Ile Met Val Gly Pro Gly Thr Gly Val Ala Pro Phe Arg
            900                 905                 910

Gly Phe Val Gln Ala Arg Lys Gln Leu Lys Glu Gln Gly Gln Ser Leu
        915                 920                 925

Gly Glu Ala His Leu Tyr Phe Gly Cys Arg Ser Pro His Glu Asp Tyr
    930                 935                 940

Leu Tyr Gln Glu Glu Leu Glu Asn Ala Gln Ser Glu Gly Ile Ile Thr
945                 950                 955                 960

Leu His Thr Ala Phe Ser Arg Met Pro Asn Gln Pro Lys Thr Tyr Val
                965                 970                 975

Gln His Val Met Glu Gln Asp Gly Lys Lys Leu Ile Glu Leu Leu Asp
            980                 985                 990

Gln Gly Ala His Phe Tyr Ile Cys  Gly Asp Gly Ser Gln  Met Ala Pro
        995                 1000                1005

Ala Val  Glu Ala Thr Leu Met  Lys Ser Tyr Ala Asp  Val His Gln
    1010                1015                1020

Val Ser  Glu Ala Asp Ala Arg  Leu Trp Leu Gln Gln  Leu Glu Glu
    1025                1030                1035

Lys Gly  Arg Tyr Ala Lys Asp  Val Trp Ala Gly
    1040                1045
```

<210> SEQ ID NO 57
<211> LENGTH: 3150
<212> TYPE: DNA
<213> ORGANISM: Artificial Sequence
<220> FEATURE:
<223> OTHER INFORMATION: P450-BM3 Variant 7 DNA sequence

<400> SEQUENCE: 57

```
atgacaatta aagaaatgcc tcagccaaaa acgtttggag agcttaaaaa tttaccgtta     60

ttaaacacag ataaaccggt tcaagctttg atgaaaattg cggatgaatt aggagaaatc    120

tttaaattcg aggcgcctgg tcgtgtaacg cgctacttat caagtcagcg tctaattaaa    180

gaagcatgcg atgaatcacg ctttgataaa aacttaagtc aagcgcttaa atttgtacgt    240

gattttgcag gagacgggtt aatcacaagc tggacgcatg aaaaaaattg gaaaaaagcg    300

cataatatct tacttccaag cttcagtcag caggcaatga aaggctatca tgcgatgatg    360

gtcgatatcg ccgtgcagct tgttcaaaag tgggagcgtc taaatgcaga tgagcatatt    420

gaagtaccgg aagacatgac acgtttaacg cttgatacaa ttggtctttg cggctttaac    480

tatcgcttta acagctttta ccgagatcag cctcatccat ttattacaag tatggtccgt    540

gcactggatg aagcaatgaa caagctgcag cgagcaaatc cagacgaccc agcttatgat    600

gaaaacaagc gccagtttca agaagatatc aaggtgatga acgacctagt agataaaatt    660
```

-continued

```
attgcagatc gcaaagcaag cggtgaacaa agcgatgatt tattaacgca catgctaaac    720
ggaaaagatc cagaaacggg tgagccgctt gatgacgaga acattcgcta tcaaattatt    780
acattcttaa ttgcgggaca cgaaacaaca agtggtcttt tatcatttgc gctgtatttc    840
ttagtgaaaa atccacatgt attacaaaaa gcagcagaag aagcagcacg agttctagta    900
gatcctgttc caagctacaa acaagtcaaa cagcttaaat atgtcggcat ggtcttaaac    960
gaagcgctgc gcttatggcc aactatccct gcgttttccc tatatgcaaa agaagatacg   1020
gtgcttggag gagaatatcc tttagaaaaa ggcgacgaac taatggttct gattcctcag   1080
cttcaccgtg ataaaacaat ttggggagac gatgtggaag agttccgtcc agagcgtttt   1140
gaaaatccaa gtgcgattcc gcagcatgcg tttaaaccgt ttggaaacgg tcagcgtgcg   1200
tgtatcggtc agcagttcgc tcttcatgaa gcaacgctgg tacttggtat gatgctaaaa   1260
cactttgact ttgaagatca tacaaactac gagctggata ttaaagaaac tttaacgtta   1320
aaacctgaag gctttgtggt aaaagcaaaa tcgaaaaaaa ttccgcttgg cggtattcct   1380
tcacctagca ctgaacagtc tgctaaaaaa gtacgcaaaa aggcagaaaa cgctcataat   1440
acgccgctgc ttgtgctata cggttcaaat atgggaacag ctgaaggaac ggcgcgtgat   1500
ttagcagata ttgcaatgag caaaggattt gcaccgcagg tcgcaacgct tgattcacac   1560
gccggaaatc ttccgcgcga aggagctgta ttaattgtaa cggcgtctta taacggtcat   1620
ccgcctgata acgcaaagca atttgtcgac tggttagacc aagcgtctgc tgatgaagta   1680
aaaggcgttc gctactccgt atttggatgc ggcgataaaa actgggctac tacgtatcaa   1740
aaagtgcctg cttttatcga tgaaacgctt gccgctaaag gggcagaaaa catcgctgac   1800
cgcggtgaag cagatgcaag cgacgacttt gaaggcacct atgaagaatg gcgtgaacac   1860
atgtggagtg acgtagcagc ctactttaac ctcgacattg aaaacagtga agataataaa   1920
tctactcttt cacttcaatt tgtcgacagc gccgcggata tgccgcttgc gaaaatgcac   1980
ggtgcgtttt caacgaacgt cgtagcaagc aaagaacttc aacagccagg cagtgcacga   2040
agcacgcgac atcttgaaat tgaacttcca aaagaagctt cttatcaaga aggagatcat   2100
ttaggtgtta ttcctcgcaa ctatgaagga atagtaaacc gtgtaacagc aaggttcggc   2160
ctagatgcat cacagcaaat ccgtctggaa gcagaagaag aaaaattagc tcatttgcca   2220
ctcgctaaaa cagtatccgt agaagagctt ctgcaatacg tggagcttca agatcctgtt   2280
acgcgcacgc agcttcgcgc aatggctgct aaaacggtct gcccgccgca taaagtagag   2340
cttgaagcct tgcttgaaaa gcaagcctac aaagaacaag tgctggcaaa acgtttaaca   2400
atgcttgaac tgcttgaaaa atacccggcg tgtgaaatga aattcagcga atttatcgcc   2460
cttctgccaa gcatacgccc gcgctattac tcgatttctt catcacctcg tgtcgatgaa   2520
aaacaagcaa gcatcacggt cagcgttgtc tcaggagaag cgtggagcgg atatggagaa   2580
tataaaggaa ttgcgtcgaa ctatcttgcc gagctgcaag aaggagatac gattacgtgc   2640
tttatttcca caccgcagtc agaatttacg ctgccaaaag accctgaaac gccgcttatc   2700
atggtcggac cgggaacagg cgtcgcgccg tttagaggct ttgtgcaggc gcgcaaacag   2760
ctaaaagaac aaggacagtc acttggagaa gcacatttat acttcggctg ccgttcacct   2820
catgaagact atctgtatca agaagagctt gaaaacgccc aaagcgaagg catcattacg   2880
cttcataccg ctttttctcg catgccaaat cagccgaaaa catacgttca gcacgtaatg   2940
gaacaagacg gcaagaaatt gattgaactt cttgatcaag gagcgcactt ctatatttgc   3000
```

-continued

```
ggagacggaa gccaaatggc acctgccgtt gaagcaacgc ttatgaaaag ctatgctgac   3060

gttcaccaag tgagtgaagc agacgctcgc ttatggctgc agcagctaga agaaaaaggc   3120

cgatacgcaa aagacgtgtg ggctgggtaa                                     3150


<210> SEQ ID NO 58
<211> LENGTH: 1049
<212> TYPE: PRT
<213> ORGANISM: Artificial Sequence
<220> FEATURE:
<223> OTHER INFORMATION: P450-BM3 Variant 7 amino acid sequence

<400> SEQUENCE: 58

Met Thr Ile Lys Glu Met Pro Gln Pro Lys Thr Phe Gly Glu Leu Lys
1               5                   10                  15

Asn Leu Pro Leu Leu Asn Thr Asp Lys Pro Val Gln Ala Leu Met Lys
            20                  25                  30

Ile Ala Asp Glu Leu Gly Glu Ile Phe Lys Phe Glu Ala Pro Gly Arg
        35                  40                  45

Val Thr Arg Tyr Leu Ser Ser Gln Arg Leu Ile Lys Glu Ala Cys Asp
    50                  55                  60

Glu Ser Arg Phe Asp Lys Asn Leu Ser Gln Ala Leu Lys Phe Val Arg
65                  70                  75                  80

Asp Phe Ala Gly Asp Gly Leu Ile Thr Ser Trp Thr His Glu Lys Asn
                85                  90                  95

Trp Lys Lys Ala His Asn Ile Leu Leu Pro Ser Phe Ser Gln Gln Ala
            100                 105                 110

Met Lys Gly Tyr His Ala Met Met Val Asp Ile Ala Val Gln Leu Val
        115                 120                 125

Gln Lys Trp Glu Arg Leu Asn Ala Asp Glu His Ile Glu Val Pro Glu
    130                 135                 140

Asp Met Thr Arg Leu Thr Leu Asp Thr Ile Gly Leu Cys Gly Phe Asn
145                 150                 155                 160

Tyr Arg Phe Asn Ser Phe Tyr Arg Asp Gln Pro His Pro Phe Ile Thr
                165                 170                 175

Ser Met Val Arg Ala Leu Asp Glu Ala Met Asn Lys Leu Gln Arg Ala
            180                 185                 190

Asn Pro Asp Asp Pro Ala Tyr Asp Glu Asn Lys Arg Gln Phe Gln Glu
        195                 200                 205

Asp Ile Lys Val Met Asn Asp Leu Val Asp Lys Ile Ile Ala Asp Arg
    210                 215                 220

Lys Ala Ser Gly Glu Gln Ser Asp Asp Leu Leu Thr His Met Leu Asn
225                 230                 235                 240

Gly Lys Asp Pro Glu Thr Gly Glu Pro Leu Asp Asp Glu Asn Ile Arg
                245                 250                 255

Tyr Gln Ile Ile Thr Phe Leu Ile Ala Gly His Glu Thr Thr Ser Gly
            260                 265                 270

Leu Leu Ser Phe Ala Leu Tyr Phe Leu Val Lys Asn Pro His Val Leu
        275                 280                 285

Gln Lys Ala Ala Glu Glu Ala Ala Arg Val Leu Val Asp Pro Val Pro
    290                 295                 300

Ser Tyr Lys Gln Val Lys Gln Leu Lys Tyr Val Gly Met Val Leu Asn
305                 310                 315                 320

Glu Ala Leu Arg Leu Trp Pro Thr Ile Pro Ala Phe Ser Leu Tyr Ala
                325                 330                 335
```

```
Lys Glu Asp Thr Val Leu Gly Gly Glu Tyr Pro Leu Glu Lys Gly Asp
            340                 345                 350

Glu Leu Met Val Leu Ile Pro Gln Leu His Arg Asp Lys Thr Ile Trp
        355                 360                 365

Gly Asp Asp Val Glu Glu Phe Arg Pro Glu Arg Phe Glu Asn Pro Ser
    370                 375                 380

Ala Ile Pro Gln His Ala Phe Lys Pro Phe Gly Asn Gly Gln Arg Ala
385                 390                 395                 400

Cys Ile Gly Gln Gln Phe Ala Leu His Glu Ala Thr Leu Val Leu Gly
                405                 410                 415

Met Met Leu Lys His Phe Asp Phe Glu Asp His Thr Asn Tyr Glu Leu
            420                 425                 430

Asp Ile Lys Glu Thr Leu Thr Leu Lys Pro Glu Gly Phe Val Val Lys
        435                 440                 445

Ala Lys Ser Lys Lys Ile Pro Leu Gly Gly Ile Pro Ser Pro Ser Thr
    450                 455                 460

Glu Gln Ser Ala Lys Lys Val Arg Lys Lys Ala Glu Asn Ala His Asn
465                 470                 475                 480

Thr Pro Leu Leu Val Leu Tyr Gly Ser Asn Met Gly Thr Ala Glu Gly
                485                 490                 495

Thr Ala Arg Asp Leu Ala Asp Ile Ala Met Ser Lys Gly Phe Ala Pro
            500                 505                 510

Gln Val Ala Thr Leu Asp Ser His Ala Gly Asn Leu Pro Arg Glu Gly
        515                 520                 525

Ala Val Leu Ile Val Thr Ala Ser Tyr Asn Gly His Pro Pro Asp Asn
    530                 535                 540

Ala Lys Gln Phe Val Asp Trp Leu Asp Gln Ala Ser Ala Asp Glu Val
545                 550                 555                 560

Lys Gly Val Arg Tyr Ser Val Phe Gly Cys Gly Asp Lys Asn Trp Ala
                565                 570                 575

Thr Thr Tyr Gln Lys Val Pro Ala Phe Ile Asp Glu Thr Leu Ala Ala
            580                 585                 590

Lys Gly Ala Glu Asn Ile Ala Asp Arg Gly Glu Ala Asp Ala Ser Asp
        595                 600                 605

Asp Phe Glu Gly Thr Tyr Glu Glu Trp Arg Glu His Met Trp Ser Asp
    610                 615                 620

Val Ala Ala Tyr Phe Asn Leu Asp Ile Glu Asn Ser Glu Asp Asn Lys
625                 630                 635                 640

Ser Thr Leu Ser Leu Gln Phe Val Asp Ser Ala Ala Asp Met Pro Leu
                645                 650                 655

Ala Lys Met His Gly Ala Phe Ser Thr Asn Val Val Ala Ser Lys Glu
            660                 665                 670

Leu Gln Gln Pro Gly Ser Ala Arg Ser Thr Arg His Leu Glu Ile Glu
        675                 680                 685

Leu Pro Lys Glu Ala Ser Tyr Gln Glu Gly Asp His Leu Gly Val Ile
    690                 695                 700

Pro Arg Asn Tyr Glu Gly Ile Val Asn Arg Val Thr Ala Arg Phe Gly
705                 710                 715                 720

Leu Asp Ala Ser Gln Gln Ile Arg Leu Glu Ala Glu Glu Glu Lys Leu
                725                 730                 735

Ala His Leu Pro Leu Ala Lys Thr Val Ser Val Glu Glu Leu Leu Gln
            740                 745                 750

Tyr Val Glu Leu Gln Asp Pro Val Thr Arg Thr Gln Leu Arg Ala Met
```

```
        755                 760                 765

Ala Ala Lys Thr Val Cys Pro Pro His Lys Val Glu Leu Glu Ala Leu
    770                 775                 780

Leu Glu Lys Gln Ala Tyr Lys Glu Gln Val Leu Ala Lys Arg Leu Thr
785                 790                 795                 800

Met Leu Glu Leu Leu Glu Lys Tyr Pro Ala Cys Glu Met Lys Phe Ser
                805                 810                 815

Glu Phe Ile Ala Leu Leu Pro Ser Ile Arg Pro Arg Tyr Tyr Ser Ile
            820                 825                 830

Ser Ser Ser Pro Arg Val Asp Glu Lys Gln Ala Ser Ile Thr Val Ser
        835                 840                 845

Val Val Ser Gly Glu Ala Trp Ser Gly Tyr Gly Glu Tyr Lys Gly Ile
    850                 855                 860

Ala Ser Asn Tyr Leu Ala Glu Leu Gln Glu Gly Asp Thr Ile Thr Cys
865                 870                 875                 880

Phe Ile Ser Thr Pro Gln Ser Glu Phe Thr Leu Pro Lys Asp Pro Glu
                885                 890                 895

Thr Pro Leu Ile Met Val Gly Pro Gly Thr Gly Val Ala Pro Phe Arg
            900                 905                 910

Gly Phe Val Gln Ala Arg Lys Gln Leu Lys Glu Gln Gly Gln Ser Leu
        915                 920                 925

Gly Glu Ala His Leu Tyr Phe Gly Cys Arg Ser Pro His Glu Asp Tyr
    930                 935                 940

Leu Tyr Gln Glu Glu Leu Glu Asn Ala Gln Ser Glu Gly Ile Ile Thr
945                 950                 955                 960

Leu His Thr Ala Phe Ser Arg Met Pro Asn Gln Pro Lys Thr Tyr Val
                965                 970                 975

Gln His Val Met Glu Gln Asp Gly Lys Lys Leu Ile Glu Leu Leu Asp
            980                 985                 990

Gln Gly Ala His Phe Tyr Ile Cys  Gly Asp Gly Ser Gln  Met Ala Pro
        995                 1000                1005

Ala Val  Glu Ala Thr Leu Met  Lys Ser Tyr Ala Asp  Val His Gln
    1010                1015                1020

Val Ser  Glu Ala Asp Ala Arg  Leu Trp Leu Gln Gln  Leu Glu Glu
    1025                1030                1035

Lys Gly  Arg Tyr Ala Lys Asp  Val Trp Ala Gly
    1040                1045
```

<210> SEQ ID NO 59
<211> LENGTH: 3150
<212> TYPE: DNA
<213> ORGANISM: Artificial Sequence
<220> FEATURE:
<223> OTHER INFORMATION: P450-BM3 Variant 17 DNA sequence

<400> SEQUENCE: 59

```
atgacaatta aagaaatgcc tcagccaaaa acgtttggag agcttaaaaa tttaccgtta      60

ttaaacacag ataaaccggt tcaagctttg atgaaaattg cggatgaatt aggagaaatc     120

tttaaattcg aggcgcctgg tcgtgtaacg cgctacttat caagtcagcg tctaattaaa     180

gaagcatgcg atgaatcacg ctttgataaa aacttaagtc aagcgcttaa atttgtacgt     240

gattttgcag gagacgggtt agttacaagc tggacgcatg aaaaaaattg gaaaaaagcg     300

cataatatct tacttccaag cttcagtcag caggcaatga aaggctatca tgcgatgatg     360

gtcgatatcg ccgtgcagct tgttcaaaag tgggagcgtc taaatgcaga tgagcatatt     420
```

```
gaagtaccgg aagacatgac acgtttaacg cttgatacaa ttggtctttg cggctttaac    480
tatcgcttta acagctttta ccgagatcag cctcatccat ttattacaag tatggtccgt    540
gcactggatg aagcaatgaa caagctgcag cgagcaaatc cagacgaccc agcttatgat    600
gaaaacaagc gccagtttca agaagatatc aaggtgatga acgacctagt agataaaatt    660
attgcagatc gcaaagcaag cggtgaacaa agcgatgatt tattaacgca catgctaaac    720
ggaaaagatc cagaaacggg tgagccgctt gatgacgaga acattcgcta tcaaattatt    780
acattcttaa ttgcgggaca cgaaacaaca agtggtcttt tatcatttgc gctgtatttc    840
ttagtgaaaa atccacatgt attacaaaaa gcagcagaag aagcagcacg agttctagta    900
gatcctgttc caagctacaa acaagtcaaa cagcttaaat atgtcggcat ggtcttaaac    960
gaagcgctgc gcttatggcc aactatccct gcgttttccc tatatgcaaa agaagatacg   1020
gtgcttggag gagaatatcc tttagaaaaa ggcgacgaac taatggttct gattcctcag   1080
cttcaccgtg ataaaacaat ttggggagac gatgtggaag agttccgtcc agagcgtttt   1140
gaaaatccaa gtgcgattcc gcagcatgcg tttaaaccgt ttggaaacgg tcagcgtgcg   1200
tgtatcggtc agcagttcgc tcttcatgaa gcaacgctgg tacttggtat gatgctaaaa   1260
cactttgact ttgaagatca tacaaactac gagctggata ttaaagaaac tttaacgtta   1320
aaacctgaag gctttgtggt aaaagcaaaa tcgaaaaaaa ttccgcttgg cggtattcct   1380
tcacctagca ctgaacagtc tgctaaaaaa gtacgcaaaa aggcagaaaa cgctcataat   1440
acgccgctgc ttgtgctata cggttcaaat atgggaacag ctgaaggaac ggcgcgtgat   1500
ttagcagata ttgcaatgag caaaggattt gcaccgcagg tcgcaacgct tgattcacac   1560
gccggaaatc ttccgcgcga aggagctgta ttaattgtaa cggcgtctta taacggtcat   1620
ccgcctgata acgcaaagca atttgtcgac tggttagacc aagcgtctgc tgatgaagta   1680
aaaggcgttc gctactccgt atttggatgc ggcgataaaa actgggctac tacgtatcaa   1740
aaagtgcctg cttttatcga tgaaacgctt gccgctaaag gggcagaaaa catcgctgac   1800
cgcggtgaag cagatgcaag cgacgacttt gaaggcacct atgaagaatg gcgtgaacac   1860
atgtggagtg acgtagcagc ctactttaac ctcgacattg aaaacagtga agataataaa   1920
tctactcttt cacttcaatt tgtcgacagc gccgcggata tgccgcttgc gaaaatgcac   1980
ggtgcgtttt caacgaacgt cgtagcaagc aaagaacttc aacagccagg cagtgcacga   2040
agcacgcgac atcttgaaat tgaacttcca aaagaagctt cttatcaaga aggagatcat   2100
ttaggtgtta ttcctcgcaa ctatgaagga atagtaaacc gtgtaacagc aaggttcggc   2160
ctagatgcat cacagcaaat ccgtctggaa gcagaagaag aaaaattagc tcatttgcca   2220
ctcgctaaaa cagtatccgt agaagagctt ctgcaatacg tggagcttca agatcctgtt   2280
acgcgcacgc agcttcgcgc aatggctgct aaaacggtct gcccgccgca taaagtagag   2340
cttgaagcct tgcttgaaaa gcaagcctac aaagaacaag tgctggcaaa acgtttaaca   2400
atgcttgaac tgcttgaaaa atacccggcg tgtgaaatga aattcagcga atttatcgcc   2460
cttctgccaa gcatacgccc gcgctattac tcgatttctt catcacctcg tgtcgatgaa   2520
aaacaagcaa gcatcacggt cagcgttgtc tcaggagaag cgtggagcgg atatggagaa   2580
tataaaggaa ttgcgtcgaa ctatcttgcc gagctgcaag aaggagatac gattacgtgc   2640
tttatttcca caccgcagtc agaatttacg ctgccaaaag accctgaaac gccgcttatc   2700
atggtcggac cgggaacagg cgtcgcgccg tttagaggct ttgtgcaggc gcgcaaacag   2760
```

```
ctaaaagaac aaggacagtc acttggagaa gcacatttat acttcggctg ccgttcacct   2820

catgaagact atctgtatca agaagagctt gaaaacgccc aaagcgaagg catcattacg   2880

cttcataccg ctttttctcg catgccaaat cagccgaaaa catacgttca gcacgtaatg   2940

gaacaagacg gcaagaaatt gattgaactt cttgatcaag gagcgcactt ctatatttgc   3000

ggagacggaa gccaaatggc acctgccgtt gaagcaacgc ttatgaaaag ctatgctgac   3060

gttcaccaag tgagtgaagc agacgctcgc ttatggctgc agcagctaga agaaaaaggc   3120

cgatacgcaa aagacgtgtg ggctgggtaa                                    3150


<210> SEQ ID NO 60
<211> LENGTH: 1049
<212> TYPE: PRT
<213> ORGANISM: Artificial Sequence
<220> FEATURE:
<223> OTHER INFORMATION: P450-BM3 Variant 17 amino acid sequence

<400> SEQUENCE: 60

Met Thr Ile Lys Glu Met Pro Gln Pro Lys Thr Phe Gly Glu Leu Lys
1               5                   10                  15

Asn Leu Pro Leu Leu Asn Thr Asp Lys Pro Val Gln Ala Leu Met Lys
            20                  25                  30

Ile Ala Asp Glu Leu Gly Glu Ile Phe Lys Phe Glu Ala Pro Gly Arg
        35                  40                  45

Val Thr Arg Tyr Leu Ser Ser Gln Arg Leu Ile Lys Glu Ala Cys Asp
    50                  55                  60

Glu Ser Arg Phe Asp Lys Asn Leu Ser Gln Ala Leu Lys Phe Val Arg
65                  70                  75                  80

Asp Phe Ala Gly Asp Gly Leu Val Thr Ser Trp Thr His Glu Lys Asn
                85                  90                  95

Trp Lys Lys Ala His Asn Ile Leu Leu Pro Ser Phe Ser Gln Gln Ala
            100                 105                 110

Met Lys Gly Tyr His Ala Met Met Val Asp Ile Ala Val Gln Leu Val
        115                 120                 125

Gln Lys Trp Glu Arg Leu Asn Ala Asp Glu His Ile Glu Val Pro Glu
    130                 135                 140

Asp Met Thr Arg Leu Thr Leu Asp Thr Ile Gly Leu Cys Gly Phe Asn
145                 150                 155                 160

Tyr Arg Phe Asn Ser Phe Tyr Arg Asp Gln Pro His Pro Phe Ile Thr
                165                 170                 175

Ser Met Val Arg Ala Leu Asp Glu Ala Met Asn Lys Leu Gln Arg Ala
            180                 185                 190

Asn Pro Asp Asp Pro Ala Tyr Asp Glu Asn Lys Arg Gln Phe Gln Glu
        195                 200                 205

Asp Ile Lys Val Met Asn Asp Leu Val Asp Lys Ile Ile Ala Asp Arg
    210                 215                 220

Lys Ala Ser Gly Glu Gln Ser Asp Asp Leu Leu Thr His Met Leu Asn
225                 230                 235                 240

Gly Lys Asp Pro Glu Thr Gly Glu Pro Leu Asp Asp Glu Asn Ile Arg
                245                 250                 255

Tyr Gln Ile Ile Thr Phe Leu Ile Ala Gly His Glu Thr Thr Ser Gly
            260                 265                 270

Leu Leu Ser Phe Ala Leu Tyr Phe Leu Val Lys Asn Pro His Val Leu
        275                 280                 285

Gln Lys Ala Ala Glu Glu Ala Ala Arg Val Leu Val Asp Pro Val Pro
```

```
    290                 295                 300

Ser Tyr Lys Gln Val Lys Gln Leu Lys Tyr Val Gly Met Val Leu Asn
305                 310                 315                 320

Glu Ala Leu Arg Leu Trp Pro Thr Ile Pro Ala Phe Ser Leu Tyr Ala
                325                 330                 335

Lys Glu Asp Thr Val Leu Gly Gly Glu Tyr Pro Leu Glu Lys Gly Asp
            340                 345                 350

Glu Leu Met Val Leu Ile Pro Gln Leu His Arg Asp Lys Thr Ile Trp
        355                 360                 365

Gly Asp Asp Val Glu Glu Phe Arg Pro Glu Arg Phe Glu Asn Pro Ser
    370                 375                 380

Ala Ile Pro Gln His Ala Phe Lys Pro Phe Gly Asn Gly Gln Arg Ala
385                 390                 395                 400

Cys Ile Gly Gln Gln Phe Ala Leu His Glu Ala Thr Leu Val Leu Gly
                405                 410                 415

Met Met Leu Lys His Phe Asp Phe Glu Asp His Thr Asn Tyr Glu Leu
            420                 425                 430

Asp Ile Lys Glu Thr Leu Thr Leu Lys Pro Glu Gly Phe Val Val Lys
        435                 440                 445

Ala Lys Ser Lys Lys Ile Pro Leu Gly Gly Ile Pro Ser Pro Ser Thr
    450                 455                 460

Glu Gln Ser Ala Lys Lys Val Arg Lys Lys Ala Glu Asn Ala His Asn
465                 470                 475                 480

Thr Pro Leu Leu Val Leu Tyr Gly Ser Asn Met Gly Thr Ala Glu Gly
                485                 490                 495

Thr Ala Arg Asp Leu Ala Asp Ile Ala Met Ser Lys Gly Phe Ala Pro
            500                 505                 510

Gln Val Ala Thr Leu Asp Ser His Ala Gly Asn Leu Pro Arg Glu Gly
        515                 520                 525

Ala Val Leu Ile Val Thr Ala Ser Tyr Asn Gly His Pro Pro Asp Asn
    530                 535                 540

Ala Lys Gln Phe Val Asp Trp Leu Asp Gln Ala Ser Ala Asp Glu Val
545                 550                 555                 560

Lys Gly Val Arg Tyr Ser Val Phe Gly Cys Gly Asp Lys Asn Trp Ala
                565                 570                 575

Thr Thr Tyr Gln Lys Val Pro Ala Phe Ile Asp Glu Thr Leu Ala Ala
            580                 585                 590

Lys Gly Ala Glu Asn Ile Ala Asp Arg Gly Glu Ala Asp Ala Ser Asp
        595                 600                 605

Asp Phe Glu Gly Thr Tyr Glu Glu Trp Arg Glu His Met Trp Ser Asp
    610                 615                 620

Val Ala Ala Tyr Phe Asn Leu Asp Ile Glu Asn Ser Glu Asp Asn Lys
625                 630                 635                 640

Ser Thr Leu Ser Leu Gln Phe Val Asp Ser Ala Ala Asp Met Pro Leu
                645                 650                 655

Ala Lys Met His Gly Ala Phe Ser Thr Asn Val Val Ala Ser Lys Glu
            660                 665                 670

Leu Gln Gln Pro Gly Ser Ala Arg Ser Thr Arg His Leu Glu Ile Glu
        675                 680                 685

Leu Pro Lys Glu Ala Ser Tyr Gln Glu Gly Asp His Leu Gly Val Ile
    690                 695                 700

Pro Arg Asn Tyr Glu Gly Ile Val Asn Arg Val Thr Ala Arg Phe Gly
705                 710                 715                 720
```

```
Leu Asp Ala Ser Gln Gln Ile Arg Leu Glu Ala Glu Glu Glu Lys Leu
                725                 730                 735

Ala His Leu Pro Leu Ala Lys Thr Val Ser Val Glu Glu Leu Leu Gln
            740                 745                 750

Tyr Val Glu Leu Gln Asp Pro Val Thr Arg Thr Gln Leu Arg Ala Met
        755                 760                 765

Ala Ala Lys Thr Val Cys Pro Pro His Lys Val Glu Leu Glu Ala Leu
    770                 775                 780

Leu Glu Lys Gln Ala Tyr Lys Glu Gln Val Leu Ala Lys Arg Leu Thr
785                 790                 795                 800

Met Leu Glu Leu Leu Glu Lys Tyr Pro Ala Cys Glu Met Lys Phe Ser
                805                 810                 815

Glu Phe Ile Ala Leu Leu Pro Ser Ile Arg Pro Arg Tyr Tyr Ser Ile
            820                 825                 830

Ser Ser Ser Pro Arg Val Asp Glu Lys Gln Ala Ser Ile Thr Val Ser
        835                 840                 845

Val Val Ser Gly Glu Ala Trp Ser Gly Tyr Gly Glu Tyr Lys Gly Ile
    850                 855                 860

Ala Ser Asn Tyr Leu Ala Glu Leu Gln Glu Gly Asp Thr Ile Thr Cys
865                 870                 875                 880

Phe Ile Ser Thr Pro Gln Ser Glu Phe Thr Leu Pro Lys Asp Pro Glu
                885                 890                 895

Thr Pro Leu Ile Met Val Gly Pro Gly Thr Gly Val Ala Pro Phe Arg
            900                 905                 910

Gly Phe Val Gln Ala Arg Lys Gln Leu Lys Glu Gln Gly Gln Ser Leu
        915                 920                 925

Gly Glu Ala His Leu Tyr Phe Gly Cys Arg Ser Pro His Glu Asp Tyr
    930                 935                 940

Leu Tyr Gln Glu Glu Leu Glu Asn Ala Gln Ser Glu Gly Ile Ile Thr
945                 950                 955                 960

Leu His Thr Ala Phe Ser Arg Met Pro Asn Gln Pro Lys Thr Tyr Val
                965                 970                 975

Gln His Val Met Glu Gln Asp Gly Lys Lys Leu Ile Glu Leu Leu Asp
            980                 985                 990

Gln Gly Ala His Phe Tyr Ile Cys  Gly Asp Gly Ser Gln  Met Ala Pro
        995                 1000                1005

Ala Val  Glu Ala Thr Leu Met  Lys Ser Tyr Ala Asp  Val His Gln
    1010                1015                1020

Val Ser  Glu Ala Asp Ala Arg  Leu Trp Leu Gln Gln  Leu Glu Glu
    1025                1030                1035

Lys Gly  Arg Tyr Ala Lys Asp  Val Trp Ala Gly
    1040                1045
```

<210> SEQ ID NO 61
<211> LENGTH: 3150
<212> TYPE: DNA
<213> ORGANISM: Artificial Sequence
<220> FEATURE:
<223> OTHER INFORMATION: P450-BM3 Variant 18 DNA sequence

<400> SEQUENCE: 61

```
atgacaatta aagaaatgcc tcagccaaaa acgtttggag agcttaaaaa tttaccgtta     60

ttaaacacag ataaaccggt tcaagctttg atgaaaattg cggatgaatt aggagaaatc    120

tttaaattcg aggcgcctgg tcgtgtaacg cgctacttat caagtcagcg tctaattaaa    180
```

-continued

```
gaagcatgcg atgaatcacg ctttgataaa aacttaagtc aagcgcttaa atttgtacgt    240
gattttgcag gagacgggtt agttacaagc tggacgcatg aaaaaaattg gaaaaaagcg    300
cataatatct tacttccaag cttcagtcag caggcaatga aaggctatca tgcgatgatg    360
gtcgatatcg ccgtgcagct tgttcaaaag tgggagcgtc taaatgcaga tgagcatatt    420
gaagtaccgg aagacatgac acgtttaacg cttgatacaa ttggtctttg cggctttaac    480
tatcgcttta acagctttta ccgagatcag cctcatccat ttattacaag tatggtccgt    540
gcactggatg aagcaatgaa caagctgcag cgagcaaatc cagacgaccc agcttatgat    600
gaaaacaagc gccagtttca agaagatatc aaggtgatga acgacctagt agataaaatt    660
attgcagatc gcaaagcaag cggtgaacaa agcgatgatt tattaacgca catgctaaac    720
ggaaaagatc cagaaacggg tgagccgctt gatgacgaga acattcgcta tcaaattatt    780
acattcttaa ttgcgggaca cgaaacaaca agtggtcttt tatcatttgc gctgtatttc    840
ttagtgaaaa atccacatgt attacaaaaa gcagcagaag aagcagcacg agttctagta    900
gatcctgttc caagctacaa acaagtcaaa cagcttaaat atgtcggcat ggtcttaaac    960
gaagcgctgc gcttatggcc aactctgcct gcgttttccc tatatgcaaa agaagatacg   1020
gtgcttggag gagaatatcc tttagaaaaa ggcgacgaac taatggttct gattcctcag   1080
cttcaccgtg ataaaacaat ttggggagac gatgtggaag agttccgtcc agagcgtttt   1140
gaaaatccaa gtgcgattcc gcagcatgcg tttaaaccgt ttggaaacgg tcagcgtgcg   1200
tgtatcggtc agcagttcgc tcttcatgaa gcaacgctgg tacttggtat gatgctaaaa   1260
cactttgact ttgaagatca tacaaactac gagctggata ttaaagaaac tttaacgtta   1320
aaacctgaag gctttgtggt aaaagcaaaa tcgaaaaaaa ttccgcttgg cggtattcct   1380
tcacctagca ctgaacagtc tgctaaaaaa gtacgcaaaa aggcagaaaa cgctcataat   1440
acgccgctgc ttgtgctata cggttcaaat atgggaacag ctgaaggaac ggcgcgtgat   1500
ttagcagata ttgcaatgag caaaggattt gcaccgcagg tcgcaacgct tgattcacac   1560
gccggaaatc ttccgcgcga aggagctgta ttaattgtaa cggcgtctta taacggtcat   1620
ccgcctgata acgcaaagca atttgtcgac tggttagacc aagcgtctgc tgatgaagta   1680
aaaggcgttc gctactccgt atttggatgc ggcgataaaa actgggctac tacgtatcaa   1740
aaagtgcctg cttttatcga tgaaacgctt gccgctaaag gggcagaaaa catcgctgac   1800
cgcggtgaag cagatgcaag cgacgacttt gaaggcacct atgaagaatg gcgtgaacac   1860
atgtggagtg acgtagcagc ctactttaac ctcgacattg aaaacagtga agataataaa   1920
tctactcttt cacttcaatt tgtcgacagc gccgcggata tgccgcttgc gaaaatgcac   1980
ggtgcgtttt caacgaacgt cgtagcaagc aaagaacttc aacagccagg cagtgcacga   2040
agcacgcgac atcttgaaat tgaacttcca aaagaagctt cttatcaaga aggagatcat   2100
ttaggtgtta ttcctcgcaa ctatgaagga atagtaaacc gtgtaacagc aaggttcggc   2160
ctagatgcat cacagcaaat ccgtctggaa gcagaagaag aaaaattagc tcatttgcca   2220
ctcgctaaaa cagtatccgt agaagagctt ctgcaatacg tggagcttca agatcctgtt   2280
acgcgcacgc agcttcgcgc aatggctgct aaaacggtct gcccgccgca taaagtagag   2340
cttgaagcct tgcttgaaaa gcaagcctac aaagaacaag tgctggcaaa acgtttaaca   2400
atgcttgaac tgcttgaaaa atacccggcg tgtgaaatga aattcagcga atttatcgcc   2460
cttctgccaa gcatacgccc gcgctattac tcgatttctt catcacctcg tgtcgatgaa   2520
```

-continued

```
aaacaagcaa gcatcacggt cagcgttgtc tcaggagaag cgtggagcgg atatggagaa   2580

tataaaggaa ttgcgtcgaa ctatcttgcc gagctgcaag aaggagatac gattacgtgc   2640

tttatttcca caccgcagtc agaatttacg ctgccaaaag accctgaaac gccgcttatc   2700

atggtcggac cgggaacagg cgtcgcgccg tttagaggct ttgtgcaggc gcgcaaacag   2760

ctaaaagaac aaggacagtc acttggagaa gcacatttat acttcggctg ccgttcacct   2820

catgaagact atctgtatca agaagagctt gaaaacgccc aaagcgaagg catcattacg   2880

cttcataccg ctttttctcg catgccaaat cagccgaaaa catacgttca gcacgtaatg   2940

gaacaagacg gcaagaaatt gattgaactt cttgatcaag gagcgcactt ctatatttgc   3000

ggagacggaa gccaaatggc acctgccgtt gaagcaacgc ttatgaaaag ctatgctgac   3060

gttcaccaag tgagtgaagc agacgctcgc ttatggctgc agcagctaga agaaaaaggc   3120

cgatacgcaa aagacgtgtg ggctgggtaa                                    3150
```

<210> SEQ ID NO 62
<211> LENGTH: 1049
<212> TYPE: PRT
<213> ORGANISM: Artificial Sequence
<220> FEATURE:
<223> OTHER INFORMATION: P450-BM3 Variant 18 amino acid sequence

<400> SEQUENCE: 62

```
Met Thr Ile Lys Glu Met Pro Gln Pro Lys Thr Phe Gly Glu Leu Lys
1               5                   10                  15

Asn Leu Pro Leu Leu Asn Thr Asp Lys Pro Val Gln Ala Leu Met Lys
            20                  25                  30

Ile Ala Asp Glu Leu Gly Glu Ile Phe Lys Phe Glu Ala Pro Gly Arg
        35                  40                  45

Val Thr Arg Tyr Leu Ser Ser Gln Arg Leu Ile Lys Glu Ala Cys Asp
    50                  55                  60

Glu Ser Arg Phe Asp Lys Asn Leu Ser Gln Ala Leu Lys Phe Val Arg
65                  70                  75                  80

Asp Phe Ala Gly Asp Gly Leu Val Thr Ser Trp Thr His Glu Lys Asn
                85                  90                  95

Trp Lys Lys Ala His Asn Ile Leu Leu Pro Ser Phe Ser Gln Gln Ala
            100                 105                 110

Met Lys Gly Tyr His Ala Met Met Val Asp Ile Ala Val Gln Leu Val
        115                 120                 125

Gln Lys Trp Glu Arg Leu Asn Ala Asp Glu His Ile Glu Val Pro Glu
    130                 135                 140

Asp Met Thr Arg Leu Thr Leu Asp Thr Ile Gly Leu Cys Gly Phe Asn
145                 150                 155                 160

Tyr Arg Phe Asn Ser Phe Tyr Arg Asp Gln Pro His Pro Phe Ile Thr
                165                 170                 175

Ser Met Val Arg Ala Leu Asp Glu Ala Met Asn Lys Leu Gln Arg Ala
            180                 185                 190

Asn Pro Asp Asp Pro Ala Tyr Asp Glu Asn Lys Arg Gln Phe Gln Glu
        195                 200                 205

Asp Ile Lys Val Met Asn Asp Leu Val Asp Lys Ile Ile Ala Asp Arg
    210                 215                 220

Lys Ala Ser Gly Glu Gln Ser Asp Asp Leu Leu Thr His Met Leu Asn
225                 230                 235                 240

Gly Lys Asp Pro Glu Thr Gly Glu Pro Leu Asp Asp Glu Asn Ile Arg
                245                 250                 255
```

-continued

```
Tyr Gln Ile Ile Thr Phe Leu Ile Ala Gly His Glu Thr Thr Ser Gly
            260                 265                 270

Leu Leu Ser Phe Ala Leu Tyr Phe Leu Val Lys Asn Pro His Val Leu
        275                 280                 285

Gln Lys Ala Ala Glu Glu Ala Ala Arg Val Leu Val Asp Pro Val Pro
    290                 295                 300

Ser Tyr Lys Gln Val Lys Gln Leu Lys Tyr Val Gly Met Val Leu Asn
305                 310                 315                 320

Glu Ala Leu Arg Leu Trp Pro Thr Leu Pro Ala Phe Ser Leu Tyr Ala
                325                 330                 335

Lys Glu Asp Thr Val Leu Gly Gly Glu Tyr Pro Leu Glu Lys Gly Asp
            340                 345                 350

Glu Leu Met Val Leu Ile Pro Gln Leu His Arg Asp Lys Thr Ile Trp
        355                 360                 365

Gly Asp Asp Val Glu Glu Phe Arg Pro Glu Arg Phe Glu Asn Pro Ser
    370                 375                 380

Ala Ile Pro Gln His Ala Phe Lys Pro Phe Gly Asn Gly Gln Arg Ala
385                 390                 395                 400

Cys Ile Gly Gln Gln Phe Ala Leu His Glu Ala Thr Leu Val Leu Gly
                405                 410                 415

Met Met Leu Lys His Phe Asp Phe Glu Asp His Thr Asn Tyr Glu Leu
            420                 425                 430

Asp Ile Lys Glu Thr Leu Thr Leu Lys Pro Glu Gly Phe Val Val Lys
        435                 440                 445

Ala Lys Ser Lys Lys Ile Pro Leu Gly Gly Ile Pro Ser Pro Ser Thr
    450                 455                 460

Glu Gln Ser Ala Lys Lys Val Arg Lys Lys Ala Glu Asn Ala His Asn
465                 470                 475                 480

Thr Pro Leu Leu Val Leu Tyr Gly Ser Asn Met Gly Thr Ala Glu Gly
                485                 490                 495

Thr Ala Arg Asp Leu Ala Asp Ile Ala Met Ser Lys Gly Phe Ala Pro
            500                 505                 510

Gln Val Ala Thr Leu Asp Ser His Ala Gly Asn Leu Pro Arg Glu Gly
        515                 520                 525

Ala Val Leu Ile Val Thr Ala Ser Tyr Asn Gly His Pro Pro Asp Asn
    530                 535                 540

Ala Lys Gln Phe Val Asp Trp Leu Asp Gln Ala Ser Ala Asp Glu Val
545                 550                 555                 560

Lys Gly Val Arg Tyr Ser Val Phe Gly Cys Gly Asp Lys Asn Trp Ala
                565                 570                 575

Thr Thr Tyr Gln Lys Val Pro Ala Phe Ile Asp Glu Thr Leu Ala Ala
            580                 585                 590

Lys Gly Ala Glu Asn Ile Ala Asp Arg Gly Glu Ala Asp Ala Ser Asp
        595                 600                 605

Asp Phe Glu Gly Thr Tyr Glu Glu Trp Arg Glu His Met Trp Ser Asp
    610                 615                 620

Val Ala Ala Tyr Phe Asn Leu Asp Ile Glu Asn Ser Glu Asp Asn Lys
625                 630                 635                 640

Ser Thr Leu Ser Leu Gln Phe Val Asp Ser Ala Ala Asp Met Pro Leu
                645                 650                 655

Ala Lys Met His Gly Ala Phe Ser Thr Asn Val Val Ala Ser Lys Glu
            660                 665                 670
```

-continued

```
Leu Gln Gln Pro Gly Ser Ala Arg Ser Thr Arg His Leu Glu Ile Glu
        675                 680                 685

Leu Pro Lys Glu Ala Ser Tyr Gln Glu Gly Asp His Leu Gly Val Ile
    690                 695                 700

Pro Arg Asn Tyr Glu Gly Ile Val Asn Arg Val Thr Ala Arg Phe Gly
705                 710                 715                 720

Leu Asp Ala Ser Gln Gln Ile Arg Leu Glu Ala Glu Glu Glu Lys Leu
                725                 730                 735

Ala His Leu Pro Leu Ala Lys Thr Val Ser Val Glu Glu Leu Leu Gln
            740                 745                 750

Tyr Val Glu Leu Gln Asp Pro Val Thr Arg Thr Gln Leu Arg Ala Met
        755                 760                 765

Ala Ala Lys Thr Val Cys Pro Pro His Lys Val Glu Leu Glu Ala Leu
    770                 775                 780

Leu Glu Lys Gln Ala Tyr Lys Glu Gln Val Leu Ala Lys Arg Leu Thr
785                 790                 795                 800

Met Leu Glu Leu Leu Glu Lys Tyr Pro Ala Cys Glu Met Lys Phe Ser
                805                 810                 815

Glu Phe Ile Ala Leu Leu Pro Ser Ile Arg Pro Arg Tyr Tyr Ser Ile
            820                 825                 830

Ser Ser Ser Pro Arg Val Asp Glu Lys Gln Ala Ser Ile Thr Val Ser
        835                 840                 845

Val Val Ser Gly Glu Ala Trp Ser Gly Tyr Gly Glu Tyr Lys Gly Ile
    850                 855                 860

Ala Ser Asn Tyr Leu Ala Glu Leu Gln Glu Gly Asp Thr Ile Thr Cys
865                 870                 875                 880

Phe Ile Ser Thr Pro Gln Ser Glu Phe Thr Leu Pro Lys Asp Pro Glu
                885                 890                 895

Thr Pro Leu Ile Met Val Gly Pro Gly Thr Gly Val Ala Pro Phe Arg
            900                 905                 910

Gly Phe Val Gln Ala Arg Lys Gln Leu Lys Glu Gln Gly Gln Ser Leu
        915                 920                 925

Gly Glu Ala His Leu Tyr Phe Gly Cys Arg Ser Pro His Glu Asp Tyr
    930                 935                 940

Leu Tyr Gln Glu Glu Leu Glu Asn Ala Gln Ser Glu Gly Ile Ile Thr
945                 950                 955                 960

Leu His Thr Ala Phe Ser Arg Met Pro Asn Gln Pro Lys Thr Tyr Val
                965                 970                 975

Gln His Val Met Glu Gln Asp Gly Lys Lys Leu Ile Glu Leu Leu Asp
            980                 985                 990

Gln Gly Ala His Phe Tyr Ile Cys  Gly Asp Gly Ser Gln  Met Ala Pro
        995                 1000                 1005

Ala Val  Glu Ala Thr Leu Met  Lys Ser Tyr Ala Asp  Val His Gln
    1010                 1015                 1020

Val Ser  Glu Ala Asp Ala Arg  Leu Trp Leu Gln Gln  Leu Glu Glu
    1025                 1030                 1035

Lys Gly  Arg Tyr Ala Lys Asp  Val Trp Ala Gly
    1040                 1045
```

<210> SEQ ID NO 63
<211> LENGTH: 3150
<212> TYPE: DNA
<213> ORGANISM: Artificial Sequence
<220> FEATURE:
<223> OTHER INFORMATION: P450-BM3 Variant 19 DNA sequence

<400> SEQUENCE: 63
atgacaatta aagaaatgcc tcagccaaaa acgtttggag agcttaaaaa tttaccgtta 60
ttaaacacag ataaaccggt tcaagctttg atgaaaattg cggatgaatt aggagaaatc 120
tttaaattcg aggcgcctgg tcgtgtaacg cgctacttat caagtcagcg tctaattaaa 180
gaagcatgcg atgaatcacg ctttgataaa aacttaagtc aagcgcttaa atttgtacgt 240
gattttgcag gagacgggtt agttacaagc tggacgcatg aaaaaaattg gaaaaaagcg 300
cataatatct tacttccaag cttcagtcag caggcaatga aaggctatca tgcgatgatg 360
gtcgatatcg ccgtgcagct tgttcaaaag tgggagcgtc taaatgcaga tgagcatatt 420
gaagtaccgg aagacatgac acgtttaacg cttgatacaa ttggtctttg cggctttaac 480
tatcgcttta acagctttta ccgagatcag cctcatccat ttattacaag tatggtccgt 540
gcactggatg aagcaatgaa caagctgcag cgagcaaatc cagacgaccc agcttatgat 600
gaaaacaagc gccagtttca agaagatatc aaggtgatga acgacctagt agataaaatt 660
attgcagatc gcaaagcaag cggtgaacaa agcgatgatt tattaacgca catgctaaac 720
ggaaaagatc cagaaacggg tgagccgctt gatgacgaga acattcgcta tcaaattatt 780
acattcttaa ttgcgggaca cgaaacaaca agtggtcttt tatcatttgc gctgtatttc 840
ttagtgaaaa atccacatgt attacaaaaa gcagcagaag aagcagcacg agttctagta 900
gatcctgttc caagctacaa acaagtcaaa cagcttaaat atgtcggcat ggtcttaaac 960
gaagcgctgc gcttatggcc aactgttcct gcgttttccc tatatgcaaa agaagatacg 1020
gtgcttggag gagaatatcc tttagaaaaa ggcgacgaac taatggttct gattcctcag 1080
cttcaccgtg ataaaacaat ttggggagac gatgtggaag agttccgtcc agagcgtttt 1140
gaaaatccaa gtgcgattcc gcagcatgcg tttaaaccgt ttggaaacgg tcagcgtgcg 1200
tgtatcggtc agcagttcgc tcttcatgaa gcaacgctgg tacttggtat gatgctaaaa 1260
cactttgact ttgaagatca tacaaactac gagctggata ttaaagaaac tttaacgtta 1320
aaacctgaag gctttgtggt aaaagcaaaa tcgaaaaaaa ttccgcttgg cggtattcct 1380
tcacctagca ctgaacagtc tgctaaaaaa gtacgcaaaa aggcagaaaa cgctcataat 1440
acgccgctgc ttgtgctata cggttcaaat atgggaacag ctgaaggaac ggcgcgtgat 1500
ttagcagata ttgcaatgag caaaggattt gcaccgcagg tcgcaacgct tgattcacac 1560
gccggaaatc ttccgcgcga aggagctgta ttaattgtaa cggcgtctta taacggtcat 1620
ccgcctgata acgcaaagca atttgtcgac tggttagacc aagcgtctgc tgatgaagta 1680
aaaggcgttc gctactccgt atttggatgc ggcgataaaa actgggctac tacgtatcaa 1740
aaagtgcctg cttttatcga tgaaacgctt gccgctaaag ggcagaaaa catcgctgac 1800
cgcggtgaag cagatgcaag cgacgacttt gaaggcacct atgaagaatg gcgtgaacac 1860
atgtggagtg acgtagcagc ctactttaac ctcgacattg aaaacagtga agataataaa 1920
tctactcttt cacttcaatt tgtcgacagc gccgcggata tgccgcttgc gaaaatgcac 1980
ggtgcgtttt caacgaacgt cgtagcaagc aaagaacttc aacagccagg cagtgcacga 2040
agcacgcgac atcttgaaat tgaacttcca aaagaagctt cttatcaaga aggagatcat 2100
ttaggtgtta ttcctcgcaa ctatgaagga atagtaaacc gtgtaacagc aaggttcggc 2160
ctagatgcat cacagcaaat ccgtctggaa gcagaagaag aaaaattagc tcatttgcca 2220
ctcgctaaaa cagtatccgt agaagagctt ctgcaatacg tggagcttca agatcctgtt 2280

```
acgcgcacgc agcttcgcgc aatggctgct aaaacggtct gcccgccgca taaagtagag   2340

cttgaagcct tgcttgaaaa gcaagcctac aaagaacaag tgctggcaaa acgtttaaca   2400

atgcttgaac tgcttgaaaa atacccggcg tgtgaaatga aattcagcga atttatcgcc   2460

cttctgccaa gcatacgccc gcgctattac tcgatttctt catcacctcg tgtcgatgaa   2520

aaacaagcaa gcatcacggt cagcgttgtc tcaggagaag cgtggagcgg atatggagaa   2580

tataaaggaa ttgcgtcgaa ctatcttgcc gagctgcaag aaggagatac gattacgtgc   2640

tttatttcca caccgcagtc agaatttacg ctgccaaaag accctgaaac gccgcttatc   2700

atggtcggac cgggaacagg cgtcgcgccg tttagaggct ttgtgcaggc gcgcaaacag   2760

ctaaaagaac aaggacagtc acttggagaa gcacatttat acttcggctg ccgttcacct   2820

catgaagact atctgtatca agaagagctt gaaaacgccc aaagcgaagg catcattacg   2880

cttcataccg ctttttctcg catgccaaat cagccgaaaa catacgttca gcacgtaatg   2940

gaacaagacg gcaagaaatt gattgaactt cttgatcaag gagcgcactt ctatatttgc   3000

ggagacggaa gccaaatggc acctgccgtt gaagcaacgc ttatgaaaag ctatgctgac   3060

gttcaccaag tgagtgaagc agacgctcgc ttatggctgc agcagctaga agaaaaaggc   3120

cgatacgcaa aagacgtgtg ggctgggtaa                                    3150


<210> SEQ ID NO 64
<211> LENGTH: 1049
<212> TYPE: PRT
<213> ORGANISM: Artificial Sequence
<220> FEATURE:
<223> OTHER INFORMATION: P450-BM3 Variant 19 amino acid sequence

<400> SEQUENCE: 64

Met Thr Ile Lys Glu Met Pro Gln Pro Lys Thr Phe Gly Glu Leu Lys
1               5                   10                  15

Asn Leu Pro Leu Leu Asn Thr Asp Lys Pro Val Gln Ala Leu Met Lys
            20                  25                  30

Ile Ala Asp Glu Leu Gly Glu Ile Phe Lys Phe Glu Ala Pro Gly Arg
        35                  40                  45

Val Thr Arg Tyr Leu Ser Ser Gln Arg Leu Ile Lys Glu Ala Cys Asp
    50                  55                  60

Glu Ser Arg Phe Asp Lys Asn Leu Ser Gln Ala Leu Lys Phe Val Arg
65                  70                  75                  80

Asp Phe Ala Gly Asp Gly Leu Val Thr Ser Trp Thr His Glu Lys Asn
                85                  90                  95

Trp Lys Lys Ala His Asn Ile Leu Leu Pro Ser Phe Ser Gln Gln Ala
            100                 105                 110

Met Lys Gly Tyr His Ala Met Met Val Asp Ile Ala Val Gln Leu Val
        115                 120                 125

Gln Lys Trp Glu Arg Leu Asn Ala Asp Glu His Ile Glu Val Pro Glu
    130                 135                 140

Asp Met Thr Arg Leu Thr Leu Asp Thr Ile Gly Leu Cys Gly Phe Asn
145                 150                 155                 160

Tyr Arg Phe Asn Ser Phe Tyr Arg Asp Gln Pro His Pro Phe Ile Thr
                165                 170                 175

Ser Met Val Arg Ala Leu Asp Glu Ala Met Asn Lys Leu Gln Arg Ala
            180                 185                 190

Asn Pro Asp Asp Pro Ala Tyr Asp Glu Asn Lys Arg Gln Phe Gln Glu
        195                 200                 205
```

-continued

```
Asp Ile Lys Val Met Asn Asp Leu Val Asp Lys Ile Ile Ala Asp Arg
    210                 215                 220

Lys Ala Ser Gly Glu Gln Ser Asp Asp Leu Leu Thr His Met Leu Asn
225                 230                 235                 240

Gly Lys Asp Pro Glu Thr Gly Glu Pro Leu Asp Asp Glu Asn Ile Arg
                245                 250                 255

Tyr Gln Ile Ile Thr Phe Leu Ile Ala Gly His Glu Thr Thr Ser Gly
            260                 265                 270

Leu Leu Ser Phe Ala Leu Tyr Phe Leu Val Lys Asn Pro His Val Leu
        275                 280                 285

Gln Lys Ala Ala Glu Glu Ala Ala Arg Val Leu Val Asp Pro Val Pro
    290                 295                 300

Ser Tyr Lys Gln Val Lys Gln Leu Lys Tyr Val Gly Met Val Leu Asn
305                 310                 315                 320

Glu Ala Leu Arg Leu Trp Pro Thr Val Pro Ala Phe Ser Leu Tyr Ala
                325                 330                 335

Lys Glu Asp Thr Val Leu Gly Gly Glu Tyr Pro Leu Glu Lys Gly Asp
            340                 345                 350

Glu Leu Met Val Leu Ile Pro Gln Leu His Arg Asp Lys Thr Ile Trp
        355                 360                 365

Gly Asp Asp Val Glu Glu Phe Arg Pro Glu Arg Phe Glu Asn Pro Ser
    370                 375                 380

Ala Ile Pro Gln His Ala Phe Lys Pro Phe Gly Asn Gly Gln Arg Ala
385                 390                 395                 400

Cys Ile Gly Gln Gln Phe Ala Leu His Glu Ala Thr Leu Val Leu Gly
                405                 410                 415

Met Met Leu Lys His Phe Asp Phe Glu Asp His Thr Asn Tyr Glu Leu
            420                 425                 430

Asp Ile Lys Glu Thr Leu Thr Leu Lys Pro Glu Gly Phe Val Val Lys
        435                 440                 445

Ala Lys Ser Lys Lys Ile Pro Leu Gly Gly Ile Pro Ser Pro Ser Thr
    450                 455                 460

Glu Gln Ser Ala Lys Lys Val Arg Lys Lys Ala Glu Asn Ala His Asn
465                 470                 475                 480

Thr Pro Leu Leu Val Leu Tyr Gly Ser Asn Met Gly Thr Ala Glu Gly
                485                 490                 495

Thr Ala Arg Asp Leu Ala Asp Ile Ala Met Ser Lys Gly Phe Ala Pro
            500                 505                 510

Gln Val Ala Thr Leu Asp Ser His Ala Gly Asn Leu Pro Arg Glu Gly
        515                 520                 525

Ala Val Leu Ile Val Thr Ala Ser Tyr Asn Gly His Pro Pro Asp Asn
    530                 535                 540

Ala Lys Gln Phe Val Asp Trp Leu Asp Gln Ala Ser Ala Asp Glu Val
545                 550                 555                 560

Lys Gly Val Arg Tyr Ser Val Phe Gly Cys Gly Asp Lys Asn Trp Ala
                565                 570                 575

Thr Thr Tyr Gln Lys Val Pro Ala Phe Ile Asp Glu Thr Leu Ala Ala
            580                 585                 590

Lys Gly Ala Glu Asn Ile Ala Asp Arg Gly Glu Ala Asp Ala Ser Asp
        595                 600                 605

Asp Phe Glu Gly Thr Tyr Glu Glu Trp Arg Glu His Met Trp Ser Asp
    610                 615                 620

Val Ala Ala Tyr Phe Asn Leu Asp Ile Glu Asn Ser Glu Asp Asn Lys
```

-continued

```
625                 630                 635                 640

Ser Thr Leu Ser Leu Gln Phe Val Asp Ser Ala Ala Asp Met Pro Leu
                645                 650                 655

Ala Lys Met His Gly Ala Phe Ser Thr Asn Val Val Ala Ser Lys Glu
            660                 665                 670

Leu Gln Gln Pro Gly Ser Ala Arg Ser Thr Arg His Leu Glu Ile Glu
        675                 680                 685

Leu Pro Lys Glu Ala Ser Tyr Gln Glu Gly Asp His Leu Gly Val Ile
    690                 695                 700

Pro Arg Asn Tyr Glu Gly Ile Val Asn Arg Val Thr Ala Arg Phe Gly
705                 710                 715                 720

Leu Asp Ala Ser Gln Gln Ile Arg Leu Glu Ala Glu Glu Glu Lys Leu
                725                 730                 735

Ala His Leu Pro Leu Ala Lys Thr Val Ser Val Glu Glu Leu Leu Gln
            740                 745                 750

Tyr Val Glu Leu Gln Asp Pro Val Thr Arg Thr Gln Leu Arg Ala Met
        755                 760                 765

Ala Ala Lys Thr Val Cys Pro Pro His Lys Val Glu Leu Glu Ala Leu
    770                 775                 780

Leu Glu Lys Gln Ala Tyr Lys Glu Gln Val Leu Ala Lys Arg Leu Thr
785                 790                 795                 800

Met Leu Glu Leu Leu Glu Lys Tyr Pro Ala Cys Glu Met Lys Phe Ser
                805                 810                 815

Glu Phe Ile Ala Leu Leu Pro Ser Ile Arg Pro Arg Tyr Tyr Ser Ile
            820                 825                 830

Ser Ser Ser Pro Arg Val Asp Glu Lys Gln Ala Ser Ile Thr Val Ser
        835                 840                 845

Val Val Ser Gly Glu Ala Trp Ser Gly Tyr Gly Glu Tyr Lys Gly Ile
    850                 855                 860

Ala Ser Asn Tyr Leu Ala Glu Leu Gln Glu Gly Asp Thr Ile Thr Cys
865                 870                 875                 880

Phe Ile Ser Thr Pro Gln Ser Glu Phe Thr Leu Pro Lys Asp Pro Glu
                885                 890                 895

Thr Pro Leu Ile Met Val Gly Pro Gly Thr Gly Val Ala Pro Phe Arg
            900                 905                 910

Gly Phe Val Gln Ala Arg Lys Gln Leu Lys Glu Gln Gly Gln Ser Leu
        915                 920                 925

Gly Glu Ala His Leu Tyr Phe Gly Cys Arg Ser Pro His Glu Asp Tyr
    930                 935                 940

Leu Tyr Gln Glu Glu Leu Glu Asn Ala Gln Ser Glu Gly Ile Ile Thr
945                 950                 955                 960

Leu His Thr Ala Phe Ser Arg Met Pro Asn Gln Pro Lys Thr Tyr Val
                965                 970                 975

Gln His Val Met Glu Gln Asp Gly Lys Lys Leu Ile Glu Leu Leu Asp
            980                 985                 990

Gln Gly Ala His Phe Tyr Ile Cys  Gly Asp Gly Ser Gln  Met Ala Pro
        995                 1000                1005

Ala Val  Glu Ala Thr Leu Met  Lys Ser Tyr Ala Asp  Val His Gln
    1010                1015                1020

Val Ser  Glu Ala Asp Ala Arg  Leu Trp Leu Gln Gln  Leu Glu Glu
    1025                1030                1035

Lys Gly  Arg Tyr Ala Lys Asp  Val Trp Ala Gly
    1040                1045
```

<210> SEQ ID NO 65
<211> LENGTH: 3150
<212> TYPE: DNA
<213> ORGANISM: Artificial Sequence
<220> FEATURE:
<223> OTHER INFORMATION: P450-BM3 Variant 20 DNA sequence

<400> SEQUENCE: 65
atgacaatta aagaaatgcc tcagccaaaa acgtttggag agcttaaaaa tttaccgtta 60
ttaaacacag ataaaccggt tcaagctttg atgaaaattg cggatgaatt aggagaaatc 120
tttaaattcg aggcgcctgg tcgtgtaacg cgctacttat caagtcagcg tctaattaaa 180
gaagcatgcg atgaatcacg ctttgataaa aacttaagtc aagcgcttaa atttgtacgt 240
gattttgcag gagacgggtt agttacaagc tggacgcatg aaaaaaattg gaaaaaagcg 300
cataatatct tacttccaag cttcagtcag caggcaatga aaggctatca tgcgatgatg 360
gtcgatatcg ccgtgcagct tgttcaaaag tgggagcgtc taaatgcaga tgagcatatt 420
gaagtaccgg aagacatgac acgtttaacg cttgatacaa ttggtctttg cggctttaac 480
tatcgcttta acagctttta ccgagatcag cctcatccat ttattacaag tatggtccgt 540
gcactggatg aagcaatgaa caagctgcag cgagcaaatc cagacgaccc agcttatgat 600
gaaaacaagc gccagtttca agaagatatc aaggtgatga acgacctagt agataaaatt 660
attgcagatc gcaaagcaag cggtgaacaa agcgatgatt tattaacgca catgctaaac 720
ggaaaagatc cagaaacggg tgagccgctt gatgacgaga acattcgcta tcaaattatt 780
acattcttaa ttgcgggaca cgaaacaaca agtggtcttt tatcatttgc gctgtatttc 840
ttagtgaaaa atccacatgt attacaaaaa gcagcagaag aagcagcacg agttctagta 900
gatcctgttc caagctacaa acaagtcaaa cagcttaaat atgtcggcat ggtcttaaac 960
gaagcgctgc gcttatggcc aacttttcct gcgttttccc tatatgcaaa agaagatacg 1020
gtgcttggag gagaatatcc tttagaaaaa ggcgacgaac taatggttct gattcctcag 1080
cttcaccgtg ataaaacaat ttggggagac gatgtggaag agttccgtcc agagcgtttt 1140
gaaaatccaa gtgcgattcc gcagcatgcg tttaaaccgt ttggaaacgg tcagcgtgcg 1200
tgtatcggtc agcagttcgc tcttcatgaa gcaacgctgg tacttggtat gatgctaaaa 1260
cactttgact ttgaagatca tacaaactac gagctggata ttaaagaaac tttaacgtta 1320
aaacctgaag gctttgtggt aaaagcaaaa tcgaaaaaaa ttccgcttgg cggtattcct 1380
tcacctagca ctgaacagtc tgctaaaaaa gtacgcaaaa aggcagaaaa cgctcataat 1440
acgccgctgc ttgtgctata cggttcaaat atgggaacag ctgaaggaac ggcgcgtgat 1500
ttagcagata ttgcaatgag caaaggattt gcaccgcagg tcgcaacgct tgattcacac 1560
gccggaaatc ttccgcgcga aggagctgta ttaattgtaa cggcgtctta taacggtcat 1620
ccgcctgata acgcaaagca atttgtcgac tggttagacc aagcgtctgc tgatgaagta 1680
aaaggcgttc gctactccgt atttggatgc ggcgataaaa actgggctac tacgtatcaa 1740
aaagtgcctg cttttatcga tgaaacgctt gccgctaaag ggcagaaaa catcgctgac 1800 cgcggtgaag cagatgcaag cgacgacttt gaaggcacct atgaagaatg gcgtgaacac 1860
atgtggagtg acgtagcagc ctactttaac ctcgacattg aaaacagtga agataataaa 1920
tctactcttt cacttcaatt tgtcgacagc gccgcggata tgccgcttgc gaaaatgcac 1980
ggtgcgtttt caacgaacgt cgtagcaagc aaagaacttc aacagccagg cagtgcacga 2040

-continued

```
agcacgcgac atcttgaaat tgaacttcca aaagaagctt cttatcaaga aggagatcat   2100

ttaggtgtta ttcctcgcaa ctatgaagga atagtaaacc gtgtaacagc aaggttcggc   2160

ctagatgcat cacagcaaat ccgtctggaa gcagaagaag aaaaattagc tcatttgcca   2220

ctcgctaaaa cagtatccgt agaagagctt ctgcaatacg tggagcttca agatcctgtt   2280

acgcgcacgc agcttcgcgc aatggctgct aaaacggtct gcccgccgca taaagtagag   2340

cttgaagcct tgcttgaaaa gcaagcctac aaagaacaag tgctggcaaa acgtttaaca   2400

atgcttgaac tgcttgaaaa atacccggcg tgtgaaatga aattcagcga atttatcgcc   2460

cttctgccaa gcatacgccc gcgctattac tcgatttctt catcacctcg tgtcgatgaa   2520

aaacaagcaa gcatcacggt cagcgttgtc tcaggagaag cgtggagcgg atatggagaa   2580

tataaaggaa ttgcgtcgaa ctatcttgcc gagctgcaag aaggagatac gattacgtgc   2640

tttatttcca caccgcagtc agaatttacg ctgccaaaag accctgaaac gccgcttatc   2700

atggtcggac cgggaacagg cgtcgcgccg tttagaggct ttgtgcaggc gcgcaaacag   2760

ctaaaagaac aaggacagtc acttggagaa gcacatttat acttcggctg ccgttcacct   2820

catgaagact atctgtatca agaagagctt gaaaacgccc aaagcgaagg catcattacg   2880

cttcataccg ctttttctcg catgccaaat cagccgaaaa catacgttca gcacgtaatg   2940

gaacaagacg gcaagaaatt gattgaactt cttgatcaag gagcgcactt ctatatttgc   3000

ggagacggaa gccaaatggc acctgccgtt gaagcaacgc ttatgaaaag ctatgctgac   3060

gttcaccaag tgagtgaagc agacgctcgc ttatggctgc agcagctaga agaaaaaggc   3120

cgatacgcaa aagacgtgtg ggctgggtaa                                 3150
```

<210> SEQ ID NO 66
<211> LENGTH: 1049
<212> TYPE: PRT
<213> ORGANISM: Artificial Sequence
<220> FEATURE:
<223> OTHER INFORMATION: P450-BM3 Variant 20 amino acid sequence

<400> SEQUENCE: 66

```
Met Thr Ile Lys Glu Met Pro Gln Pro Lys Thr Phe Gly Glu Leu Lys
1               5                   10                  15

Asn Leu Pro Leu Leu Asn Thr Asp Lys Pro Val Gln Ala Leu Met Lys
            20                  25                  30

Ile Ala Asp Glu Leu Gly Glu Ile Phe Lys Phe Glu Ala Pro Gly Arg
        35                  40                  45

Val Thr Arg Tyr Leu Ser Ser Gln Arg Leu Ile Lys Glu Ala Cys Asp
    50                  55                  60

Glu Ser Arg Phe Asp Lys Asn Leu Ser Gln Ala Leu Lys Phe Val Arg
65                  70                  75                  80

Asp Phe Ala Gly Asp Gly Leu Val Thr Ser Trp Thr His Glu Lys Asn
                85                  90                  95

Trp Lys Lys Ala His Asn Ile Leu Leu Pro Ser Phe Ser Gln Gln Ala
            100                 105                 110

Met Lys Gly Tyr His Ala Met Met Val Asp Ile Ala Val Gln Leu Val
        115                 120                 125

Gln Lys Trp Glu Arg Leu Asn Ala Asp Glu His Ile Glu Val Pro Glu
    130                 135                 140

Asp Met Thr Arg Leu Thr Leu Asp Thr Ile Gly Leu Cys Gly Phe Asn
145                 150                 155                 160

Tyr Arg Phe Asn Ser Phe Tyr Arg Asp Gln Pro His Pro Phe Ile Thr
```

-continued

```
                165                 170                 175

Ser Met Val Arg Ala Leu Asp Glu Ala Met Asn Lys Leu Gln Arg Ala
            180                 185                 190

Asn Pro Asp Asp Pro Ala Tyr Asp Glu Asn Lys Arg Gln Phe Gln Glu
        195                 200                 205

Asp Ile Lys Val Met Asn Asp Leu Val Asp Lys Ile Ile Ala Asp Arg
    210                 215                 220

Lys Ala Ser Gly Glu Gln Ser Asp Asp Leu Leu Thr His Met Leu Asn
225                 230                 235                 240

Gly Lys Asp Pro Glu Thr Gly Glu Pro Leu Asp Asp Glu Asn Ile Arg
                245                 250                 255

Tyr Gln Ile Ile Thr Phe Leu Ile Ala Gly His Glu Thr Thr Ser Gly
            260                 265                 270

Leu Leu Ser Phe Ala Leu Tyr Phe Leu Val Lys Asn Pro His Val Leu
        275                 280                 285

Gln Lys Ala Ala Glu Glu Ala Ala Arg Val Leu Val Asp Pro Val Pro
    290                 295                 300

Ser Tyr Lys Gln Val Lys Gln Leu Lys Tyr Val Gly Met Val Leu Asn
305                 310                 315                 320

Glu Ala Leu Arg Leu Trp Pro Thr Phe Pro Ala Phe Ser Leu Tyr Ala
                325                 330                 335

Lys Glu Asp Thr Val Leu Gly Gly Glu Tyr Pro Leu Glu Lys Gly Asp
            340                 345                 350

Glu Leu Met Val Leu Ile Pro Gln Leu His Arg Asp Lys Thr Ile Trp
        355                 360                 365

Gly Asp Asp Val Glu Glu Phe Arg Pro Glu Arg Phe Glu Asn Pro Ser
    370                 375                 380

Ala Ile Pro Gln His Ala Phe Lys Pro Phe Gly Asn Gly Gln Arg Ala
385                 390                 395                 400

Cys Ile Gly Gln Gln Phe Ala Leu His Glu Ala Thr Leu Val Leu Gly
                405                 410                 415

Met Met Leu Lys His Phe Asp Phe Glu Asp His Thr Asn Tyr Glu Leu
            420                 425                 430

Asp Ile Lys Glu Thr Leu Thr Leu Lys Pro Glu Gly Phe Val Val Lys
        435                 440                 445

Ala Lys Ser Lys Lys Ile Pro Leu Gly Gly Ile Pro Ser Pro Ser Thr
    450                 455                 460

Glu Gln Ser Ala Lys Lys Val Arg Lys Lys Ala Glu Asn Ala His Asn
465                 470                 475                 480

Thr Pro Leu Leu Val Leu Tyr Gly Ser Asn Met Gly Thr Ala Glu Gly
                485                 490                 495

Thr Ala Arg Asp Leu Ala Asp Ile Ala Met Ser Lys Gly Phe Ala Pro
            500                 505                 510

Gln Val Ala Thr Leu Asp Ser His Ala Gly Asn Leu Pro Arg Glu Gly
        515                 520                 525

Ala Val Leu Ile Val Thr Ala Ser Tyr Asn Gly His Pro Pro Asp Asn
    530                 535                 540

Ala Lys Gln Phe Val Asp Trp Leu Asp Gln Ala Ser Ala Asp Glu Val
545                 550                 555                 560

Lys Gly Val Arg Tyr Ser Val Phe Gly Cys Gly Asp Lys Asn Trp Ala
                565                 570                 575

Thr Thr Tyr Gln Lys Val Pro Ala Phe Ile Asp Glu Thr Leu Ala Ala
            580                 585                 590
```

```
Lys Gly Ala Glu Asn Ile Ala Asp Arg Gly Glu Ala Asp Ala Ser Asp
        595                 600                 605

Asp Phe Glu Gly Thr Tyr Glu Glu Trp Arg Glu His Met Trp Ser Asp
    610                 615                 620

Val Ala Ala Tyr Phe Asn Leu Asp Ile Glu Asn Ser Glu Asp Asn Lys
625                 630                 635                 640

Ser Thr Leu Ser Leu Gln Phe Val Asp Ser Ala Ala Asp Met Pro Leu
                645                 650                 655

Ala Lys Met His Gly Ala Phe Ser Thr Asn Val Val Ala Ser Lys Glu
            660                 665                 670

Leu Gln Gln Pro Gly Ser Ala Arg Ser Thr Arg His Leu Glu Ile Glu
        675                 680                 685

Leu Pro Lys Glu Ala Ser Tyr Gln Glu Gly Asp His Leu Gly Val Ile
    690                 695                 700

Pro Arg Asn Tyr Glu Gly Ile Val Asn Arg Val Thr Ala Arg Phe Gly
705                 710                 715                 720

Leu Asp Ala Ser Gln Gln Ile Arg Leu Glu Ala Glu Glu Glu Lys Leu
                725                 730                 735

Ala His Leu Pro Leu Ala Lys Thr Val Ser Val Glu Glu Leu Leu Gln
            740                 745                 750

Tyr Val Glu Leu Gln Asp Pro Val Thr Arg Thr Gln Leu Arg Ala Met
        755                 760                 765

Ala Ala Lys Thr Val Cys Pro Pro His Lys Val Glu Leu Glu Ala Leu
    770                 775                 780

Leu Glu Lys Gln Ala Tyr Lys Glu Gln Val Leu Ala Lys Arg Leu Thr
785                 790                 795                 800

Met Leu Glu Leu Leu Glu Lys Tyr Pro Ala Cys Glu Met Lys Phe Ser
                805                 810                 815

Glu Phe Ile Ala Leu Leu Pro Ser Ile Arg Pro Arg Tyr Tyr Ser Ile
            820                 825                 830

Ser Ser Ser Pro Arg Val Asp Glu Lys Gln Ala Ser Ile Thr Val Ser
        835                 840                 845

Val Val Ser Gly Glu Ala Trp Ser Gly Tyr Gly Glu Tyr Lys Gly Ile
    850                 855                 860

Ala Ser Asn Tyr Leu Ala Glu Leu Gln Glu Gly Asp Thr Ile Thr Cys
865                 870                 875                 880

Phe Ile Ser Thr Pro Gln Ser Glu Phe Thr Leu Pro Lys Asp Pro Glu
                885                 890                 895

Thr Pro Leu Ile Met Val Gly Pro Gly Thr Gly Val Ala Pro Phe Arg
            900                 905                 910

Gly Phe Val Gln Ala Arg Lys Gln Leu Lys Glu Gln Gly Gln Ser Leu
        915                 920                 925

Gly Glu Ala His Leu Tyr Phe Gly Cys Arg Ser Pro His Glu Asp Tyr
    930                 935                 940

Leu Tyr Gln Glu Glu Leu Glu Asn Ala Gln Ser Glu Gly Ile Ile Thr
945                 950                 955                 960

Leu His Thr Ala Phe Ser Arg Met Pro Asn Gln Pro Lys Thr Tyr Val
                965                 970                 975

Gln His Val Met Glu Gln Asp Gly Lys Lys Leu Ile Glu Leu Leu Asp
            980                 985                 990

Gln Gly Ala His Phe Tyr Ile Cys  Gly Asp Gly Ser Gln  Met Ala Pro
        995                 1000                1005
```

-continued

```
Ala Val Glu Ala Thr Leu Met Lys Ser Tyr Ala Asp Val His Gln
    1010                1015                1020

Val Ser Glu Ala Asp Ala Arg Leu Trp Leu Gln Gln Leu Glu Glu
    1025                1030                1035

Lys Gly Arg Tyr Ala Lys Asp Val Trp Ala Gly
    1040                1045
```

<210> SEQ ID NO 67
<211> LENGTH: 3150
<212> TYPE: DNA
<213> ORGANISM: Artificial Sequence
<220> FEATURE:
<223> OTHER INFORMATION: P450-BM3 Variant 23 DNA sequence

<400> SEQUENCE: 67

```
atgacaatta aagaaatgcc tcagccaaaa acgtttggag agcttaaaaa tttaccgtta     60
ttaaacacag ataaaccggt tcaagctttg atgaaaattg cggatgaatt aggagaaatc    120
tttaaattcg aggcgcctgg tcgtgtaacg cgctacttat caagtcagcg tctaattaaa    180
gaagcatgcg atgaatcacg ctttgataaa aacttaagtc aagcgcttaa atttgtacgt    240
gattttgcag gagacgggtt atttacaagc tggacgcatg aaaaaaattg gaaaaaagcg    300
cataatatct tacttccaag cttcagtcag caggcaatga aaggctatca tgcgatgatg    360
gtcgatatcg ccgtgcagct tgttcaaaag tgggagcgtc taaatgcaga tgagcatatt    420
gaagtaccgg aagacatgac acgtttaacg cttgatacaa ttggtctttg cggctttaac    480
tatcgcttta acagctttta ccgagatcag cctcatccat ttattacaag tatggtccgt    540
gcactggatg aagcaatgaa caagctgcag cgagcaaatc cagacgaccc agcttatgat    600
gaaaacaagc gccagtttca agaagatatc aaggtgatga acgacctagt agataaaatt    660
attgcagatc gcaaagcaag cggtgaacaa agcgatgatt tattaacgca catgctaaac    720
ggaaaagatc cagaaacggg tgagccgctt gatgacgaga acattcgcta tcaaattatt    780
acattcttaa ttgcgggaca cgaaacaaca agtggtcttt tatcatttgc gctgtatttc    840
ttagtgaaaa atccacatgt attacaaaaa gcagcagaag aagcagcacg agttctagta    900
gatcctgttc caagctacaa acaagtcaaa cagcttaaat atgtcggcat ggtcttaaac    960
gaagcgctgc gcttatggcc aactgttcct gcgttttccc tatatgcaaa agaagatacg   1020
gtgcttggag gagaatatcc tttagaaaaa ggcgacgaac taatggttct gattcctcag   1080
cttcaccgtg ataaaacaat ttggggagac gatgtggaag agttccgtcc agagcgtttt   1140
gaaaatccaa gtgcgattcc gcagcatgcg tttaaaccgt ttggaaacgg tcagcgtgcg   1200
tgtatcggtc agcagttcgc tcttcatgaa gcaacgctgg tacttggtat gatgctaaaa   1260
cactttgact ttgaagatca tacaaactac gagctggata ttaaagaaac tttaacgtta   1320
aaacctgaag gctttgtggt aaaagcaaaa tcgaaaaaaa ttccgcttgg cggtattcct   1380
tcacctagca ctgaacagtc tgctaaaaaa gtacgcaaaa aggcagaaaa cgctcataat   1440
acgccgctgc ttgtgctata cggttcaaat atgggaacag ctgaaggaac ggcgcgtgat   1500
ttagcagata ttgcaatgag caaaggattt gcaccgcagg tcgcaacgct tgattcacac   1560
gccggaaatc ttccgcgcga aggagctgta ttaattgtaa cggcgtctta taacggtcat   1620
ccgcctgata acgcaaagca atttgtcgac tggttagacc aagcgtctgc tgatgaagta   1680
aaaggcgttc gctactccgt atttggatgc ggcgataaaa actgggctac tacgtatcaa   1740
aaagtgcctg cttttatcga tgaaacgctt gccgctaaag ggcagaaaa catcgctgac    1800
```

```
cgcggtgaag cagatgcaag cgacgacttt gaaggcacct atgaagaatg gcgtgaacac   1860
atgtggagtg acgtagcagc ctactttaac ctcgacattg aaaacagtga agataataaa   1920
tctactcttt cacttcaatt tgtcgacagc gccgcggata tgccgcttgc gaaaatgcac   1980
ggtgcgtttt caacgaacgt cgtagcaagc aaagaacttc aacagccagg cagtgcacga   2040
agcacgcgac atcttgaaat tgaacttcca aaagaagctt cttatcaaga aggagatcat   2100
ttaggtgtta ttcctcgcaa ctatgaagga atagtaaacc gtgtaacagc aaggttcggc   2160
ctagatgcat cacagcaaat ccgtctggaa gcagaagaag aaaaattagc tcatttgcca   2220
ctcgctaaaa cagtatccgt agaagagctt ctgcaatacg tggagcttca agatcctgtt   2280
acgcgcacgc agcttcgcgc aatggctgct aaaacggtct gcccgccgca taaagtagag   2340
cttgaagcct tgcttgaaaa gcaagcctac aaagaacaag tgctggcaaa acgtttaaca   2400
atgcttgaac tgcttgaaaa atacccggcg tgtgaaatga aattcagcga atttatcgcc   2460
cttctgccaa gcatacgccc gcgctattac tcgatttctt catcacctcg tgtcgatgaa   2520
aaacaagcaa gcatcacggt cagcgttgtc tcaggagaag cgtggagcgg atatggagaa   2580
tataaaggaa ttgcgtcgaa ctatcttgcc gagctgcaag aaggagatac gattacgtgc   2640
tttatttcca caccgcagtc agaatttacg ctgccaaaag accctgaaac gccgcttatc   2700
atggtcggac cgggaacagg cgtcgcgccg tttagaggct ttgtgcaggc gcgcaaacag   2760
ctaaaagaac aaggacagtc acttggagaa gcacatttat acttcggctg ccgttcacct   2820
catgaagact atctgtatca agaagagctt gaaaacgccc aaagcgaagg catcattacg   2880
cttcataccg ctttttctcg catgccaaat cagccgaaaa catacgttca gcacgtaatg   2940
gaacaagacg gcaagaaatt gattgaactt cttgatcaag gagcgcactt ctatatttgc   3000
ggagacggaa gccaaatggc acctgccgtt gaagcaacgc ttatgaaaag ctatgctgac   3060
gttcaccaag tgagtgaagc agacgctcgc ttatggctgc agcagctaga agaaaaaggc   3120
cgatacgcaa aagacgtgtg ggctgggtaa                                    3150
```

<210> SEQ ID NO 68
<211> LENGTH: 1049
<212> TYPE: PRT
<213> ORGANISM: Artificial Sequence
<220> FEATURE:
<223> OTHER INFORMATION: P450-BM3 Variant 23 amino acid sequence

<400> SEQUENCE: 68

```
Met Thr Ile Lys Glu Met Pro Gln Pro Lys Thr Phe Gly Glu Leu Lys
1               5                   10                  15

Asn Leu Pro Leu Leu Asn Thr Asp Lys Pro Val Gln Ala Leu Met Lys
            20                  25                  30

Ile Ala Asp Glu Leu Gly Glu Ile Phe Lys Phe Glu Ala Pro Gly Arg
        35                  40                  45

Val Thr Arg Tyr Leu Ser Ser Gln Arg Leu Ile Lys Glu Ala Cys Asp
    50                  55                  60

Glu Ser Arg Phe Asp Lys Asn Leu Ser Gln Ala Leu Lys Phe Val Arg
65                  70                  75                  80

Asp Phe Ala Gly Asp Gly Leu Phe Thr Ser Trp Thr His Glu Lys Asn
                85                  90                  95

Trp Lys Lys Ala His Asn Ile Leu Leu Pro Ser Phe Ser Gln Gln Ala
            100                 105                 110

Met Lys Gly Tyr His Ala Met Met Val Asp Ile Ala Val Gln Leu Val
        115                 120                 125
```

```
Gln Lys Trp Glu Arg Leu Asn Ala Asp Glu His Ile Glu Val Pro Glu
    130                 135                 140

Asp Met Thr Arg Leu Thr Leu Asp Thr Ile Gly Leu Cys Gly Phe Asn
145                 150                 155                 160

Tyr Arg Phe Asn Ser Phe Tyr Arg Asp Gln Pro His Pro Phe Ile Thr
                165                 170                 175

Ser Met Val Arg Ala Leu Asp Glu Ala Met Asn Lys Leu Gln Arg Ala
            180                 185                 190

Asn Pro Asp Asp Pro Ala Tyr Asp Glu Asn Lys Arg Gln Phe Gln Glu
        195                 200                 205

Asp Ile Lys Val Met Asn Asp Leu Val Asp Lys Ile Ile Ala Asp Arg
    210                 215                 220

Lys Ala Ser Gly Glu Gln Ser Asp Asp Leu Leu Thr His Met Leu Asn
225                 230                 235                 240

Gly Lys Asp Pro Glu Thr Gly Glu Pro Leu Asp Asp Glu Asn Ile Arg
                245                 250                 255

Tyr Gln Ile Ile Thr Phe Leu Ile Ala Gly His Glu Thr Thr Ser Gly
            260                 265                 270

Leu Leu Ser Phe Ala Leu Tyr Phe Leu Val Lys Asn Pro His Val Leu
        275                 280                 285

Gln Lys Ala Ala Glu Glu Ala Ala Arg Val Leu Val Asp Pro Val Pro
    290                 295                 300

Ser Tyr Lys Gln Val Lys Gln Leu Lys Tyr Val Gly Met Val Leu Asn
305                 310                 315                 320

Glu Ala Leu Arg Leu Trp Pro Thr Val Pro Ala Phe Ser Leu Tyr Ala
                325                 330                 335

Lys Glu Asp Thr Val Leu Gly Gly Glu Tyr Pro Leu Glu Lys Gly Asp
            340                 345                 350

Glu Leu Met Val Leu Ile Pro Gln Leu His Arg Asp Lys Thr Ile Trp
        355                 360                 365

Gly Asp Asp Val Glu Glu Phe Arg Pro Glu Arg Phe Glu Asn Pro Ser
    370                 375                 380

Ala Ile Pro Gln His Ala Phe Lys Pro Phe Gly Asn Gly Gln Arg Ala
385                 390                 395                 400

Cys Ile Gly Gln Gln Phe Ala Leu His Glu Ala Thr Leu Val Leu Gly
                405                 410                 415

Met Met Leu Lys His Phe Asp Phe Glu Asp His Thr Asn Tyr Glu Leu
            420                 425                 430

Asp Ile Lys Glu Thr Leu Thr Leu Lys Pro Glu Gly Phe Val Val Lys
        435                 440                 445

Ala Lys Ser Lys Lys Ile Pro Leu Gly Gly Ile Pro Ser Pro Ser Thr
    450                 455                 460

Glu Gln Ser Ala Lys Lys Val Arg Lys Lys Ala Glu Asn Ala His Asn
465                 470                 475                 480

Thr Pro Leu Leu Val Leu Tyr Gly Ser Asn Met Gly Thr Ala Glu Gly
                485                 490                 495

Thr Ala Arg Asp Leu Ala Asp Ile Ala Met Ser Lys Gly Phe Ala Pro
            500                 505                 510

Gln Val Ala Thr Leu Asp Ser His Ala Gly Asn Leu Pro Arg Glu Gly
        515                 520                 525

Ala Val Leu Ile Val Thr Ala Ser Tyr Asn Gly His Pro Pro Asp Asn
    530                 535                 540
```

```
Ala Lys Gln Phe Val Asp Trp Leu Asp Gln Ala Ser Ala Asp Glu Val
545                 550                 555                 560

Lys Gly Val Arg Tyr Ser Val Phe Gly Cys Gly Asp Lys Asn Trp Ala
                565                 570                 575

Thr Thr Tyr Gln Lys Val Pro Ala Phe Ile Asp Glu Thr Leu Ala Ala
            580                 585                 590

Lys Gly Ala Glu Asn Ile Ala Asp Arg Gly Glu Ala Asp Ala Ser Asp
        595                 600                 605

Asp Phe Glu Gly Thr Tyr Glu Glu Trp Arg Glu His Met Trp Ser Asp
    610                 615                 620

Val Ala Ala Tyr Phe Asn Leu Asp Ile Glu Asn Ser Glu Asp Asn Lys
625                 630                 635                 640

Ser Thr Leu Ser Leu Gln Phe Val Asp Ser Ala Ala Asp Met Pro Leu
                645                 650                 655

Ala Lys Met His Gly Ala Phe Ser Thr Asn Val Val Ala Ser Lys Glu
            660                 665                 670

Leu Gln Gln Pro Gly Ser Ala Arg Ser Thr Arg His Leu Glu Ile Glu
        675                 680                 685

Leu Pro Lys Glu Ala Ser Tyr Gln Glu Gly Asp His Leu Gly Val Ile
    690                 695                 700

Pro Arg Asn Tyr Glu Gly Ile Val Asn Arg Val Thr Ala Arg Phe Gly
705                 710                 715                 720

Leu Asp Ala Ser Gln Gln Ile Arg Leu Glu Ala Glu Glu Glu Lys Leu
                725                 730                 735

Ala His Leu Pro Leu Ala Lys Thr Val Ser Val Glu Glu Leu Leu Gln
            740                 745                 750

Tyr Val Glu Leu Gln Asp Pro Val Thr Arg Thr Gln Leu Arg Ala Met
        755                 760                 765

Ala Ala Lys Thr Val Cys Pro Pro His Lys Val Glu Leu Glu Ala Leu
    770                 775                 780

Leu Glu Lys Gln Ala Tyr Lys Glu Gln Val Leu Ala Lys Arg Leu Thr
785                 790                 795                 800

Met Leu Glu Leu Leu Glu Lys Tyr Pro Ala Cys Glu Met Lys Phe Ser
                805                 810                 815

Glu Phe Ile Ala Leu Leu Pro Ser Ile Arg Pro Arg Tyr Tyr Ser Ile
            820                 825                 830

Ser Ser Ser Pro Arg Val Asp Glu Lys Gln Ala Ser Ile Thr Val Ser
        835                 840                 845

Val Val Ser Gly Glu Ala Trp Ser Gly Tyr Gly Glu Tyr Lys Gly Ile
    850                 855                 860

Ala Ser Asn Tyr Leu Ala Glu Leu Gln Glu Gly Asp Thr Ile Thr Cys
865                 870                 875                 880

Phe Ile Ser Thr Pro Gln Ser Glu Phe Thr Leu Pro Lys Asp Pro Glu
                885                 890                 895

Thr Pro Leu Ile Met Val Gly Pro Gly Thr Gly Val Ala Pro Phe Arg
            900                 905                 910

Gly Phe Val Gln Ala Arg Lys Gln Leu Lys Glu Gln Gly Gln Ser Leu
        915                 920                 925

Gly Glu Ala His Leu Tyr Phe Gly Cys Arg Ser Pro His Glu Asp Tyr
    930                 935                 940

Leu Tyr Gln Glu Glu Leu Glu Asn Ala Gln Ser Glu Gly Ile Ile Thr
945                 950                 955                 960

Leu His Thr Ala Phe Ser Arg Met Pro Asn Gln Pro Lys Thr Tyr Val
```

-continued

```
                965                 970                 975

Gln His Val Met Glu Gln Asp Gly Lys Lys Leu Ile Glu Leu Leu Asp
            980                 985                 990

Gln Gly Ala His Phe Tyr Ile Cys  Gly Asp Gly Ser Gln  Met Ala Pro
        995                 1000                 1005

Ala Val  Glu Ala Thr Leu Met  Lys Ser Tyr Ala Asp  Val His Gln
    1010                 1015                 1020

Val Ser  Glu Ala Asp Ala Arg  Leu Trp Leu Gln Gln  Leu Glu Glu
    1025                 1030                 1035

Lys Gly  Arg Tyr Ala Lys Asp  Val Trp Ala Gly
    1040                 1045


<210> SEQ ID NO 69
<211> LENGTH: 2051
<212> TYPE: DNA
<213> ORGANISM: Santalum album

<400> SEQUENCE: 69

atgtacgtat ccatcagcaa tgatcgacct tataaaggag ccgagacact ctcaccttca     60

atccactcat ccctacattc ttttgctaac tcctttgttg ccagcaagta tatctcttac    120

gttaaacgtt ttacttcctc aacatgtctc cggcaacagc cgttatcctc actctcctcg    180

tggccctagg gctatccatc cttttgcggc ggcgccaaaa aagaaataat ctacctcccg    240

gtccacccgc tttaccgatc atcggaaaca tccacatatt ggggaccctt cctcaccaga    300

gcctctacaa cttggccaag aagtatggtc ccatcatgtc aatgaggctg gggctcgtgc    360

cggctgttgt gatatcctct ccggaggccg ccgagctcgt cctcaagacc cacgatatcg    420

ttttcgccag ccggcccaga ctccaagttg cggactactt ccattacggg acaaagggcg    480

tcatcctgac ggagtatggt acatattggc gcaacatgcg aaggctgtgc accgtgaagc    540

ttctcaacac ggtgaaaatc gattctttcg cagggacaag gaagaaggag gtggcatcgt    600

tcgtgcagtc ccttaaggag gcttcggtgg cacacaaaat ggtgaatttg agcgcgaggg    660

tggcgaacgt cattgaaaac atggtgtgcc ttatggtgat cgggcgaagt agcgatgaga    720

ggtttaagct aaaggaggtc atccaggagg cagcgcagtt ggcgggagct ttcaatatag    780

gggattatgt tccattcctt atgccccttg acctacaggg attaactcgg cgcataaagt    840

caggaagtaa agctttcgac gacatcttgg aagtcataat cgacgagcac gtgcaagaca    900

ttaaggacca tgatgatgaa caacatggag acttcattga tgtgttgctg gcaatgatga    960

acaagcccat ggattcgcgg gagggtctta gtatcattga ccgaacaaac atcaaagcga   1020

tcctagtgga catgattgga gctgcaatgg acacttcaac aagtggcgtc gagtgggcga   1080

tttcagagct catcaagcat ccgcgggtaa tgaaaaagct ccaagacgag gtcaaaactg   1140

tcatcggaat gaataggatg gtcgaggagg ccgacttgcc taagctacca tacctcgaca   1200

tggtagtgaa agagaccatg aggttacacc ctcctggacc attgctcgtg ccccgagagt   1260

ccatggaaga catcacaatc aacggatact acatacctaa gaaatcgcga atcattgtca   1320

acgcctgggc aattgggcgt gatacaaacg cctggtctaa taacgcgcac gagttcttcc   1380

cagagaggtt tatgagtagc aatgtggact tacagggaca agatttccaa cttatcccat   1440

tcgggtcagg tcggagaggg tgccccggga tgcgcctagg cctcacaacc gttcgattag   1500

tgttagcgca gctcattcat tgtttcgact tggagcttcc taagggaacc gtggcgaccg   1560

acttggacat gagtgagaaa ttcgggttgg caatgcccag agcccagcac ttgcttgcat   1620
```

-continued

```
ttccaaccta tcgcttggag tcctaaacca ttgaggaaga tgcgtttata tttcatattg   1680

cagtgttaca ataagtagca gtcgttttca tggtgaagag gcaattcccc ctacactacc   1740

tgtcttatgc tatgcccctc cccaactttc accgtatgtg tcttgtcatc atgtatcatg   1800

tccacatcaa taagatatta tatagaaatt gtcggtacgc caagatcgga ctcaatatgt   1860

atcagctttg agctctgtac acaaaatttg atacacgaac agagaaggtc gcgaattttg   1920

ggccactcgt ctcagatata taccctcaa gtggctaatg ggagatccc tctcctttgc   1980

atttaaagcc tctgcttccc gaaccctagc ccacaaaatt ttggccgaaa ccggataggc   2040

atacacgaca g                                                        2051
```

<210> SEQ ID NO 70
<211> LENGTH: 1503
<212> TYPE: DNA
<213> ORGANISM: Santalum album

<400> SEQUENCE: 70

```
atgtctccgg caacagccgt tatcctcact ctcctcgtgg ccctagggct atccatcctt     60

ttgcggcggc gccaaaaaag aaataatcta cctcccggtc cacccgcttt accgatcatc    120

ggaaacatcc acatattggg gacccttcct caccagagcc tctacaactt ggccaagaag    180

tatggtccca tcatgtcaat gaggctgggg ctcgtgccgg ctgttgtgat atcctctccg    240

gaggccgccg agctcgtcct caagacccac gatatcgttt tcgccagccg gcccagactc    300

caagttgcgg actacttcca ttacgggaca aagggcgtca tcctgacgga gtatggtaca    360

tattggcgca acatgcgaag gctgtgcacc gtgaagcttc tcaacacggt gaaaatcgat    420

tctttcgcag ggacaaggaa gaaggaggtg gcatcgttcg tgcagtccct taaggaggct    480

tcggtggcac acaaaatggt gaatttgagc gcgagggtgg cgaacgtcat tgaaaacatg    540

gtgtgcctta tggtgatcgg gcgaagtagc gatgagaggt ttaagctaaa ggaggtcatc    600

caggaggcag cgcagttggc gggagctttc aatatagggg attatgttcc attccttatg    660

ccccttgacc tacagggatt aactcggcgc ataaagtcag gaagtaaagc tttcgacgac    720

atcttggaag tcataatcga cgagcacgtg caagacatta aggaccatga tgatgaacaa    780

catggagact tcattgatgt gttgctggca atgatgaaca agcccatgga ttcgcgggag    840

ggtcttagta tcattgaccg aacaaacatc aaagcgatcc tagtggacat gattggagct    900

gcaatggaca cttcaacaag tggcgtcgag tgggcgattt cagagctcat caagcatccg    960

cgggtaatga aaaagctcca agacgaggtc aaaactgtca tcggaatgaa taggatggtc   1020

gaggaggccg acttgcctaa gctaccatac ctcgacatgg tagtgaaaga gaccatgagg   1080

ttacaccctc ctggaccatt gctcgtgccc cgagagtcca tggaagacat cacaatcaac   1140

ggatactaca tacctaagaa atcgcgaatc attgtcaacg cctgggcaat tgggcgtgat   1200

acaaacgcct ggtctaataa cgcgcacgag ttcttcccag agaggtttat gagtagcaat   1260

gtggacttac agggacaaga tttccaactt atcccattcg ggtcaggtcg gagagggtgc   1320

cccgggatgc gcctaggcct cacaaccgtt cgattagtgt tagcgcagct cattcattgt   1380

ttcgacttgg agcttcctaa gggaaccgtg gcgaccgact tggacatgag tgagaaattc   1440

gggttggcaa tgcccagagc ccagcacttg cttgcatttc caacctatcg cttggagtcc   1500

taa                                                                 1503
```

<210> SEQ ID NO 71
<211> LENGTH: 500

<212> TYPE: PRT
<213> ORGANISM: Santalum album

<400> SEQUENCE: 71

```
Met Ser Pro Ala Thr Ala Val Ile Leu Thr Leu Leu Val Ala Leu Gly
1               5                   10                  15

Leu Ser Ile Leu Leu Arg Arg Arg Gln Lys Arg Asn Asn Leu Pro Pro
            20                  25                  30

Gly Pro Pro Ala Leu Pro Ile Ile Gly Asn Ile His Ile Leu Gly Thr
        35                  40                  45

Leu Pro His Gln Ser Leu Tyr Asn Leu Ala Lys Lys Tyr Gly Pro Ile
    50                  55                  60

Met Ser Met Arg Leu Gly Leu Val Pro Ala Val Val Ile Ser Ser Pro
65                  70                  75                  80

Glu Ala Ala Glu Leu Val Leu Lys Thr His Asp Ile Val Phe Ala Ser
                85                  90                  95

Arg Pro Arg Leu Gln Val Ala Asp Tyr Phe His Tyr Gly Thr Lys Gly
            100                 105                 110

Val Ile Leu Thr Glu Tyr Gly Thr Tyr Trp Arg Asn Met Arg Arg Leu
        115                 120                 125

Cys Thr Val Lys Leu Leu Asn Thr Val Lys Ile Asp Ser Phe Ala Gly
    130                 135                 140

Thr Arg Lys Lys Glu Val Ala Ser Phe Val Gln Ser Leu Lys Glu Ala
145                 150                 155                 160

Ser Val Ala His Lys Met Val Asn Leu Ser Ala Arg Val Ala Asn Val
                165                 170                 175

Ile Glu Asn Met Val Cys Leu Met Val Ile Gly Arg Ser Ser Asp Glu
            180                 185                 190

Arg Phe Lys Leu Lys Glu Val Ile Gln Glu Ala Ala Gln Leu Ala Gly
        195                 200                 205

Ala Phe Asn Ile Gly Asp Tyr Val Pro Phe Leu Met Pro Leu Asp Leu
    210                 215                 220

Gln Gly Leu Thr Arg Arg Ile Lys Ser Gly Ser Lys Ala Phe Asp Asp
225                 230                 235                 240

Ile Leu Glu Val Ile Ile Asp Glu His Val Gln Asp Ile Lys Asp His
                245                 250                 255

Asp Asp Glu Gln His Gly Asp Phe Ile Asp Val Leu Leu Ala Met Met
            260                 265                 270

Asn Lys Pro Met Asp Ser Arg Glu Gly Leu Ser Ile Ile Asp Arg Thr
        275                 280                 285

Asn Ile Lys Ala Ile Leu Val Asp Met Ile Gly Ala Ala Met Asp Thr
    290                 295                 300

Ser Thr Ser Gly Val Glu Trp Ala Ile Ser Glu Leu Ile Lys His Pro
305                 310                 315                 320

Arg Val Met Lys Lys Leu Gln Asp Glu Val Lys Thr Val Ile Gly Met
                325                 330                 335

Asn Arg Met Val Glu Glu Ala Asp Leu Pro Lys Leu Pro Tyr Leu Asp
            340                 345                 350

Met Val Val Lys Glu Thr Met Arg Leu His Pro Pro Gly Pro Leu Leu
        355                 360                 365

Val Pro Arg Glu Ser Met Glu Asp Ile Thr Ile Asn Gly Tyr Tyr Ile
    370                 375                 380

Pro Lys Lys Ser Arg Ile Ile Val Asn Ala Trp Ala Ile Gly Arg Asp
385                 390                 395                 400
```

```
Thr Asn Ala Trp Ser Asn Asn Ala His Glu Phe Phe Pro Glu Arg Phe
                405                 410                 415

Met Ser Ser Asn Val Asp Leu Gln Gly Gln Asp Phe Gln Leu Ile Pro
            420                 425                 430

Phe Gly Ser Gly Arg Arg Gly Cys Pro Gly Met Arg Leu Gly Leu Thr
        435                 440                 445

Thr Val Arg Leu Val Leu Ala Gln Leu Ile His Cys Phe Asp Leu Glu
    450                 455                 460

Leu Pro Lys Gly Thr Val Ala Thr Asp Leu Asp Met Ser Glu Lys Phe
465                 470                 475                 480

Gly Leu Ala Met Pro Arg Ala Gln His Leu Leu Ala Phe Pro Thr Tyr
                485                 490                 495

Arg Leu Glu Ser
            500


<210> SEQ ID NO 72
<211> LENGTH: 1534
<212> TYPE: DNA
<213> ORGANISM: Artificial Sequence
<220> FEATURE:
<223> OTHER INFORMATION: SaCP120293, optimized DNA sequence for SaCP816

<400> SEQUENCE: 72

aggaggtaaa acatatggca ctgttgttgg cggttttctg gagcgctttg attattctgg     60

ttagcatctt attgcgtcgt cgtcaaaaac gcaacaattt gccaccgggc ccaccggccc    120

tgccgatcat cggtaacatt cacattctgg gcaccctgcc gcaccagagc ctgtacaatc    180

tggcgaagaa gtacggtccg atcatgtcca tgcgtttggg cttggttccg gcggtggtca    240

tcagcagccc ggaagcggcc gagctggtcc tgaaaaccca cgacatcgtt tttgcttctc    300

gccctcgtct gcaagttgca gattactttc actatggcac caaaggcgtg attctgaccg    360

aatatggtac ctactggcgt aacatgcgtc gcctgtgcac ggtcaaactg ctgaacaccg    420

ttaagattga tagctttgca ggcacccgca agaaagaagt cgctagcttc gttcagagcc    480

tgaaagaagc aagcgtggcg cacaaaatgg ttaacctgtc cgcacgcgtc gctaatgtta    540

ttgagaatat ggtttgtctg atggttattg gtagatcgtc tgacgagcgt ttcaagctga    600

aagaagtgat ccaagaagcg gcacagctgg cgggtgcctt caatattggt gactatgtcc    660

cgtttctgat gccgctggat ctgcagggcc tgactcgccg tatcaagagc ggtagcaagg    720

cattcgatga catcctcgag gtcattatcg acgagcatgt gcaagacatt aaagatcatg    780

acgatgagca gcatggtgac ttcatcgacg tgctgctggc gatgatgaat aagccgatgg    840

attctcgtga gggtctgtcc atcattgatc gcacgaacat taaagcgatc ctggtggata    900

tgatcggtgc cgcgatggac acgagcacca gcggtgtgga gtgggcgatt tcggagctga    960

ttaagcatcc tcgtgtcatg aagaaactgc aagacgaagt gaaaaccgta atcggtatga   1020

accgcatggt ggaagaagcg gatctgccga aactgccgta cctggacatg gttgtcaagg   1080

aaacgatgcg tctgcatccg ccaggcccgc tgctggtgcc gcgtgaaagc atggaagata   1140

ttacgatcaa cggttactat atcccgaaga aatcccgcat tattgtgaat gcatgggcga   1200

tcggccgtga caccaacgcc tggagcaata atgcgcacga gtttttccct gagcgtttta   1260

tgagctctaa cgttgatctg caaggccagg acttccagct gatcccgttc ggtagcggtc   1320

gtcgcggttg tccgggcatg cgtctgggtc tgacgacggt ccgcttggtg ctggcccaac   1380

tgattcactg cttcgacctg gagcttccga agggcaccgt cgcgactgac ctggatatga   1440
```

```
gcgagaagtt tggtctggca atgccgcgtg cgcagcactt actggccttt ccgacctacc   1500

gtctggagag ctaagtcgac accatggaaa gctt                               1534


<210> SEQ ID NO 73
<211> LENGTH: 499
<212> TYPE: PRT
<213> ORGANISM: Artificial Sequence
<220> FEATURE:
<223> OTHER INFORMATION: SaCP120293 amino acid sequence, N-terminal
      modified SaCP816

<400> SEQUENCE: 73

Met Ala Leu Leu Leu Ala Val Phe Trp Ser Ala Leu Ile Ile Leu Val
1               5                   10                  15

Ser Ile Leu Leu Arg Arg Arg Gln Lys Arg Asn Asn Leu Pro Pro Gly
            20                  25                  30

Pro Pro Ala Leu Pro Ile Ile Gly Asn Ile His Ile Leu Gly Thr Leu
        35                  40                  45

Pro His Gln Ser Leu Tyr Asn Leu Ala Lys Lys Tyr Gly Pro Ile Met
    50                  55                  60

Ser Met Arg Leu Gly Leu Val Pro Ala Val Val Ile Ser Ser Pro Glu
65                  70                  75                  80

Ala Ala Glu Leu Val Leu Lys Thr His Asp Ile Val Phe Ala Ser Arg
                85                  90                  95

Pro Arg Leu Gln Val Ala Asp Tyr Phe His Tyr Gly Thr Lys Gly Val
            100                 105                 110

Ile Leu Thr Glu Tyr Gly Thr Tyr Trp Arg Asn Met Arg Arg Leu Cys
        115                 120                 125

Thr Val Lys Leu Leu Asn Thr Val Lys Ile Asp Ser Phe Ala Gly Thr
    130                 135                 140

Arg Lys Lys Glu Val Ala Ser Phe Val Gln Ser Leu Lys Glu Ala Ser
145                 150                 155                 160

Val Ala His Lys Met Val Asn Leu Ser Ala Arg Val Ala Asn Val Ile
                165                 170                 175

Glu Asn Met Val Cys Leu Met Val Ile Gly Arg Ser Ser Asp Glu Arg
            180                 185                 190

Phe Lys Leu Lys Glu Val Ile Gln Glu Ala Ala Gln Leu Ala Gly Ala
        195                 200                 205

Phe Asn Ile Gly Asp Tyr Val Pro Phe Leu Met Pro Leu Asp Leu Gln
    210                 215                 220

Gly Leu Thr Arg Arg Ile Lys Ser Gly Ser Lys Ala Phe Asp Asp Ile
225                 230                 235                 240

Leu Glu Val Ile Ile Asp Glu His Val Gln Asp Ile Lys Asp His Asp
                245                 250                 255

Asp Glu Gln His Gly Asp Phe Ile Asp Val Leu Leu Ala Met Met Asn
            260                 265                 270

Lys Pro Met Asp Ser Arg Glu Gly Leu Ser Ile Ile Asp Arg Thr Asn
        275                 280                 285

Ile Lys Ala Ile Leu Val Asp Met Ile Gly Ala Ala Met Asp Thr Ser
    290                 295                 300

Thr Ser Gly Val Glu Trp Ala Ile Ser Glu Leu Ile Lys His Pro Arg
305                 310                 315                 320

Val Met Lys Lys Leu Gln Asp Glu Val Lys Thr Val Ile Gly Met Asn
                325                 330                 335
```

```
Arg Met Val Glu Glu Ala Asp Leu Pro Lys Leu Pro Tyr Leu Asp Met
            340                 345                 350

Val Val Lys Glu Thr Met Arg Leu His Pro Pro Gly Pro Leu Leu Val
        355                 360                 365

Pro Arg Glu Ser Met Glu Asp Ile Thr Ile Asn Gly Tyr Tyr Ile Pro
    370                 375                 380

Lys Lys Ser Arg Ile Ile Val Asn Ala Trp Ala Ile Gly Arg Asp Thr
385                 390                 395                 400

Asn Ala Trp Ser Asn Asn Ala His Glu Phe Phe Pro Glu Arg Phe Met
                405                 410                 415

Ser Ser Asn Val Asp Leu Gln Gly Gln Asp Phe Gln Leu Ile Pro Phe
            420                 425                 430

Gly Ser Gly Arg Arg Gly Cys Pro Gly Met Arg Leu Gly Leu Thr Thr
        435                 440                 445

Val Arg Leu Val Leu Ala Gln Leu Ile His Cys Phe Asp Leu Glu Leu
    450                 455                 460

Pro Lys Gly Thr Val Ala Thr Asp Leu Asp Met Ser Glu Lys Phe Gly
465                 470                 475                 480

Leu Ala Met Pro Arg Ala Gln His Leu Leu Ala Phe Pro Thr Tyr Arg
                485                 490                 495

Leu Glu Ser
```

<210> SEQ ID NO 74
<211> LENGTH: 3672
<212> TYPE: DNA
<213> ORGANISM: Artificial Sequence
<220> FEATURE:
<223> OTHER INFORMATION: synthetic operon encoding for SaCP816 and CPRm

<400> SEQUENCE: 74

```
catatggcac tgttgttggc ggttttctgg agcgctttga ttattctggt tagcatctta      60

ttgcgtcgtc gtcaaaaacg caacaatttg ccaccgggcc caccggccct gccgatcatc     120

ggtaacattc acattctggg caccctgccg caccagagcc tgtacaatct ggcgaagaag     180

tacggtccga tcatgtccat gcgtttgggc ttggttccgg cggtggtcat cagcagcccg     240

gaagcggccg agctggtcct gaaaacccac gacatcgttt ttgcttctcg ccctcgtctg     300

caagttgcag attactttca ctatggcacc aaaggcgtga ttctgaccga atatggtacc     360

tactggcgta acatgcgtcg cctgtgcacg gtcaaactgc tgaacaccgt taagattgat     420

agctttgcag gcacccgcaa gaaagaagtc gctagcttcg ttcagagcct gaaagaagca     480

agcgtggcgc acaaaatggt taacctgtcc gcacgcgtcg ctaatgttat tgagaatatg     540

gtttgtctga tggttattgg tagatcgtct gacgagcgtt tcaagctgaa agaagtgatc     600

caagaagcgg cacagctggc gggtgccttc aatattggtg actatgtccc gtttctgatg     660

ccgctggatc tgcagggcct gactcgccgt atcaagagcg gtagcaaggc attcgatgac     720

atcctcgagg tcattatcga cgagcatgtg caagacatta aagatcatga cgatgagcag     780

catggtgact tcatcgacgt gctgctggcg atgatgaata agccgatgga ttctcgtgag     840

ggtctgtcca tcattgatcg cacgaacatt aaagcgatcc tggtggatat gatcggtgcc     900

gcgatggaca cgagcaccag cggtgtggag tgggcgattt cggagctgat taagcatcct     960

cgtgtcatga agaaactgca agacgaagtg aaaaccgtaa tcggtatgaa ccgcatggtg    1020

gaagaagcgg atctgccgaa actgccgtac ctggacatgg ttgtcaagga aacgatgcgt    1080

ctgcatccgc caggcccgct gctggtgccg cgtgaaagca tggaagatat tacgatcaac    1140
```

ggttactata tcccgaagaa atcccgcatt attgtgaatg catgggcgat cggccgtgac 1200
accaacgcct ggagcaataa tgcgcacgag tttttccctg agcgttttat gagctctaac 1260
gttgatctgc aaggccagga cttccagctg atcccgttcg gtagcggtcg tcgcggttgt 1320
ccgggcatgc gtctgggtct gacgacggtc cgcttggtgc tggcccaact gattcactgc 1380
ttcgacctgg agcttccgaa gggcaccgtc gcgactgacc tggatatgag cgagaagttt 1440
ggtctggcaa tgccgcgtgc gcagcactta ctggcctttc cgacctaccg tctggagagc 1500
taagtcgact aactttaaga aggagatata tccatggaac ctagctctca gaaactgtct 1560
ccgttggaat ttgttgctgc tatcctgaag ggcgactaca gcagcggtca ggttgaaggt 1620
ggtccaccgc caggtctggc agctatgttg atggaaaata aggatttggt gatggttctg 1680
acgacgtccg tggcagtcct gatcggctgt gtcgtggtcc tggcatggcg tcgtgcggca 1740
ggtagcggta agtacaagca acctgaactg cctaaactgg tggtcccgaa agcagccgaa 1800
ccggaggagg cagaggatga taaaaccaag atcagcgtgt ttttcggcac ccaaaccggt 1860
acggcagaag gtttcgcgaa ggcttttgtt gaagaggcca aggcgcgtta tcagcaggcc 1920
cgtttcaaag ttatcgacct ggacgactat gcggcagacg atgacgagta cgaagagaaa 1980
ctgaagaagg aaaacttggc attcttcttc ttggcgtcct acggtgacgg cgagccgacg 2040
gacaacgcgg cacgctttta caaatggttt acggagggta aggaccgtgg tgaatggctg 2100
aacaatctgc agtacggcgt ttttggtctg ggtaaccgtc aatatgagca tttcaataag 2160
atcgccattg tcgtcgatga tctgatcttc gagcaaggtg gcaagaagct ggttccggtg 2220
ggtctgggtg acgatgacca gtgcattgag gatgattttg cggcgtggcg tgaactggtc 2280
tggccggaac tggataaact gctgcgtaac gaagacgacg ctaccgtggc aaccccgtac 2340
agcgccgctg tgctgcaata ccgcgtggtt ttccacgatc acattgacgg cctgattagc 2400
gaaaacggta gcccgaacgg tcatgctaat ggcaataccg tgtacgatgc gcaacacccg 2460
tgccgtagca acgtcgcggt caagaaggaa ttgcatactc cggcgagcga tcgcagctgc 2520
acccacctgg aatttaacat tagcggtacc ggcctgatgt acgagacggg tgaccacgtc 2580
ggtgtgtatt gcgagaacct gttggaaacc gtggaggagg ccgagaagtt gttgaacctg 2640
agcccgcaga cgtacttctc cgttcacacc gacaacgagg acggtacgcc gttgagcggc 2700
agcagcctgc cgccaccgtt tccgccgtgc accttgcgca cggcattgac caaatacgca 2760
gacttgactt ctgcaccgaa aaagtcggtg ctggtggcgc tggccgagta cgcatctgac 2820
cagggtgaag cggatcgttt gcgtttcttg gcgagcccga gcggcaaaga ggaatatgca 2880
cagtacatct tggcaagcca gcgcacgctg ctggaggtca tggcggagtt cccgtcggcg 2940
aaaccgccgc tgggtgtctt tttcgcgggt gtcgctccgc gcctgcagcc gcgtttctat 3000
tccattagct ctagcccgaa gatcgcaccg ttccgtattc acgtgacctg cgccctggtt 3060
tatgacaaat cccctaccgg tcgcgttcat aagggcatct gtagcacgtg gatgaaaaat 3120
gcggtcccgc tggaagaaag caacgattgt tcctgggctc cgatcttcgt ccgcaacagc 3180
aacttcaagc tgccgaccga cccgaaggtt ccgattatca tgattggtcc gggtaccggt 3240
ctggcccctt ttcgtggctt tttgcaagag cgcttggcgt tgaaagagag cggtgctgaa 3300
ttgggtccgg cgatcttgtt ctttggttgc cgtaaccgta aaatggactt tatttacgag 3360
gatgaactga atgatttcgt caaagcgggc gttgtcagcg agctgatcgt cgcttttagc 3420
cgcgaaggcc cgatgaaaga atacgtgcaa cacaaaatga gccaacgtgc ctccgatgtg 3480
tggaacatca ttagcgacgg tggttatgtt tatgtttgcg gtgacgcgaa gggtatggct 3540
cgtgatgttc accgtaccct gcataccatc gcacaggagc aaggtagcat gtccagctcg 3600
gaggccgaag gtatggtcaa aaacctgcaa accaccggtc gttacctgcg tgatgtgtgg 3660
taataaaagc tt 3672

<210> SEQ ID NO 75
<211> LENGTH: 5349
<212> TYPE: DNA
<213> ORGANISM: Artificial Sequence
<220> FEATURE:
<223> OTHER INFORMATION: Synthetic operon encoding for SaCP816, CPRm and ClASS

<400> SEQUENCE: 75
catatggcac tgttgttggc ggttttctgg agcgctttga ttattctggt tagcatctta 60
ttgcgtcgtc gtcaaaaacg caacaatttg ccaccgggcc caccggccct gccgatcatc 120
ggtaacattc acattctggg caccctgccg caccagagcc tgtacaatct ggcgaagaag 180
tacggtccga tcatgtccat gcgtttgggc ttggttccgg cggtggtcat cagcagcccg 240
gaagcggccg agctggtcct gaaaacccac gacatcgttt ttgcttctcg ccctcgtctg 300
caagttgcag attactttca ctatggcacc aaaggcgtga ttctgaccga atatggtacc 360
tactggcgta acatgcgtcg cctgtgcacg gtcaaactgc tgaacaccgt taagattgat 420
agctttgcag gcacccgcaa gaaagaagtc gctagcttcg ttcagagcct gaaagaagca 480
agcgtggcgc acaaaatggt taacctgtcc gcacgcgtcg ctaatgttat tgagaatatg 540
gtttgtctga tggttattgg tagatcgtct gacgagcgtt tcaagctgaa agaagtgatc 600
caagaagcgg cacagctggc gggtgccttc aatattggtg actatgtccc gtttctgatg 660
ccgctggatc tgcagggcct gactcgccgt atcaagagcg gtagcaaggc attcgatgac 720
atcctcgagg tcattatcga cgagcatgtg caagacatta aagatcatga cgatgagcag 780
catggtgact tcatcgacgt gctgctggcg atgatgaata agccgatgga ttctcgtgag 840
ggtctgtcca tcattgatcg cacgaacatt aaagcgatcc tggtggatat gatcggtgcc 900
gcgatggaca cgagcaccag cggtgtggag tgggcgattt cggagctgat taagcatcct 960
cgtgtcatga agaaactgca agacgaagtg aaaaccgtaa tcggtatgaa ccgcatggtg 1020
gaagaagcgg atctgccgaa actgccgtac ctggacatgg ttgtcaagga aacgatgcgt 1080
ctgcatccgc caggcccgct gctggtgccg cgtgaaagca tggaagatat tacgatcaac 1140
ggttactata tcccgaagaa atcccgcatt attgtgaatg catgggcgat cggccgtgac 1200
accaacgcct ggagcaataa tgcgcacgag tttttccctg agcgttttat gagctctaac 1260
gttgatctgc aaggccagga cttccagctg atcccgttcg gtagcggtcg tcgcggttgt 1320
ccgggcatgc gtctgggtct gacgacggtc cgcttggtgc tggcccaact gattcactgc 1380
ttcgacctgg agcttccgaa gggcaccgtc gcgactgacc tggatatgag cgagaagttt 1440
ggtctggcaa tgccgcgtgc gcagcactta ctggcctttc cgacctaccg tctggagagc 1500
taagtcgact aactttaaga aggagatata tccatggaac ctagctctca gaaactgtct 1560
ccgttggaat ttgttgctgc tatcctgaag ggcgactaca gcagcggtca ggttgaaggt 1620
ggtccaccgc caggtctggc agctatgttg atggaaaata aggatttggt gatggttctg 1680
acgacgtccg tggcagtcct gatcggctgt gtcgtggtcc tggcatggcg tcgtgcggca 1740
ggtagcggta agtacaagca acctgaactg cctaaactgg tggtcccgaa agcagccgaa 1800

-continued ccggaggagg cagaggatga taaaaccaag atcagcgtgt ttttcggcac ccaaaccggt 1860
acggcagaag gtttcgcgaa ggcttttgtt gaagaggcca aggcgcgtta tcagcaggcc 1920
cgtttcaaag ttatcgacct ggacgactat gcggcagacg atgacgagta cgaagagaaa 1980
ctgaagaagg aaaacttggc attcttcttc ttggcgtcct acggtgacgg cgagccgacg 2040
gacaacgcgg cacgctttta caaatggttt acggagggta aggaccgtgg tgaatggctg 2100
aacaatctgc agtacggcgt ttttggtctg ggtaaccgtc aatatgagca tttcaataag 2160
atcgccattg tcgtcgatga tctgatcttc gagcaaggtg gcaagaagct ggttccggtg 2220
ggtctgggtg acgatgacca gtgcattgag gatgattttg cggcgtggcg tgaactggtc 2280
tggccggaac tggataaact gctgcgtaac gaagacgacg ctaccgtggc aaccccgtac 2340
agcgccgctg tgctgcaata ccgcgtggtt ttccacgatc acattgacgg cctgattagc 2400
gaaaacggta gcccgaacgg tcatgctaat ggcaataccg tgtacgatgc gcaacacccg 2460
tgccgtagca acgtcgcggt caagaaggaa ttgcatactc cggcgagcga tcgcagctgc 2520
acccacctgg aatttaacat tagcggtacc ggcctgatgt acgagacggg tgaccacgtc 2580
ggtgtgtatt gcgagaacct gttggaaacc gtggaggagg ccgagaagtt gttgaacctg 2640
agcccgcaga cgtacttctc cgttcacacc gacaacgagg acggtacgcc gttgagcggc 2700
agcagcctgc cgccaccgtt tccgccgtgc accttgcgca cggcattgac caaatacgca 2760
gacttgactt ctgcaccgaa aaagtcggtg ctggtggcgc tggccgagta cgcatctgac 2820
cagggtgaag cggatcgttt gcgtttcttg gcgagcccga gcggcaaaga ggaatatgca 2880
cagtacatct tggcaagcca gcgcacgctg ctggaggtca tggcggagtt cccgtcggcg 2940
aaaccgccgc tgggtgtctt tttcgcgggt gtcgctccgc gcctgcagcc gcgtttctat 3000
tccattagct ctagcccgaa gatcgcaccg ttccgtattc acgtgacctg cgccctggtt 3060
tatgacaaat cccctaccgg tcgcgttcat aagggcatct gtagcacgtg gatgaaaaat 3120
gcggtcccgc tggaagaaag caacgattgt tcctgggctc cgatcttcgt ccgcaacagc 3180
aacttcaagc tgccgaccga cccgaaggtt ccgattatca tgattggtcc gggtaccggt 3240
ctggcccctt ttcgtggctt tttgcaagag cgcttggcgt tgaaagagag cggtgctgaa 3300
ttgggtccgg cgatcttgtt ctttggttgc cgtaaccgta aaatggactt tatttacgag 3360
gatgaactga atgatttcgt caaagcgggc gttgtcagcg agctgatcgt cgcttttagc 3420
cgcgaaggcc cgatgaaaga atacgtgcaa cacaaaatga gccaacgtgc ctccgatgtg 3480
tggaacatca ttagcgacgg tggttatgtt tatgtttgcg gtgacgcgaa gggtatggct 3540
cgtgatgttc accgtaccct gcataccatc gcacaggagc aaggtagcat gtccagctcg 3600
gaggccgaag gtatggtcaa aaacctgcaa accaccggtc gttacctgcg tgatgtgtgg 3660
taataaaagc ttgaaggaga tatactaatg tctacccagc aggttagctc cgagaatatc 3720
gttcgcaacg cggcgaactt ccacccgaat atctggggta atcatttctt gacgtgtcca 3780
agccagacga tcgattcttg gacgcaacaa caccataaag agctgaaaga agaggtccgc 3840
aagatgatgg tgagcgacgc aaacaaaccg gcacaacgtc tgcgtctgat tgacaccgtt 3900
caacgtttgg gcgtggcgta tcatttcgaa aaagaaatcg atgacgctct ggaaaagatc 3960
ggtcacgatc cgtttgacga taaggatgac ctgtatatcg ttagcctgtg ttttcgcctg 4020
ctgcgtcagc atggcatcaa gattagctgc gatgtttttg agaagttcaa agacgacgat 4080
ggcaagttta aggcttccct gatgaatgat gtccaaggta tgctgtcgtt gtatgaagcg 4140
gcccacctgg caattcatgg cgaggacatc ctggatgagg ctattgtctt tacgaccacc 4200
cacctgaaga gcaccgtttc taactccccg gtcaattcca cctttgcgga acagattcgc 4260
cacagcctgc gtgtgccgct gcgtaaggca gtcccgcgtt tggagagccg ctacttcctg 4320
gatatctata gccgtgacga cctgcacgac aagactctgc tgaactttgc caaactggac 4380
ttcaacatcc tgcaggcgat gcaccagaaa gaggcaagcg agatgacccg ttggtggcgt 4440
gatttcgatt tcctgaagaa gctgccgtac attcgtgatc gcgtggttga actgtacttt 4500
tggattttgg tcggtgtgag ctaccaaccg aaattcagca cgggtcgtat ctttttgagc 4560
aagattatct gtctggaaac cctggtggac gacacgtttg atgcgtacgg tactttcgac 4620
gaactggcca ttttcaccga ggccgttacg cgttgggacc tgggtcatcg cgacgcgctg 4680
cctgagtaca tgaaattcat tttcaagacc ctgattgatg tgtacagcga ggcggaacaa 4740
gagctggcaa aagagggccg ctcctatagc attcactatg cgatccgtag cttccaggag 4800
ttggtcatga agtacttttg cgaggcgaaa tggctgaata agggttatgt tccgagcctg 4860
gatgactaca agagcgtcag cctgcgcagc atcggcttcc tgccgatcgc cgtggcttct 4920
tttgttttca tgggcgacat tgctacgaaa gaggtttttg agtgggaaat gaataacccg 4980
aaaatcatca tcgcagccga aaccattttc cgctttctgg atgacattgc aggtcatcgc 5040
ttcgaacaaa aacgtgagca cagcccgagc gcaatcgagt gctacaaaaa ccaacatggt 5100
gtctcggaag aagaggcagt gaaagcgctg agcttggagg tcgccaattc gtggaaagac 5160
attaacgaag agctgctgct gaaccctatg gcaattccac tgccgttgct gcaggtgatc 5220
ctggatttga gccgtagcgc ggacttcatg tacggtaatg cgcaggaccg tttcacgcac 5280
tccaccatga tgaaagatca agttgacctg gttctgaaag atccggtgaa actggacgat 5340
taagaattc 5349

<210> SEQ ID NO 76
<211> LENGTH: 5402
<212> TYPE: DNA
<213> ORGANISM: Artificial Sequence
<220> FEATURE:
<223> OTHER INFORMATION: synthetic operon encoding for SaCP816, CPRm and SaSAS

<400> SEQUENCE: 76
catatggcac tgttgttggc ggttttctgg agcgctttga ttattctggt tagcatctta 60
ttgcgtcgtc gtcaaaaacg caacaatttg ccaccgggcc caccggccct gccgatcatc 120
ggtaacattc acattctggg caccctgccg caccagagcc tgtacaatct ggcgaagaag 180
tacggtccga tcatgtccat gcgtttgggc ttggttccgg cggtggtcat cagcagcccg 240
gaagcggccg agctggtcct gaaaacccac gacatcgttt ttgcttctcg ccctcgtctg 300
caagttgcag attactttca ctatggcacc aaaggcgtga ttctgaccga atatggtacc 360
tactggcgta acatgcgtcg cctgtgcacg gtcaaactgc tgaacaccgt taagattgat 420
agctttgcag gcacccgcaa gaaagaagtc gctagcttcg ttcagagcct gaaagaagca 480
agcgtggcgc acaaaatggt taacctgtcc gcacgcgtcg ctaatgttat tgagaatatg 540
gtttgtctga tggttattgg tagatcgtct gacgagcgtt tcaagctgaa agaagtgatc 600
caagaagcgg cacagctggc gggtgccttc aatattggtg actatgtccc gtttctgatg 660
ccgctggatc tgcagggcct gactcgccgt atcaagagcg gtagcaaggc attcgatgac 720
atcctcgagg tcattatcga cgagcatgtg caagacatta aagatcatga cgatgagcag 780
catggtgact tcatcgacgt gctgctggcg atgatgaata agccgatgga ttctcgtgag 840

-continued

```
ggtctgtcca tcattgatcg cacgaacatt aaagcgatcc tggtggatat gatcggtgcc    900
gcgatggaca cgagcaccag cggtgtggag tgggcgattt cggagctgat taagcatcct    960
cgtgtcatga agaaactgca agacgaagtg aaaaccgtaa tcggtatgaa ccgcatggtg   1020
gaagaagcgg atctgccgaa actgccgtac ctggacatgg ttgtcaagga aacgatgcgt   1080
ctgcatccgc caggcccgct gctggtgccg cgtgaaagca tggaagatat tacgatcaac   1140
ggttactata tcccgaagaa atcccgcatt attgtgaatg catgggcgat cggccgtgac   1200
accaacgcct ggagcaataa tgcgcacgag tttttccctg agcgttttat gagctctaac   1260
gttgatctgc aaggccagga cttccagctg atcccgttcg gtagcggtcg tcgcggttgt   1320
ccgggcatgc gtctgggtct gacgacggtc cgcttggtgc tggcccaact gattcactgc   1380
ttcgacctgg agcttccgaa gggcaccgtc gcgactgacc tggatatgag cgagaagttt   1440
ggtctggcaa tgccgcgtgc gcagcactta ctggcctttc cgacctaccg tctggagagc   1500
taagtcgact aactttaaga aggagatata tccatggaac ctagctctca gaaactgtct   1560
ccgttggaat ttgttgctgc tatcctgaag ggcgactaca gcagcggtca ggttgaaggt   1620
ggtccaccgc caggtctggc agctatgttg atggaaaata aggatttggt gatggttctg   1680
acgacgtccg tggcagtcct gatcggctgt gtcgtggtcc tggcatggcg tcgtgcggca   1740
ggtagcggta agtacaagca acctgaactg cctaaactgg tggtcccgaa agcagccgaa   1800
ccggaggagg cagaggatga taaaaccaag atcagcgtgt tttcggcac ccaaaccggt   1860
acggcagaag gtttcgcgaa ggcttttgtt gaagaggcca aggcgcgtta tcagcaggcc   1920
cgtttcaaag ttatcgacct ggacgactat gcggcagacg atgacgagta cgaagagaaa   1980
ctgaagaagg aaaacttggc attcttcttc ttggcgtcct acggtgacgg cgagccgacg   2040
gacaacgcgg cacgctttta caaatggttt acggagggta aggaccgtgg tgaatggctg   2100
aacaatctgc agtacggcgt ttttggtctg ggtaaccgtc aatatgagca tttcaataag   2160
atcgccattg tcgtcgatga tctgatcttc gagcaaggtg gcaagaagct ggttccggtg   2220
ggtctgggtg acgatgacca gtgcattgag gatgattttg cggcgtggcg tgaactggtc   2280
tggccggaac tggataaact gctgcgtaac gaagacgacg ctaccgtggc aaccccgtac   2340
agcgccgctg tgctgcaata ccgcgtggtt ttccacgatc acattgacgg cctgattagc   2400
gaaaacggta gcccgaacgg tcatgctaat ggcaataccg tgtacgatgc gcaacacccg   2460
tgccgtagca acgtcgcggt caagaaggaa ttgcatactc cggcgagcga tcgcagctgc   2520
acccacctgg aatttaacat tagcggtacc ggcctgatgt acgagacggg tgaccacgtc   2580
ggtgtgtatt gcgagaacct gttggaaacc gtggaggagg ccgagaagtt gttgaacctg   2640
agcccgcaga cgtacttctc cgttcacacc gacaacgagg acggtacgcc gttgagcggc   2700
agcagcctgc cgccaccgtt tccgccgtgc accttgcgca cggcattgac caaatacgca   2760
gacttgactt ctgcaccgaa aaagtcggtg ctggtggcgc tggccgagta cgcatctgac   2820
cagggtgaag cggatcgttt gcgtttcttg gcgagcccga gcggcaaaga ggaatatgca   2880
cagtacatct tggcaagcca gcgcacgctg ctggaggtca tggcggagtt cccgtcggcg   2940
aaaccgccgc tgggtgtctt tttcgcgggt gtcgctccgc gcctgcagcc gcgtttctat   3000
tccattagct ctagcccgaa gatcgcaccg ttccgtattc acgtgacctg cgccctggtt   3060
tatgacaaat cccctaccgg tcgcgttcat aagggcatct gtagcacgtg gatgaaaaat   3120
gcggtcccgc tggaagaaag caacgattgt tcctgggctc cgatcttcgt ccgcaacagc   3180
```

-continued

```
aacttcaagc tgccgaccga cccgaaggtt ccgattatca tgattggtcc gggtaccggt   3240
ctggcccctt ttcgtggctt tttgcaagag cgcttggcgt tgaaagagag cggtgctgaa   3300
ttgggtccgg cgatcttgtt ctttggttgc cgtaaccgta aaatggactt tatttacgag   3360
gatgaactga atgatttcgt caaagcgggc gttgtcagcg agctgatcgt cgcttttagc   3420
cgcgaaggcc cgatgaaaga atacgtgcaa cacaaaatga gccaacgtgc ctccgatgtg   3480
tggaacatca ttagcgacgg tggttatgtt tatgtttgcg gtgacgcgaa gggtatggct   3540
cgtgatgttc accgtaccct gcataccatc gcacaggagc aaggtagcat gtccagctcg   3600
gaggccgaag gtatggtcaa aaacctgcaa accaccggtc gttacctgcg tgatgtgtgg   3660
taataaaagc ttaggaggta aaacatatgg acagcagcac cgccaccgca atgaccgcac   3720
cattcatcga cccgacggat catgtgaatc tgaaaaccga cacggatgcg agcgaaaatc   3780
gtcgtatggg taactacaag ccgagcattt ggaactacga ttttctgcag tccctggcga   3840
cgcaccacaa cattgttgaa gagcgtcacc tgaagctggc agagaaactg aaaggtcaag   3900
tgaaattcat gttcggtgcg ccgatggagc cattggctaa gttggagctg gttgatgtgg   3960
tgcaacgctt gggtctgaac cacctgttcg agactgaaat caaagaagct ctgttcagca   4020
tctacaaaga tggcagcaat ggctggtggt ttggccatct gcatgctacc tctttgcgct   4080
tccgtctgtt gcgccaatgt ggcctgttta tcccgcagga cgttttcaaa acctttcaaa   4140
acaagaccgg tgagtttgac atgaagctgt gggacaacgt taagggcctg ctgagcctgt   4200
acgaggcgag ctacctgggc tggaagggcg agaacatctt ggatgaagca aaggcgttca   4260
cgaccaagtg cctgaagagc gcatgggaga acattagcga gaagtggctg gcgaagcgtg   4320
ttaaacatgc gttggcgctg ccgctgcact ggcgtgttcc gcgtattgaa gcacgctggt   4380
ttatcgaggt gtacgaacaa gaggccaata tgaatccgac gctgctgaaa ctggcgaaac   4440
tggacttcaa catggtccaa agcattcacc agaaagaaat cggtgaactg gcccgctggt   4500
gggttactac cggcctggac aagctggatt tcgcacgcaa caatctgttg cagtcttata   4560
tgtggagctg cgccatcgcg tccgacccga aattcaaact ggcgcgtgaa accattgtcg   4620
agatcggttc cgtgttgacg gttgtcgacg acggctatga tgtgtacggt tctatggatg   4680
agctggacct gtacaccagc tcggtggagc gttggtcctg tgtcaaaatt gacaagctgc   4740
ctaatacgct gaagctgatc tttatgtcta tgttcaacaa aaccaacgag gtgggtctgc   4800
gtgttcaaca cgagcgtggt tacaatagca tcccgacctt cattaaggcg tgggtggaac   4860
agtgtaagag ctatcaaaaa gaggcgcgtt ggtttcatgg tggtcacacg cctccgctgg   4920
aagaatacag cctgaacggt ctggtcagca ttggttttcc gctgttgctg atcaccggct   4980
atgttgcgat tgctgagaat gaagcagccc tggataaagt ccacccgctg ccggacctgc   5040
tgcattattc cagcttgctg agccgtctga ttaatgatat cggcactagc ccggatgaaa   5100
tggcgcgtgg tgacaatctg aagagcattc actgctatat gaatgaaacc ggtgccagcg   5160
aagaggtcgc acgcgagcac atcaaaggcg tcatcgaaga gaattggaaa attctgaacc   5220
agtgttgctt tgaccagtcc cagttccagg agccgttcat cacgtttaac ctgaacagcg   5280
tgcgcggctc gcatttcttc tatgaatttg gtgatggttt tggtgttacc gacagctgga   5340
ccaaggtgga tatgaaaagc gtcctgattg atccgattcc gctgggtgaa gagtaagctt   5400
gc                                                                  5402
```

<210> SEQ ID NO 77
<211> LENGTH: 1880

<212> TYPE: DNA
<213> ORGANISM: Santalum album

<400> SEQUENCE: 77
atataaaagc aatagagaaa cgcactttcc cacaccatcc caccagtaag tcactttgcc 60
caagtcccta atacggtgga aagggcaaaa aaaaataacg gaaagggtaa aatatcccgc 120
aaatgtctcc gaccactgtc gccgtcgccg tcgccatcat cggagcactc tggctcctca 180
cgcgaaagcg ccggaagggg ccgggcctcc cgccaggccc acgggcctac ccgatcatcg 240
ggaacctcca catgatgggc cagctcccgc accacaacct ccgcgagctg gcccgggagt 300
acggccccat catgtcgatg cggctcggcc tcgtccccgc catcgtggtc tcctccccgg 360
aggcggcgca gctcttcctg aagacgcatg atacggtgtt cgcgagccgg ccgaagacgg 420
agacggcgaa gtacttccac tacgggatca agggtctcat cctgaccgag tacgggccgt 480
actggcgcaa catccggcgg ctgagcacgg tcaagctgct gaacgcggcg aagatcgatt 540
cgttcgcggc gatgaggcgg agcgaggtgg agaggctggt ggcgtcggtg agggggtcgg 600
cggtgcggcg ggaggtggtg gacgtgagct cgaaggtggc ggaggcaatg gagaacatgg 660
tgtgtcagat ggtgattggg aggagtgggg acgataggtt taagctgaag gagacgtttc 720
aggaggggac tcagttggcc ggagctttca attttgggga gttcgttccc tttctcctgc 780
cacttgacct tcagggaata acacggcgca taaaagaagt aagcacgagg ttcaacaaaa 840
tcttggattt aatcgtcgac gagcacatca gagacgccgc tggaaccaaa aattccggcg 900
gtcgagacag cgacaacttc ctcgacgtcc tcctttccct aatgaacacc tccatcagcg 960
actccaacga caccggcgac aacaaccgca acaacgtcat tgaacgagac aacatcaaag 1020
cgatcctcac cgatatgctc ggcgccgcca tggacacctc cgccagcacc gtcgagtgga 1080
ccatctccga gctcttccgc cacccaaaaa caatgcaaaa gctccaggcc gagattcggg 1140
gtgtcgtggg cccgacccgg aacgtgtctg aagacgacct cccaaagctc acttacctgg 1200
acatggtggt gaaggagggg atgcggcttc acccggcggt gccgctgctc ctcccccacg 1260
agtccctgga ggaggcgaca atcgatggtt attacattcc gaaggggtct cggatcctga 1320
tcaatgtgtg ggccatcggg cgcgacccga aggcctggcc tgatcgcccg gaggagttca 1380
tcccggagag gtttgagaaa agcaatgtgg atgtgctggg gagggatttc caactccttc 1440
cgttcggctc gggccgtaga gggtgcgccg ggattcggtt agggttgatt ttcgtgcgat 1500
tggtgctagc tcagctggtg cattgtttcg attgggagct cgcccgcaac atggcttcgt 1560
caccggagaa gttggacatg gaagagaagt tcgggctagc tgtgcataga gttaaccatt 1620
tgaaagcact gccgacttat cgcttggaat gctaaaagtt gctttctacc tatatatata 1680
cactcgctag gaaataaatg atgttttcaa atggaataat tttctttttt aatgaaatag 1740
cataagtatt gttggttgtt atttaccaaa aaaaaagaag tattgtcggt tgtttacgat 1800
ggtggtatta atgtgttttg atgcatgggt atatccatca ttttatttta acttagctaa 1860
tttttgagtt attgatgtat 1880

<210> SEQ ID NO 78
<211> LENGTH: 1533
<212> TYPE: DNA
<213> ORGANISM: Santalum album

<400> SEQUENCE: 78
atgtctccga ccactgtcgc cgtcgccgtc gccatcatcg gagcactctg gctcctcacg 60

-continued

```
cgaaagcgcc ggaaggggcc gggcctcccg ccaggcccac gggcctaccc gatcatcggg    120

aacctccaca tgatgggcca gctcccgcac cacaacctcc gcgagctggc ccgggagtac    180

ggccccatca tgtcgatgcg gctcggcctc gtccccgcca tcgtggtctc ctccccggag    240

gcggcgcagc tcttcctgaa gacgcatgat acggtgttcg cgagccggcc gaagacggag    300

acggcgaagt acttccacta cgggatcaag ggtctcatcc tgaccgagta cgggccgtac    360

tggcgcaaca tccggcggct gagcacggtc aagctgctga acgcggcgaa gatcgattcg    420

ttcgcggcga tgaggcggag cgaggtggag aggctggtgg cgtcggtgag ggggtcggcg    480

gtgcggcggg aggtggtgga cgtgagctcg aaggtggcgg aggcaatgga gaacatggtg    540

tgtcagatgg tgattgggag gagtggggac gataggttta agctgaagga gacgtttcag    600

gaggggactc agttggccgg agctttcaat tttggggagt tcgttccctt tctcctgcca    660

cttgaccttc agggaataac acggcgcata aaagaagtaa gcacgaggtt caacaaaatc    720

ttggatttaa tcgtcgacga gcacatcaga gacgccgctg gaaccaaaaa ttccggcggt    780

cgagacagcg acaacttcct cgacgtcctc ctttccctaa tgaacacctc catcagcgac    840

tccaacgaca ccggcgacaa caaccgcaac aacgtcattg aacgagacaa catcaaagcg    900

atcctcaccg atatgctcgg cgccgccatg gacacctccg ccagcaccgt cgagtggacc    960

atctccgagc tcttccgcca cccaaaaaca atgcaaaagc tccaggccga gattcggggt   1020

gtcgtgggcc cgacccggaa cgtgtctgaa gacgacctcc caaagctcac ttacctggac   1080

atggtggtga aggaggggat gcggcttcac ccggcggtgc cgctgctcct cccccacgag   1140

tccctggagg aggcgacaat cgatggttat tacattccga aggggtctcg gatcctgatc   1200

aatgtgtggg ccatcggggcg cgacccgaag gcctggcctg atcgcccgga ggagttcatc   1260

ccggagaggt ttgagaaaag caatgtggat gtgctgggga gggatttcca actccttccg   1320

ttcggctcgg gccgtagagg gtgcgccggg attcggttag ggttgatttt cgtgcgattg   1380

gtgctagctc agctggtgca ttgtttcgat tgggagctcg cccgcaacat ggcttcgtca   1440

ccggagaagt tggacatgga agagaagttc gggctagctg tgcatagagt taaccatttg   1500

aaagcactgc cgacttatcg cttggaatgc taa                                 1533
```

<210> SEQ ID NO 79
<211> LENGTH: 510
<212> TYPE: PRT
<213> ORGANISM: Santalum album

<400> SEQUENCE: 79

```
Met Ser Pro Thr Thr Val Ala Val Ala Val Ala Ile Ile Gly Ala Leu
1               5                   10                  15

Trp Leu Leu Thr Arg Lys Arg Arg Lys Gly Pro Gly Leu Pro Pro Gly
            20                  25                  30

Pro Arg Ala Tyr Pro Ile Ile Gly Asn Leu His Met Met Gly Gln Leu
        35                  40                  45

Pro His His Asn Leu Arg Glu Leu Ala Arg Glu Tyr Gly Pro Ile Met
    50                  55                  60

Ser Met Arg Leu Gly Leu Val Pro Ala Ile Val Val Ser Ser Pro Glu
65                  70                  75                  80

Ala Ala Gln Leu Phe Leu Lys Thr His Asp Thr Val Phe Ala Ser Arg
                85                  90                  95

Pro Lys Thr Glu Thr Ala Lys Tyr Phe His Tyr Gly Ile Lys Gly Leu
            100                 105                 110
```

-continued

```
Ile Leu Thr Glu Tyr Gly Pro Tyr Trp Arg Asn Ile Arg Arg Leu Ser
        115                 120                 125

Thr Val Lys Leu Leu Asn Ala Ala Lys Ile Asp Ser Phe Ala Ala Met
    130                 135                 140

Arg Arg Ser Glu Val Glu Arg Leu Val Ala Ser Val Arg Gly Ser Ala
145                 150                 155                 160

Val Arg Arg Glu Val Val Asp Val Ser Ser Lys Val Ala Glu Ala Met
                165                 170                 175

Glu Asn Met Val Cys Gln Met Val Ile Gly Arg Ser Gly Asp Asp Arg
            180                 185                 190

Phe Lys Leu Lys Glu Thr Phe Gln Glu Gly Thr Gln Leu Ala Gly Ala
        195                 200                 205

Phe Asn Phe Gly Glu Phe Val Pro Phe Leu Leu Pro Leu Asp Leu Gln
    210                 215                 220

Gly Ile Thr Arg Arg Ile Lys Glu Val Ser Thr Arg Phe Asn Lys Ile
225                 230                 235                 240

Leu Asp Leu Ile Val Asp Glu His Ile Arg Asp Ala Ala Gly Thr Lys
                245                 250                 255

Asn Ser Gly Gly Arg Asp Ser Asp Asn Phe Leu Asp Val Leu Leu Ser
            260                 265                 270

Leu Met Asn Thr Ser Ile Ser Asp Ser Asn Asp Thr Gly Asp Asn Asn
        275                 280                 285

Arg Asn Asn Val Ile Glu Arg Asp Asn Ile Lys Ala Ile Leu Thr Asp
    290                 295                 300

Met Leu Gly Ala Ala Met Asp Thr Ser Ala Ser Thr Val Glu Trp Thr
305                 310                 315                 320

Ile Ser Glu Leu Phe Arg His Pro Lys Thr Met Gln Lys Leu Gln Ala
                325                 330                 335

Glu Ile Arg Gly Val Val Gly Pro Thr Arg Asn Val Ser Glu Asp Asp
            340                 345                 350

Leu Pro Lys Leu Thr Tyr Leu Asp Met Val Val Lys Glu Gly Met Arg
        355                 360                 365

Leu His Pro Ala Val Pro Leu Leu Leu Pro His Glu Ser Leu Glu Glu
    370                 375                 380

Ala Thr Ile Asp Gly Tyr Tyr Ile Pro Lys Gly Ser Arg Ile Leu Ile
385                 390                 395                 400

Asn Val Trp Ala Ile Gly Arg Asp Pro Lys Ala Trp Pro Asp Arg Pro
                405                 410                 415

Glu Glu Phe Ile Pro Glu Arg Phe Glu Lys Ser Asn Val Asp Val Leu
            420                 425                 430

Gly Arg Asp Phe Gln Leu Leu Pro Phe Gly Ser Gly Arg Arg Gly Cys
        435                 440                 445

Ala Gly Ile Arg Leu Gly Leu Ile Phe Val Arg Leu Val Leu Ala Gln
    450                 455                 460

Leu Val His Cys Phe Asp Trp Glu Leu Ala Arg Asn Met Ala Ser Ser
465                 470                 475                 480

Pro Glu Lys Leu Asp Met Glu Glu Lys Phe Gly Leu Ala Val His Arg
                485                 490                 495

Val Asn His Leu Lys Ala Leu Pro Thr Tyr Arg Leu Glu Cys
            500                 505                 510
```

<210> SEQ ID NO 80
<211> LENGTH: 1555
<212> TYPE: DNA

-continued

<213> ORGANISM: Artificial Sequence
<220> FEATURE:
<223> OTHER INFORMATION: SaCP120292, optimized cDNA encoding for N-term
modified SaCP10374

<400> SEQUENCE: 80

```
aggaggtaaa acatatggca ctgctgctgg ctgtcttttg gagcgcactg attattctga     60

cccgcaaacg ccgcaaaggt ccgggtctgc caccgggtcc gcgtgcgtac ccgattattg    120

gcaatctgca catgatgggc cagctgccac accacaattt gcgtgagctg gcacgtgagt    180

atggtccgat tatgagcatg cgcctgggtc tggtgccggc aatcgtggtt agctctcctg    240

aggctgcgca gctgttcctc aagacgcatg ataccgtttt cgcgagccgt ccaaagaccg    300

agactgccaa atacttccat tacggtatca aaggtctgat cctgaccgag tatggcccgt    360

actggcgcaa tattcgtcgt ttgagcaccg ttaagctgtt gaatgccgcg aaaatcgata    420

gcttcgcggc tatgcgtaga agcgaagttg aacgcctggt cgcgtccgtt cgtggttcgg    480

cggttcgtcg tgaggttgtg gacgtcagca gcaaagtggc ggaagctatg gagaatatgg    540

tctgccagat ggttatcggc cgttcaggtg acgatcgttt taagctgaaa gaaacctttc    600

aagagggcac ccaactggca ggcgcgttca attttggtga gtttgtgccg tttctgctgc    660

cgctggactt gcaaggtatt acccgtcgca tcaaagaagt cagcactcgt ttcaataaga    720

ttttggacct gatcgttgac gagcacattc gcgatgccgc tggtaccaaa aacagcggcg    780

gtcgtgatag cgacaatttt ctggatgttc tgctgtcctt gatgaacacc tctattagcg    840

atagcaatga cacgggtgac aacaaccgta acaacgtgat cgagcgtgat aacattaaag    900

cgatcctgac ggacatgctg ggtgcagcga tggacacgag cgcgagcacg gtcgagtgga    960

cgatctccga actgtttcgc cacccgaaaa ccatgcagaa gctgcaagca gaaatccgtg   1020

gtgtcgtggg cccgacccgc aatgtgagcg aagatgactt gccgaagctg acctatctgg   1080

acatggtcgt taaggaaggc atgcgtttgc atccggccgt gccgctgctt ctgccgcatg   1140

agtctctgga agaagccacg atcgatggct actacattcc gaagggttcc cgcattctga   1200

tcaacgtctg ggcgattggt cgcgacccga aggcctggcc ggatcgtcct gaagagttca   1260

tcccggagcg tttcgagaaa agcaacgtgg atgtgctggg ccgtgacttc cagctgctgc   1320

cgtttggttc gggtcgtcgc ggttgtgcag gcattcgcct gggcctgatc ttcgtacgtc   1380

tggttctggc acagttagtt cactgtttcg actgggaact ggcgcgcaac atggcgagca   1440

gcccggagaa gttggatatg gaagagaagt tcggcctggc ggtgcatcgt gtcaaccacc   1500

tgaaagccct gccgacgtat cgtctggagt gctaagtcga caccatggaa agctt         1555
```

<210> SEQ ID NO 81
<211> LENGTH: 506
<212> TYPE: PRT
<213> ORGANISM: Artificial Sequence
<220> FEATURE:
<223> OTHER INFORMATION: SaCP10374opt, N-terminal modified, amino acid
sequence

<400> SEQUENCE: 81

```
Met Ala Leu Leu Leu Ala Val Phe Trp Ser Ala Leu Ile Ile Leu Thr
1               5                   10                  15

Arg Lys Arg Arg Lys Gly Pro Gly Leu Pro Pro Gly Pro Arg Ala Tyr
            20                  25                  30

Pro Ile Ile Gly Asn Leu His Met Met Gly Gln Leu Pro His His Asn
        35                  40                  45
```

-continued

```
Leu Arg Glu Leu Ala Arg Glu Tyr Gly Pro Ile Met Ser Met Arg Leu
    50                  55                  60

Gly Leu Val Pro Ala Ile Val Val Ser Ser Pro Glu Ala Ala Gln Leu
65                  70                  75                  80

Phe Leu Lys Thr His Asp Thr Val Phe Ala Ser Arg Pro Lys Thr Glu
                85                  90                  95

Thr Ala Lys Tyr Phe His Tyr Gly Ile Lys Gly Leu Ile Leu Thr Glu
            100                 105                 110

Tyr Gly Pro Tyr Trp Arg Asn Ile Arg Arg Leu Ser Thr Val Lys Leu
        115                 120                 125

Leu Asn Ala Ala Lys Ile Asp Ser Phe Ala Ala Met Arg Arg Ser Glu
    130                 135                 140

Val Glu Arg Leu Val Ala Ser Val Arg Gly Ser Ala Val Arg Arg Glu
145                 150                 155                 160

Val Val Asp Val Ser Ser Lys Val Ala Glu Ala Met Glu Asn Met Val
                165                 170                 175

Cys Gln Met Val Ile Gly Arg Ser Gly Asp Asp Arg Phe Lys Leu Lys
            180                 185                 190

Glu Thr Phe Gln Glu Gly Thr Gln Leu Ala Gly Ala Phe Asn Phe Gly
        195                 200                 205

Glu Phe Val Pro Phe Leu Leu Pro Leu Asp Leu Gln Gly Ile Thr Arg
    210                 215                 220

Arg Ile Lys Glu Val Ser Thr Arg Phe Asn Lys Ile Leu Asp Leu Ile
225                 230                 235                 240

Val Asp Glu His Ile Arg Asp Ala Ala Gly Thr Lys Asn Ser Gly Gly
                245                 250                 255

Arg Asp Ser Asp Asn Phe Leu Asp Val Leu Leu Ser Leu Met Asn Thr
            260                 265                 270

Ser Ile Ser Asp Ser Asn Asp Thr Gly Asp Asn Asn Arg Asn Asn Val
        275                 280                 285

Ile Glu Arg Asp Asn Ile Lys Ala Ile Leu Thr Asp Met Leu Gly Ala
    290                 295                 300

Ala Met Asp Thr Ser Ala Ser Thr Val Glu Trp Thr Ile Ser Glu Leu
305                 310                 315                 320

Phe Arg His Pro Lys Thr Met Gln Lys Leu Gln Ala Glu Ile Arg Gly
                325                 330                 335

Val Val Gly Pro Thr Arg Asn Val Ser Glu Asp Asp Leu Pro Lys Leu
            340                 345                 350

Thr Tyr Leu Asp Met Val Val Lys Glu Gly Met Arg Leu His Pro Ala
        355                 360                 365

Val Pro Leu Leu Leu Pro His Glu Ser Leu Glu Glu Ala Thr Ile Asp
    370                 375                 380

Gly Tyr Tyr Ile Pro Lys Gly Ser Arg Ile Leu Ile Asn Val Trp Ala
385                 390                 395                 400

Ile Gly Arg Asp Pro Lys Ala Trp Pro Asp Arg Pro Glu Glu Phe Ile
                405                 410                 415

Pro Glu Arg Phe Glu Lys Ser Asn Val Asp Val Leu Gly Arg Asp Phe
            420                 425                 430

Gln Leu Leu Pro Phe Gly Ser Gly Arg Arg Gly Cys Ala Gly Ile Arg
        435                 440                 445

Leu Gly Leu Ile Phe Val Arg Leu Val Leu Ala Gln Leu Val His Cys
    450                 455                 460

Phe Asp Trp Glu Leu Ala Arg Asn Met Ala Ser Ser Pro Glu Lys Leu
```

-continued 465 470 475 480

Asp Met Glu Glu Lys Phe Gly Leu Ala Val His Arg Val Asn His Leu
485 490 495

Lys Ala Leu Pro Thr Tyr Arg Leu Glu Cys
500 505

<210> SEQ ID NO 82
<211> LENGTH: 3693
<212> TYPE: DNA
<213> ORGANISM: Artificial Sequence
<220> FEATURE:
<223> OTHER INFORMATION: SaCP10374-CPRm, synthetic operon encoding for SaCP10374 and CPRm

<400> SEQUENCE: 82
catatggcac tgctgctggc tgtcttttgg agcgcactga ttattctgac ccgcaaacgc 60
cgcaaaggtc cgggtctgcc accgggtccg cgtgcgtacc cgattattgg caatctgcac 120
atgatgggcc agctgccaca ccacaatttg cgtgagctgg cacgtgagta tggtccgatt 180
atgagcatgc gcctgggtct ggtgccggca atcgtggtta gctctcctga ggctgcgcag 240
ctgttcctca agacgcatga taccgttttc gcgagccgtc caaagaccga gactgccaaa 300
tacttccatt acggtatcaa aggtctgatc ctgaccgagt atggcccgta ctggcgcaat 360
attcgtcgtt tgagcaccgt taagctgttg aatgccgcga aaatcgatag cttcgcggct 420
atgcgtagaa gcgaagttga acgcctggtc gcgtccgttc gtggttcggc ggttcgtcgt 480
gaggttgtgg acgtcagcag caaagtggcg gaagctatgg agaatatggt ctgccagatg 540
gttatcggcc gttcaggtga cgatcgtttt aagctgaaag aaacctttca agagggcacc 600
caactggcag gcgcgttcaa ttttggtgag tttgtgccgt ttctgctgcc gctggacttg 660
caaggtatta cccgtcgcat caaagaagtc agcactcgtt tcaataagat tttggacctg 720
atcgttgacg agcacattcg cgatgccgct ggtaccaaaa acagcggcgg tcgtgatagc 780
gacaattttc tggatgttct gctgtccttg atgaacacct ctattagcga tagcaatgac 840
acgggtgaca acaaccgtaa caacgtgatc gagcgtgata acattaaagc gatcctgacg 900
gacatgctgg gtgcagcgat ggacacgagc gcgagcacgg tcgagtggac gatctccgaa 960
ctgtttcgcc acccgaaaac catgcagaag ctgcaagcag aaatccgtgg tgtcgtgggc 1020
ccgacccgca atgtgagcga agatgacttg ccgaagctga cctatctgga catggtcgtt 1080
aaggaaggca tgcgtttgca tccggccgtg ccgctgcttc tgccgcatga gtctctggaa 1140
gaagccacga tcgatggcta ctacattccg aagggttccc gcattctgat caacgtctgg 1200
gcgattggtc gcgacccgaa ggcctggccg gatcgtcctg aagagttcat cccggagcgt 1260
ttcgagaaaa gcaacgtgga tgtgctgggc cgtgacttcc agctgctgcc gtttggttcg 1320
ggtcgtcgcg gttgtgcagg cattcgcctg ggcctgatct tcgtacgtct ggttctggca 1380
cagttagttc actgtttcga ctgggaactg gcgcgcaaca tggcgagcag cccggagaag 1440
ttggatatgg aagagaagtt cggcctggcg gtgcatcgtg tcaaccacct gaaagccctg 1500
ccgacgtatc gtctggagtg ctaagtcgac taactttaag aaggagatat atccatggaa 1560
cctagctctc agaaactgtc tccgttggaa tttgttgctg ctatcctgaa gggcgactac 1620
agcagcggtc aggttgaagg tggtccaccg ccaggtctgg cagctatgtt gatggaaaat 1680
aaggatttgg tgatggttct gacgacgtcc gtggcagtcc tgatcggctg tgtcgtggtc 1740
ctggcatggc gtcgtgcggc aggtagcggt aagtacaagc aacctgaact gcctaaactg 1800
gtggtcccga aagcagccga accggaggag gcagaggatg ataaaaccaa gatcagcgtg 1860
tttttcggca cccaaaccgg tacggcagaa ggtttcgcga aggcttttgt tgaagaggcc 1920
aaggcgcgtt atcagcaggc ccgtttcaaa gttatcgacc tggacgacta tgcggcagac 1980
gatgacgagt acgaagagaa actgaagaag gaaaacttgg cattcttctt cttggcgtcc 2040
tacggtgacg gcgagccgac ggacaacgcg gcacgctttt acaaatggtt tacggagggt 2100
aaggaccgtg gtgaatggct gaacaatctg cagtacggcg tttttggtct gggtaaccgt 2160
caatatgagc atttcaataa gatcgccatt gtcgtcgatg atctgatctt cgagcaaggt 2220
ggcaagaagc tggttccggt gggtctgggt gacgatgacc agtgcattga ggatgatttt 2280
gcggcgtggc gtgaactggt ctggccggaa ctggataaac tgctgcgtaa cgaagacgac 2340
gctaccgtgg caaccccgta cagcgccgct gtgctgcaat accgcgtggt tttccacgat 2400
cacattgacg gcctgattag cgaaaacggt agcccgaacg gtcatgctaa tggcaatacc 2460
gtgtacgatg cgcaacaccc gtgccgtagc aacgtcgcgg tcaagaagga attgcatact 2520
ccggcgagcg atcgcagctg cacccacctg gaatttaaca ttagcggtac cggcctgatg 2580
tacgagacgg gtgaccacgt cggtgtgtat tgcgagaacc tgttggaaac cgtggaggag 2640
gccgagaagt tgttgaacct gagcccgcag acgtacttct ccgttcacac cgacaacgag 2700
gacggtacgc cgttgagcgg cagcagcctg ccgccaccgt ttccgccgtg caccttgcgc 2760
acggcattga ccaaatacgc agacttgact tctgcaccga aaaagtcggt gctggtggcg 2820
ctggccgagt acgcatctga ccagggtgaa gcggatcgtt tgcgtttctt ggcgagcccg 2880
agcggcaaag aggaatatgc acagtacatc ttggcaagcc agcgcacgct gctggaggtc 2940
atggcggagt tcccgtcggc gaaaccgccg ctgggtgtct tttcgcgggg tgtcgctccg 3000
cgcctgcagc cgcgtttcta ttccattagc tctagcccga agatcgcacc gttccgtatt 3060
cacgtgacct gcgccctggt ttatgacaaa tcccctaccg gtcgcgttca taagggcatc 3120
tgtagcacgt ggatgaaaaa tgcggtcccg ctggaagaaa gcaacgattg ttcctgggct 3180
ccgatcttcg tccgcaacag caacttcaag ctgccgaccg acccgaaggt tccgattatc 3240
atgattggtc cgggtaccgg tctggcccct tttcgtggct tttgcaaga gcgcttggcg 3300 ttgaaagaga gcggtgctga attgggtccg gcgatcttgt tctttggttg ccgtaaccgt 3360
aaaatggact ttatttacga ggatgaactg aatgatttcg tcaaagcggg cgttgtcagc 3420
gagctgatcg tcgcttttag ccgcgaaggc ccgatgaaag aatacgtgca acacaaaatg 3480
agccaacgtg cctccgatgt gtggaacatc attagcgacg gtggttatgt ttatgtttgc 3540
ggtgacgcga agggtatggc tcgtgatgtt caccgtaccc tgcataccat cgcacaggag 3600
caaggtagca tgtccagctc ggaggccgaa ggtatggtca aaaacctgca aaccaccggt 3660
cgttacctgc gtgatgtgtg gtaataaaag ctt 3693

<210> SEQ ID NO 83
<211> LENGTH: 5339
<212> TYPE: DNA
<213> ORGANISM: Artificial Sequence
<220> FEATURE:
<223> OTHER INFORMATION: SaCP816-CPRm-SaTPs647, synthetic operon
encoding for SaCP816, CPRm and a sesquisabiene B synthase

<400> SEQUENCE: 83
catatggcac tgttgttggc ggttttctgg agcgctttga ttattctggt tagcatctta 60
ttgcgtcgtc gtcaaaaacg caacaatttg ccaccgggcc caccggccct gccgatcatc 120

```
ggtaacattc acattctggg caccctgccg caccagagcc tgtacaatct ggcgaagaag    180
tacggtccga tcatgtccat gcgtttgggc ttggttccgg cggtggtcat cagcagcccg    240
gaagcggccg agctggtcct gaaaacccac gacatcgttt ttgcttctcg ccctcgtctg    300
caagttgcag attactttca ctatggcacc aaaggcgtga ttctgaccga atatggtacc    360
tactggcgta acatgcgtcg cctgtgcacg gtcaaactgc tgaacaccgt taagattgat    420
agctttgcag gcacccgcaa gaaagaagtc gctagcttcg ttcagagcct gaaagaagca    480
agcgtggcgc acaaaatggt taacctgtcc gcacgcgtcg ctaatgttat tgagaatatg    540
gtttgtctga tggttattgg tagatcgtct gacgagcgtt tcaagctgaa agaagtgatc    600
caagaagcgg cacagctggc gggtgccttc aatattggtg actatgtccc gtttctgatg    660
ccgctggatc tgcagggcct gactcgccgt atcaagagcg gtagcaaggc attcgatgac    720
atcctcgagg tcattatcga cgagcatgtg caagacatta aagatcatga cgatgagcag    780
catggtgact tcatcgacgt gctgctggcg atgatgaata agccgatgga ttctcgtgag    840
ggtctgtcca tcattgatcg cacgaacatt aaagcgatcc tggtggatat gatcggtgcc    900
gcgatggaca cgagcaccag cggtgtggag tgggcgattt cggagctgat taagcatcct    960
cgtgtcatga agaaactgca agacgaagtg aaaaccgtaa tcggtatgaa ccgcatggtg   1020
gaagaagcgg atctgccgaa actgccgtac ctggacatgg ttgtcaagga aacgatgcgt   1080
ctgcatccgc caggcccgct gctggtgccg cgtgaaagca tggaagatat tacgatcaac   1140
ggttactata tcccgaagaa atcccgcatt attgtgaatg catgggcgat cggccgtgac   1200
accaacgcct ggagcaataa tgcgcacgag tttttccctg agcgttttat gagctctaac   1260
gttgatctgc aaggccagga cttccagctg atcccgttcg gtagcggtcg tcgcggttgt   1320
ccgggcatgc gtctgggtct gacgacggtc cgcttggtgc tggcccaact gattcactgc   1380
ttcgacctgg agcttccgaa gggcaccgtc gcgactgacc tggatatgag cgagaagttt   1440
ggtctggcaa tgccgcgtgc gcagcactta ctggcctttc cgacctaccg tctggagagc   1500
taagtcgact aactttaaga aggagatata tccatggaac ctagctctca gaaactgtct   1560
ccgttggaat ttgttgctgc tatcctgaag ggcgactaca gcagcggtca ggttgaaggt   1620
ggtccaccgc caggtctggc agctatgttg atggaaaata aggatttggt gatggttctg   1680
acgacgtccg tggcagtcct gatcggctgt gtcgtggtcc tggcatggcg tcgtgcggca   1740
ggtagcggta agtacaagca acctgaactg cctaaactgg tggtcccgaa agcagccgaa   1800
ccggaggagg cagaggatga taaaaccaag atcagcgtgt ttttcggcac ccaaaccggt   1860
acggcagaag gtttcgcgaa ggcttttgtt gaagaggcca aggcgcgtta tcagcaggcc   1920
cgtttcaaag ttatcgacct ggacgactat gcggcagacg atgacgagta cgaagagaaa   1980
ctgaagaagg aaaacttggc attcttcttc ttggcgtcct acggtgacgg cgagccgacg   2040
gacaacgcgg cacgctttta caaatggttt acggagggta aggaccgtgg tgaatggctg   2100
aacaatctgc agtacggcgt ttttggtctg ggtaaccgtc aatatgagca tttcaataag   2160
atcgccattg tcgtcgatga tctgatcttc gagcaaggtg gcaagaagct ggttccggtg   2220
ggtctgggtg acgatgacca gtgcattgag gatgattttg cggcgtggcg tgaactggtc   2280
tggccggaac tggataaact gctgcgtaac gaagacgacg ctaccgtggc aaccccgtac   2340
agcgccgctg tgctgcaata ccgcgtggtt ttccacgatc acattgacgg cctgattagc   2400
gaaaacggta gcccgaacgg tcatgctaat ggcaataccg tgtacgatgc gcaacacccg   2460
tgccgtagca acgtcgcggt caagaaggaa ttgcatactc cggcgagcga tcgcagctgc   2520
```

```
acccacctgg aatttaacat tagcggtacc ggcctgatgt acgagacggg tgaccacgtc   2580
ggtgtgtatt gcgagaacct gttggaaacc gtggaggagg ccgagaagtt gttgaacctg   2640
agcccgcaga cgtacttctc cgttcacacc gacaacgagg acggtacgcc gttgagcggc   2700
agcagcctgc cgccaccgtt tccgccgtgc accttgcgca cggcattgac caaatacgca   2760
gacttgactt ctgcaccgaa aaagtcggtg ctggtggcgc tggccgagta cgcatctgac   2820
cagggtgaag cggatcgttt gcgtttcttg gcgagcccga gcggcaaaga ggaatatgca   2880
cagtacatct tggcaagcca gcgcacgctg ctggaggtca tggcggagtt cccgtcggcg   2940
aaaccgccgc tgggtgtctt tttcgcgggt gtcgctccgc gcctgcagcc gcgtttctat   3000
tccattagct ctagcccgaa gatcgcaccg ttccgtattc acgtgacctg cgccctggtt   3060
tatgacaaat cccctaccgg tcgcgttcat aagggcatct gtagcacgtg gatgaaaaat   3120
gcggtcccgc tggaagaaag caacgattgt tcctgggctc cgatcttcgt ccgcaacagc   3180
aacttcaagc tgccgaccga cccgaaggtt ccgattatca tgattggtcc gggtaccggt   3240
ctggcccctt ttcgtggctt tttgcaagag cgcttggcgt tgaaagagag cggtgctgaa   3300
ttgggtccgg cgatcttgtt ctttggttgc cgtaaccgta aaatggactt tatttacgag   3360
gatgaactga atgatttcgt caaagcgggc gttgtcagcg agctgatcgt cgcttttagc   3420
cgcgaaggcc cgatgaaaga atacgtgcaa cacaaaatga gccaacgtgc ctccgatgtg   3480
tggaacatca ttagcgacgg tggttatgtt tatgtttgcg gtgacgcgaa gggtatggct   3540
cgtgatgttc accgtaccct gcataccatc gcacaggagc aaggtagcat gtccagctcg   3600
gaggccgaag gtatggtcaa aaacctgcaa accaccggtc gttacctgcg tgatgtgtgg   3660
taataaaagc ttaggaggta aaaatggcga ccgttgtgga tgattctagc gtcgttcgtc   3720
gttctgcaaa ctacccgccg aatttgtggg actatgagtt cctgcaatcc ctgggtgacc   3780
agtgtacggt cgaagaaaaa cacctgaagc tggccgacaa gttgaaagaa gaagttaaat   3840
ccctgattaa acagacgatg gagccgctgg caaaactgga gttcatcgat accgtgcgtc   3900
gtttgggttt gaaatatcag tttgagaccg aggtgaagga ggccgttgtt atggttagca   3960
aatatgagaa tgatgcgtgg tggattgata atctgcacgc taccagcctg cgtttccgca   4020
tcatgcgtga gaatggtatc ttcgtgccgc aagatgtgtt tgaacgtttc aaagataccg   4080
acggctttaa aaaccaactg tgcgaagacg tgaagggtct gttgtctctg tatgaggcga   4140
gctttctggg ttgggagggc gaggatatct tggatgaggc acgcaccttt gcgaccagca   4200
agctgaagag cattgaaggc aaaattccga gcccgagcct ggctaagaaa gtgagccacg   4260
cgctggactt gcctctgcac tggcgtacca ttcgctacga agcgcgctgg ttcatcgaca   4320
cctacggtga agaagaggac gtgaatctga cgttgctgcg ttacgccaaa ctggacttca   4380
acattgttca atctttttac caaaaagaga tcggccgtct gtcccgctgg tgggtgggta   4440
ctggcctgga taaaatgccg tttgctcgta atggtctgat tcagagctat atgtacgcaa   4500
ttggtatgct gttcgagcct aacctgggcg aggtgcgtga gatggaggcg aaggtcggcg   4560
ccttgattac cacgatcgac gacgtgtatg acgtttacgg cacgatggag gagttggagc   4620
tgttcaccga tattaccaat cgttgggaca tcagcaaagc ggatcaactg ccgcgtaaca   4680
tccgcatgcc gctgctgacg atgttcaaca ccagcaatga tatcggttat tgggctctga   4740
aagagcgtgg tttcaatggc attccgtgta ccgcaaaagt ctggtccgac caactgaaga   4800
gctacaccaa ggaggctaaa tggttccacg aaggccataa accgactctg gaggagtatc   4860
```

-continued

```
tggacaatgc gctggtcagc atcggcttcc cgaacctgct ggtcacgtct tatctgttga   4920

ccgttgagaa tccgaccaaa gaaaagctgg actatgtgaa cagcctgccg ttgttcgttc   4980

gcgcgagctg catcctgtgt cgtatcatta acgatctggg tacgagcccg gatgaaatgg   5040

agcgtggtga caatctgaaa agcatccagt gctatatgaa cgaaaccggt gcgagccaag   5100

aggttgcgcg tgagcacatc gaaggcctgg ttcgtatgtg gtggaaacgt ctgaacaagt   5160

gcctgtttga gccgagcccg ttcactgagc cgttcctgag ctttacgatt aacgtggtcc   5220

gtggtagcca ctttttctat cagtacggcg atggctacgg caacgcagag agctggacca   5280

agaaccaggg tatgtcggtg ctgatccacc cgattaccct ggatgaagag taagaattc    5339
```

<210> SEQ ID NO 84
<211> LENGTH: 5360
<212> TYPE: DNA
<213> ORGANISM: Artificial Sequence
<220> FEATURE:
<223> OTHER INFORMATION: SaCP10374-CPRm-saTPs647, synthetic operon encoding for SaCP10374, CPRm and a sesquisabiene B synthase

<400> SEQUENCE: 84

```
catatggcac tgctgctggc tgtcttttgg agcgcactga ttattctgac ccgcaaacgc     60

cgcaaaggtc cgggtctgcc accgggtccg cgtgcgtacc cgattattgg caatctgcac    120

atgatgggcc agctgccaca ccacaatttg cgtgagctgg cacgtgagta tggtccgatt    180

atgagcatgc gcctgggtct ggtgccggca atcgtggtta gctctcctga ggctgcgcag    240

ctgttcctca agacgcatga taccgttttc gcgagccgtc caaagaccga gactgccaaa    300

tacttccatt acggtatcaa aggtctgatc ctgaccgagt atggcccgta ctggcgcaat    360

attcgtcgtt tgagcaccgt taagctgttg aatgccgcga aaatcgatag cttcgcggct    420

atgcgtagaa gcgaagttga acgcctggtc gcgtccgttc gtggttcggc ggttcgtcgt    480

gaggttgtgg acgtcagcag caaagtggcg gaagctatgg agaatatggt ctgccagatg    540

gttatcggcc gttcaggtga cgatcgtttt aagctgaaag aaacctttca agagggcacc    600

caactggcag gcgcgttcaa ttttggtgag tttgtgccgt ttctgctgcc gctggacttg    660

caaggtatta cccgtcgcat caaagaagtc agcactcgtt tcaataagat tttggacctg    720

atcgttgacg agcacattcg cgatgccgct ggtaccaaaa acagcggcgg tcgtgatagc    780

gacaattttc tggatgttct gctgtccttg atgaacacct ctattagcga tagcaatgac    840

acgggtgaca acaaccgtaa caacgtgatc gagcgtgata acattaaagc gatcctgacg    900

gacatgctgg gtgcagcgat ggacacgagc gcgagcacgg tcgagtggac gatctccgaa    960

ctgtttcgcc acccgaaaac catgcagaag ctgcaagcag aaatccgtgg tgtcgtgggc   1020

ccgacccgca atgtgagcga agatgacttg ccgaagctga cctatctgga catggtcgtt   1080

aaggaaggca tgcgtttgca tccggccgtg ccgctgcttc tgccgcatga gtctctggaa   1140

gaagccacga tcgatggcta ctacattccg aagggttccc gcattctgat caacgtctgg   1200

gcgattggtc gcgacccgaa ggcctggccg gatcgtcctg aagagttcat cccggagcgt   1260

ttcgagaaaa gcaacgtgga tgtgctgggc cgtgacttcc agctgctgcc gtttggttcg   1320

ggtcgtcgcg gttgtgcagg cattcgcctg ggcctgatct tcgtacgtct ggttctggca   1380

cagttagttc actgtttcga ctgggaactg gcgcgcaaca tggcgagcag cccggagaag   1440

ttggatatgg aagagaagtt cggcctggcg gtgcatcgtg tcaaccacct gaaagccctg   1500

ccgacgtatc gtctggagag ctaagtcgac taactttaag aaggagatat atccatggaa   1560
```

-continued

```
cctagctctc agaaactgtc tccgttggaa tttgttgctg ctatcctgaa gggcgactac   1620
agcagcggtc aggttgaagg tggtccaccg ccaggtctgg cagctatgtt gatggaaaat   1680
aaggatttgg tgatggttct gacgacgtcc gtggcagtcc tgatcggctg tgtcgtggtc   1740
ctggcatggc gtcgtgcggc aggtagcggt aagtacaagc aacctgaact gcctaaactg   1800
gtggtcccga aagcagccga accggaggag gcagaggatg ataaaaccaa gatcagcgtg   1860
tttttcggca cccaaaccgg tacggcagaa ggtttcgcga aggcttttgt tgaagaggcc   1920
aaggcgcgtt atcagcaggc ccgtttcaaa gttatcgacc tggacgacta tgcggcagac   1980
gatgacgagt acgaagagaa actgaagaag gaaaacttgg cattcttctt cttggcgtcc   2040
tacggtgacg gcgagccgac ggacaacgcg gcacgctttt acaaatggtt tacggagggt   2100
aaggaccgtg gtgaatggct gaacaatctg cagtacggcg tttttggtct gggtaaccgt   2160
caatatgagc atttcaataa gatcgccatt gtcgtcgatg atctgatctt cgagcaaggt   2220
ggcaagaagc tggttccggt gggtctgggt gacgatgacc agtgcattga ggatgatttt   2280
gcggcgtggc gtgaactggt ctggccggaa ctggataaac tgctgcgtaa cgaagacgac   2340
gctaccgtgg caaccccgta cagcgccgct gtgctgcaat accgcgtggt tttccacgat   2400
cacattgacg gcctgattag cgaaaacggt agcccgaacg gtcatgctaa tggcaatacc   2460
gtgtacgatg cgcaacaccc gtgccgtagc aacgtcgcgg tcaagaagga attgcatact   2520
ccggcgagcg atcgcagctg cacccacctg gaatttaaca ttagcggtac cggcctgatg   2580
tacgagacgg gtgaccacgt cggtgtgtat tgcgagaacc tgttggaaac cgtggaggag   2640
gccgagaagt tgttgaacct gagcccgcag acgtacttct ccgttcacac cgacaacgag   2700
gacggtacgc cgttgagcgg cagcagcctg ccgccaccgt ttccgccgtg caccttgcgc   2760
acggcattga ccaaatacgc agacttgact tctgcaccga aaaagtcggt gctggtggcg   2820
ctggccgagt acgcatctga ccagggtgaa gcggatcgtt tgcgtttctt ggcgagcccg   2880
agcggcaaag aggaatatgc acagtacatc ttggcaagcc agcgcacgct gctggaggtc   2940
atggcggagt tcccgtcggc gaaaccgccg ctgggtgtct tttcgcgggg tgtcgctccg   3000
cgcctgcagc cgcgtttcta ttccattagc tctagcccga agatcgcacc gttccgtatt   3060
cacgtgacct gcgccctggt ttatgacaaa tcccctaccg gtcgcgttca taagggcatc   3120
tgtagcacgt ggatgaaaaa tgcggtcccg ctggaagaaa gcaacgattg ttcctgggct   3180
ccgatcttcg tccgcaacag caacttcaag ctgccgaccg acccgaaggt tccgattatc   3240
atgattggtc cgggtaccgg tctggcccct tttcgtggct tttgcaaga gcgcttggcg   3300
ttgaaagaga gcggtgctga attgggtccg gcgatcttgt tctttggttg ccgtaaccgt   3360
aaaatggact ttatttacga ggatgaactg aatgatttcg tcaaagcggg cgttgtcagc   3420
gagctgatcg tcgcttttag ccgcgaaggc ccgatgaaag aatacgtgca acacaaaatg   3480
agccaacgtg cctccgatgt gtggaacatc attagcgacg gtggttatgt ttatgtttgc   3540
ggtgacgcga agggtatggc tcgtgatgtt caccgtaccc tgcataccat cgcacaggag   3600
caaggtagca tgtccagctc ggaggccgaa ggtatggtca aaaacctgca aaccaccggt   3660
cgttacctgc gtgatgtgtg gtaataaaag cttaggaggt aaaaatggcg accgttgtgg   3720
atgattctag cgtcgttcgt cgttctgcaa actacccgcc gaatttgtgg gactatgagt   3780
tcctgcaatc cctgggtgac cagtgtacgg tcgaagaaaa acacctgaag ctggccgaca   3840
agttgaaaga agaagttaaa tccctgatta aacagacgat ggagccgctg gcaaaactgg   3900
agttcatcga taccgtgcgt cgtttgggtt tgaaatatca gtttgagacc gaggtgaagg   3960
```

aggccgttgt tatggttagc aaatatgaga atgatgcgtg gtggattgat aatctgcacg 4020
ctaccagcct gcgtttccgc atcatgcgtg agaatggtat cttcgtgccg caagatgtgt 4080
ttgaacgttt caaagatacc gacggcttta aaaaccaact gtgcgaagac gtgaagggtc 4140
tgttgtctct gtatgaggcg agctttctgg gttgggaggg cgaggatatc ttggatgagg 4200
cacgcacctt tgcgaccagc aagctgaaga gcattgaagg caaaattccg agcccgagcc 4260
tggctaagaa agtgagccac gcgctggact tgcctctgca ctggcgtacc attcgctacg 4320
aagcgcgctg gttcatcgac acctacggtg aagaagagga cgtgaatctg acgttgctgc 4380
gttacgccaa actggacttc aacattgttc aatcttttta ccaaaaagag atcggccgtc 4440
tgtcccgctg gtgggtgggt actggcctgg ataaaatgcc gtttgctcgt aatggtctga 4500
ttcagagcta tatgtacgca attggtatgc tgttcgagcc taacctgggc gaggtgcgtg 4560
agatggaggc gaaggtcggc gccttgatta ccacgatcga cgacgtgtat gacgtttacg 4620
gcacgatgga ggagttggag ctgttcaccg atattaccaa tcgttgggac atcagcaaag 4680
cggatcaact gccgcgtaac atccgcatgc cgctgctgac gatgttcaac accagcaatg 4740
atatcggtta ttgggctctg aaagagcgtg gtttcaatgg cattccgtgt accgcaaaag 4800
tctggtccga ccaactgaag agctacacca aggaggctaa atggttccac gaaggccata 4860
aaccgactct ggaggagtat ctggacaatg cgctggtcag catcggcttc ccgaacctgc 4920
tggtcacgtc ttatctgttg accgttgaga atccgaccaa agaaaagctg gactatgtga 4980
acagcctgcc gttgttcgtt cgcgcgagct gcatcctgtg tcgtatcatt aacgatctgg 5040
gtacgagccc ggatgaaatg gagcgtggtg acaatctgaa aagcatccag tgctatatga 5100
acgaaaccgg tgcgagccaa gaggttgcgc gtgagcacat cgaaggcctg gttcgtatgt 5160
ggtggaaacg tctgaacaag tgcctgtttg agccgagccc gttcactgag ccgttcctga 5220
gctttacgat taacgtggtc cgtggtagcc actttttcta tcagtacggc gatggctacg 5280
gcaacgcaga gagctggacc aagaaccagg gtatgtcggt gctgatccac ccgattaccc 5340
tggatgaaga gtaagaattc 5360

<210> SEQ ID NO 85
<211> LENGTH: 5420
<212> TYPE: DNA
<213> ORGANISM: Artificial Sequence
<220> FEATURE:
<223> OTHER INFORMATION: SaCP816-CPRm-SaTPs30, synthetic operon encoding for SaCP816, CPRm and a Beta-bisabolene synthase

<400> SEQUENCE: 85
catatggcac tgttgttggc ggttttctgg agcgctttga ttattctggt tagcatctta 60
ttgcgtcgtc gtcaaaaacg caacaatttg ccaccgggcc caccggccct gccgatcatc 120
ggtaacattc acattctggg caccctgccg caccagagcc tgtacaatct ggcgaagaag 180
tacggtccga tcatgtccat gcgtttgggc ttggttccgg cggtggtcat cagcagcccg 240
gaagcggccg agctggtcct gaaaacccac gacatcgttt ttgcttctcg ccctcgtctg 300
caagttgcag attactttca ctatggcacc aaaggcgtga ttctgaccga atatggtacc 360
tactggcgta acatgcgtcg cctgtgcacg gtcaaactgc tgaacaccgt taagattgat 420
agctttgcag gcacccgcaa gaaagaagtc gctagcttcg ttcagagcct gaaagaagca 480
agcgtggcgc acaaaatggt taacctgtcc gcacgcgtcg ctaatgttat tgagaatatg 540
gtttgtctga tggttattgg tagatcgtct gacgagcgtt tcaagctgaa agaagtgatc 600

-continued

```
caagaagcgg cacagctggc gggtgccttc aatattggtg actatgtccc gtttctgatg    660
ccgctggatc tgcagggcct gactcgccgt atcaagagcg gtagcaaggc attcgatgac    720
atcctcgagg tcattatcga cgagcatgtg caagacatta aagatcatga cgatgagcag    780
catggtgact tcatcgacgt gctgctggcg atgatgaata agccgatgga ttctcgtgag    840
ggtctgtcca tcattgatcg cacgaacatt aaagcgatcc tggtggatat gatcggtgcc    900
gcgatggaca cgagcaccag cggtgtggag tgggcgattt cggagctgat taagcatcct    960
cgtgtcatga agaaactgca agacgaagtg aaaaccgtaa tcggtatgaa ccgcatggtg   1020
gaagaagcgg atctgccgaa actgccgtac ctggacatgg ttgtcaagga aacgatgcgt   1080
ctgcatccgc caggcccgct gctggtgccg cgtgaaagca tggaagatat tacgatcaac   1140
ggttactata tcccgaagaa atcccgcatt attgtgaatg catgggcgat cggccgtgac   1200
accaacgcct ggagcaataa tgcgcacgag tttttccctg agcgttttat gagctctaac   1260
gttgatctgc aaggccagga cttccagctg atcccgttcg gtagcggtcg tcgcggttgt   1320
ccgggcatgc gtctgggtct gacgacggtc cgcttggtgc tggcccaact gattcactgc   1380
ttcgacctgg agcttccgaa gggcaccgtc gcgactgacc tggatatgag cgagaagttt   1440
ggtctggcaa tgccgcgtgc gcagcactta ctggcctttc cgacctaccg tctggagagc   1500
taagtcgact aactttaaga aggagatata tccatggaac ctagctctca gaaactgtct   1560
ccgttggaat ttgttgctgc tatcctgaag ggcgactaca gcagcggtca ggttgaaggt   1620
ggtccaccgc caggtctggc agctatgttg atggaaaata aggatttggt gatggttctg   1680
acgacgtccg tggcagtcct gatcggctgt gtcgtggtcc tggcatggcg tcgtgcggca   1740
ggtagcggta agtacaagca acctgaactg cctaaactgg tggtcccgaa agcagccgaa   1800
ccggaggagg cagaggatga taaaaccaag atcagcgtgt tttcggcac ccaaaccggt    1860
acggcagaag gtttcgcgaa ggcttttgtt gaagaggcca aggcgcgtta tcagcaggcc   1920
cgtttcaaag ttatcgacct ggacgactat gcggcagacg atgacgagta cgaagagaaa   1980
ctgaagaagg aaaacttggc attcttcttc ttggcgtcct acggtgacgg cgagccgacg   2040
gacaacgcgg cacgctttta caaatggttt acggagggta aggaccgtgg tgaatggctg   2100
aacaatctgc agtacggcgt ttttggtctg ggtaaccgtc aatatgagca tttcaataag   2160
atcgccattg tcgtcgatga tctgatcttc gagcaaggtg gcaagaagct ggttccggtg   2220
ggtctgggtg acgatgacca gtgcattgag gatgattttg cggcgtggcg tgaactggtc   2280
tggccggaac tggataaact gctgcgtaac gaagacgacg ctaccgtggc aaccccgtac   2340
agcgccgctg tgctgcaata ccgcgtggtt ttccacgatc acattgacgg cctgattagc   2400
gaaaacggta gcccgaacgg tcatgctaat ggcaataccg tgtacgatgc gcaacacccg   2460
tgccgtagca acgtcgcggt caagaaggaa ttgcatactc cggcgagcga tcgcagctgc   2520
acccacctgg aatttaacat tagcggtacc ggcctgatgt acgagacggg tgaccacgtc   2580
ggtgtgtatt gcgagaacct gttggaaacc gtggaggagg ccgagaagtt gttgaacctg   2640
agcccgcaga cgtacttctc cgttcacacc gacaacgagg acggtacgcc gttgagcggc   2700
agcagcctgc cgccaccgtt tccgccgtgc accttgcgca cggcattgac caaatacgca   2760
gacttgactt ctgcaccgaa aaagtcggtg ctggtggcgc tggccgagta cgcatctgac   2820
cagggtgaag cggatcgttt gcgtttcttg gcgagcccga gcggcaaaga ggaatatgca   2880
cagtacatct tggcaagcca gcgcacgctg ctggaggtca tggcggagtt cccgtcggcg   2940
```

-continued

```
aaaccgccgc tgggtgtctt tttcgcgggt gtcgctccgc gcctgcagcc gcgtttctat   3000
tccattagct ctagcccgaa gatcgcaccg ttccgtattc acgtgacctg cgccctggtt   3060
tatgacaaat cccctaccgg tcgcgttcat aagggcatct gtagcacgtg gatgaaaaat   3120
gcggtcccgc tggaagaaag caacgattgt tcctgggctc cgatcttcgt ccgcaacagc   3180
aacttcaagc tgccgaccga cccgaaggtt ccgattatca tgattggtcc gggtaccggt   3240
ctggcccctt ttcgtggctt tttgcaagag cgcttggcgt tgaaagagag cggtgctgaa   3300
ttgggtccgg cgatcttgtt ctttggttgc cgtaaccgta aaatggactt tatttacgag   3360
gatgaactga atgatttcgt caaagcgggc gttgtcagcg agctgatcgt cgcttttagc   3420
cgcgaaggcc cgatgaaaga atacgtgcaa cacaaaatga gccaacgtgc ctccgatgtg   3480
tggaacatca ttagcgacgg tggttatgtt tatgtttgcg gtgacgcgaa gggtatggct   3540
cgtgatgttc accgtaccct gcataccatc gcacaggagc aaggtagcat gtccagctcg   3600
gaggccgaag gtatggtcaa aaacctgcaa accaccggtc gttacctgcg tgatgtgtgg   3660
taataaaagc ttaggaggta aaaatggacg cattcgcaac gagcccgacc agcgcactga   3720
ttaaggcggt taactgcatc gcgcacgtga ccccgatggc aggtgaagat tcctccgaaa   3780
accgccgtgc atcgaactac aaaccgagca cctgggacta tgaatttctg caaagcctgg   3840
ccacgagcca taacaccgtc caggaaaagc acatgaagat ggctgagaaa ttgaaggaag   3900
aggtgaagag catgatcaag ggtcagatgg agccggtggc gaagttggaa ctgatcaaca   3960
tcctgcagcg tctgggtttg aaatatcgct ttgaatccga gatcaaggaa gagctgtttt   4020
ccctgtacaa ggacggtact gatgcgtggt gggttgataa tctgcatgca acggcgctgc   4080
gttttagact gctgcgcgag aatggtattt tcgtgccgca agaagtattc gaaactttaa   4140
aggataagag cggtaagttt aagagccagc tgtgcaagga cgttcgtggt ctgctgagct   4200
tgtacgaggc gtcctacctg ggttgggagg gtgaggactt gctggacgag gccaagaagt   4260
tcagcaccac caacctgaac aatgtgaaag aaagcatcag cagcaacact ctgggtcgct   4320
tggtcaagca cgccctgaac ctgccgctgc actggtctgc ggcacgttac gaggcgagat   4380
ggtttattga cgagtacgaa aaagaagaaa acgttaaccc gaacctgctg aagtacgcga   4440
agtttgactt taacatcgtt cagagcattc accaacgtga gctcggtaac ctcgcgcgtt   4500
ggtgggtaga aaccggcctg gataaactga gcttcgtgcg caatacgttg atgcagaatt   4560
tcatgtgggg ctgtgcgatg gtgttcgaac cgcagtacgg caaggttcgc gatgcggccg   4620
tcaagcaggc cagcctgatt gcgatggtcg acgacgtgta tgacgtttat ggcagcctgg   4680
aagaactgga aatctttacc gatatcgtgg accgttggga tatcaccggt atcgacaagc   4740
tgccgcgtaa catctctatg attctgctga cgatgttcaa taccgcgaat cagattggtt   4800
acgacttgct gcgtgaccgc ggttttaacg gcatcccgca cattgctcag gcgtgggcca   4860
ccctgtgtaa gaaatatctg aaagaggcga agtggtatca tagcggttac aagccaactc   4920
tggaggagta cctggaaaac ggtcttgttt ctattagctt tgtgctgagc cttgttaccg   4980
catatctgca gaccgaaacc ctggagaatc tgacgtatga gtccgctgcg tacgtgaata   5040
gcgtaccgcc actggtccgc tacagcggcc tgctgaatcg tctgtacaac gatctcggta   5100
cgtcaagcgc agaaattgca cgtggtgaca ccctgaaaag catccagtgt tatatgaccc   5160
aaaccggtgc aaccgaggaa gcagcgcgcg agcacattaa aggtctggtt cacgaagcgt   5220
ggaagggcat gaacaaatgc ttgttcgagc agacgccatt cgcggagccg tttgtcggtt   5280
tcaacgtcaa taccgtccgc ggttcccaat tcttctacca gcatggcgac ggctacgcgg   5340
```

ttacggaaag ctggacgaag gacctgagcc tgtcggtgct gattcacccg atcccgctga 5400
atgaagagga ctaagaattc 5420

<210> SEQ ID NO 86
<211> LENGTH: 5441
<212> TYPE: DNA
<213> ORGANISM: Artificial Sequence
<220> FEATURE:
<223> OTHER INFORMATION: SaCP10374-CPRm-SaTPs30, synthetic operon encoding for SaCP10374, CPRm and a Beta-bisabolene synthase

<400> SEQUENCE: 86
catatggcac tgctgctggc tgtcttttgg agcgcactga ttattctgac ccgcaaacgc 60
cgcaaaggtc cgggtctgcc accgggtccg cgtgcgtacc cgattattgg caatctgcac 120
atgatgggcc agctgccaca ccacaatttg cgtgagctgg cacgtgagta tggtccgatt 180
atgagcatgc gcctgggtct ggtgccggca atcgtggtta gctctcctga ggctgcgcag 240
ctgttcctca agacgcatga taccgttttc gcgagccgtc caaagaccga gactgccaaa 300
tacttccatt acggtatcaa aggtctgatc ctgaccgagt atggcccgta ctggcgcaat 360
attcgtcgtt tgagcaccgt taagctgttg aatgccgcga aaatcgatag cttcgcggct 420
atgcgtagaa gcgaagttga acgcctggtc gcgtccgttc gtggttcggc ggttcgtcgt 480
gaggttgtgg acgtcagcag caaagtggcg gaagctatgg agaatatggt ctgccagatg 540
gttatcggcc gttcaggtga cgatcgtttt aagctgaaag aaacctttca agagggcacc 600
caactggcag gcgcgttcaa ttttggtgag tttgtgccgt ttctgctgcc gctggacttg 660
caaggtatta cccgtcgcat caaagaagtc agcactcgtt tcaataagat tttggacctg 720
atcgttgacg agcacattcg cgatgccgct ggtaccaaaa acagcggcgg tcgtgatagc 780
gacaattttc tggatgttct gctgtccttg atgaacacct ctattagcga tagcaatgac 840
acgggtgaca acaaccgtaa caacgtgatc gagcgtgata acattaaagc gatcctgacg 900
gacatgctgg gtgcagcgat ggacacgagc gcgagcacgg tcgagtggac gatctccgaa 960
ctgtttcgcc acccgaaaac catgcagaag ctgcaagcag aaatccgtgg tgtcgtgggc 1020
ccgacccgca atgtgagcga agatgacttg ccgaagctga cctatctgga catggtcgtt 1080
aaggaaggca tgcgtttgca tccggccgtg ccgctgcttc tgccgcatga gtctctggaa 1140
gaagccacga tcgatggcta ctacattccg aagggttccc gcattctgat caacgtctgg 1200
gcgattggtc gcgacccgaa ggcctggccg gatcgtcctg aagagttcat cccggagcgt 1260
ttcgagaaaa gcaacgtgga tgtgctgggc cgtgacttcc agctgctgcc gtttggttcg 1320
ggtcgtcgcg gttgtgcagg cattcgcctg ggcctgatct tcgtacgtct ggttctggca 1380
cagttagttc actgtttcga ctgggaactg gcgcgcaaca tggcgagcag cccggagaag 1440
ttggatatgg aagagaagtt cggcctggcg gtgcatcgtg tcaaccacct gaaagccctg 1500
ccgacgtatc gtctggagag ctaagtcgac taactttaag aaggagatat atccatggaa 1560
cctagctctc agaaactgtc tccgttggaa tttgttgctg ctatcctgaa gggcgactac 1620
agcagcggtc aggttgaagg tggtccaccg ccaggtctgg cagctatgtt gatggaaaat 1680
aaggatttgg tgatggttct gacgacgtcc gtggcagtcc tgatcggctg tgtcgtggtc 1740
ctggcatggc gtcgtgcggc aggtagcggt aagtacaagc aacctgaact gcctaaactg 1800
gtggtcccga aagcagccga accggaggag gcagaggatg ataaaaccaa gatcagcgtg 1860
tttttcggca cccaaaccgg tacggcagaa ggtttcgcga aggcttttgt tgaagaggcc 1920

```
aaggcgcgtt atcagcaggc ccgtttcaaa gttatcgacc tggacgacta tgcggcagac   1980
gatgacgagt acgaagagaa actgaagaag gaaaacttgg cattcttctt cttggcgtcc   2040
tacggtgacg gcgagccgac ggacaacgcg gcacgctttt acaaatggtt tacggagggt   2100
aaggaccgtg gtgaatggct gaacaatctg cagtacggcg tttttggtct gggtaaccgt   2160
caatatgagc atttcaataa gatcgccatt gtcgtcgatg atctgatctt cgagcaaggt   2220
ggcaagaagc tggttccggt gggtctgggt gacgatgacc agtgcattga ggatgatttt   2280
gcggcgtggc gtgaactggt ctggccggaa ctggataaac tgctgcgtaa cgaagacgac   2340
gctaccgtgg caaccccgta cagcgccgct gtgctgcaat accgcgtggt tttccacgat   2400
cacattgacg gcctgattag cgaaaacggt agcccgaacg gtcatgctaa tggcaatacc   2460
gtgtacgatg cgcaacaccc gtgccgtagc aacgtcgcgg tcaagaagga attgcatact   2520
ccggcgagcg atcgcagctg cacccacctg gaatttaaca ttagcggtac cggcctgatg   2580
tacgagacgg gtgaccacgt cggtgtgtat tgcgagaacc tgttggaaac cgtggaggag   2640
gccgagaagt tgttgaacct gagcccgcag acgtacttct ccgttcacac cgacaacgag   2700
gacggtacgc cgttgagcgg cagcagcctg ccgccaccgt ttccgccgtg caccttgcgc   2760
acggcattga ccaaatacgc agacttgact tctgcaccga aaaagtcggt gctggtggcg   2820
ctggccgagt acgcatctga ccagggtgaa gcggatcgtt tgcgtttctt ggcgagcccg   2880
agcggcaaag aggaatatgc acagtacatc ttggcaagcc agcgcacgct gctggaggtc   2940
atggcggagt tcccgtcggc gaaaccgccg ctgggtgtct tttcgcgggg tgtcgctccg   3000
cgcctgcagc cgcgtttcta ttccattagc tctagcccga agatcgcacc gttccgtatt   3060
cacgtgacct gcgccctggt ttatgacaaa tcccctaccg gtcgcgttca taagggcatc   3120
tgtagcacgt ggatgaaaaa tgcggtcccg ctggaagaaa gcaacgattg ttcctgggct   3180
ccgatcttcg tccgcaacag caacttcaag ctgccgaccg acccgaaggt tccgattatc   3240
atgattggtc cgggtaccgg tctggcccct tttcgtggct tttgcaaga gcgcttggcg    3300
ttgaaagaga gcggtgctga attgggtccg gcgatcttgt tctttggttg ccgtaaccgt   3360
aaaatggact ttatttacga ggatgaactg aatgatttcg tcaaagcggg cgttgtcagc   3420
gagctgatcg tcgcttttag ccgcgaaggc ccgatgaaag aatacgtgca acacaaaatg   3480
agccaacgtg cctccgatgt gtggaacatc attagcgacg gtggttatgt ttatgtttgc   3540
ggtgacgcga agggtatggc tcgtgatgtt caccgtaccc tgcataccat cgcacaggag   3600
caaggtagca tgtccagctc ggaggccgaa ggtatggtca aaaacctgca aaccaccggt   3660
cgttacctgc gtgatgtgtg gtaataaaag cttaggaggt aaaaatggac gcattcgcaa   3720
cgagcccgac cagcgcactg attaaggcgg ttaactgcat cgcgcacgtg accccgatgg   3780
caggtgaaga ttcctccgaa aaccgccgtg catcgaacta caaaccgagc acctgggact   3840
atgaatttct gcaaagcctg gccacgagcc ataacaccgt ccaggaaaag cacatgaaga   3900
tggctgagaa attgaaggaa gaggtgaaga gcatgatcaa gggtcagatg gagccggtgg   3960
cgaagttgga actgatcaac atcctgcagc gtctgggttt gaaatatcgc tttgaatccg   4020
agatcaagga agagctgttt tccctgtaca aggacggtac tgatgcgtgg tgggttgata   4080
atctgcatgc aacggcgctg cgttttagac tgctgcgcga gaatggtatt ttcgtgccgc   4140
aagaagtatt cgaaacttta aaggataaga gcggtaagtt taagagccag ctgtgcaagg   4200
acgttcgtgg tctgctgagc ttgtacgagg cgtcctacct gggttgggag ggtgaggact   4260
```

-continued

```
tgctggacga ggccaagaag ttcagcacca ccaacctgaa caatgtgaaa gaaagcatca   4320

gcagcaacac tctgggtcgc ttggtcaagc acgccctgaa cctgccgctg cactggtctg   4380

cggcacgtta cgaggcgaga tggtttattg acgagtacga aaaagaagaa aacgttaacc   4440

cgaacctgct gaagtacgcg aagtttgact ttaacatcgt tcagagcatt caccaacgtg   4500

agctcggtaa cctcgcgcgt tggtgggtag aaaccggcct ggataaactg agcttcgtgc   4560

gcaatacgtt gatgcagaat ttcatgtggg gctgtgcgat ggtgttcgaa ccgcagtacg   4620

gcaaggttcg cgatgcggcc gtcaagcagg ccagcctgat tgcgatggtc gacgacgtgt   4680

atgacgttta tggcagcctg gaagaactgg aaatctttac cgatatcgtg gaccgttggg   4740

atatcaccgg tatcgacaag ctgccgcgta acatctctat gattctgctg acgatgttca   4800

ataccgcgaa tcagattggt tacgacttgc tgcgtgaccg cggttttaac ggcatcccgc   4860

acattgctca ggcgtgggcc accctgtgta agaaatatct gaaagaggcg aagtggtatc   4920

atagcggtta caagccaact ctggaggagt acctggaaaa cggtcttgtt tctattagct   4980

ttgtgctgag ccttgttacc gcatatctgc agaccgaaac cctggagaat ctgacgtatg   5040

agtccgctgc gtacgtgaat agcgtaccgc cactggtccg ctacagcggc ctgctgaatc   5100

gtctgtacaa cgatctcggt acgtcaagcg cagaaattgc acgtggtgac accctgaaaa   5160

gcatccagtg ttatatgacc caaaccggtg caaccgagga agcagcgcgc gagcacatta   5220

aaggtctggt tcacgaagcg tggaagggca tgaacaaatg cttgttcgag cagacgccat   5280

tcgcggagcc gtttgtcggt ttcaacgtca ataccgtccg cggttcccaa ttcttctacc   5340

agcatggcga cggctacgcg gttacggaaa gctggacgaa ggacctgagc ctgtcggtgc   5400

tgattcaccc gatcccgctg aatgaagagg actaagaatt c                       5441
```

<210> SEQ ID NO 87
<211> LENGTH: 5414
<212> TYPE: DNA
<213> ORGANISM: Artificial Sequence
<220> FEATURE:
<223> OTHER INFORMATION: SaCP816-CPRm-AaBFS, synthetic operon encoding for SaCP816, CPRm and a Beta-farnesene synthase

<400> SEQUENCE: 87

```
catatggcac tgttgttggc ggttttctgg agcgctttga ttattctggt tagcatctta     60

ttgcgtcgtc gtcaaaaacg caacaatttg ccaccgggcc caccggccct gccgatcatc    120

ggtaacattc acattctggg caccctgccg caccagagcc tgtacaatct ggcgaagaag    180

tacggtccga tcatgtccat gcgtttgggc ttggttccgg cggtggtcat cagcagcccg    240

gaagcggccg agctggtcct gaaaacccac gacatcgttt ttgcttctcg ccctcgtctg    300

caagttgcag attactttca ctatggcacc aaaggcgtga ttctgaccga atatggtacc    360

tactggcgta acatgcgtcg cctgtgcacg gtcaaactgc tgaacaccgt taagattgat    420

agctttgcag gcacccgcaa gaaagaagtc gctagcttcg ttcagagcct gaaagaagca    480

agcgtggcgc acaaaatggt taacctgtcc gcacgcgtcg ctaatgttat tgagaatatg    540

gtttgtctga tggttattgg tagatcgtct gacgagcgtt tcaagctgaa agaagtgatc    600

caagaagcgg cacagctggc gggtgccttc aatattggtg actatgtccc gtttctgatg    660

ccgctggatc tgcagggcct gactcgccgt atcaagagcg gtagcaaggc attcgatgac    720

atcctcgagg tcattatcga cgagcatgtg caagacatta aagatcatga cgatgagcag    780

catggtgact tcatcgacgt gctgctggcg atgatgaata agccgatgga ttctcgtgag    840
```

-continued

```
ggtctgtcca tcattgatcg cacgaacatt aaagcgatcc tggtggatat gatcggtgcc    900
gcgatggaca cgagcaccag cggtgtggag tgggcgattt cggagctgat taagcatcct    960
cgtgtcatga agaaactgca agacgaagtg aaaaccgtaa tcggtatgaa ccgcatggtg   1020
gaagaagcgg atctgccgaa actgccgtac ctggacatgg ttgtcaagga aacgatgcgt   1080
ctgcatccgc caggcccgct gctggtgccg cgtgaaagca tggaagatat tacgatcaac   1140
ggttactata tcccgaagaa atcccgcatt attgtgaatg catgggcgat cggccgtgac   1200
accaacgcct ggagcaataa tgcgcacgag tttttccctg agcgttttat gagctctaac   1260
gttgatctgc aaggccagga cttccagctg atcccgttcg gtagcggtcg tcgcggttgt   1320
ccgggcatgc gtctgggtct gacgacggtc cgcttggtgc tggcccaact gattcactgc   1380
ttcgacctgg agcttccgaa gggcaccgtc gcgactgacc tggatatgag cgagaagttt   1440
ggtctggcaa tgccgcgtgc gcagcactta ctggcctttc cgacctaccg tctggagagc   1500
taagtcgact aactttaaga aggagatata tccatggaac ctagctctca gaaactgtct   1560
ccgttggaat ttgttgctgc tatcctgaag ggcgactaca gcagcggtca ggttgaaggt   1620
ggtccaccgc caggtctggc agctatgttg atggaaaata aggatttggt gatggttctg   1680
acgacgtccg tggcagtcct gatcggctgt gtcgtggtcc tggcatggcg tcgtgcggca   1740
ggtagcggta agtacaagca acctgaactg cctaaactgg tggtcccgaa agcagccgaa   1800
ccggaggagg cagaggatga taaaaccaag atcagcgtgt ttttcggcac ccaaaccggt   1860
acggcagaag gtttcgcgaa ggcttttgtt gaagaggcca aggcgcgtta tcagcaggcc   1920
cgtttcaaag ttatcgacct ggacgactat gcggcagacg atgacgagta cgaagagaaa   1980
ctgaagaagg aaaacttggc attcttcttc ttggcgtcct acggtgacgg cgagccgacg   2040
gacaacgcgg cacgctttta caaatggttt acggagggta aggaccgtgg tgaatggctg   2100
aacaatctgc agtacggcgt ttttggtctg ggtaaccgtc aatatgagca tttcaataag   2160
atcgccattg tcgtcgatga tctgatcttc gagcaaggtg gcaagaagct ggttccggtg   2220
ggtctgggtg acgatgacca gtgcattgag gatgattttg cggcgtggcg tgaactggtc   2280
tggccggaac tggataaact gctgcgtaac gaagacgacg ctaccgtggc aaccccgtac   2340
agcgccgctg tgctgcaata ccgcgtggtt ttccacgatc acattgacgg cctgattagc   2400
gaaaacggta gcccgaacgg tcatgctaat ggcaataccg tgtacgatgc gcaacacccg   2460
tgccgtagca acgtcgcggt caagaaggaa ttgcatactc cggcgagcga tcgcagctgc   2520
acccacctgg aatttaacat tagcggtacc ggcctgatgt acgagacggg tgaccacgtc   2580
ggtgtgtatt gcgagaacct gttggaaacc gtggaggagg ccgagaagtt gttgaacctg   2640
agcccgcaga cgtacttctc cgttcacacc gacaacgagg acggtacgcc gttgagcggc   2700
agcagcctgc cgccaccgtt tccgccgtgc accttgcgca cggcattgac caaatacgca   2760
gacttgactt ctgcaccgaa aaagtcggtg ctggtggcgc tggccgagta cgcatctgac   2820
cagggtgaag cggatcgttt gcgtttcttg gcgagcccga gcggcaaaga ggaatatgca   2880
cagtacatct tggcaagcca gcgcacgctg ctggaggtca tggcggagtt cccgtcggcg   2940
aaaccgccgc tgggtgtctt tttcgcgggt gtcgctccgc gcctgcagcc gcgtttctat   3000
tccattagct ctagcccgaa gatcgcaccg ttccgtattc acgtgacctg cgccctggtt   3060
tatgacaaat cccctaccgg tcgcgttcat aagggcatct gtagcacgtg gatgaaaaat   3120
gcggtcccgc tggaagaaag caacgattgt tcctgggctc cgatcttcgt ccgcaacagc   3180
aacttcaagc tgccgaccga cccgaaggtt ccgattatca tgattggtcc gggtaccggt   3240
```

ctggcccctt ttcgtggctt tttgcaagag cgcttggcgt tgaaagagag cggtgctgaa 3300
ttgggtccgg cgatcttgtt ctttggttgc cgtaaccgta aaatggactt tatttacgag 3360
gatgaactga atgatttcgt caaagcgggc gttgtcagcg agctgatcgt cgcttttagc 3420
cgcgaaggcc cgatgaaaga atacgtgcaa cacaaaatga gccaacgtgc ctccgatgtg 3480
tggaacatca ttagcgacgg tggttatgtt tatgtttgcg gtgacgcgaa gggtatggct 3540
cgtgatgttc accgtaccct gcataccatc gcacaggagc aaggtagcat gtccagctcg 3600
gaggccgaag gtatggtcaa aaacctgcaa accaccggtc gttacctgcg tgatgtgtgg 3660
taataaaagc ttaggaggta aaaatgtcta ccctgccaat ttcttctgtg tcctttagct 3720
ccagcacttc gccactggtt gtcgatgaca aggtgagcac gaaaccggat gtgatccgtc 3780
acacgatgaa cttcaacgcg agcatttggg gcgatcaatt cctgacctat gacgagccgg 3840
aagatctggt aatgaagaaa caactggttg aggaacttaa agaagaagtg aagaaagaat 3900
tgatcaccat caagggtagc aacgagccga tgcaacatgt caagctgatc gagttgatcg 3960
acgcagttca acgcctgggc attgcctacc actttgaaga agagattgaa gaggccctgc 4020
agcacattca tgtcacctac ggtgagcagt gggtggacaa agagaatttg caatccatca 4080
gcctgtggtt tcgtctgctg cgtcaacagg gcttcaacgt gagcagcggt gtgtttaaag 4140
atttcatgga cgaaaagggt aagtttaaag agtccctgtg caatgatgca cagggtattt 4200
tggcgctgta tgaggccgca ttcatgcgcg ttgaagatga aaccattctg gacaacgctc 4260
tggagttcac caaggtgcat ctggacatca tcgctaagga cccgagctgt gattctagcc 4320
tgcgcacgca gattcaccag gctctgaagc agccgctgcg ccgtcgcctg gcacgtattg 4380
aggcgttaca ctatatgccg atctatcagc aagagactag ccatgacgaa gttctgctga 4440
aactggcaaa gctggacttt agcgttctgc agagcatgca caagaaagaa ctcagccata 4500
tttgcaagtg gtggaaagat ctggatctgc agaataagct gccgtacgtt cgtgaccgtg 4560
tcgttgaggg ctatttctgg atcttgagca tttactacga gccgcaacat gcgcgtaccc 4620
gtatgttcct gatgaaaacc tgtatgtggt tggttgtgct ggacgacacg tttgataact 4680
acggcacgta cgaagagttg gagattttca cccaagcggt agaacgttgg agcatctcgt 4740
gtctggacat gctgcctgag tatatgaagc tgatctacca ggaactggtc aatttacacg 4800
tcgagatgga agagagcctg gagaaagaag gcaagaccta tcagattcac tatgtgaaag 4860
aaatggcgaa agaactggtc cgcaactacc tggttgaggc gcgctggctg aaagagggct 4920
acatgccgac cctggaagag tatatgagcg tgagcatggt cacgggtacg tacggtctga 4980
tgatcgcccg cagctacgtc ggtcgtggcg acatcgttac cgaagatacc ttcaaatggg 5040
tttctagcta cccgccgatt atcaaggcaa gctgcgttat cgtgcgtttg atggatgata 5100
ttgttagcca caaagaagaa caagagcgtg gtcatgttgc tagcagcatt gagtgctaca 5160
gcaaagagtc cggtgcaagc gaagaagaag cgtgcgagta tatcagccgt aaggtcgagg 5220
acgcgtggaa agtcattaat cgcgagtccc tgcgtccgac cgcggttccg tttccgctgc 5280
tgatgcctgc gattaatctg gcgcgtatgt gtgaggtcct gtacagcgtg aatgacggtt 5340
ttacgcacgc cgagggtgat atgaaaagct atatgaagtc attctttgtg cacccgatgg 5400
ttgtgtaaga attc 5414

<210> SEQ ID NO 88
<211> LENGTH: 5435
<212> TYPE: DNA

<213> ORGANISM: Artificial Sequence
<220> FEATURE:
<223> OTHER INFORMATION: SaCP10374-CPRm-AaBFS, synthetic operon encoding
for SaCP10374, CPRm and a Beta-farnesene synthase

<400> SEQUENCE: 88
catatggcac tgctgctggc tgtcttttgg agcgcactga ttattctgac ccgcaaacgc 60
cgcaaaggtc cgggtctgcc accgggtccg cgtgcgtacc cgattattgg caatctgcac 120
atgatgggcc agctgccaca ccacaatttg cgtgagctgg cacgtgagta tggtccgatt 180
atgagcatgc gcctgggtct ggtgccggca atcgtggtta gctctcctga ggctgcgcag 240
ctgttcctca agacgcatga taccgttttc gcgagccgtc caaagaccga gactgccaaa 300
tacttccatt acggtatcaa aggtctgatc ctgaccgagt atggcccgta ctggcgcaat 360
attcgtcgtt tgagcaccgt taagctgttg aatgccgcga aaatcgatag cttcgcggct 420
atgcgtagaa gcgaagttga acgcctggtc gcgtccgttc gtggttcggc ggttcgtcgt 480
gaggttgtgg acgtcagcag caaagtggcg gaagctatgg agaatatggt ctgccagatg 540
gttatcggcc gttcaggtga cgatcgtttt aagctgaaag aaacctttca agagggcacc 600
caactggcag gcgcgttcaa ttttggtgag tttgtgccgt ttctgctgcc gctggacttg 660
caaggtatta cccgtcgcat caaagaagtc agcactcgtt tcaataagat tttggacctg 720
atcgttgacg agcacattcg cgatgccgct ggtaccaaaa acagcggcgg tcgtgatagc 780 gacaatttc tggatgttct gctgtccttg atgaacacct ctattagcga tagcaatgac 840
acgggtgaca acaaccgtaa caacgtgatc gagcgtgata acattaaagc gatcctgacg 900
gacatgctgg gtgcagcgat ggacacgagc gcgagcacgg tcgagtggac gatctccgaa 960
ctgtttcgcc acccgaaaac catgcagaag ctgcaagcag aaatccgtgg tgtcgtgggc 1020
ccgacccgca atgtgagcga agatgacttg ccgaagctga cctatctgga catggtcgtt 1080
aaggaaggca tgcgtttgca tccggccgtg ccgctgcttc tgccgcatga gtctctggaa 1140
gaagccacga tcgatggcta ctacattccg aagggttccc gcattctgat caacgtctgg 1200
gcgattggtc gcgacccgaa ggcctggccg gatcgtcctg aagagttcat cccggagcgt 1260
ttcgagaaaa gcaacgtgga tgtgctgggc cgtgacttcc agctgctgcc gtttggttcg 1320
ggtcgtcgcg gttgtgcagg cattcgcctg ggcctgatct tcgtacgtct ggttctggca 1380
cagttagttc actgtttcga ctgggaactg gcgcgcaaca tggcgagcag cccggagaag 1440
ttggatatgg aagagaagtt cggcctggcg gtgcatcgtg tcaaccacct gaaagccctg 1500
ccgacgtatc gtctggagag ctaagtcgac taactttaag aaggagatat atccatggaa 1560
cctagctctc agaaactgtc tccgttggaa tttgttgctg ctatcctgaa gggcgactac 1620
agcagcggtc aggttgaagg tggtccaccg ccaggtctgg cagctatgtt gatggaaaat 1680
aaggatttgg tgatggttct gacgacgtcc gtggcagtcc tgatcggctg tgtcgtggtc 1740
ctggcatggc gtcgtgcggc aggtagcggt aagtacaagc aacctgaact gcctaaactg 1800
gtggtcccga aagcagccga accggaggag gcagaggatg ataaaaccaa gatcagcgtg 1860
tttttcggca cccaaaccgg tacggcagaa ggtttcgcga aggcttttgt tgaagaggcc 1920
aaggcgcgtt atcagcaggc ccgtttcaaa gttatcgacc tggacgacta tgcggcagac 1980
gatgacgagt acgaagagaa actgaagaag gaaaacttgg cattcttctt cttggcgtcc 2040
tacggtgacg gcgagccgac ggacaacgcg gcacgctttt acaaatggtt tacggagggt 2100
aaggaccgtg gtgaatggct gaacaatctg cagtacggcg tttttggtct gggtaaccgt 2160

-continued

```
caatatgagc atttcaataa gatcgccatt gtcgtcgatg atctgatctt cgagcaaggt   2220
ggcaagaagc tggttccggt gggtctgggt gacgatgacc agtgcattga ggatgatttt   2280
gcggcgtggc gtgaactggt ctggccggaa ctggataaac tgctgcgtaa cgaagacgac   2340
gctaccgtgg caaccccgta cagcgccgct gtgctgcaat accgcgtggt tttccacgat   2400
cacattgacg gcctgattag cgaaaacggt agcccgaacg gtcatgctaa tggcaatacc   2460
gtgtacgatg cgcaacaccc gtgccgtagc aacgtcgcgg tcaagaagga attgcatact   2520
ccggcgagcg atcgcagctg cacccacctg gaatttaaca ttagcggtac cggcctgatg   2580
tacgagacgg gtgaccacgt cggtgtgtat tgcgagaacc tgttggaaac cgtggaggag   2640
gccgagaagt tgttgaacct gagcccgcag acgtacttct ccgttcacac cgacaacgag   2700
gacggtacgc cgttgagcgg cagcagcctg ccgccaccgt ttccgccgtg caccttgcgc   2760
acggcattga ccaaatacgc agacttgact tctgcaccga aaaagtcggt gctggtggcg   2820
ctggccgagt acgcatctga ccagggtgaa gcggatcgtt tgcgtttctt ggcgagcccg   2880
agcggcaaag aggaatatgc acagtacatc ttggcaagcc agcgcacgct gctggaggtc   2940
atggcggagt tcccgtcggc gaaaccgccg ctgggtgtct tttcgcgggg tgtcgctccg   3000
cgcctgcagc cgcgtttcta ttccattagc tctagcccga agatcgcacc gttccgtatt   3060
cacgtgacct gcgccctggt ttatgacaaa tcccctaccg gtcgcgttca taagggcatc   3120
tgtagcacgt ggatgaaaaa tgcggtcccg ctggaagaaa gcaacgattg ttcctgggct   3180
ccgatcttcg tccgcaacag caacttcaag ctgccgaccg acccgaaggt tccgattatc   3240
atgattggtc cgggtaccgg tctggcccct tttcgtggct tttgcaaga gcgcttggcg    3300
ttgaaagaga gcggtgctga attgggtccg gcgatcttgt tctttggttg ccgtaaccgt   3360
aaaatggact ttatttacga ggatgaactg aatgatttcg tcaaagcggg cgttgtcagc   3420
gagctgatcg tcgcttttag ccgcgaaggc ccgatgaaag aatacgtgca acacaaaatg   3480
agccaacgtg cctccgatgt gtggaacatc attagcgacg gtggttatgt ttatgtttgc   3540
ggtgacgcga agggtatggc tcgtgatgtt caccgtaccc tgcataccat cgcacaggag   3600
caaggtagca tgtccagctc ggaggccgaa ggtatggtca aaaacctgca aaccaccggt   3660
cgttacctgc gtgatgtgtg gtaataaaag cttaggaggt aaaaatgtct accctgccaa   3720
tttcttctgt gtcctttagc tccagcactt cgccactggt tgtcgatgac aaggtgagca   3780
cgaaaccgga tgtgatccgt cacacgatga acttcaacgc gagcatttgg ggcgatcaat   3840
tcctgaccta tgacgagccg gaagatctgg taatgaagaa acaactggtt gaggaactta   3900
aagaagaagt gaagaaagaa ttgatcacca tcaagggtag caacgagccg atgcaacatg   3960
tcaagctgat cgagttgatc gacgcagttc aacgcctggg cattgcctac cactttgaag   4020
aagagattga agaggccctg cagcacattc atgtcaccta cggtgagcag tgggtggaca   4080
aagagaattt gcaatccatc agcctgtggt ttcgtctgct gcgtcaacag ggcttcaacg   4140
tgagcagcgg tgtgtttaaa gatttcatgg acgaaaaggg taagtttaaa gagtccctgt   4200
gcaatgatgc acagggtatt ttggcgctgt atgaggccgc attcatgcgc gttgaagatg   4260
aaaccattct ggacaacgct ctggagttca ccaaggtgca tctggacatc atcgctaagg   4320
acccgagctg tgattctagc ctgcgcacgc agattcacca ggctctgaag cagccgctgc   4380
gccgtcgcct ggcacgtatt gaggcgttac actatatgcc gatctatcag caagagacta   4440
gccatgacga agttctgctg aaactggcaa agctggactt tagcgttctg cagagcatgc   4500
acaagaaaga actcagccat atttgcaagt ggtggaaaga tctggatctg cagaataagc   4560
```

tgccgtacgt tcgtgaccgt gtcgttgagg gctatttctg gatcttgagc atttactacg 4620
agccgcaaca tgcgcgtacc cgtatgttcc tgatgaaaac ctgtatgtgg ttggttgtgc 4680
tggacgacac gtttgataac tacggcacgt acgaagagtt ggagattttc acccaagcgg 4740
tagaacgttg gagcatctcg tgtctggaca tgctgcctga gtatatgaag ctgatctacc 4800
aggaactggt caatttacac gtcgagatgg aagagagcct ggagaaagaa ggcaagacct 4860
atcagattca ctatgtgaaa gaaatggcga aagaactggt ccgcaactac ctggttgagg 4920
cgcgctggct gaaagagggc tacatgccga ccctggaaga gtatatgagc gtgagcatgg 4980
tcacgggtac gtacggtctg atgatcgccc gcagctacgt cggtcgtggc gacatcgtta 5040
ccgaagatac cttcaaatgg gtttctagct acccgccgat tatcaaggca agctgcgtta 5100
tcgtgcgttt gatggatgat attgttagcc acaaagaaga acaagagcgt ggtcatgttg 5160
ctagcagcat tgagtgctac agcaaagagt ccggtgcaag cgaagaagaa gcgtgcgagt 5220
atatcagccg taaggtcgag gacgcgtgga aagtcattaa tcgcgagtcc ctgcgtccga 5280
ccgcggttcc gtttccgctg ctgatgcctg cgattaatct ggcgcgtatg tgtgaggtcc 5340
tgtacagcgt gaatgacggt tttacgcacg ccgagggtga tatgaaaagc tatatgaagt 5400
cattctttgt gcacccgatg gttgtgtaag aattc 5435

<210> SEQ ID NO 89
<211> LENGTH: 5432
<212> TYPE: DNA
<213> ORGANISM: Artificial Sequence
<220> FEATURE:
<223> OTHER INFORMATION: SaCP816-CPRm-PaAFS, synthetic operon encoding for SaCP816, CPRm and an alpha-farnesene synthase

<400> SEQUENCE: 89
catatggcac tgttgttggc ggttttctgg agcgctttga ttattctggt tagcatctta 60
ttgcgtcgtc gtcaaaaacg caacaatttg ccaccgggcc caccggccct gccgatcatc 120
ggtaacattc acattctggg caccctgccg caccagagcc tgtacaatct ggcgaagaag 180
tacggtccga tcatgtccat gcgtttgggc ttggttccgg cggtggtcat cagcagcccg 240
gaagcggccg agctggtcct gaaaacccac gacatcgttt ttgcttctcg ccctcgtctg 300
caagttgcag attactttca ctatggcacc aaaggcgtga ttctgaccga atatggtacc 360
tactggcgta acatgcgtcg cctgtgcacg gtcaaactgc tgaacaccgt taagattgat 420
agctttgcag gcacccgcaa gaaagaagtc gctagcttcg ttcagagcct gaaagaagca 480
agcgtggcgc acaaaatggt taacctgtcc gcacgcgtcg ctaatgttat tgagaatatg 540
gtttgtctga tggttattgg tagatcgtct gacgagcgtt tcaagctgaa agaagtgatc 600
caagaagcgg cacagctggc gggtgccttc aatattggtg actatgtccc gtttctgatg 660
ccgctggatc tgcagggcct gactcgccgt atcaagagcg gtagcaaggc attcgatgac 720
atcctcgagg tcattatcga cgagcatgtg caagacatta aagatcatga cgatgagcag 780
catggtgact tcatcgacgt gctgctggcg atgatgaata agccgatgga ttctcgtgag 840
ggtctgtcca tcattgatcg cacgaacatt aaagcgatcc tggtggatat gatcggtgcc 900
gcgatggaca cgagcaccag cggtgtggag tgggcgattt cggagctgat taagcatcct 960
cgtgtcatga agaaactgca agacgaagtg aaaaccgtaa tcggtatgaa ccgcatggtg 1020
gaagaagcgg atctgccgaa actgccgtac ctggacatgg ttgtcaagga aacgatgcgt 1080
ctgcatccgc caggcccgct gctggtgccg cgtgaaagca tggaagatat tacgatcaac 1140

```
ggttactata tcccgaagaa atcccgcatt attgtgaatg catgggcgat cggccgtgac   1200
accaacgcct ggagcaataa tgcgcacgag tttttccctg agcgttttat gagctctaac   1260
gttgatctgc aaggccagga cttccagctg atcccgttcg gtagcggtcg tcgcggttgt   1320
ccgggcatgc gtctgggtct gacgacggtc cgcttggtgc tggcccaact gattcactgc   1380
ttcgacctgg agcttccgaa gggcaccgtc gcgactgacc tggatatgag cgagaagttt   1440
ggtctggcaa tgccgcgtgc gcagcactta ctggcctttc cgacctaccg tctggagagc   1500
taagtcgact aactttaaga aggagatata tccatggaac ctagctctca gaaactgtct   1560
ccgttggaat ttgttgctgc tatcctgaag ggcgactaca gcagcggtca ggttgaaggt   1620
ggtccaccgc caggtctggc agctatgttg atggaaaata aggatttggt gatggttctg   1680
acgacgtccg tggcagtcct gatcggctgt gtcgtggtcc tggcatggcg tcgtgcggca   1740
ggtagcggta agtacaagca acctgaactg cctaaactgg tggtcccgaa agcagccgaa   1800
ccggaggagg cagaggatga taaaaccaag atcagcgtgt tttcggcac ccaaaccggt   1860
acggcagaag gtttcgcgaa ggcttttgtt gaagaggcca aggcgcgtta tcagcaggcc   1920
cgtttcaaag ttatcgacct ggacgactat gcggcagacg atgacgagta cgaagagaaa   1980
ctgaagaagg aaaacttggc attcttcttc ttggcgtcct acggtgacgg cgagccgacg   2040
gacaacgcgg cacgctttta caaatggttt acggagggta aggaccgtgg tgaatggctg   2100
aacaatctgc agtacggcgt tttggtctg ggtaaccgtc aatatgagca tttcaataag   2160
atcgccattg tcgtcgatga tctgatcttc gagcaaggtg gcaagaagct ggttccggtg   2220
ggtctgggtg acgatgacca gtgcattgag gatgattttg cggcgtggcg tgaactggtc   2280
tggccggaac tggataaact gctgcgtaac gaagacgacg ctaccgtggc aaccccgtac   2340
agcgccgctg tgctgcaata ccgcgtggtt ttccacgatc acattgacgg cctgattagc   2400
gaaaacggta gcccgaacgg tcatgctaat ggcaataccg tgtacgatgc gcaacacccg   2460
tgccgtagca acgtcgcggt caagaaggaa ttgcatactc cggcgagcga tcgcagctgc   2520
acccacctgg aatttaacat tagcggtacc ggcctgatgt acgagacggg tgaccacgtc   2580
ggtgtgtatt gcgagaacct gttggaaacc gtggaggagg ccgagaagtt gttgaacctg   2640
agcccgcaga cgtacttctc cgttcacacc gacaacgagg acggtacgcc gttgagcggc   2700
agcagcctgc cgccaccgtt tccgccgtgc accttgcgca cggcattgac caaatacgca   2760
gacttgactt ctgcaccgaa aaagtcggtg ctggtggcgc tggccgagta cgcatctgac   2820
cagggtgaag cggatcgttt gcgtttcttg gcgagcccga gcggcaaaga ggaatatgca   2880
cagtacatct tggcaagcca gcgcacgctg ctggaggtca tggcggagtt cccgtcggcg   2940
aaaccgccgc tgggtgtctt tttcgcgggt gtcgctccgc gcctgcagcc gcgtttctat   3000
tccattagct ctagcccgaa gatcgcaccg ttccgtattc acgtgacctg cgccctggtt   3060
tatgacaaat cccctaccgg tcgcgttcat aagggcatct gtagcacgtg gatgaaaaat   3120
gcggtcccgc tggaagaaag caacgattgt tcctgggctc cgatcttcgt ccgcaacagc   3180
aacttcaagc tgccgaccga cccgaaggtt ccgattatca tgattggtcc gggtaccggt   3240
ctggcccctt ttcgtggctt tttgcaagag cgcttggcgt tgaaagagag cggtgctgaa   3300
ttgggtccgg cgatcttgtt ctttggttgc cgtaaccgta aaatggactt tatttacgag   3360
gatgaactga atgatttcgt caaagcgggc gttgtcagcg agctgatcgt cgcttttagc   3420
cgcgaaggcc cgatgaaaga atacgtgcaa cacaaaatga gccaacgtgc ctccgatgtg   3480
```

```
tggaacatca ttagcgacgg tggttatgtt tatgtttgcg gtgacgcgaa gggtatggct   3540

cgtgatgttc accgtaccct gcataccatc gcacaggagc aaggtagcat gtccagctcg   3600

gaggccgaag gtatggtcaa aaacctgcaa accaccggtc gttacctgcg tgatgtgtgg   3660

taataaaagc ttaggaggta aaaatggatc tggcagtgga aatcgcaatg gacctggcag   3720

tggatgatgt tgaacgccgt gtgggtgact atcattccaa tctgtgggac gacgacttca   3780

tccaaagcct gagcaccccg tatggcgcca gctcttaccg cgagcgtgcg gagcgcttgg   3840

tcggcgaggt caaagaaatg tttacgagca tcagcatcga ggatggtgag ctgacctctg   3900

acttgcttca acgcctgtgg atggttgaca acgttgagcg cctgggcatt agccgtcact   3960

tcgagaatga aatcaaggct gcaattgatt acgtctacag ctattggtcc gacaagggta   4020

ttgtccgtgg tagagatagc gccgtgccgg atctgaacag cattgctctg ggtttccgta   4080

cgttgcgtct gcatggttac accgttagca gcgatgtttt caaggtcttt caagaccgca   4140

aaggtgagtt tgcatgtagc gcgattccga cggaaggtga catcaaaggc gtactgaatc   4200

tgctgcgtgc aagctacatc gcgttccctg gtgagaaagt gatggagaaa gcgcagacct   4260

ttgccgcaac ttatctgaaa gaagcactgc agaagatcca agtgtctagc ctgagccgcg   4320

agatcgaata cgttctggag tatggctggc tgaccaattt tccgcgcctg gaagcgcgta   4380

actacatcga cgttttcggt gaggaaattt gtccgtactt caagaaaccg tgtattatgg   4440

ttgataagct gctggaactg gcgaaactgg agttcaattt gtttcactcg ctgcaacaga   4500

ccgagctgaa acacgtttcc cgttggtgga aggatagcgg ctttagccag ctgaccttca   4560

cgcgtcatcg tcacgtggag ttttacaccc tggctagctg tattgcaatt gaaccgaaac   4620

attctgcgtt tcgtttgggt ttcgcgaagg tctgctacct gggcattgtg ctggacgata   4680

tctatgacac gttcggtaaa atgaaagaac tggagttatt cacggcggca atcaagcgtt   4740

gggacccgag cacgaccgag tgcctgcctg agtatatgaa aggtgtctac atggcgtttt   4800

acaactgcgt taatgaactg gcgctgcaag ccgagaaaac ccagggccgt gacatgttga   4860

actatgcacg taaggcgtgg gaagccctgt tcgatgcgtt cctggaagaa gcgaagtgga   4920

ttagctccgg ctatctgccg acctttgagg aatacctgga gaacggcaaa gtgtccttcg   4980

gttatcgtgc tgccactctg cagccaatcc tgaccctgga cattccgttg ccgctgcaca   5040

tcttgcagca gatcgatttc ccgagccgct ttaatgacct ggccagctca attttgcgtc   5100

tgcgcggtga tatctgcggt tatcaagccg agcgttctcg tggcgaagag gcgagcagca   5160

ttagctgcta catgaaggac aatccgggtt ccaccgagga agatgcgctg agccacatta   5220

acgcgatgat ttcggacaac atcaacgaac tgaattggga gctgctgaag ccgaacagca   5280

atgttccaat cagcagcaaa aagcacgctt tcgatatcct gcgtgcgttt taccatctct   5340

ataagtaccg tgatggtttt agcattgcga agattgaaac gaagaacctg gtgatgcgca   5400

ccgtcctgga gccggtcccg atgtaagaat tc                                 5432
```

<210> SEQ ID NO 90
<211> LENGTH: 5453
<212> TYPE: DNA
<213> ORGANISM: Artificial Sequence
<220> FEATURE:
<223> OTHER INFORMATION: SaCP10374-CPRm-PaAFS, synthetic operon encoding for SaCP10374, CPRm and an alpha-farnesene synthase

<400> SEQUENCE: 90

```
catatggcac tgctgctggc tgtcttttgg agcgcactga ttattctgac ccgcaaacgc     60
```

-continued

```
cgcaaaggtc cgggtctgcc accgggtccg cgtgcgtacc cgattattgg caatctgcac    120
atgatgggcc agctgccaca ccacaatttg cgtgagctgg cacgtgagta tggtccgatt    180
atgagcatgc gcctgggtct ggtgccggca atcgtggtta gctctcctga ggctgcgcag    240
ctgttcctca agacgcatga taccgttttc gcgagccgtc caaagaccga gactgccaaa    300
tacttccatt acggtatcaa aggtctgatc ctgaccgagt atggcccgta ctggcgcaat    360
attcgtcgtt tgagcaccgt taagctgttg aatgccgcga aaatcgatag cttcgcggct    420
atgcgtagaa gcgaagttga acgcctggtc gcgtccgttc gtggttcggc ggttcgtcgt    480
gaggttgtgg acgtcagcag caaagtggcg gaagctatgg agaatatggt ctgccagatg    540
gttatcggcc gttcaggtga cgatcgtttt aagctgaaag aaacctttca agagggcacc    600
caactggcag gcgcgttcaa ttttggtgag tttgtgccgt ttctgctgcc gctggacttg    660
caaggtatta cccgtcgcat caaagaagtc agcactcgtt tcaataagat tttggacctg    720
atcgttgacg agcacattcg cgatgccgct ggtaccaaaa acagcggcgg tcgtgatagc    780
gacaatttc tggatgttct gctgtccttg atgaacacct ctattagcga tagcaatgac    840
acgggtgaca acaaccgtaa caacgtgatc gagcgtgata acattaaagc gatcctgacg    900
gacatgctgg gtgcagcgat ggacacgagc gcgagcacgg tcgagtggac gatctccgaa    960
ctgtttcgcc acccgaaaac catgcagaag ctgcaagcag aaatccgtgg tgtcgtgggc   1020
ccgacccgca atgtgagcga agatgacttg ccgaagctga cctatctgga catggtcgtt   1080
aaggaaggca tgcgtttgca tccggccgtg ccgctgcttc tgccgcatga gtctctggaa   1140
gaagccacga tcgatggcta ctacattccg aagggttccc gcattctgat caacgtctgg   1200
gcgattggtc gcgacccgaa ggcctggccg gatcgtcctg aagagttcat cccggagcgt   1260
ttcgagaaaa gcaacgtgga tgtgctgggc cgtgacttcc agctgctgcc gtttggttcg   1320
ggtcgtcgcg gttgtgcagg cattcgcctg ggcctgatct tcgtacgtct ggttctggca   1380
cagttagttc actgtttcga ctgggaactg gcgcgcaaca tggcgagcag cccggagaag   1440
ttggatatgg aagagaagtt cggcctggcg gtgcatcgtg tcaaccacct gaaagccctg   1500
ccgacgtatc gtctggagtg ctaagtcgac taactttaag aaggagatat atccatggaa   1560
cctagctctc agaaactgtc tccgttggaa tttgttgctg ctatcctgaa gggcgactac   1620
agcagcggtc aggttgaagg tggtccaccg ccaggtctgg cagctatgtt gatggaaaat   1680
aaggatttgg tgatggttct gacgacgtcc gtggcagtcc tgatcggctg tgtcgtggtc   1740
ctggcatggc gtcgtgcggc aggtagcggt aagtacaagc aacctgaact gcctaaactg   1800
gtggtcccga aagcagccga accggaggag gcagaggatg ataaaaccaa gatcagcgtg   1860
tttttcggca cccaaaccgg tacggcagaa ggtttcgcga aggcttttgt tgaagaggcc   1920
aaggcgcgtt atcagcaggc ccgtttcaaa gttatcgacc tggacgacta tgcggcagac   1980
gatgacgagt acgaagagaa actgaagaag gaaaacttgg cattcttctt cttggcgtcc   2040
tacggtgacg gcgagccgac ggacaacgcg gcacgctttt acaaatggtt tacggagggt   2100
aaggaccgtg gtgaatggct gaacaatctg cagtacggcg tttttggtct gggtaaccgt   2160
caatatgagc atttcaataa gatcgccatt gtcgtcgatg atctgatctt cgagcaaggt   2220
ggcaagaagc tggttccggt gggtctgggt gacgatgacc agtgcattga ggatgatttt   2280
gcggcgtggc gtgaactggt ctggccggaa ctggataaac tgctgcgtaa cgaagacgac   2340
gctaccgtgg caaccccgta cagcgccgct gtgctgcaat accgcgtggt tttccacgat   2400
cacattgacg gcctgattag cgaaaacggt agcccgaacg gtcatgctaa tggcaatacc   2460
```

-continued

```
gtgtacgatg cgcaacaccc gtgccgtagc aacgtcgcgg tcaagaagga attgcatact   2520
ccggcgagcg atcgcagctg cacccacctg gaatttaaca ttagcggtac cggcctgatg   2580
tacgagacgg gtgaccacgt cggtgtgtat tgcgagaacc tgttggaaac cgtggaggag   2640
gccgagaagt tgttgaacct gagcccgcag acgtacttct ccgttcacac cgacaacgag   2700
gacggtacgc cgttgagcgg cagcagcctg ccgccaccgt ttccgccgtg caccttgcgc   2760
acggcattga ccaaatacgc agacttgact tctgcaccga aaaagtcggt gctggtggcg   2820
ctggccgagt acgcatctga ccagggtgaa gcggatcgtt tgcgtttctt ggcgagcccg   2880
agcggcaaag aggaatatgc acagtacatc ttggcaagcc agcgcacgct gctggaggtc   2940
atggcggagt tcccgtcggc gaaaccgccg ctgggtgtct tttcgcgggg tgtcgctccg   3000
cgcctgcagc cgcgtttcta ttccattagc tctagcccga agatcgcacc gttccgtatt   3060
cacgtgacct gcgccctggt ttatgacaaa tcccctaccg gtcgcgttca taagggcatc   3120
tgtagcacgt ggatgaaaaa tgcggtcccg ctggaagaaa gcaacgattg ttcctgggct   3180
ccgatcttcg tccgcaacag caacttcaag ctgccgaccg acccgaaggt tccgattatc   3240
atgattggtc cgggtaccgg tctggcccct tttcgtggct tttgcaaga gcgcttggcg    3300
ttgaaagaga gcggtgctga attgggtccg gcgatcttgt tctttggttg ccgtaaccgt   3360
aaaatggact ttatttacga ggatgaactg aatgatttcg tcaaagcggg cgttgtcagc   3420
gagctgatcg tcgcttttag ccgcgaaggc ccgatgaaag aatacgtgca acacaaaatg   3480
agccaacgtg cctccgatgt gtggaacatc attagcgacg gtggttatgt ttatgtttgc   3540
ggtgacgcga agggtatggc tcgtgatgtt caccgtaccc tgcataccat cgcacaggag   3600
caaggtagca tgtccagctc ggaggccgaa ggtatggtca aaaacctgca aaccaccggt   3660
cgttacctgc gtgatgtgtg gtaataaaag cttaggaggt aaaaatggat ctggcagtgg   3720
aaatcgcaat ggacctggca gtggatgatg ttgaacgccg tgtgggtgac tatcattcca   3780
atctgtggga cgacgacttc atccaaagcc tgagcacccc gtatggcgcc agctcttacc   3840
gcgagcgtgc ggagcgcttg gtcggcgagg tcaaagaaat gtttacgagc atcagcatcg   3900
aggatggtga gctgacctct gacttgcttc aacgcctgtg gatggttgac aacgttgagc   3960
gcctgggcat tagccgtcac ttcgagaatg aaatcaaggc tgcaattgat tacgtctaca   4020
gctattggtc cgacaagggt attgtccgtg gtagagatag cgccgtgccg gatctgaaca   4080
gcattgctct gggtttccgt acgttgcgtc tgcatggtta caccgttagc agcgatgttt   4140
tcaaggtctt tcaagaccgc aaaggtgagt ttgcatgtag cgcgattccg acggaaggtg   4200
acatcaaagg cgtactgaat ctgctgcgtg caagctacat cgcgttccct ggtgagaaag   4260
tgatggagaa agcgcagacc tttgccgcaa cttatctgaa agaagcactg cagaagatcc   4320
aagtgtctag cctgagccgc gagatcgaat acgttctgga gtatggctgg ctgaccaatt   4380
ttccgcgcct ggaagcgcgt aactacatcg acgttttcgg tgaggaaatt tgtccgtact   4440
tcaagaaacc gtgtattatg gttgataagc tgctggaact ggcgaaactg gagttcaatt   4500
tgtttcactc gctgcaacag accgagctga aacacgtttc ccgttggtgg aaggatagcg   4560
gctttagcca gctgaccttc acgcgtcatc gtcacgtgga gttttacacc ctggctagct   4620
gtattgcaat tgaaccgaaa cattctgcgt ttcgtttggg tttcgcgaag gtctgctacc   4680
tgggcattgt gctggacgat atctatgaca cgttcggtaa aatgaaagaa ctggagttat   4740
tcacggcggc aatcaagcgt tgggacccga gcacgaccga gtgcctgcct gagtatatga   4800
```

```
aaggtgtcta catggcgttt tacaactgcg ttaatgaact ggcgctgcaa gccgagaaaa   4860

cccagggccg tgacatgttg aactatgcac gtaaggcgtg ggaagccctg ttcgatgcgt   4920

tcctggaaga agcgaagtgg attagctccg gctatctgcc gacctttgag gaatacctgg   4980

agaacggcaa agtgtccttc ggttatcgtg ctgccactct gcagccaatc ctgaccctgg   5040

acattccgtt gccgctgcac atcttgcagc agatcgattt cccgagccgc tttaatgacc   5100

tggccagctc aattttgcgt ctgcgcggtg atatctgcgg ttatcaagcc gagcgttctc   5160

gtggcgaaga ggcgagcagc attagctgct acatgaagga caatccgggt tccaccgagg   5220

aagatgcgct gagccacatt aacgcgatga tttcggacaa catcaacgaa ctgaattggg   5280

agctgctgaa gccgaacagc aatgttccaa tcagcagcaa aaagcacgct ttcgatatcc   5340

tgcgtgcgtt ttaccatctc tataagtacc gtgatggttt tagcattgcg aagattgaaa   5400

cgaagaacct ggtgatgcgc accgtcctgg agccggtccc gatgtaagaa ttc          5453
```

<210> SEQ ID NO 91
<211> LENGTH: 5370
<212> TYPE: DNA
<213> ORGANISM: Artificial Sequence
<220> FEATURE:
<223> OTHER INFORMATION: SaCP10374-CPRm-ClTps2, synthetic operon
      encoding for SaCP10374, CPRm and an alpha-santalene synthase

<400> SEQUENCE: 91

```
catatggcac tgctgctggc tgtcttttgg agcgcactga ttattctgac ccgcaaacgc     60

cgcaaaggtc cgggtctgcc accgggtccg cgtgcgtacc cgattattgg caatctgcac    120

atgatgggcc agctgccaca ccacaatttg cgtgagctgg cacgtgagta tggtccgatt    180

atgagcatgc gcctgggtct ggtgccggca atcgtggtta gctctcctga ggctgcgcag    240

ctgttcctca agacgcatga taccgttttc gcgagccgtc caaagaccga gactgccaaa    300

tacttccatt acggtatcaa aggtctgatc ctgaccgagt atggcccgta ctggcgcaat    360

attcgtcgtt tgagcaccgt taagctgttg aatgccgcga aaatcgatag cttcgcggct    420

atgcgtagaa gcgaagttga acgcctggtc gcgtccgttc gtggttcggc ggttcgtcgt    480

gaggttgtgg acgtcagcag caaagtggcg gaagctatgg agaatatggt ctgccagatg    540

gttatcggcc gttcaggtga cgatcgtttt aagctgaaag aaacctttca agagggcacc    600

caactggcag gcgcgttcaa ttttggtgag tttgtgccgt ttctgctgcc gctggacttg    660

caaggtatta cccgtcgcat caaagaagtc agcactcgtt tcaataagat tttggacctg    720

atcgttgacg agcacattcg cgatgccgct ggtaccaaaa acagcggcgg tcgtgatagc    780

gacaattttc tggatgttct gctgtccttg atgaacacct ctattagcga tagcaatgac    840

acgggtgaca acaaccgtaa caacgtgatc gagcgtgata acattaaagc gatcctgacg    900

gacatgctgg gtgcagcgat ggacacgagc gcgagcacgg tcgagtggac gatctccgaa    960

ctgtttcgcc acccgaaaac catgcagaag ctgcaagcag aaatccgtgg tgtcgtgggc   1020

ccgacccgca atgtgagcga agatgacttg ccgaagctga cctatctgga catggtcgtt   1080

aaggaaggca tgcgtttgca tccggccgtg ccgctgcttc tgccgcatga gtctctggaa   1140

gaagccacga tcgatggcta ctacattccg aagggttccc gcattctgat caacgtctgg   1200

gcgattggtc gcgacccgaa ggcctggccg gatcgtcctg aagagttcat cccggagcgt   1260

ttcgagaaaa gcaacgtgga tgtgctgggc cgtgacttcc agctgctgcc gtttggttcg   1320

ggtcgtcgcg gttgtgcagg cattcgcctg ggcctgatct tcgtacgtct ggttctggca   1380
```

-continued

```
cagttagttc actgtttcga ctgggaactg gcgcgcaaca tggcgagcag cccggagaag   1440
ttggatatgg aagagaagtt cggcctggcg gtgcatcgtg tcaaccacct gaaagccctg   1500
ccgacgtatc gtctggagtg ctaagtcgac taactttaag aaggagatat atccatggaa   1560
cctagctctc agaaactgtc tccgttggaa tttgttgctg ctatcctgaa gggcgactac   1620
agcagcggtc aggttgaagg tggtccaccg ccaggtctgg cagctatgtt gatggaaaat   1680
aaggatttgg tgatggttct gacgacgtcc gtggcagtcc tgatcggctg tgtcgtggtc   1740
ctggcatggc gtcgtgcggc aggtagcggt aagtacaagc aacctgaact gcctaaactg   1800
gtggtcccga aagcagccga accggaggag gcagaggatg ataaaaccaa gatcagcgtg   1860
tttttcggca cccaaaccgg tacggcagaa ggtttcgcga aggcttttgt tgaagaggcc   1920
aaggcgcgtt atcagcaggc ccgtttcaaa gttatcgacc tggacgacta tgcggcagac   1980
gatgacgagt acgaagagaa actgaagaag gaaaacttgg cattcttctt cttggcgtcc   2040
tacggtgacg gcgagccgac ggacaacgcg gcacgctttt acaaatggtt tacggagggt   2100
aaggaccgtg gtgaatggct gaacaatctg cagtacggcg tttttggtct gggtaaccgt   2160
caatatgagc atttcaataa gatcgccatt gtcgtcgatg atctgatctt cgagcaaggt   2220
ggcaagaagc tggttccggt gggtctgggt gacgatgacc agtgcattga ggatgatttt   2280
gcggcgtggc gtgaactggt ctggccggaa ctggataaac tgctgcgtaa cgaagacgac   2340
gctaccgtgg caaccccgta cagcgccgct gtgctgcaat accgcgtggt tttccacgat   2400
cacattgacg gcctgattag cgaaaacggt agcccgaacg gtcatgctaa tggcaatacc   2460
gtgtacgatg cgcaacaccc gtgccgtagc aacgtcgcgg tcaagaagga attgcatact   2520
ccggcgagcg atcgcagctg cacccacctg gaatttaaca ttagcggtac cggcctgatg   2580
tacgagacgg gtgaccacgt cggtgtgtat tgcgagaacc tgttggaaac cgtggaggag   2640
gccgagaagt tgttgaacct gagcccgcag acgtacttct ccgttcacac cgacaacgag   2700
gacggtacgc cgttgagcgg cagcagcctg ccgccaccgt ttccgccgtg caccttgcgc   2760
acggcattga ccaaatacgc agacttgact tctgcaccga aaaagtcggt gctggtggcg   2820
ctggccgagt acgcatctga ccagggtgaa gcggatcgtt tgcgtttctt ggcgagcccg   2880
agcggcaaag aggaatatgc acagtacatc ttggcaagcc agcgcacgct gctggaggtc   2940
atggcggagt tcccgtcggc gaaaccgccg ctgggtgtct tttcgcgggg tgtcgctccg   3000
cgcctgcagc cgcgtttcta ttccattagc tctagcccga agatcgcacc gttccgtatt   3060
cacgtgacct gcgccctggt ttatgacaaa tcccctaccg gtcgcgttca taagggcatc   3120
tgtagcacgt ggatgaaaaa tgcggtcccg ctggaagaaa gcaacgattg ttcctgggct   3180
ccgatcttcg tccgcaacag caacttcaag ctgccgaccg acccgaaggt tccgattatc   3240
atgattggtc cgggtaccgg tctggcccct tttcgtggct ttttgcaaga gcgcttggcg   3300
ttgaaagaga gcggtgctga attgggtccg gcgatcttgt tctttggttg ccgtaaccgt   3360
aaaatggact ttatttacga ggatgaactg aatgatttcg tcaaagcggg cgttgtcagc   3420
gagctgatcg tcgcttttag ccgcgaaggc ccgatgaaag aatacgtgca acacaaaatg   3480
agccaacgtg cctccgatgt gtggaacatc attagcgacg gtggttatgt ttatgtttgc   3540
ggtgacgcga agggtatggc tcgtgatgtt caccgtaccc tgcataccat cgcacaggag   3600
caaggtagca tgtccagctc ggaggccgaa ggtatggtca aaaacctgca aaccaccggt   3660
cgttacctgc gtgatgtgtg gtaataaaag cttgaaggag atatactaat gtctacccag   3720
caggttagct ccgagaatat cgttcgcaac gcggcgaact tccacccgaa tatctggggt   3780
```

aatcatttct tgacgtgtcc aagccagacg atcgattctt ggacgcaaca acaccataaa 3840
gagctgaaag aagaggtccg caagatgatg gtgagcgacg caaacaaacc ggcacaacgt 3900
ctgcgtctga ttgacaccgt tcaacgtttg ggcgtggcgt atcatttcga aaaagaaatc 3960
gatgacgctc tggaaaagat cggtcacgat ccgtttgacg ataaggatga cctgtatatc 4020
gttagcctgt gttttcgcct gctgcgtcag catggcatca agattagctg cgatgttttt 4080
gagaagttca aagacgacga tggcaagttt aaggcttccc tgatgaatga tgtccaaggt 4140
atgctgtcgt tgtatgaagc ggcccacctg gcaattcatg gcgaggacat cctggatgag 4200
gctattgtct ttacgaccac ccacctgaag agcaccgttt ctaactcccc ggtcaattcc 4260
acctttgcgg aacagattcg ccacagcctg cgtgtgccgc tgcgtaaggc agtcccgcgt 4320
ttggagagcc gctacttcct ggatatctat agccgtgacg acctgcacga caagactctg 4380
ctgaactttg ccaaactgga cttcaacatc ctgcaggcga tgcaccagaa agaggcaagc 4440
gagatgaccc gttggtggcg tgatttcgat ttcctgaaga agctgccgta cattcgtgat 4500
cgcgtggttg aactgtactt ttggattttg gtcggtgtga gctaccaacc gaaattcagc 4560
acgggtcgta tctttttgag caagattatc tgtctggaaa ccctggtgga cgacacgttt 4620
gatgcgtacg gtactttcga cgaactggcc attttcaccg aggccgttac gcgttgggac 4680
ctgggtcatc gcgacgcgct gcctgagtac atgaaattca ttttcaagac cctgattgat 4740
gtgtacagcg aggcggaaca agagctggca aaagagggcc gctcctatag cattcactat 4800
gcgatccgta gcttccagga gttggtcatg aagtactttt gcgaggcgaa atggctgaat 4860
aagggttatg ttccgagcct ggatgactac aagagcgtca gcctgcgcag catcggcttc 4920
ctgccgatcg ccgtggcttc ttttgttttc atgggcgaca ttgctacgaa agaggttttt 4980
gagtgggaaa tgaataaccc gaaaatcatc atcgcagccg aaaccatttt ccgctttctg 5040
gatgacattg caggtcatcg cttcgaacaa aaacgtgagc acagcccgag cgcaatcgag 5100
tgctacaaaa accaacatgg tgtctcggaa gaagaggcag tgaaagcgct gagcttggag 5160
gtcgccaatt cgtggaaaga cattaacgaa gagctgctgc tgaaccctat ggcaattcca 5220
ctgccgttgc tgcaggtgat cctggatttg agccgtagcg cggacttcat gtacggtaat 5280
gcgcaggacc gtttcacgca ctccaccatg atgaaagatc aagttgacct ggttctgaaa 5340
gatccggtga aactggacga ttaagaattc 5370

<210> SEQ ID NO 92
<211> LENGTH: 5423
<212> TYPE: DNA
<213> ORGANISM: Artificial Sequence
<220> FEATURE:
<223> OTHER INFORMATION: SaCP10374-CPRm-SaTps8201, synthetic operon encoding for SaCP10374, CPRm and an alpha-/beta-santalene synthase

<400> SEQUENCE: 92
catatggcac tgctgctggc tgtcttttgg agcgcactga ttattctgac ccgcaaacgc 60
cgcaaaggtc cgggtctgcc accgggtccg cgtgcgtacc cgattattgg caatctgcac 120
atgatgggcc agctgccaca ccacaatttg cgtgagctgg cacgtgagta tggtccgatt 180
atgagcatgc gcctgggtct ggtgccggca atcgtggtta gctctcctga ggctgcgcag 240
ctgttcctca agacgcatga taccgttttc gcgagccgtc caaagaccga gactgccaaa 300
tacttccatt acggtatcaa aggtctgatc ctgaccgagt atggcccgta ctggcgcaat 360
attcgtcgtt tgagcaccgt taagctgttg aatgccgcga aaatcgatag cttcgcggct 420

-continued

```
atgcgtagaa gcgaagttga acgcctggtc gcgtccgttc gtggttcggc ggttcgtcgt    480
gaggttgtgg acgtcagcag caaagtggcg gaagctatgg agaatatggt ctgccagatg    540
gttatcggcc gttcaggtga cgatcgtttt aagctgaaag aaacctttca agagggcacc    600
caactggcag gcgcgttcaa ttttggtgag tttgtgccgt ttctgctgcc gctggacttg    660
caaggtatta cccgtcgcat caaagaagtc agcactcgtt tcaataagat tttggacctg    720
atcgttgacg agcacattcg cgatgccgct ggtaccaaaa acagcggcgg tcgtgatagc    780
gacaattttc tggatgttct gctgtccttg atgaacacct ctattagcga tagcaatgac    840
acgggtgaca acaaccgtaa caacgtgatc gagcgtgata acattaaagc gatcctgacg    900
gacatgctgg gtgcagcgat ggacacgagc gcgagcacgg tcgagtggac gatctccgaa    960
ctgtttcgcc acccgaaaac catgcagaag ctgcaagcag aaatccgtgg tgtcgtgggc   1020
ccgacccgca atgtgagcga agatgacttg ccgaagctga cctatctgga catggtcgtt   1080
aaggaaggca tgcgtttgca tccggccgtg ccgctgcttc tgccgcatga gtctctggaa   1140
gaagccacga tcgatggcta ctacattccg aagggttccc gcattctgat caacgtctgg   1200
gcgattggtc gcgacccgaa ggcctggccg gatcgtcctg aagagttcat cccggagcgt   1260
ttcgagaaaa gcaacgtgga tgtgctgggc cgtgacttcc agctgctgcc gtttggttcg   1320
ggtcgtcgcg gttgtgcagg cattcgcctg ggcctgatct tcgtacgtct ggttctggca   1380
cagttagttc actgtttcga ctgggaactg gcgcgcaaca tggcgagcag cccggagaag   1440
ttggatatgg aagagaagtt cggcctggcg gtgcatcgtg tcaaccacct gaaagccctg   1500
ccgacgtatc gtctggagtg ctaagtcgac taactttaag aaggagatat atccatggaa   1560
cctagctctc agaaactgtc tccgttggaa tttgttgctg ctatcctgaa gggcgactac   1620
agcagcggtc aggttgaagg tggtccaccg ccaggtctgg cagctatgtt gatggaaaat   1680
aaggatttgg tgatggttct gacgacgtcc gtggcagtcc tgatcggctg tgtcgtggtc   1740
ctggcatggc gtcgtgcggc aggtagcggt aagtacaagc aacctgaact gcctaaactg   1800
gtggtcccga aagcagccga accggaggag gcagaggatg ataaaaccaa gatcagcgtg   1860
tttttcggca cccaaaccgg tacggcagaa ggtttcgcga aggcttttgt tgaagaggcc   1920
aaggcgcgtt atcagcaggc ccgtttcaaa gttatcgacc tggacgacta tgcggcagac   1980
gatgacgagt acgaagagaa actgaagaag gaaaacttgg cattcttctt cttggcgtcc   2040
tacggtgacg gcgagccgac ggacaacgcg gcacgctttt acaaatggtt tacggagggt   2100
aaggaccgtg gtgaatggct gaacaatctg cagtacggcg tttttggtct gggtaaccgt   2160
caatatgagc atttcaataa gatcgccatt gtcgtcgatg atctgatctt cgagcaaggt   2220
ggcaagaagc tggttccggt gggtctgggt gacgatgacc agtgcattga ggatgatttt   2280
gcggcgtggc gtgaactggt ctggccggaa ctggataaac tgctgcgtaa cgaagacgac   2340
gctaccgtgg caaccccgta cagcgccgct gtgctgcaat accgcgtggt tttccacgat   2400
cacattgacg gcctgattag cgaaaacggt agcccgaacg gtcatgctaa tggcaatacc   2460
gtgtacgatg cgcaacaccc gtgccgtagc aacgtcgcgg tcaagaagga attgcatact   2520
ccggcgagcg atcgcagctg cacccacctg gaatttaaca ttagcggtac cggcctgatg   2580
tacgagacgg gtgaccacgt cggtgtgtat tgcgagaacc tgttggaaac cgtggaggag   2640
gccgagaagt tgttgaacct gagcccgcag acgtacttct ccgttcacac cgacaacgag   2700
gacggtacgc cgttgagcgg cagcagcctg ccgccaccgt ttccgccgtg caccttgcgc   2760
```

```
acggcattga ccaaatacgc agacttgact tctgcaccga aaaagtcggt gctggtggcg   2820
ctggccgagt acgcatctga ccagggtgaa gcggatcgtt tgcgtttctt ggcgagcccg   2880
agcggcaaag aggaatatgc acagtacatc ttggcaagcc agcgcacgct gctggaggtc   2940
atggcggagt tcccgtcggc gaaaccgccg ctgggtgtct ttttcgcggg tgtcgctccg   3000
cgcctgcagc cgcgtttcta ttccattagc tctagcccga agatcgcacc gttccgtatt   3060
cacgtgacct gcgccctggt ttatgacaaa tcccctaccg gtcgcgttca taagggcatc   3120
tgtagcacgt ggatgaaaaa tgcggtcccg ctggaagaaa gcaacgattg ttcctgggct   3180
ccgatcttcg tccgcaacag caacttcaag ctgccgaccg acccgaaggt tccgattatc   3240
atgattggtc cgggtaccgg tctggcccct tttcgtggct tttgcaaga gcgcttggcg   3300
ttgaaagaga gcggtgctga attgggtccg gcgatcttgt tctttggttg ccgtaaccgt   3360
aaaatggact ttatttacga ggatgaactg aatgatttcg tcaaagcggg cgttgtcagc   3420
gagctgatcg tcgcttttag ccgcgaaggc ccgatgaaag aatacgtgca acacaaaatg   3480
agccaacgtg cctccgatgt gtggaacatc attagcgacg gtggttatgt ttatgtttgc   3540
ggtgacgcga agggtatggc tcgtgatgtt caccgtaccc tgcataccat cgcacaggag   3600
caaggtagca tgtccagctc ggaggccgaa ggtatggtca aaaacctgca aaccaccggt   3660
cgttacctgc gtgatgtgtg gtaataaaag cttaggaggt aaaacatatg gacagcagca   3720
ccgccaccgc aatgaccgca ccattcatcg acccgacgga tcatgtgaat ctgaaaaccg   3780
acacggatgc gagcgaaaat cgtcgtatgg gtaactacaa gccgagcatt tggaactacg   3840
attttctgca gtccctggcg acgcaccaca acattgttga agagcgtcac ctgaagctgg   3900
cagagaaact gaaaggtcaa gtgaaattca tgttcggtgc gccgatggag ccattggcta   3960
agttggagct ggttgatgtg gtgcaacgct tgggtctgaa ccacctgttc gagactgaaa   4020
tcaaagaagc tctgttcagc atctacaaag atggcagcaa tggctggtgg tttggccatc   4080
tgcatgctac ctctttgcgc ttccgtctgt tgcgccaatg tggcctgttt atcccgcagg   4140
acgttttcaa aacctttcaa aacaagaccg gtgagtttga catgaagctg tgcgacaacg   4200
ttaagggcct gctgagcctg tacgaggcga gctacctggg ctggaagggc gagaacatct   4260
tggatgaagc aaaggcgttc acgaccaagt gcctgaagag cgcatgggag aacattagcg   4320
agaagtggct ggcgaagcgt gttaaacatg cgttggcgct gccgctgcac tggcgtgttc   4380
cgcgtattga agcacgctgg tttatcgagg cctacgaaca agaggccaat atgaatccga   4440
cgctgctgaa actggcgaaa ctggacttca acatggtcca aagcattcac cagaaagaaa   4500
tcggtgaact ggcccgctgg tgggttacta ccggcctgga caagctggcg ttcgcacgca   4560
acaatctgtt gcagtcttat atgtggagct gcgccatcgc gtccgacccg aaattcaaac   4620
tggcgcgtga aaccattgtc gagatcggtt ccgtgttgac ggttgtcgac gacggctatg   4680
atgtgtacgg ttctatcgat gagctggacc tgtacaccag ctcggtggag cgttggtcct   4740
gtgtcgagat tgacaagctg cctaatacgc tgaagctgat ctttatgtct atgttcaaca   4800
aaaccaacga ggtgggtctg cgtgttcaac acgagcgtgg ttacaatagc atcccgacct   4860
tcattaaggc gtgggtggaa cagtgtaaga gctatcaaaa agaggcgcgt tggtttcatg   4920
gtggtcacac gcctccgctg gaagaataca gcctgaacgg tctggtcagc attggttttc   4980
cgctgttgct gatcaccggc tatgttgcga ttgctgagaa tgaagcagcc ctggataaag   5040
tccacccgct gccggacctg ctgcattatt ccagcttgct gagccgtctg attaatgata   5100
tcggcactag cccggatgaa atggcgcgtg gtgacaatct gaagagcatt cactgctata   5160
```

tgaatgaaac cggtgccagc gaagaggtcg cacgcgagca catcaaaggc gtcatcgaag 5220
agaattggaa aattctgaac cagtgttgct ttgaccagtc ccagttccag gagccgttca 5280
tcacgtttaa cctgaacagc gtgcgcggct cgcatttctt ctatgaattt ggtgatggtt 5340
ttggtgttac cgacagctgg accaaggtgg atatgaaaag cgtcctgatt gatccgattc 5400
cgctgggtga agagtaagaa ttc 5423

<210> SEQ ID NO 93
<211> LENGTH: 53
<212> TYPE: DNA
<213> ORGANISM: Artificial Sequence
<220> FEATURE:
<223> OTHER INFORMATION: mutagenesis reverse primer AV8-L358-rev
<220> FEATURE:
<221> NAME/KEY: misc_feature
<222> LOCATION: (22)..(22)
<223> OTHER INFORMATION: n is a, c, g, or t

<400> SEQUENCE: 93
cacgcggcat caccagcgga vncggcggat gcaggcgcag ggtttcttta atc 53

<210> SEQ ID NO 94
<211> LENGTH: 40
<212> TYPE: DNA
<213> ORGANISM: Artificial Sequence
<220> FEATURE:
<223> OTHER INFORMATION: primer AV8-pcw-fw

<400> SEQUENCE: 94
catcgatgct taggaggtca tatggctctg ttattagcag 40

<210> SEQ ID NO 95
<211> LENGTH: 25
<212> TYPE: DNA
<213> ORGANISM: Artificial Sequence
<220> FEATURE:
<223> OTHER INFORMATION: primer AV8-L358-fw

<400> SEQUENCE: 95
tccgctggtg atgccgcgtg agtgc 25

<210> SEQ ID NO 96
<211> LENGTH: 38
<212> TYPE: DNA
<213> ORGANISM: Artificial Sequence
<220> FEATURE:
<223> OTHER INFORMATION: primer AV8-CPR-rev

<400> SEQUENCE: 96
atatatctcc ttcttaaagt tagtcgactc attaggtg 38

<210> SEQ ID NO 97
<211> LENGTH: 65
<212> TYPE: DNA
<213> ORGANISM: Artificial Sequence
<220> FEATURE:
<223> OTHER INFORMATION: foward primer CPRm_aaBFS_Inf1

<400> SEQUENCE: 97
ttacctgcgt gatgtgtggt aataaaagct taggaggtaa aaatgtctac cctgccaatt 60
tcttc 65

<210> SEQ ID NO 98

<211> LENGTH: 63
<212> TYPE: DNA
<213> ORGANISM: Artificial Sequence
<220> FEATURE:
<223> OTHER INFORMATION: reverse primer AaBFS_Inf2

<400> SEQUENCE: 98
atgtttgaca gcttatcatc gataagctga attcttacac aaccatcggg tgcacaaaga 60
atg 63

<210> SEQ ID NO 99
<211> LENGTH: 65
<212> TYPE: DNA
<213> ORGANISM: Artificial Sequence
<220> FEATURE:
<223> OTHER INFORMATION: foward primer CPRm_PaAFS_Inf1

<400> SEQUENCE: 99
ttacctgcgt gatgtgtggt aataaaagct taggaggtaa aaatggatct ggcagtggaa 60
atcgc 65

<210> SEQ ID NO 100
<211> LENGTH: 66
<212> TYPE: DNA
<213> ORGANISM: Artificial Sequence
<220> FEATURE:
<223> OTHER INFORMATION: reverse primer PaAFS_Inf2

<400> SEQUENCE: 100
ctcatgtttg acagcttatc atcgataagc tgaattctta catcgggacc ggctccagga 60
cggtgc 66

<210> SEQ ID NO 101
<211> LENGTH: 60
<212> TYPE: DNA
<213> ORGANISM: Artificial Sequence
<220> FEATURE:
<223> OTHER INFORMATION: primer foward CPRm_Tps647_inf1

<400> SEQUENCE: 101
gcgtgatgtg tggtaataaa agcttaggag gtaaaaatgg cgaccgttgt ggatgattct 60

<210> SEQ ID NO 102
<211> LENGTH: 53
<212> TYPE: DNA
<213> ORGANISM: Artificial Sequence
<220> FEATURE:
<223> OTHER INFORMATION: primer reverse Tps647_Inf2

<400> SEQUENCE: 102
gcttatcatc gataagctga attcttactc ttcatccagg gtaatcgggt gga 53

<210> SEQ ID NO 103
<211> LENGTH: 58
<212> TYPE: DNA
<213> ORGANISM: Artificial Sequence
<220> FEATURE:
<223> OTHER INFORMATION: primer foward CPRm_Tps30_Inf1

<400> SEQUENCE: 103
gcgtgatgtg tggtaataaa agcttaggag gtaaaaatgg acgcattcgc aacgagcc 58

<210> SEQ ID NO 104
<211> LENGTH: 59

-continued

```
<212> TYPE: DNA
<213> ORGANISM: Artificial Sequence
<220> FEATURE:
<223> OTHER INFORMATION: primer reverse Tps30_Inf2

<400> SEQUENCE: 104

gtgatgtgtg gtaataaaaa gctgaattct tagtcctctt cattcagcgg gatcgggtg      59
```